(12) United States Patent
Chen et al.

(10) Patent No.: US 6,861,423 B2
(45) Date of Patent: Mar. 1, 2005

(54) METHODS OF TREATING P38 KINASE-MEDIATED DISORDERS WITH PYRIDO[2,3-D]PYRIMIDIN-7-ONE COMPOUNDS

(75) Inventors: Jian Jeffrey Chen, Santa Clara, CA (US); James Patrick Dunn, Los Altos, CA (US); David Michael Goldstein, San Jose, CA (US); Julie Anne Lim, San Mateo, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 80 days.

(21) Appl. No.: 10/230,723

(22) Filed: Aug. 29, 2002

(65) Prior Publication Data

US 2003/0153586 A1 Aug. 14, 2003

Related U.S. Application Data

(63) Continuation of application No. 09/943,407, filed on Aug. 30, 2001, now Pat. No. 6,506,749.
(60) Provisional application No. 60/229,584, filed on Aug. 31, 2000, and provisional application No. 60/229,577, filed on Aug. 31, 2000.

(51) Int. Cl.[7] .................. A61K 31/535; A61K 31/52
(52) U.S. Cl. ................. 514/234.2; 514/264.11
(58) Field of Search .................... 514/234.2, 264.11

(56) References Cited

U.S. PATENT DOCUMENTS

| 5,620,981 A | 4/1997 | Blankley et al. |
| 5,733,914 A | 3/1998 | Blankley et al. |
| 5,945,422 A | 8/1999 | Doherty et al. |

FOREIGN PATENT DOCUMENTS

| WO | WO 96/15128 A2 | 5/1996 |
| WO | WO 96/34867 A1 | 11/1996 |
| WO | WO 99/61444 A2 | 12/1999 |

OTHER PUBLICATIONS

Boehm and Adams, "New inhibitors of p38 kinase," *Expert Opinion on Therapeutic Patents*, vol. 10:1 (2000), pp 25–37.
Trumpp–Kallmeyer, et al., Development of a Binding Model to Protein Tyrosine Kinases for Substituted Pyrido[2,3-d] pyrimidine Inhibitors, *J. Medicinal Chemistry*, vol. 41 (1998), pp 1752–1763.

Klutchko, et al., "2–Substituted Aminopyrido[2,3–d] pyrimidin–7(8H)–ones. Structure–Activity Relationships Against Selected Tyrosine Kinases and in Vitro and in Vivo Anticancer Activity," *J. Medicinal Chemistry*, vol. 41 (1998), pp 3276–3292.

Boschelli, et al., "Synthesis and Tyrosine Kinase Inhibitory Activity of a Series of 2–Amino–8H–pyrido[2,3–d]pyrid-midines: Identification of Potent Selective Platelet–Derived Growth Factor Receptor Tyrosine Kinase Inhibitors," *J. Medicinal Chemistry*, vol. 41 (1998), pp 4365–4377.

*Primary Examiner*—Rebecca Cook
(74) *Attorney, Agent, or Firm*—Grant D. Green

(57) ABSTRACT

Disorders mediated by p38 kinase inhibitors are treated with compounds of the formula:

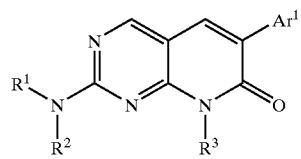

or salts thereof, wherein:

$R^1$ is hydrogen or alkyl;

$R^2$ is substituted cycloalkyl, heterosubstituted cycloalkyl, helcroalkylsubstituted cycloalkyl, heterosubstituted cycloalkyl-alkly, heterocyclyl, heterocyclyl spiro cycloalkyl, aralkoxy, alkoxy, -alkylene-S(O)$_n$-alkyl (where is 1 or 2) or —SO$_2$Ar$^2$;

$R^3$ is hydrogen, amino, monoalkylamino, dialkylamino, acylamino, —NR$^8$—C(=O)—R$^b$ (where R$^a$ is hydrogen or alkyl and R$^h$ is heterocyclyl or heteroalkyl), alkyl, cycloalkyl, phthalimidoalkyl, aryl, aralkyl, haloalkyl, heteroalkyl, cyanoalkyl, -alkylene-C(O) R (where R is hydrogen, alkyl, hydroxy, alkoxy, amino, monoalkylamino or dialkylamino) or acyl; and each of Ar$^1$ and Ar$^2$ is independently aryl.

24 Claims, No Drawings

METHODS OF TREATING P38 KINASE-MEDIATED DISORDERS WITH PYRIDO[2,3-D]PYRIMIDIN-7-ONE COMPOUNDS

CROSS-REFERENCE TO RELATED APPLICATIONS

This application is a continuation application of U.S. application Ser. No. 09/943,407, filed Aug. 30, 2001, now U.S. Pat. No. 6,506,749 and claims the benefit under 35 U.S.C. 119 (e) of U.S. Provisional Applications Ser. No. 60/229,584, filed on Aug. 31, 2000, and Ser. No. 60/229,577, filed Aug. 31, 2000, the disclosure of which is herein incorporated by reference. This patent application also incorporates by reference the entire disclosure of U.S. patent application Ser. No. 09/943,338, filed Aug. 30, 2001 allowed.

FIELD OF THE INVENTION

The present invention relates to 7-oxo-pyridopyrimidines. In particular, the present invention provides 2,6-disubstituted 7-oxo-pyrido[2,3-d]pyrimidines, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents*, (2000) 10(1).

Certain pyrido[2,3-d]pyrimidines are disclosed as inhibitors of protein tyrosine kinase mediated cellular proliferation in WO 96/34867, published Nov. 7, 1996 (Warner Lambert).

The inhibition of these cytokines by inhibition of the p38 kinase is of benefit in controlling, reducing and alleviating many of these disease states.

SUMMARY OF THE INVENTION

One aspect of the present invention provides compounds represented by the Formula:

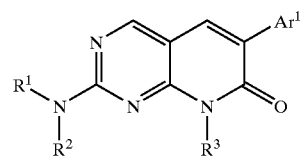

in which:

$R^1$ is hydrogen or alkyl;

$R^2$ is substituted cycloalkyl, heterosubstituted cycloalkyl, heteroalkylsubstituted cycloalkyl, heterosubstituted cycloalkyl-alkyl, heterocyclyl, heterocyclyl spiro cycloalkyl, aralkoxy, alkoxy, alkyl-S(O)$_n$-alkylene- (where n is 1 or 2) or SO$_2$Ar$^2$;

$R^3$ is hydrogen, amino, monoalkylamino, dialkylamino, acylamino, —NR$^a$—C(=O)—R$^b$ (where R$^a$ is hydrogen or alkyl and R$^b$ is heterocyclyl or heteroalkyl), alkyl, cycloalkyl, phthalimidoalkyl, aryl, aralkyl, haloalkyl, heteroalkyl, cyanoalkyl, -alkylene-C(O)—R (where R is hydrogen, alkyl, hydroxy, alkoxy, amino, monoalkylamino or dialkylamino) or acyl; and each of Ar$^1$ and Ar$^2$ is independently aryl.

The compounds of Formula I and their aforementioned salts are inhibitors of protein kinases, and exhibit effective activity against p38 in vivo. Therefore, the compounds can be used for the treatment of diseases mediated by the pro-inflammatory cytokines such as TNF and IL-1.

Thus, another aspect of the present invention provides methods for the treatment of p38 mediated diseases or conditions in which a therapeutically effective amount of a compound of Formula I is administered to a patient in need of such treatment.

Yet another aspect of the present invention provides methods for preparing the compounds described above.

Still yet another aspect of the present invention provides methods for preparing medicaments useful for the treatment of the p38 mediated diseases and conditions.

Definitions

Unless otherwise stated, the following terms used in the specification and claims have the meanings given below:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylsulfonyl-alkyl" means a radical $R^a$—S(O)$_2$—$R^b$—, where $R^a$ is alkyl and $R^b$ is alkylene as defined herein.

"Alkylthio" means a radical —SR where R is an alkyl as defined above e.g., methylthio, ethylthio, propylthio, butylthio, and the like.

"Aralkoxy" means a radical —O—$R^a$—$R^b$, where $R^a$ is alkylene and $R^b$ is aryl as defined above.

"Aryl" means a monovalent monocyclic or bicyclic aromatic hydrocarbon radical which is optionally substituted independently with one or more substituents, preferably one, two or three, substituents preferably selected from the group consisting of alkyl, hydroxy, alkoxy, haloalkyl, haloalkoxy, heteroalkyl, halo, nitro, cyano, amino, monoalkylamio, dialkylamino, methylenedioxy, ethylenedioxy and acyl. More specifically the term aryl includes, but is not limited to, phenyl, chlorophenyl, methoxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Cycloalkylalkyl" means a radical —$R^aR^b$ where $R^a$ is an alkylene group and $R^b$ is cycloalkyl group as defined herein, e.g., cyclohexylmethyl, and the like.

"Substituted cycloalkyl" means a cycloalkyl radical as defined herein with one, two or three (preferably one) ring hydrogen atoms independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl).

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl radical as defined herein wherein one, two or three hydrogen atoms have been replaced with a substituent independently selected from the group consisting of —O$R^a$, —N$R^bR^c$, and —S(O)$_n R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C=O), imino, hydroximino (=NOH), NR'SO$_2R^d$ (where R' is hydrogen or alkyl and $R^d$ is alkyl, cycloalkyl, amino, monoalkylamino or dialkylamino), —X—C(O)R (where X is O or NR', R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterosubstituted cycloalkyl-alkyl" means a radical $R^aR^b$— where $R^a$ is a heterosubstituted cycloalkyl radical and $R^b$ is an alkylene radical.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, three or four substituents selected from alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R (where R is OR or NR'R" and R is hydrogen, alkyl or haloalkyl, and R' and R" are independently hydrogen or alkyl, or R' and R" together with the nitrogen atom to which they are attached form a ring), or —S(O)$_n$R (where n is an integer from 0 to 2) such that when n is 0, R is hydrogen, alkyl, haloalkyl, cycloalkyl, or cycloalkylalkyl, and when n is 1 or 2, R is alkyl, cycloalkyl, cycloalkylalkyl, amino, acylamino, monoalkylamino or dialkylamino. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, N-methanesulfonyl-piperidin-4-yl, and the derivatives thereof.

"Heterocyclylalkyl" means a radical —$R^aR^b$ where $R^a$ is an alkylene group and $R^b$ is a heterocyclyl group as defined above with the understanding that $R^b$ is attached to $R^a$ via a carbon atom of the heterocyclyl ring, e.g., tetrahydropyran-2-ylmethyl, 2- or 3-piperidinylmethyl, and the like.

"Heterocyclyl spiro cycloalkyl" means a spiro radical consisting of a cycloalkyl ring and a heterocyclic ring with each ring having 5 to 8 ring atoms and the two rings having only one carbon atom in common, with the understanding that the point of attachment of the heterocyclyl spiro cycloalkyl radical is via the cycloalkyl ring. The spiro radical is formed when two hydrogen atoms from the same carbon atom of the cycloalkyl radical are replaced with a heterocyclyl group as defined herein, and may be optionally substituted with alkyl, hydroxy, hydroxyalkyl, or oxo. Examples include, but are not limited to, for example, 1,4-dioxaspiro[4.5]decan-8-yl, 1,3-diazaspiro[4.5]decan-8-yl, 2,4-dione-1,3-diaza-spiro[4.5]decan-8-yl, 1,5-dioxaspiro[5.5]undecan-9-yl, (3-hydroxymethyl-3-methyl)-1,5-dioxa-spiro[5.5]undecan-9-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monoalkylamino" means a radical —NHR where R is an alkyl, hydroxyalkyl, cycloalkyl, or cycloalkylalkyl group as defined above, e.g., methylamino, (1-methylethyl)amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Phthalimidoalkyl" means a radical of the formula —$R^a$—$R^b$, wherein $R^a$ is alkylene as defined herein and $R^b$ is phthalimido radical attached to $R^a$ via the nitrogen atom.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "treating", "contacting" or "reacting" when referring to a chemical reaction, means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

DETAILED DESCRIPTION

One aspect of the present invention provides compounds represented by the formula:

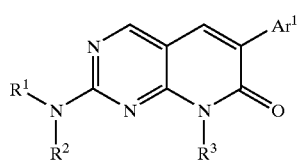

I where:
R$^1$ is hydrogen or alkyl;
R$^2$ is substituted cycloalkyl, heterosubstituted cycloalkyl, heteroalkylsubstituted cycloalkyl, heterosubstituted cycloalkyl-alkyl, heterocyclyl, heterocyclyl spiro cycloalkyl, aralkoxy, alkoxy, alkyl-S(O)$_n$-alkylene- (where n is 1 or 2) or SO$_2$Ar$^2$;
R$^3$ is hydrogen, amino, monoalkylamino, dialkylamino, acylamino, —NR$^a$—C(=O)—R$^b$ (where R$^a$ is hydrogen or alkyl and R$^b$ is heterocyclyl or heteroalkyl), alkyl, cycloalkyl, phthalimidoalkyl, aryl, aralkyl, haloalkyl, heteroalkyl, cyanoalkyl, -alkylene-C(O)—R (where R is hydrogen, alkyl, hydroxy, alkoxy, amino, monoalkylamino or dialkylamino)or acyl; and
each of Ar$^1$ and Ar$^2$ is independently an aryl.

Particularly preferred compounds of Formula I are those represented by the Formula II:

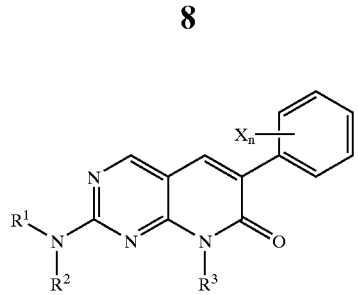

II where n is 1 or 2 and X is hydrogen, alkyl, halo, nitro, cyano or methoxy, particularly halo, alkyl or methoxy, with substitution at the 2-position being preferred.

More preferred compounds of Formula I are represented by the Formula III:

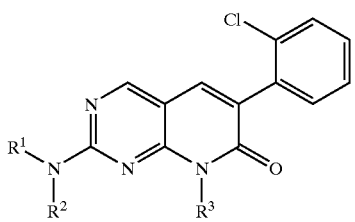

III

In reference to compounds of Formula I:

Preferably, R$^1$ is hydrogen or alkyl. More preferably, R$^1$ is hydrogen.

Preferably, R$^2$ is alkylsulfonyl-alkyl, aralkoxy, alkoxy, heterosubstituted cycloalkyl, heteroalkylsubstituted cycloalkyl, heterosubstituted cycloalkyl-alkyl or heterocyclyl. More preferably R$^2$ is heterosubstituted cycloalkyl or heterocyclyl, e.g. 4-substituted cyclohexyl, substituted piperidinyl, morpholino, optionally substituted piperazinyl, tetrahydrofuryl, tetrahydrothiofuryl, S-oxo-tetrahydrothiofuryl, S,S-dioxo-tetrahydrothiofuryl, tetrahydrothiopyranyl, S-oxo-tetrahydrothiopyranyl, S,S-dioxo-tetrahydrohtiopyranyl, (1,1-dimethyl-2-methylsulfonyl)ethyl, (1,1-dimethyl-3-methylsulfonyl) propyl, benzyloxy or tetrahydropyranyl.

Preferably, R$^3$ of compounds of Formula I is hydrogen, amino, monoalkylamino, dialkylamino, acylamino, —NR$^a$—C(=O)—R$^b$ (where R$^a$ is hydrogen or alkyl and R$^b$ is heterocyclyl or heteroalkyl), alkyl, haloalkyl, cycloalkyl, cyanomethyl, phthalimidoalkyl, heteroalkyl, aryl, aralkyl or -alkylene-C(O)—R (where R is hydrogen, alkyl, hydroxy, alkoxy, amino, monoalkylamino or dialkylamino). Most preferably R$^3$ is hydrogen, amino, dimethylamino, isopropylamino, (morpholinoformyl)amino (i.e., —NR$^a$—C(=O)—R$^b$ where R$^a$ is hydrogen and R$^b$ is morpholino), methyl, 2,2,2-trifluoroethyl, cyclopropyl, cyanomethyl, phthalimidoalkyl, 2-hydroxyethyl, 4-fluorophenyl, benzyl, carboxymethyl or methoxycarbonylmethyl. Even more preferably, R$^3$ is hydrogen or methyl.

It should be appreciated that when R$^3$ is hydrogen, the compounds can exist in tautomeric form as follows:

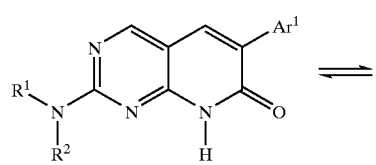

⇌

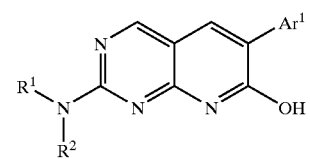

Thus, in addition to the compounds described above, the present invention includes all tautomeric forms. Furthermore, the present invention also includes all pharmaceutically acceptable salts of those compounds along with prodrug forms of the compounds and all stereoisomers whether in a pure chiral form or a racemic mixture or other form of mixture.

Still further, combinations of the preferred groups described above will form other preferred embodiments; thus, for example, preferred substituents $R^1$, $R^2$ and $R^3$ of Formula I are also preferred substituents of compounds of Formulas II and III.

Some of the representative compounds of Formula I are shown in Table 1 below.

TABLE 1

Representative compounds of Formula I

| Cpd # | STRUCTURE | Melting Point | Mass spec |
|---|---|---|---|
| 1 | 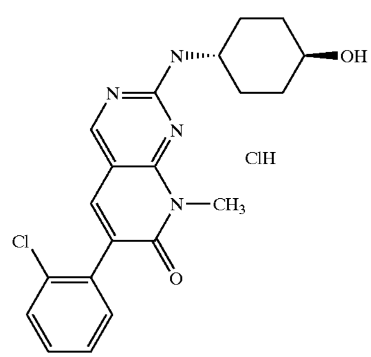 | 163.4–171.1° C. (salt) | (M + H) + 385 |
| 2 | 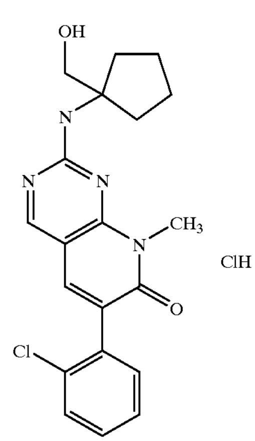 | 213.7–214.6° C. (salt) | (M + H) + 385 |

TABLE 1-continued
Representative compounds of Formula I
| Cpd # | STRUCTURE | Melting Point | Mass spec |
|---|---|---|---|
| 3 | 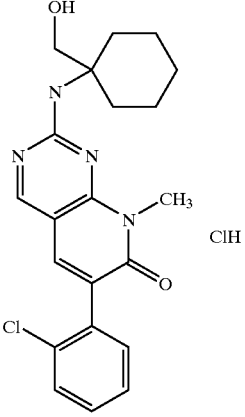 | 185–188.6° C. (salt) | (M + H) + 399 |
| 4 | 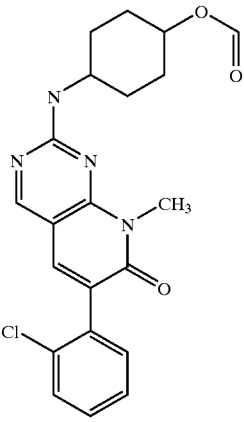 | 196.1–196.6° C. | MH+ = 413 |
| 5 | 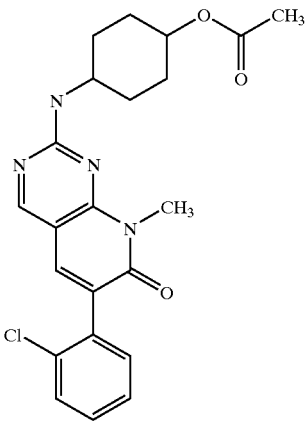 | 200.9–201.2° C. | MH+ = 427 |
| 6 | 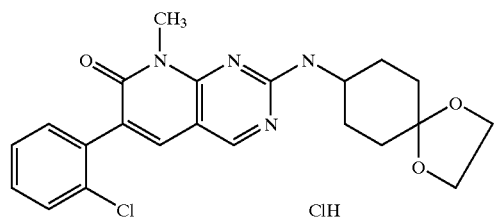 | | M+. 427 |

TABLE 1-continued

Representative compounds of Formula I

| Cpd # | STRUCTURE | Melting Point | Mass spec |
|---|---|---|---|
| 7 | 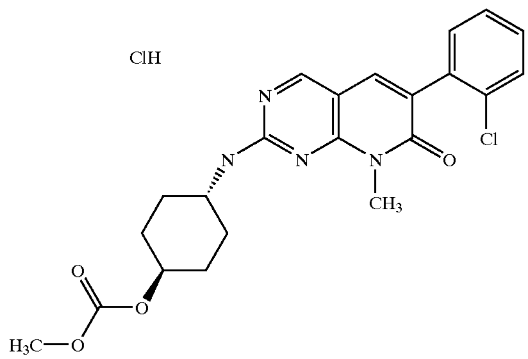 | 213.9–214.4° C. | MH+ = 443 |
| 8 | 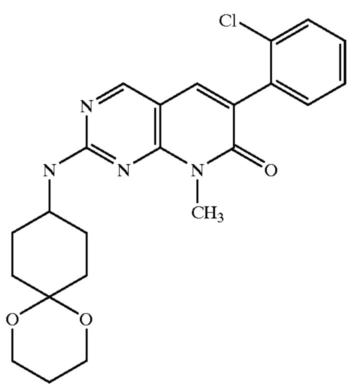 | 196.1–196.5° C. | MH+ = 441 |
| 9 | 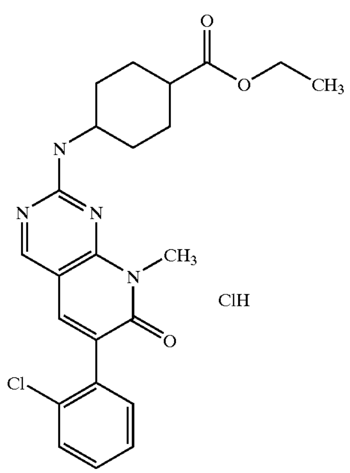 | 192.1–198.3° C. (salt) | (M + H) + 441 |
| 10 | 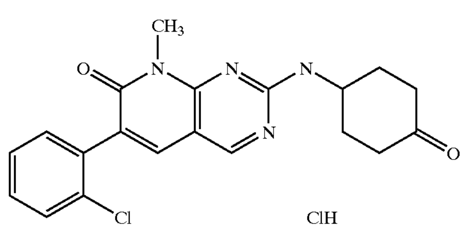 | | MH+ = 383 |

TABLE 1-continued
Representative compounds of Formula I
| Cpd # | STRUCTURE | Melting Point | Mass spec |
|---|---|---|---|
| 11 | 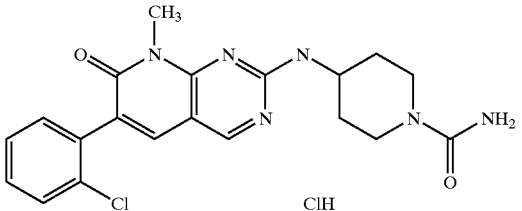 | 192–202° C. (salt) | M+. 413 |
| 12 | 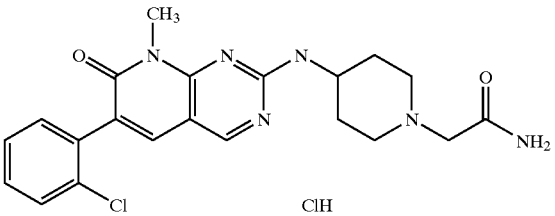 | | M+. 427 |
| 13 | 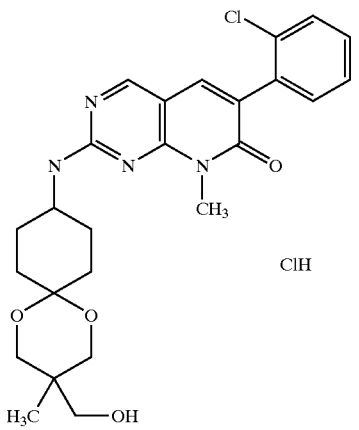 | 180.3–181.2° C. (salt) | M+ = 485 |
| 14 | 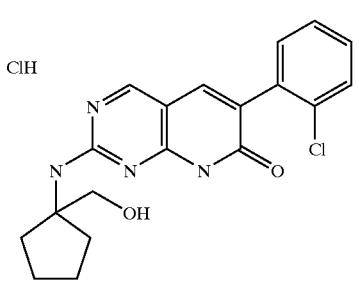 | 290–293° C. (salt) | MH+ = 371 |

TABLE 1-continued
Representative compounds of Formula I
| Cpd # | STRUCTURE | Melting Point | Mass spec |
|---|---|---|---|
| 15 | 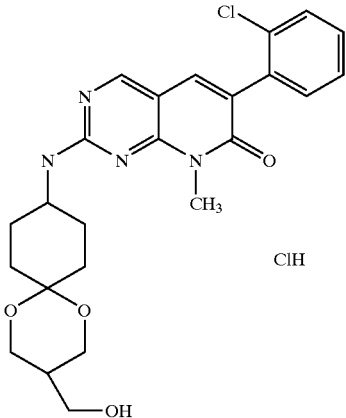 | 146–150° C. (salt) | M+ = 471 |
| 16 | 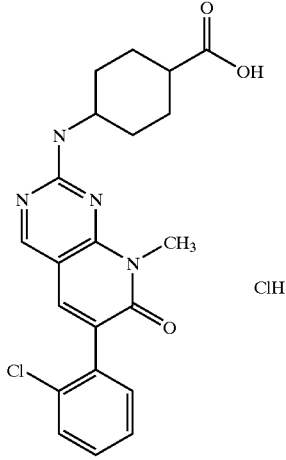 | 263.6–264.2° C. (salt) | (M + H) + 413 |
| 17 | 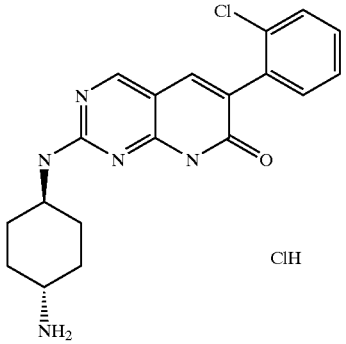 | >300° C. (salt) | M + H+ = 370 |

TABLE 1-continued
Representative compounds of Formula I
| Cpd # | STRUCTURE | Melting Point | Mass spec |
|---|---|---|---|
| 18 | 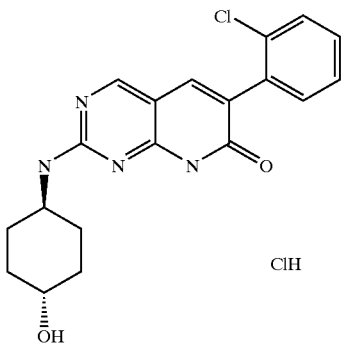 | 191.1–194.3° C. | M + H+ = 371 |
| 19 | 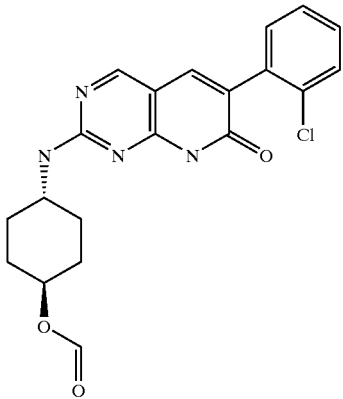 | >300° C. | MH+ = 399 |
| 20 | 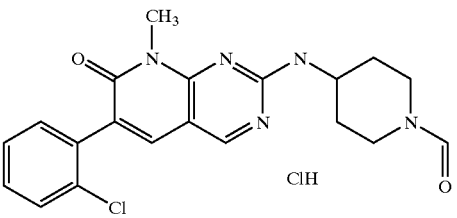 | 143–148° C. (salt) | M+. 398 |
| 21 | 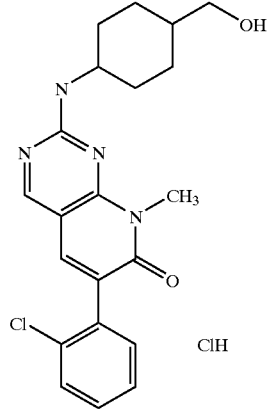 | 153.6–157° C. (salt) | (M + H) + 399 |

TABLE 1-continued
Representative compounds of Formula I
| Cpd # | STRUCTURE | Melting Point | Mass spec |
|---|---|---|---|
| 22 | 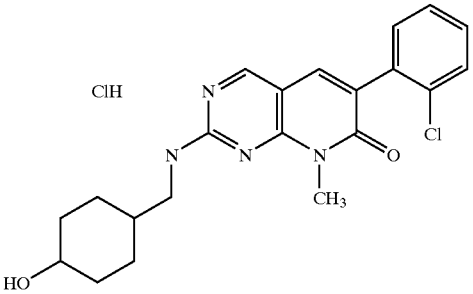 | 148–151.5° C. (salt) | MH+ = 399 |
| 23 | 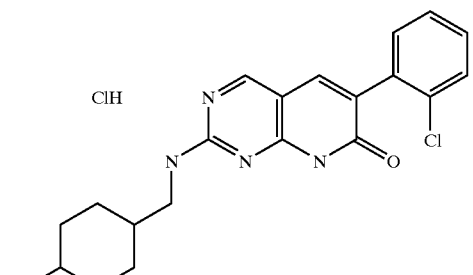 | 205–213° C. (salt) | MH+ = 385 |
| 24 | 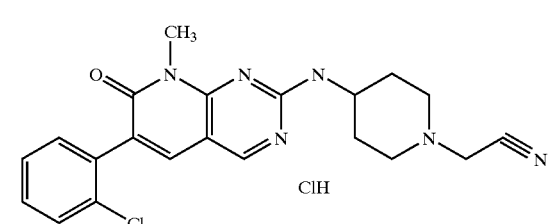 | 228.3–228.9° C. (salt) | M+. 409 |
| 25 | 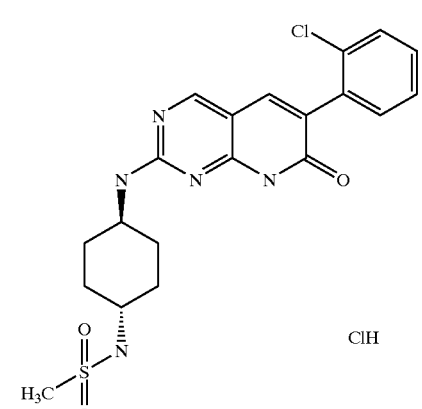 | >300° C. (salt) | M + H+ = 448 |

TABLE 1-continued
Representative compounds of Formula I
| Cpd # | STRUCTURE | Melting Point | Mass spec |
|---|---|---|---|
| 26 | 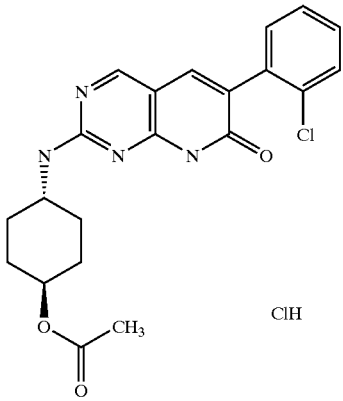 | >300° C. (salt) | MH+ = 413 |
| 27 | 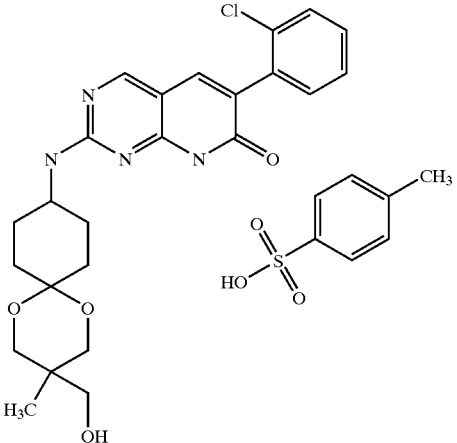 | 223.–226.5° C. (salt) | MH+ = 470 |
| 28 | 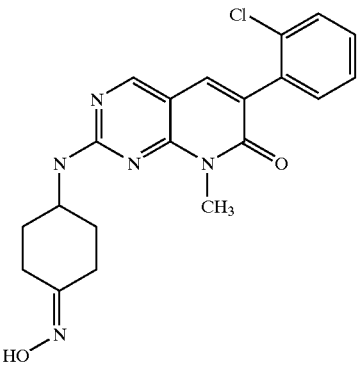 | >300° C. | M+ = 398 |

TABLE 1-continued
Representative compounds of Formula I
| Cpd # | STRUCTURE | Melting Point | Mass spec |
|---|---|---|---|
| 29 | 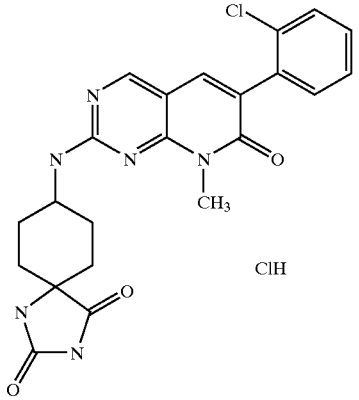 | >300° C. (salt) | MH+ = 453 |
| 30 | 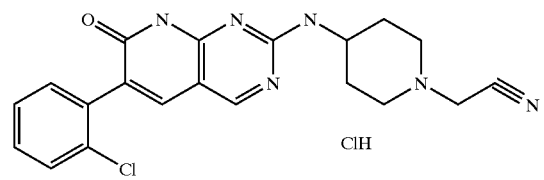 | | M+. 395 |
| 31 | 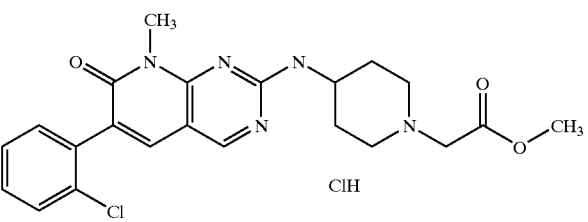 | 150–168° C. (salt) | M+. 442 |
| 32 | 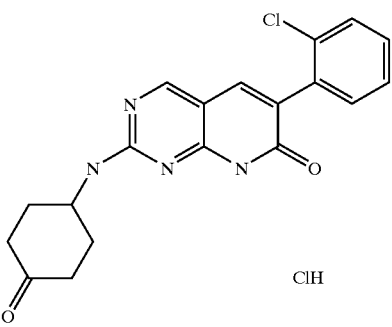 | 265.5–269.9° C. (salt) | MH+ = 369 |
| 33 | 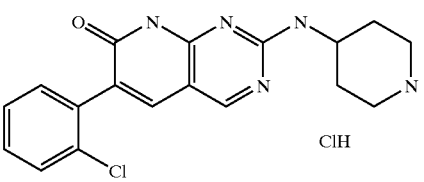 | >300° C. (salt) | |

TABLE 1-continued

Representative compounds of Formula I

| Cpd # | STRUCTURE | Melting Point | Mass spec |
|---|---|---|---|
| 34 | 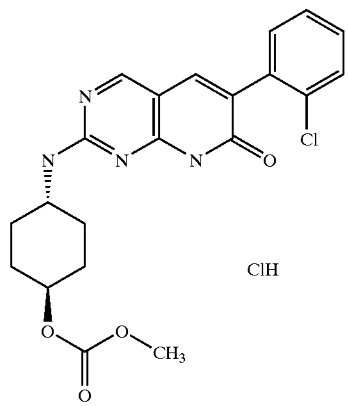 | | MH+ = 429 |
| 35 | 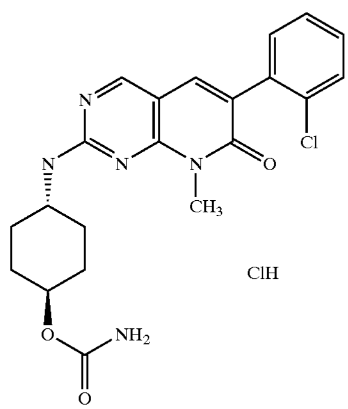 | 234.7–235.4° C. (salt) | MH+ = 428 |
| 36 | 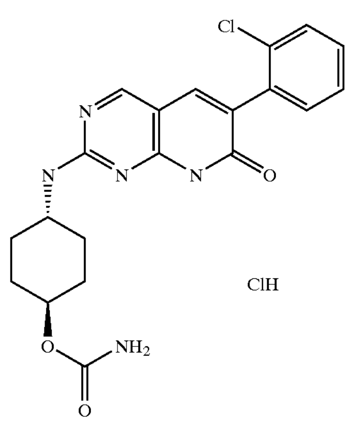 | 291–293.5° C. (salt) | MH+ = 414 |

TABLE 1-continued
Representative compounds of Formula I
| Cpd # | STRUCTURE | Melting Point | Mass spec |
|---|---|---|---|
| 37 | 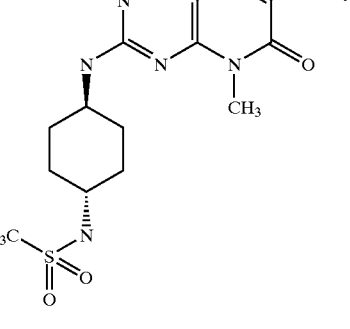 | 260.9–261.1° C. | M + H+ = 462 |
| 38 | 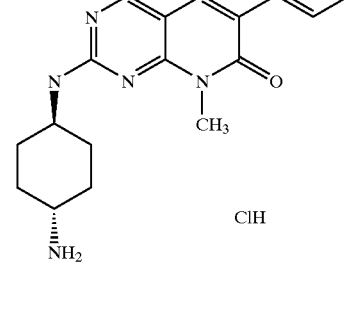 | 190.3–191.4° C. | M + H+ = 384 |
| 39 | 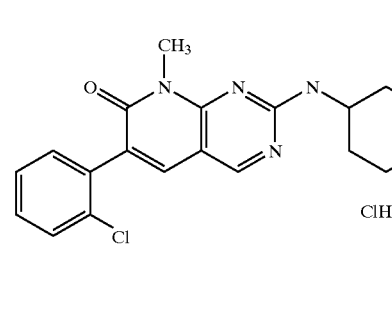 | >300° C. (salt) | |
| 40 | 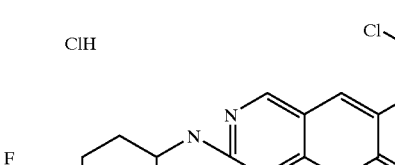 | 260–265° C. (salt) | (M + H)+ = 438 |

TABLE 1-continued
Representative compounds of Formula I
| Cpd # | STRUCTURE | Melting Point | Mass spec |
|---|---|---|---|
| 41 | 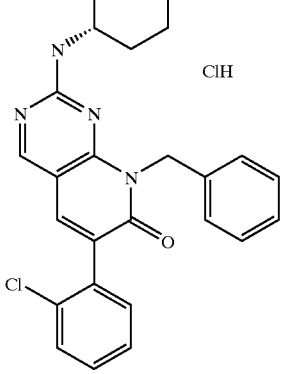 | 202–206° C. (salt) | (M + H) + 461 |
| 42 | 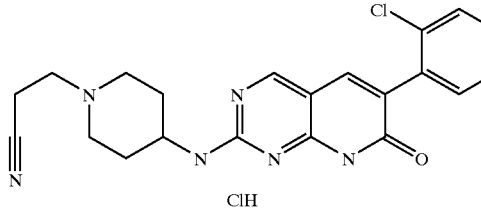 | 217.5–219.5° C. (salt) | MH+ = 408 |
| 43 | 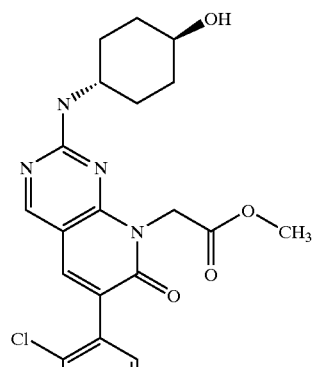 | 118–130° C. | (M + H) + 443 |
| 44 | 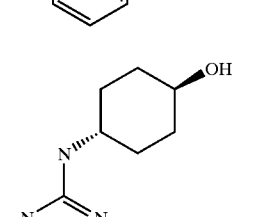 | 232.1–233.4° C. (salt) | (M + H) + 410 |

TABLE 1-continued
Representative compounds of Formula I
| Cpd # | STRUCTURE | Melting Point | Mass spec |
|---|---|---|---|
| 45 | 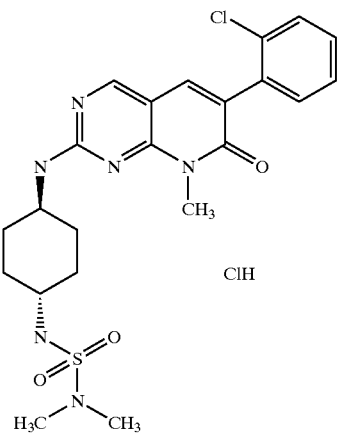 | 226.5–229° C. | M + H+ = 491 |
| 46 | 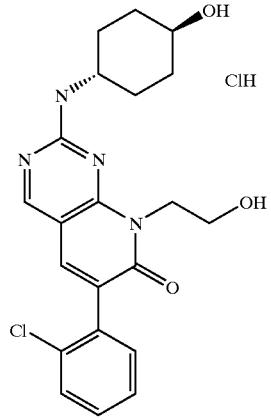 | 210.5–212° C. (salt) | (M + H) + 415 |
| 47 | 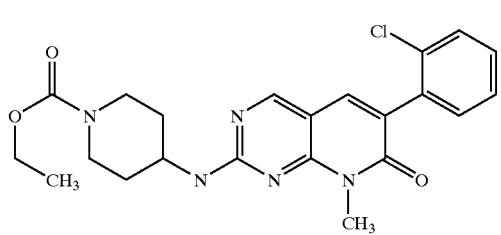 | 190–191° C. (salt) | M+ = 441.9 |
| 48 | 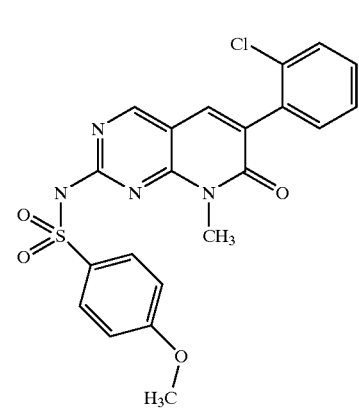 | >300° C. | MH+ = 457 |

TABLE 1-continued
Representative compounds of Formula I
| Cpd # | STRUCTURE | Melting Point | Mass spec |
|---|---|---|---|
| 49 | 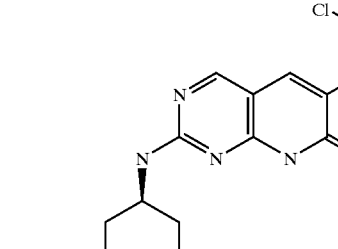 | 103–120° C. (salt) | |
| 50 | 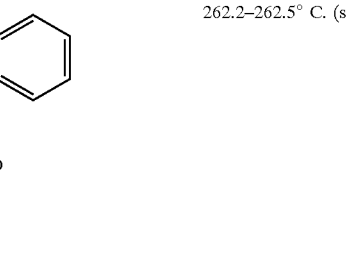 | 262.2–262.5° C. (salt) | M + H+ = 477 |
| 51 | 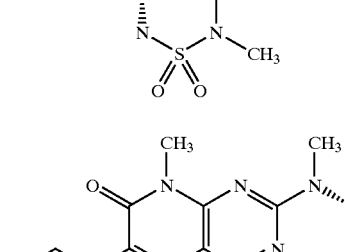 | 182.3–183.1° C. (salt) | |
| 52 | 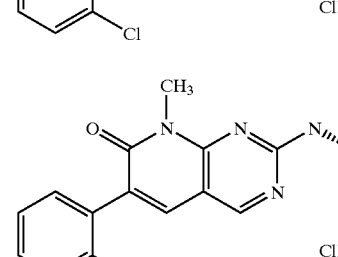 | 218.2–218.5° C. (salt) | |
| 53 | 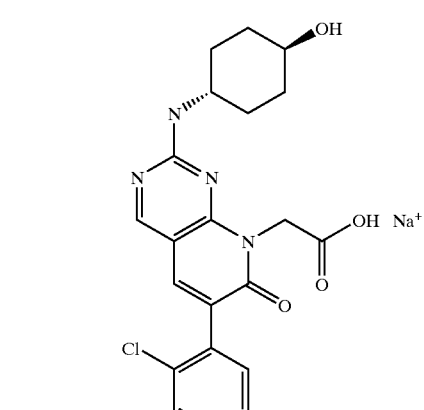 | 260–265° C. (salt) | (M + H) + 429 |

TABLE 1-continued

Representative compounds of Formula I

| Cpd # | STRUCTURE | Melting Point | Mass spec |
|---|---|---|---|
| 54 | 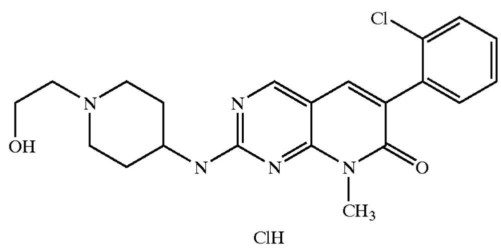 | 265.9–266.6° C. | MH+ = 414 |
| 55 | 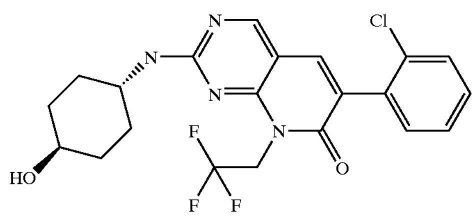 | 227.2–230.4° C. | (M + H) + 453 |
| 56 | 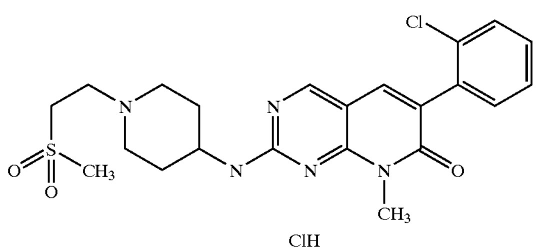 | 204.6–205.6° C. (salt) | MH+ = 476 |
| 57 | 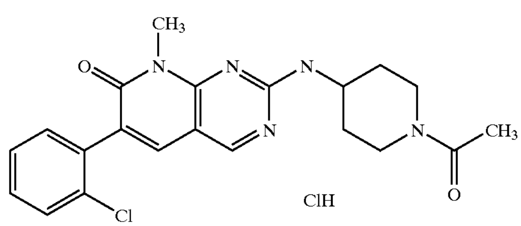 | 215.3–218.6 C. (salt) | M+. 427 |
| 58 | 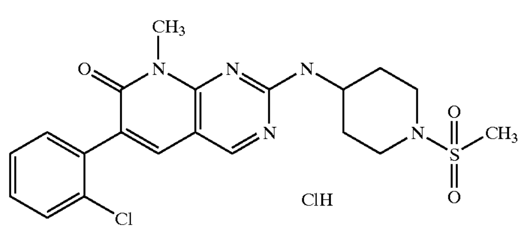 | 185.0–194.0 C. (salt) | M+ = 427 |
| 59 | 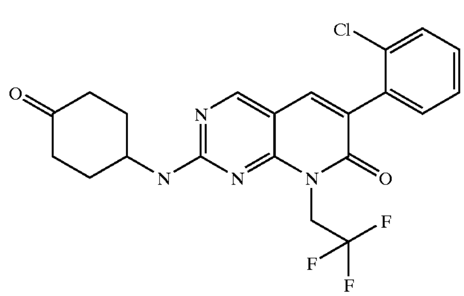 | 251.2–252 C. | (M + H) = 451 |

TABLE 1-continued
Representative compounds of Formula I
| Cpd # | STRUCTURE | Melting Point | Mass spec |
|---|---|---|---|
| 60 | 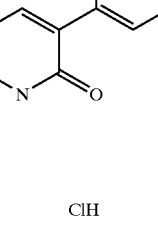 | 294.6–296.8 C. (salt) | M + H+ = 428 |
| 61 | 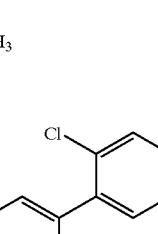 | >300 C. (salt) | M + H+ = 412 |
| 62 | 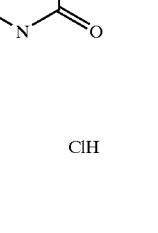 | 207.2–208 C. (salt) | MH+ = 477 |
| 63 | 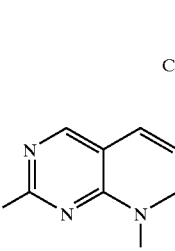 | 217.2–218.9 C. (salt) | (M + H) + 371 |

TABLE 1-continued

Representative compounds of Formula I

| Cpd # | STRUCTURE | Melting Point | Mass spec |
|---|---|---|---|
| 64 | 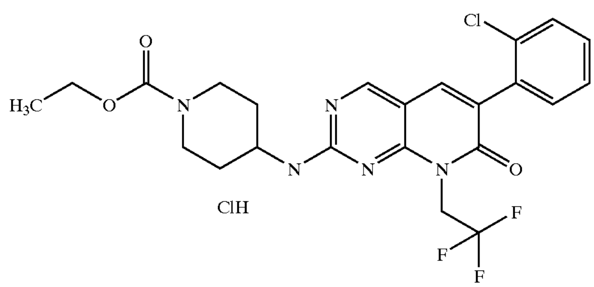 | 194.2–221.4 C. | (M + H)+ = 510 |
| 65 | 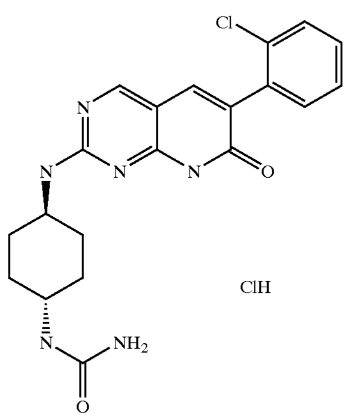 | >300 C. (salt) | M + H+ = 413 |
| 66 | 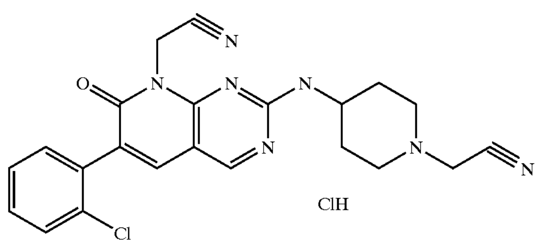 | 143.0–158.5 C. (salt) | |
| 67 | 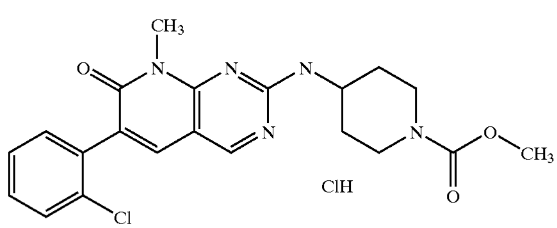 | 133.5–136.5 C. (salt) | |

TABLE 1-continued
Representative compounds of Formula I
| Cpd # | STRUCTURE | Melting Point | Mass spec |
|---|---|---|---|
| 68 | 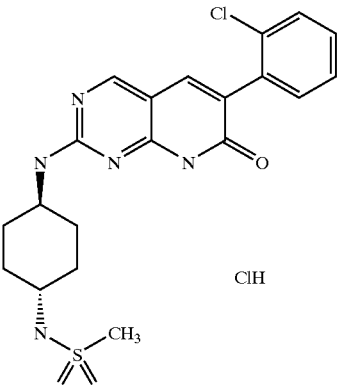 | >300 C. (salt) | |
| 69 | 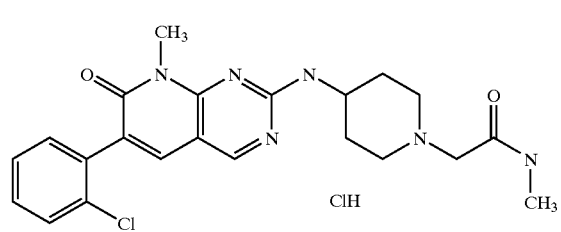 | 64.0–102.6 C. (salt) | |
| 70 | 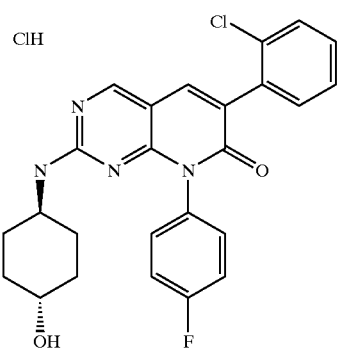 | 248.7–249.9 C. | MH+ = 465 |
| 71 | 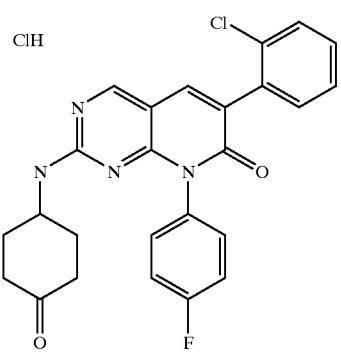 | 242.7–243.6 C. | MH+ = 463 |

TABLE 1-continued
Representative compounds of Formula I
| Cpd # | STRUCTURE | Melting Point | Mass spec |
|---|---|---|---|
| 72 | 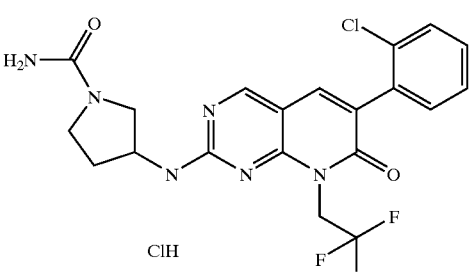 | 164.5–168.0 C. | (M + H)+ = 467 |
| 73 | 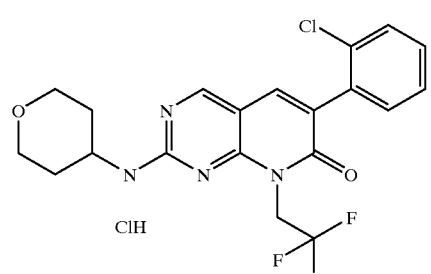 | 200.9–202.1 C. | (M + H)+ = 439 |
| 74 | 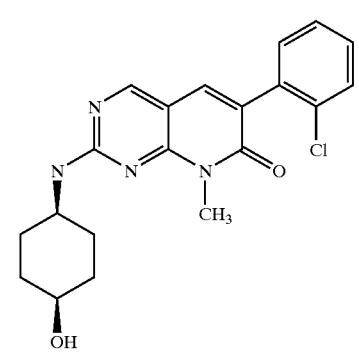 | 209.5–216.5 C. | M + H+ = 385 |
| 75 | 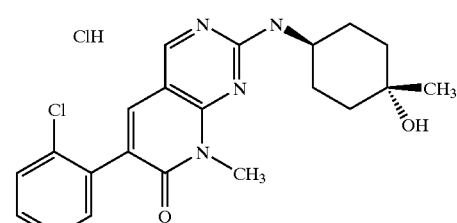 | 155–168 C. (salt) | MH+ = 399 |
| 76 | 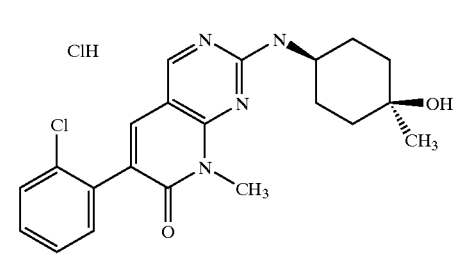 | 156–169 C. (salt) | MH+ = 399 |

TABLE 1-continued

Representative compounds of Formula I

| Cpd # | STRUCTURE | Melting Point | Mass spec |
|---|---|---|---|
| 77 | 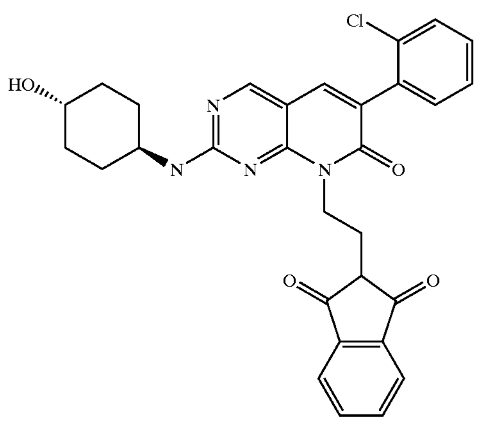 | 208–210 C. | MH+ = 544 |
| 78 | 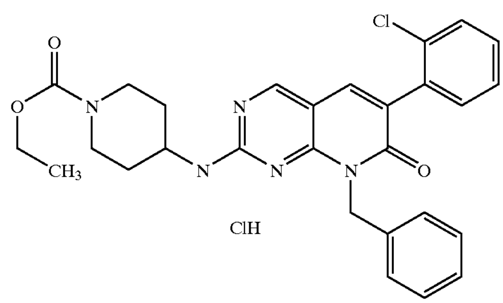 | 162–173 C. (salt) | MH+ = 518 |
| 79 | 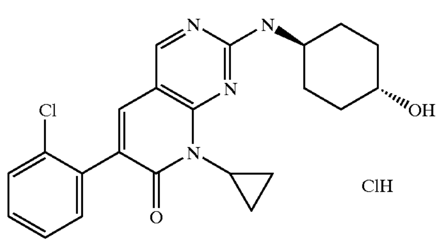 | 241.7–242.3 C. | MH+ = 411 |
| 80 | 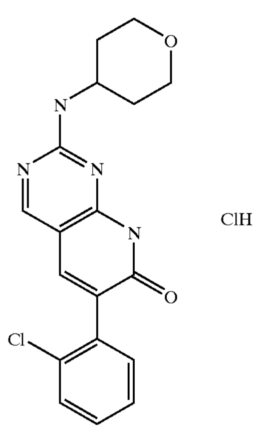 | >300 C. (salt) | (M + H) + 357 |

TABLE 1-continued
Representative compounds of Formula I
| Cpd # | STRUCTURE | Melting Point | Mass spec |
|---|---|---|---|
| 81 | 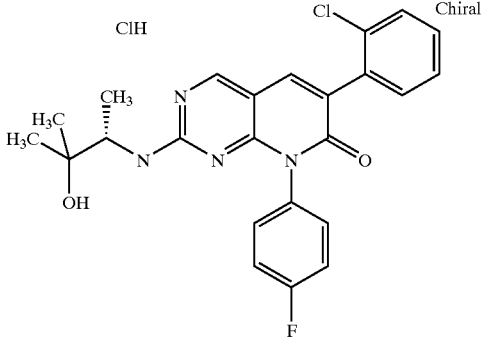 | 142.0–149.0 | |
| 82 | 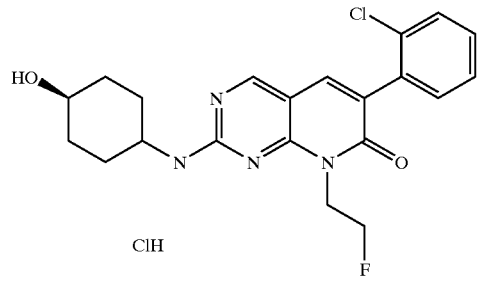 | 198.0–200.0 | |
| 83 | 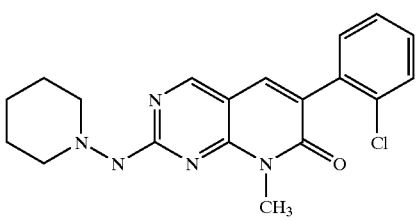 | 247.4–248.2 | |
| 84 | 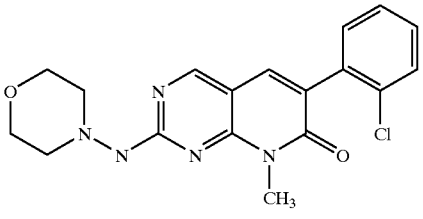 | 243.5–244.0 | |
| 85 | 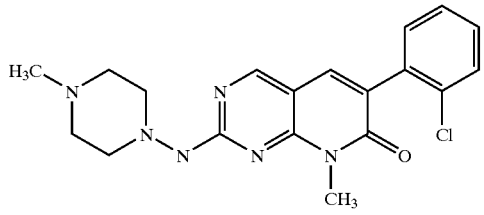 | 125.7–128.1 | |

TABLE 1-continued

Representative compounds of Formula I

| Cpd # | STRUCTURE | Melting Point | Mass spec |
|---|---|---|---|
| 86 | 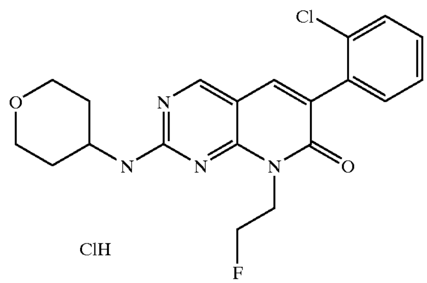 | 156.0–168.0 | |
| 87 | 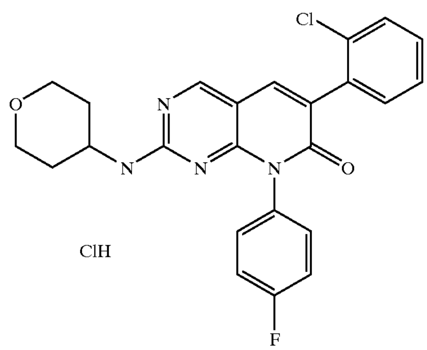 | 150.0–154.0 | |
| 88 | 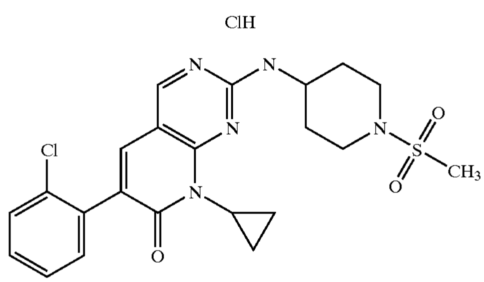 | 128–141.5 | |
| 89 | 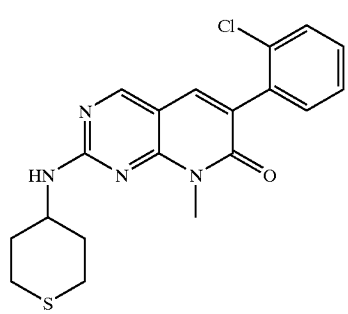 | 232.1–233.1° C. (HCl salt) | |
| 90 | 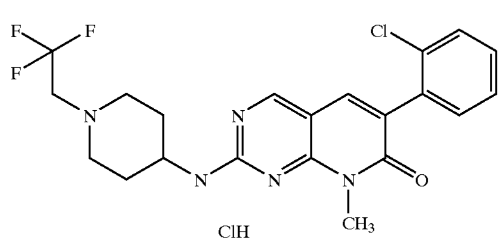 | 180.0–183.0 | |

TABLE 1-continued

Representative compounds of Formula I

| Cpd # | STRUCTURE | Melting Point | Mass spec |
|---|---|---|---|
| 91 | 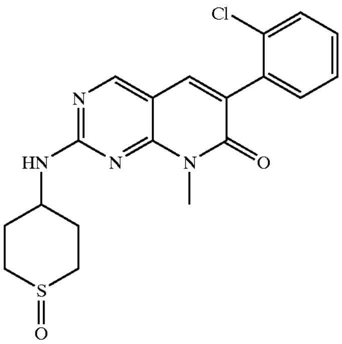 | 205.6–207.3° C. | MH+ = 403 |
| 92 | 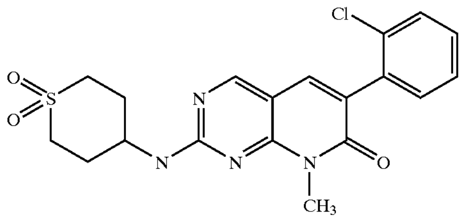 | 143.0–152.2 | |
| 93 | 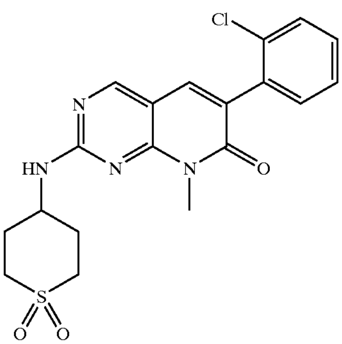 | 218.4–224.2° C. | MH+ = 419 |
| 94 | 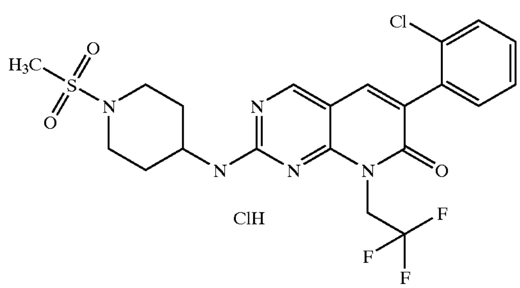 | 148.6–151.6 | |
| 95 | 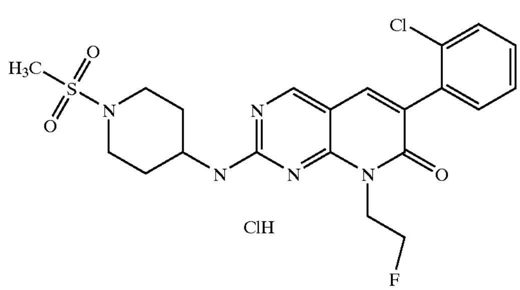 | 187.7–188.4 | |

TABLE 1-continued

Representative compounds of Formula I

| Cpd # | STRUCTURE | Melting Point | Mass spec |
|---|---|---|---|
| 96 | 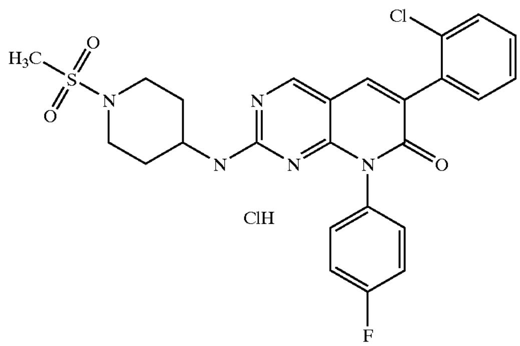 | 165.0–169.0 | |
| 97 | 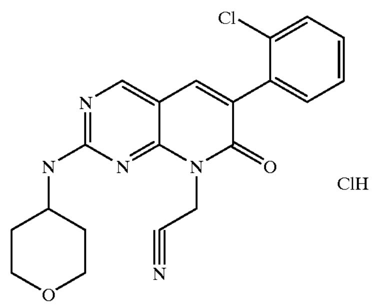 | 230.2–230.4 | |
| 98 | 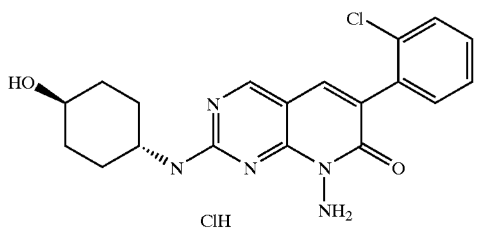 | | (M + H) = 386 |
| 99 | 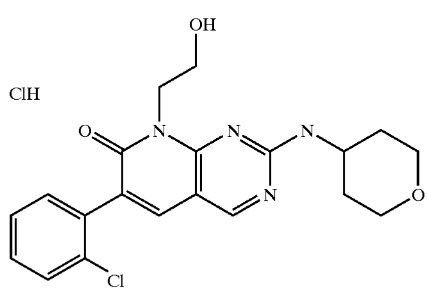 | 217.0–220.0 | |
| 100 | 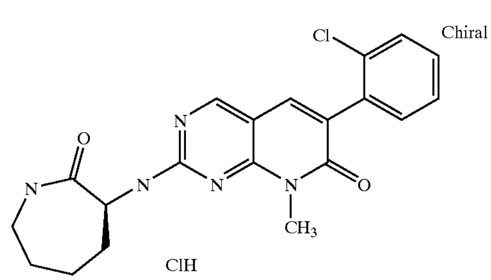 | 140–144 | |

TABLE 1-continued
Representative compounds of Formula I
| Cpd # | STRUCTURE | Melting Point | Mass spec |
|---|---|---|---|
| 101 | 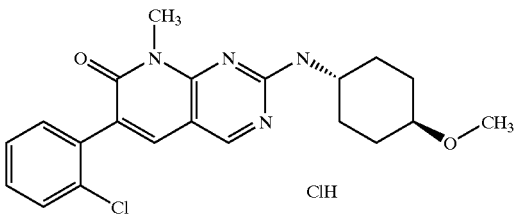 ClH | 189.0–192.0 | |
| 102 | 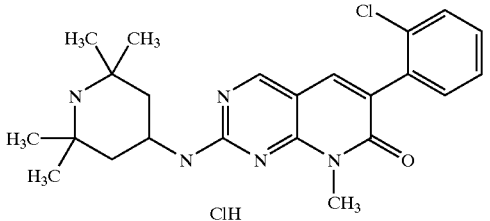 ClH | >300 | |
| 103 | 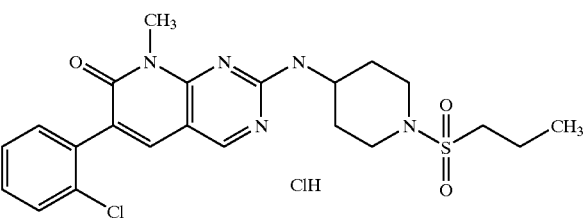 ClH | 193.3–194.1 | |
| 104 | 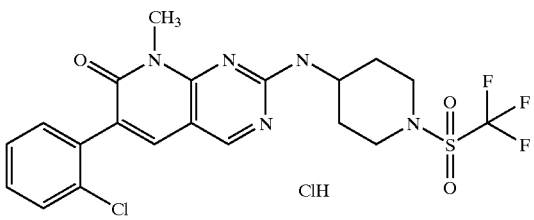 ClH | 134.0–140.0 | |
| 105 | 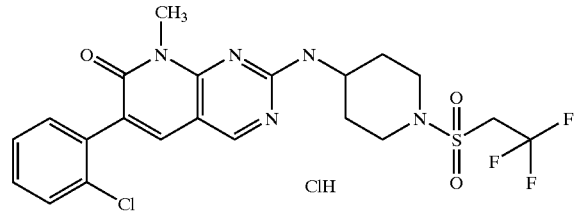 ClH | 215.0–219.0 | |
| 106 | 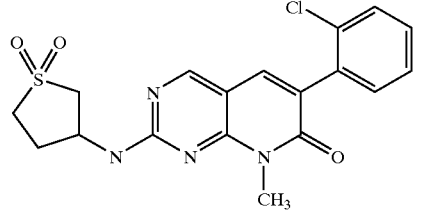 ClH | 256.0–260.0 | |

TABLE 1-continued

Representative compounds of Formula I

| Cpd # | STRUCTURE | Melting Point | Mass spec |
|---|---|---|---|
| 107 | 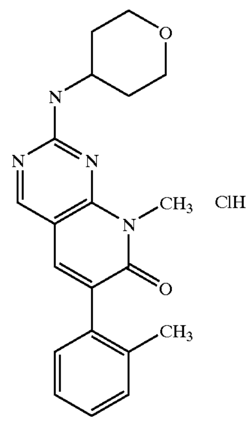 | 222.9–225.9 | |
| 108 | 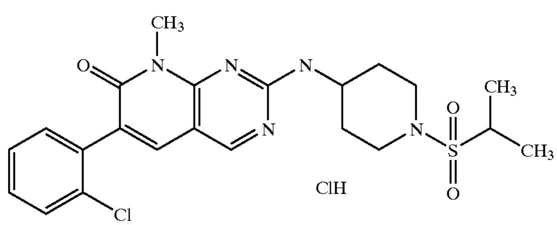 | 132.0–136.0 | |
| 109 | 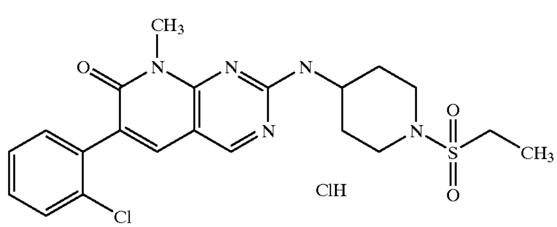 | 144.0–150.0 | |
| 110 | 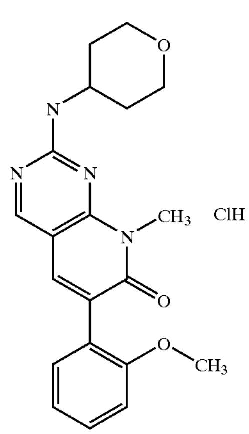 | 212–213.7 | |

TABLE 1-continued

Representative compounds of Formula I

| Cpd # | STRUCTURE | Melting Point | Mass spec |
|---|---|---|---|
| 111 | 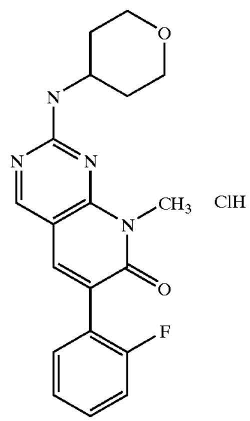 | 210.7–211.9 | |
| 112 | 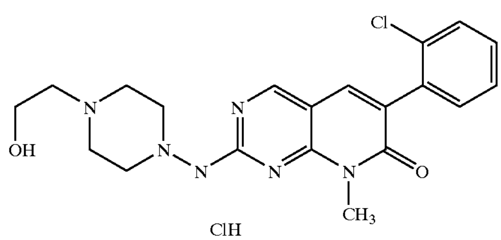 | 274.4–274.8 | |
| 113 | 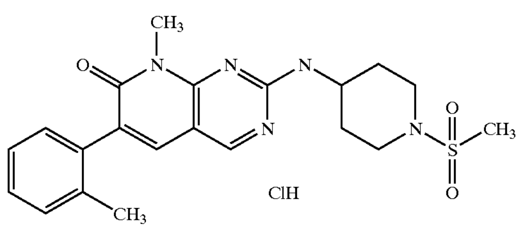 | 221.4–221.8 | |
| 114 | 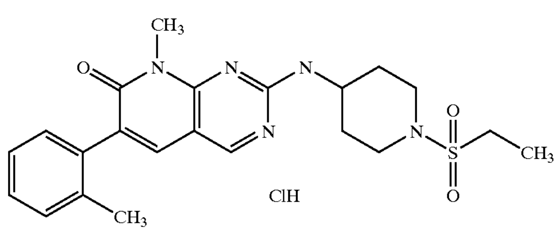 | 218.5–219.3 | |
| 115 | 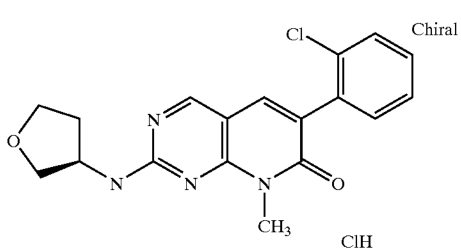 | 193.9–194.5 | |

TABLE 1-continued
Representative compounds of Formula I
| Cpd # | STRUCTURE | Melting Point | Mass spec |
|---|---|---|---|
| 116 | 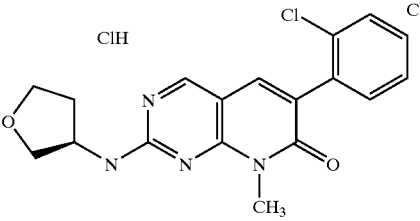 | 171.9–173 | |
| 117 | 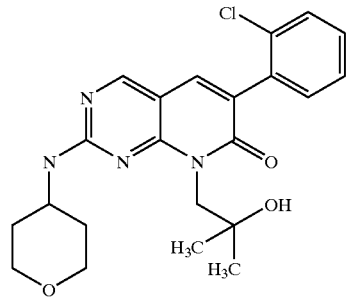 | 189–191.5 | |
| 118 | 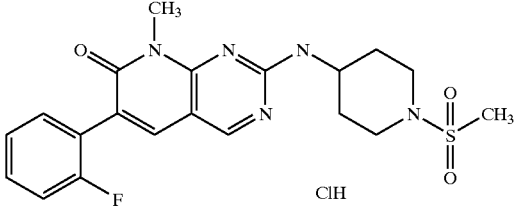 | 205.0–207.5 | |
| 119 | 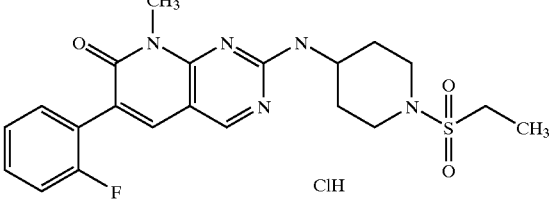 | 192.5–195.0 | |
| 120 | 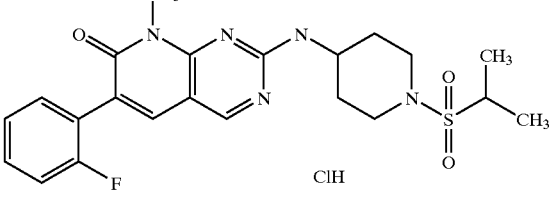 | 204.0–209.0 | |
| 121 | 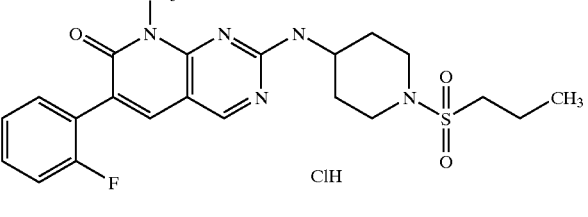 | 206.0–209.0 | |

TABLE 1-continued
Representative compounds of Formula I
| Cpd # | STRUCTURE | Melting Point | Mass spec |
|---|---|---|---|
| 122 | 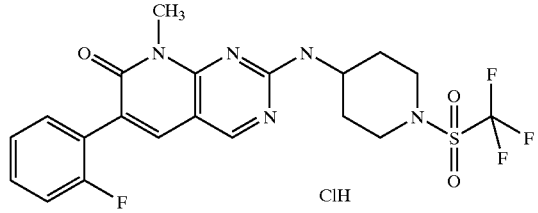 | 213.5–221.0 | |
| 123 | 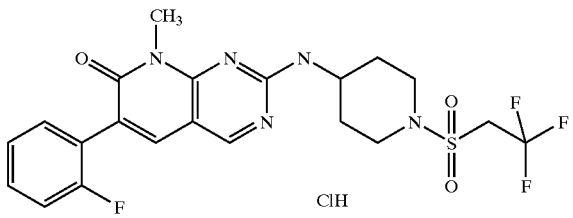 | 225.9–226.4 | |
| 124 | 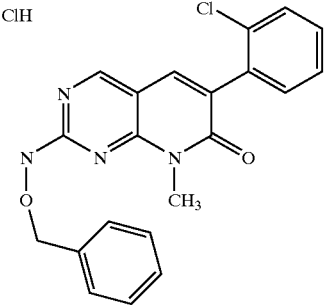 | 199.2–199.5 | |
| 125 | 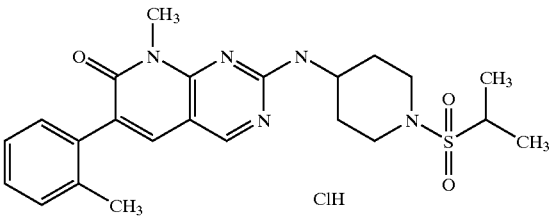 | 142.0–149.0 | |
| 126 | 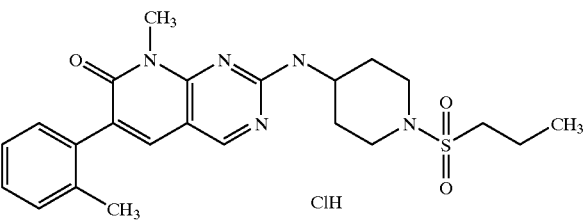 | 211.7–212.6 | |
| 127 | 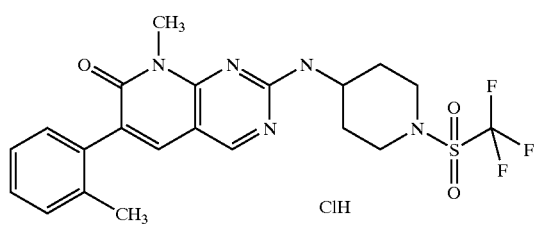 | 153.0–162.0 | |

TABLE 1-continued

Representative compounds of Formula I

| Cpd # | STRUCTURE | Melting Point | Mass spec |
|---|---|---|---|
| 128 | 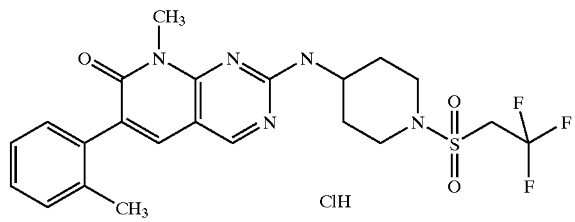 | 200.0–204.0 | |
| 129 | 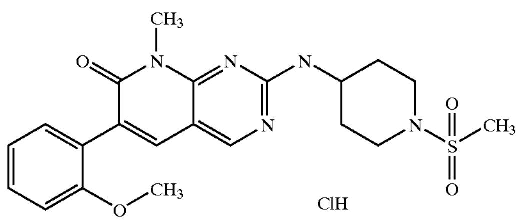 | 202.7–204.3 | |
| 130 | 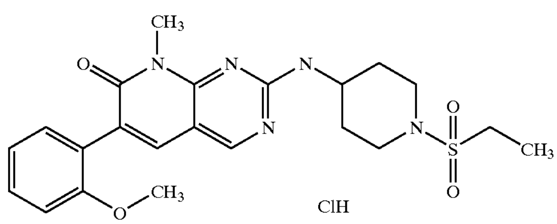 | 120.3–139.7 | |
| 131 | 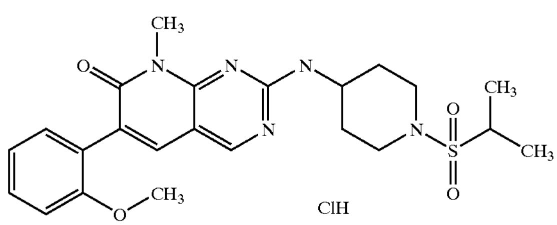 | 157.0–163.1 | |
| 132 | 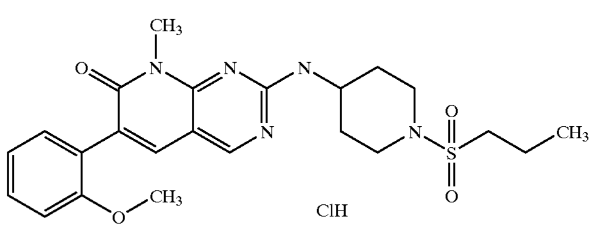 | 59.7–63.8 | |
| 133 | 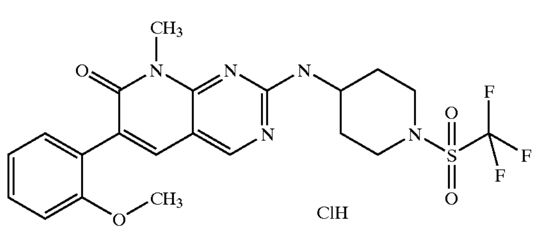 | 140.8–147.3 | |

TABLE 1-continued

Representative compounds of Formula I

| Cpd # | STRUCTURE | Melting Point | Mass spec |
|---|---|---|---|
| 134 | 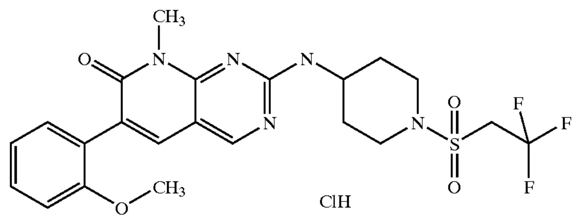 | 194.7–196.0 | |
| 135 | 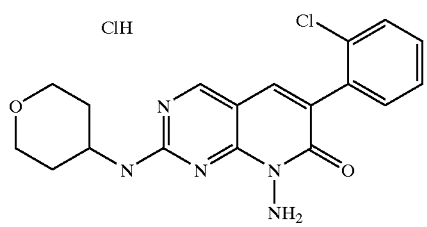 | 207.1 to 215.9 | |
| 136 | 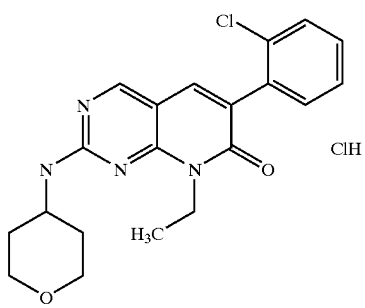 | 185.3–190.1 | |
| 137 | 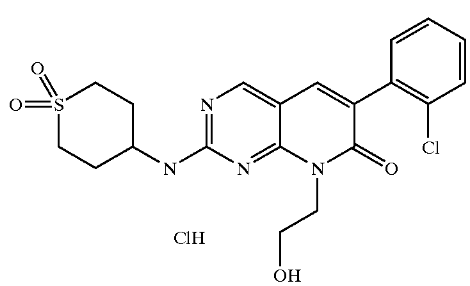 | 182.0–186.0 | |
| 138 | 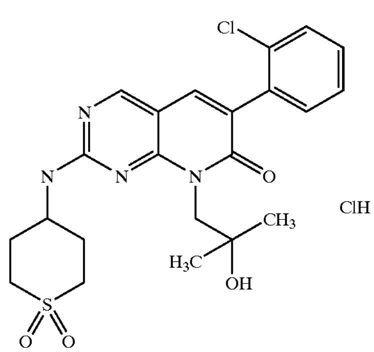 | 223.7–230.2 | |

TABLE 1-continued

Representative compounds of Formula I

| Cpd # | STRUCTURE | Melting Point | Mass spec |
|---|---|---|---|
| 139 | 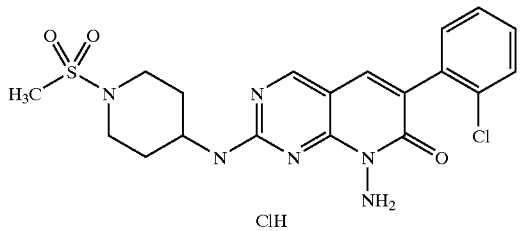 | 180.7–213.2 | |
| 140 | 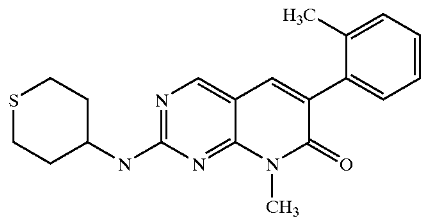 | 186.6–188.1 | |
| 141 | 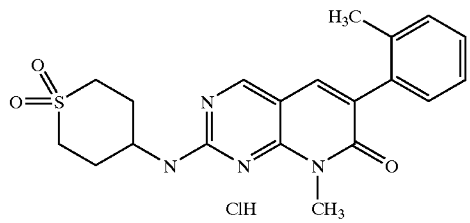 | 240.0–258.0 | |
| 142 | 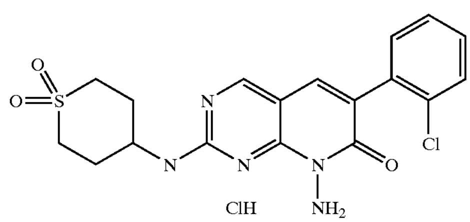 | 240.0–243.0 | |
| 143 | 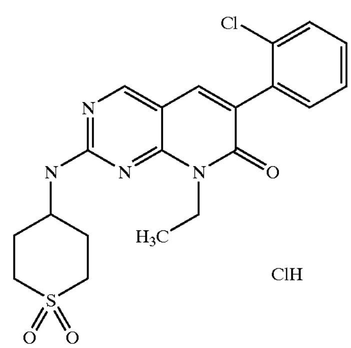 | 285.2–286.7 | |
| 144 | 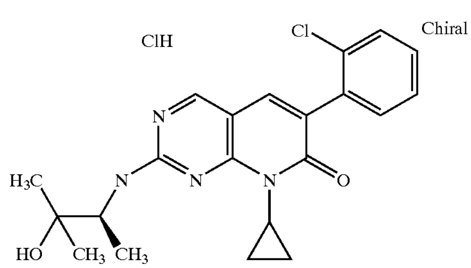 | Chiral | 436.36 (M + H) |

TABLE 1-continued

Representative compounds of Formula I

| Cpd # | STRUCTURE | Melting Point | Mass spec |
|---|---|---|---|
| 145 | 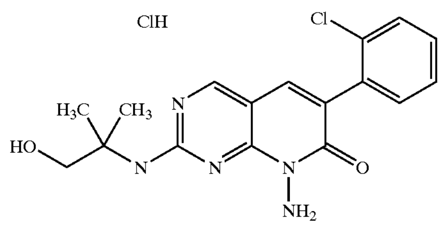 | 145.0–163.0 | |
| 146 | 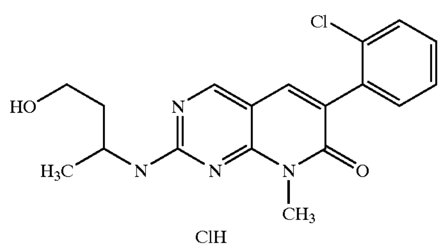 | 180.7–189.2 | |
| 147 | 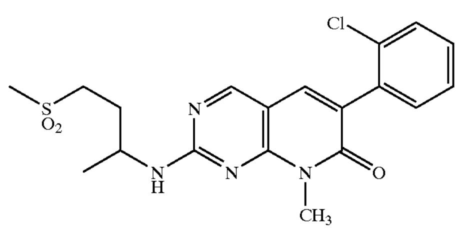 | 160.1–167.0 | |
| 148 | 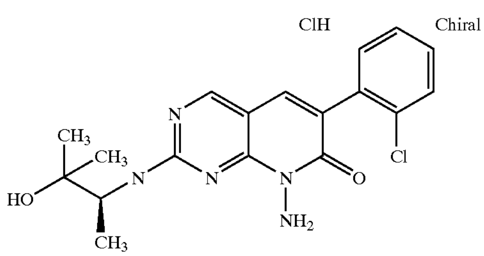 | >300 | |
| 149 | 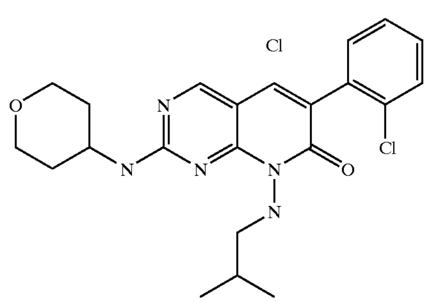 | 111.3 to 117.5 | |

TABLE 1-continued

Representative compounds of Formula I

| Cpd # | STRUCTURE | Melting Point | Mass spec |
|---|---|---|---|
| 150 | 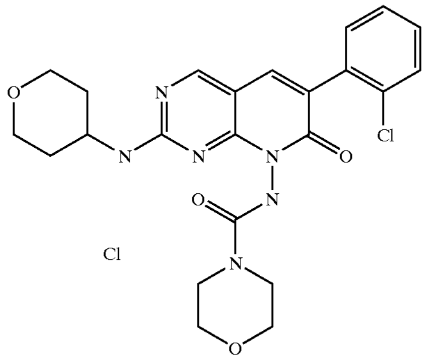 | | |
| 151 | 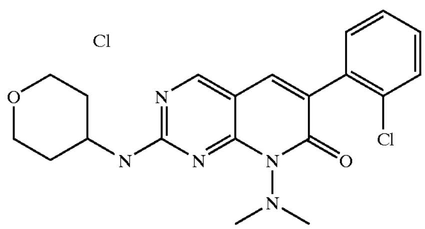 | | |

The $IC_{50}$ of Compounds of Formula I in the in vitro p38 assay is less than 10 µM, preferably less than 5 µM, more preferably less than 3 µM, and most preferably less than 1 µM. In particular, Compounds of Formula I in Table I have $IC_{50}$ in the in vitro p38 assay of from about 4.76 µM to about 0.0003 µM.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. Furthermore, as stated above, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge et al, "Pharmaceutical Salts," *J. of Pharmaceutical Science*, 1977, 66, 1–19).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

Processes for Preparing the Compounds

The compounds of the present invention can be prepared by a variety of methods, using procedures well known to those of skill in the art. In one aspect of the present invention, a method for preparing compounds of Formula I is shown in Scheme 1 below:

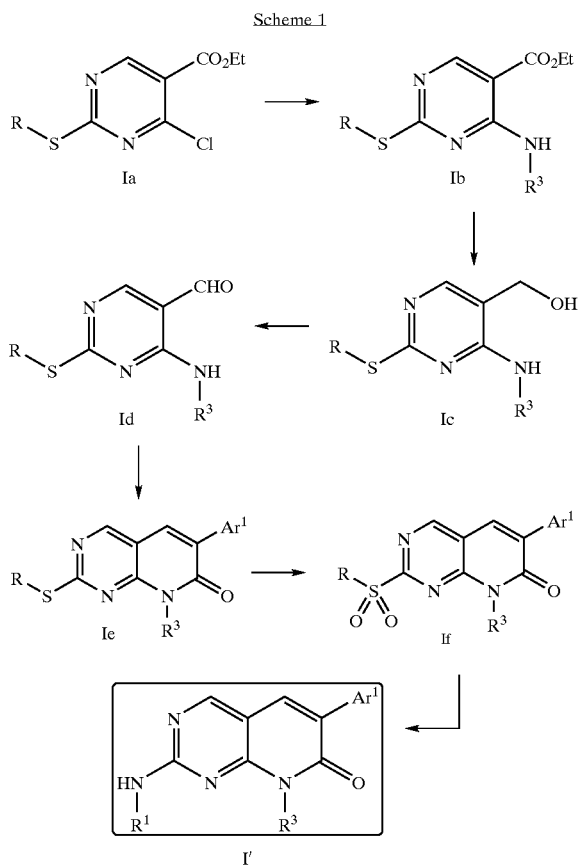

Treatment of a compound of Formula Ia with a primary amine ($R^3$—$NH_2$) provides a compound of Formula Ib. This reaction is conveniently carried out in a solvent which is inert under the reaction conditions, preferably a halogenated aliphatic hydrocarbon, especially dichoromethane, an optionally halogenated aromatic hydrocarbon, or an open-chain or cyclic ether such as tetrahydrofuran, a formamide or a lower alkanol. Suitably, the reaction is carried out at about −20° C. to about 120° C.

Reduction of a compound of Formula Ib provides an alcohol of Formula Ic. This reduction is typically carried out using lithium aluminum hydride in a manner well known to those of skill in the art (e.g., in a solvent which is inert under the conditions of the reduction, preferably an open-chain or cyclic ether, especially tetrahydrofuran, at about −20° C. to about 70° C., preferably at about 0° C. to about room temperature).

Oxidation of an alcohol of Formula Ic in the next step provides a carboxaldehyde of Formula Id. The oxidation is typically carried out with manganese dioxide, although numerous other methods can also be employed (see, for example, Advanced Organic Chemistry, $4^{TH}$ ed., March, John Wiley & Sons, New York (1992)). Depending on the oxidizing agent employed, the reaction is carried out conveniently in a solvent which is inert under the specific oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of Formula Id with an aryl substituted acetate, $Ar^1$—$CH_2$—$CO_2R$ (where R is an alkyl group) in a presence of a base provides a compound of Formula Ie. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; amines, such as secondary and tertiary amines; and resin bound amines such as 1,3,4,6,7,8-hexahydro-2H pyrimido[1,2-a]pyrimidine. Conveniently, the reaction is carried out in a solvent which is relatively polar but inert under the reaction conditions, preferably an amide such as dimethyl formamide, N-substituted pyrrolidinone, especially 1-methyl-2-pyrrolidinone, and at a temperature of about 70° C. to about 150° C., especially at or near the reflux temperature of the solvent to assist in the noted azeotropic removal of water.

Oxidation of Ie with an oxidizing agent, e.g. a peracid such as 3-chloroperbenzoic acid (i.e., MCPBA) or Oxone®, provides a sulfone (If) which can be converted to a variety of target compounds. Typically the oxidation of Ie is carried out in a solvent which is inert under the conditions of the oxidation. For example, when MCPBA is used as the oxidizing agent, the solvent is preferably a halogenated aliphatic hydrocarbon, especially chloroform. When Oxone® is used as the oxidizing agent, the solvent can be water, methanol or a mixture of an organic solvent (such as methanol, acetonitrile or tetrahydrofuran) and water. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature. Alternatively, the oxidation can be carried under catalytic conditions with rhenium/peroxide based reagents. See, for example, "Oxidation of Sulfoxides by Hydrogen Peroxide, Catalyzed by Methyltrioxorhenium(VII)", Lahti, David W.; Espenson, James H, Inorg. Chem. 2000, 39(10) pp.2164–2167; "Rhenium oxo complexes in catalytic oxidations," Catal. Today, 2000, 55(4), pp317–363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, J. Org. Chem., 1998, 63(5), pp1740–1741, which are incorporated herein by reference in their entirety.

Reaction of the compound If with an amine ($R^2$—$NH_2$) provides the compounds of Formula I' (i.e. compounds I, wherein $R^1$ is hydrogen). Further alkylation of I' then provides compounds of Formula I, where $R^1$ is not hydrogen. The reaction can be carried out in the presence or absence of solvent. Conveniently, the reaction is carried out at temperatures of from about 0° C. to about 200° C., more preferably about room temperature to about 150° C. Alternatively, in some cases rather than using the sulfone If, the sulfide Ie or the corresponding sulfoxide can be reacted directly an amine ($R^1$—$NH_2$) to provide the compounds of Formula I'. Furthermore, If may also be alkylated with an amine of $R^1R^2NH$ directly to provide a compound of Formula I where $R^1$ and $R^2$ are as described in the Summary of the Invention.

Accordingly, the present invention provides a method of preparing compounds of Formula I, by treating a compound of general Formula Ie or If with an amine ($R^1$—$NH_2$) and optionally reacting the resulting product with $R^1$—L, where $R^1$ is defined above, but excludes hydrogen, and L is a leaving group.

Alternatively, the carboxaldehyde of the Compound of Formula Ie can be prepared as shown in Scheme II below, which eliminates a need for an ester reduction and an alcohol oxidation in Scheme I:

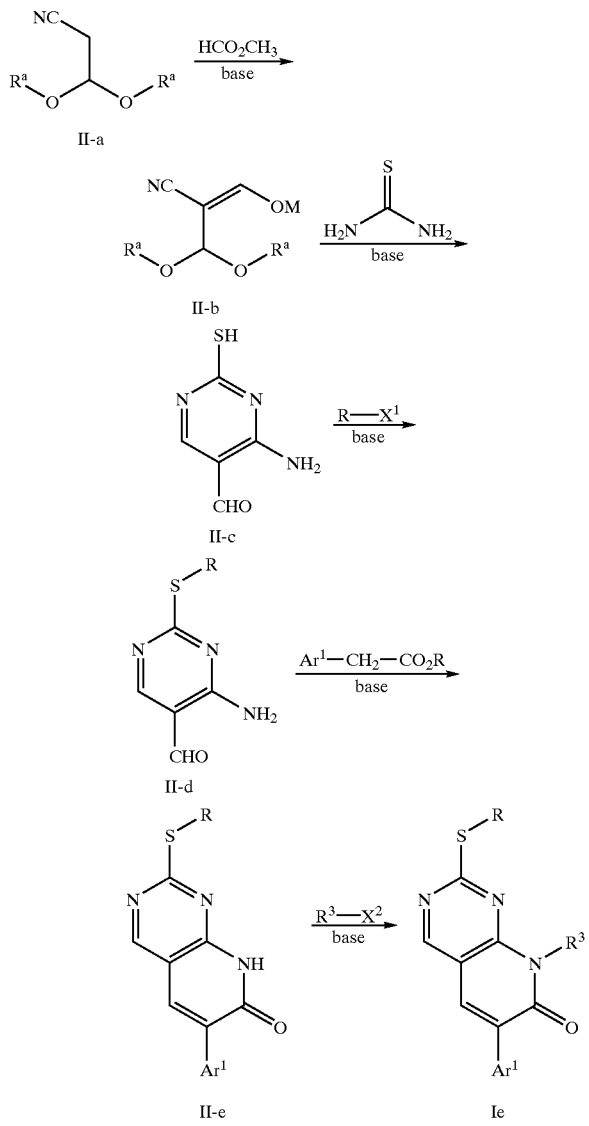

Treatment of a compound of Formula II-a (where each $R^8$ is independently alkyl) with an alkyl formate (e.g., methylformate) in the presence of a base provides a compound of Formula II-b (where M is a metal). This reaction is conveniently carried out at a temperature range of from about 0° C. to about 100° C. Typically, an ether, such as THF, and other solvents which are inert to the reaction conditions is used. Suitable bases include alkoxides, such as tert-butoxides, and other relatively non-nucleophilic bases that are capable of deprotonating the compound of Formula II-a.

Cyclization of a compound of Formula II-b with thiourea in the presence of a base affords a pyrimidine of Formula II-c. Typically, this cyclization reaction is conducted in an alcoholic solvent under refluxing conditions using a corresponding alkoxide as a base.

Alkylation of a compound of Formula II-c with an alkylating agent $R$—$X^1$ (where R is an alkyl group and $X^1$ is a leaving group, such as halide) in the presence of a base then provides a compound of Formula II-d. Suitable bases include a relatively non-nucleophilic bases including carbonates, such as potassium carbonate, lithium carbonate, and sodium carbonate; and bicarbonates, such as potassium bicarbonate, lithium bicarbonate, and sodium bicarbonate. Conveniently, the reaction is carried out in a relatively polar solvent that inert under the reaction conditions, preferably acetone, dimethylformamide (DMF) or methylpyrrolidinone (MP).

Reaction of a compound of Formula II-d with an aryl substituted acetate $Ar^1$—$CH_2$—$CO_2R$ (where R is an alkyl group) under similar conditions as that described for preparation of a compound of Formula Ie in Scheme I above, then provides a compound of Formula II-e. While the alkylation of a compound of Formula II-c is generally conducted prior to the reaction with an aryl substituted acetate, the order of these two reactions are not crucial and can be reversed. Thus, a compound of Formula II-c can be reacted with an aryl substituted acetate $Ar^1$—$CH_2$—$CO_2R$ and the resulting product can be alkylated with an alkylating agent R—$X^1$ to provide a compound of Formula II-e.

Alkylation of the amine group of a compound of Formula II-e with an alkylating agent $R^3$—$X^2$ (where $R^3$ is those defined above and $X^2$ is a leaving group, such as halide) then provides a compound of Ie which can be further converted to a compound of Formula I' as described in Scheme I.

Thus, another aspect of the present invention provides a method of preparing a pyrimidine compound of Formula II-c by reacting an acetal of the Formula II-a with with an alkyl formate and reacting the resulting product with a thiourea.

Yet another aspect of the present invention provides a method for preparing a compound of Formula II-e, by reacting a compound of Formula II-c with an alkylating agent or an aryl substituted acetate, and reacting the resulting product with an aryl substituted acetate or an alkylating agent, respectively.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of Formula I and the pharmaceutically acceptable salts of basic compounds of Formula I with acids can be used as medicaments, e.g., in the form of pharmaceutical preparations. The pharmaceutical preparations can be administered enterally, e.g., orally in the form of tablets, coated tablets, dragées, hard and soft gelatine capsules, solutions, emulsions or suspensions, nasally, e.g., in the form of nasal sprays, or rectally, e.g., in the form of suppositories. However, they may also be administered parenterally, e.g., in the form of injection solutions.

The compounds of Formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of Formula I and their aforementioned pharmaceutically acceptable salts.

Medicaments which contain a compound of Formula I or a pharmaceutically acceptable salt of a basic compound of Formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of Formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of Formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthopathics, gouty arthritis, osteoarthritis, systemic lupus erythematosus and juvenile arthritis, and other arthritic conditions. Such compounds would be useful for the treatment of pulmonary disorders or lung inflammation, including adult respiratory distress syndrome, pulmonary sarcoidosis, asthma, silicosis, chronic obstructive pulmonary disease, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

Additional objects, advantages, and novel features of this invention will become apparent to those skilled in the art upon examination of the following illustrative examples thereof, which are not intended to be limiting.

Unless otherwise stated, all temperatures including melting points (i.e., Mpts.) are in degrees celsius (°C.).

Example 1

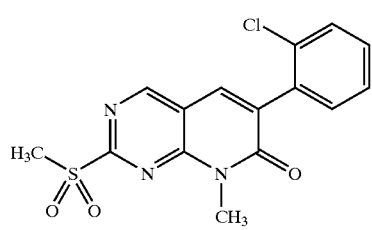

Sulfone 1

This example illustrates a method for preparing sulfone 1 from ethyl 4-chloro-2-methylthiopyrimidine-5-carboxylate.

Step 1 Preparation of ethyl 4-methylamino-2-methylthiopyrimidine-5-carboxylate

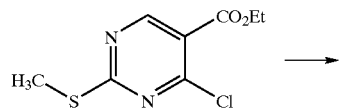

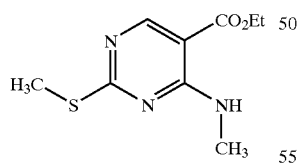

To a 0° C. solution of 20 g (86 mmol) of ethyl 4-chloro-2-methylthiopyrimidine-5-carboxylate (Aldrich Chemical Co., Milwaukee, Wis., USA) in 250 mL of dichloromethane was slowly added 35 mL (281 mmol) of a 33% solution of methylamine in ethanol. After stirring for 30 minutes, 150 mL of water was added and the phases were separated. The organic phase was dried over magnesium sulfate and filtered. The filtrate was evaporated under reduced pressure to give 19 g (97%) of ethyl 4-methylamino-2-methylthiopyrimidine-5-carboxylate as a white solid.

Step 2 Preparation of 4-methylamino-2-methylthiopyrimidine-5-methanol

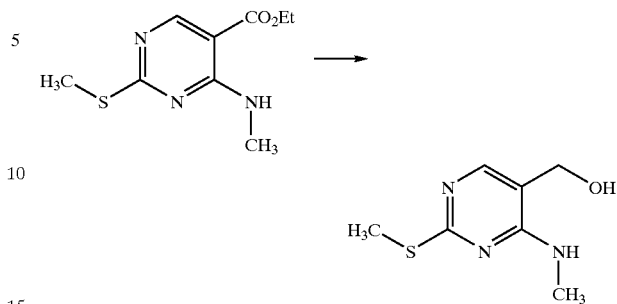

To a suspension of lithium aluminum hydride (8.2 g, 215 mmol) in 300 mL of dry tetrahydrofuran cooled in an ice-bath was added a solution of 46 g (215 mmol) of ethyl 4-methylamino-2-methylthio-pyrimidine-5-carboxylate in 450 mL of dry tetrahydrofuran. The reaction mixture was stirred for 15 minutes and quenched by adding 18 mL of water. 8.5 mL of 15% sodium hydroxide solution was added dropwise, followed by 25.5 mL of water. The resulting suspension was stirred for 17 hours at room temperature and then filtered. The filter residue was washed twice with 100 mL of tetrahydrofuran. The filtrate was combined and concentrated under reduced pressure. The residue was suspended in 200 mL of ethylacetate/hexane (1:2) and the solid was filtered and dried to give 32.7 g (82%) of 4-methylamino-2-methylthiopyrimidine-5-methanol as a yellow solid.

Step 3 Preparation of 4-methylamino-2-methylthiopyrimidine-5-carboxaldehyde

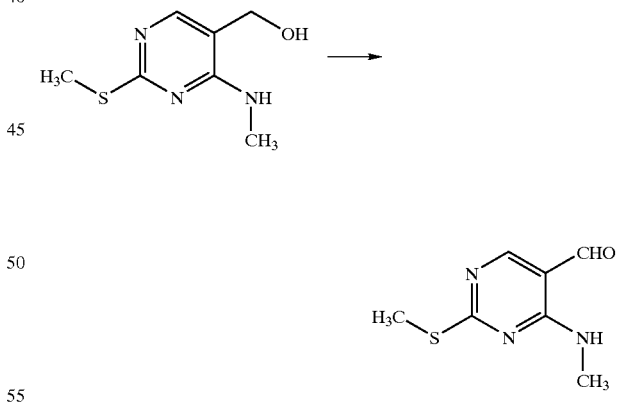

To a solution of 4-methylamino-2-methylthiopyrimidine-5-methanol (20 g, 108 mmol) in 1 L of dichloromethane was added 87 g (1 mol) of manganese dioxide. The resulting mixture was stirred for 24 hours and filtered through a filter aid. The filter residue was washed with 100 mL of dichloromethane. The filtrates were combined and concentrated under reduced pressure to give 15.8 g (80%) of 4-methylamino-2-methylthiopyrimidine-5-carboxaldehyde as a white solid.

Step 4

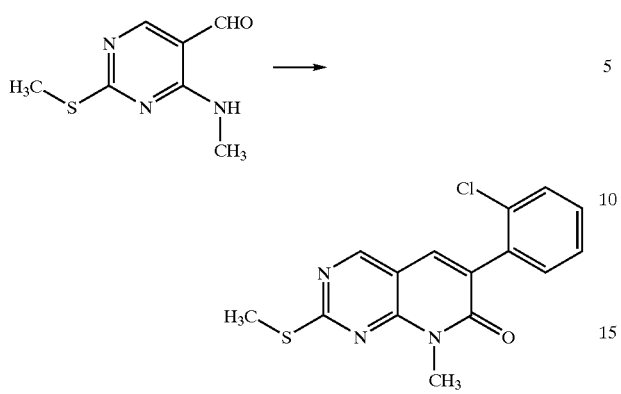

To a mixture of 3.3 g (18.1 mmol) of 4-methylamino-2-methylthiopyrimidine-5-carboxaldehyde, 4.0 g (20.1 mmol) of ethyl-2-chlorophenylacetate in 30 mL of NMP was added 1.5 g of resin, polymer bound 1,3,4,6,7,8-hexahydro-2H-pyrimido[1,2-a]pyrimidine. The reaction mixture was stirred at 120° C. for 48 h, cooled to room temperature, filtered, washed with NMP and ethyl acetate and suspended in water. The product was isolated by filtration. Additional product was obtained by extracting the filtrate with ethyl acetate. The combined product was washed with 5% aqueous HCl and water and dried to give 4.0 g of sulfide (mass spec. MH$^+$= 318. Mpt. 193.0–193.4).

Step 5

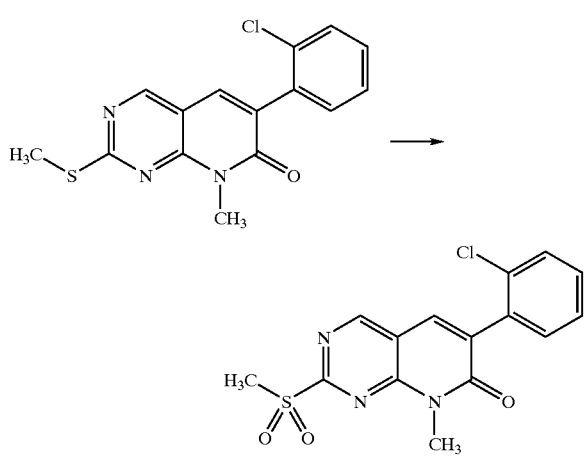

A solution of 13.5 g (42.5 mmol) of sulfide in chloroform was cooled in ice and treated with 20.5 g (91 mmol) of 3-chloroperbenzoic acid. The mixture was stirred at room temperature for 16 hours, then washed with saturated aqueous sodium bicarbonate solution and the phases were separated. The organic phase was dried over magnesium sulfate, filtered, and concentrated under reduced pressure. The product was stirred in ethyl ether, filtered and dried to give 13.1 g of sulfone 1 (mass spec. MH$^+$=350. MP=232.6–232.8° C.).

Example 2

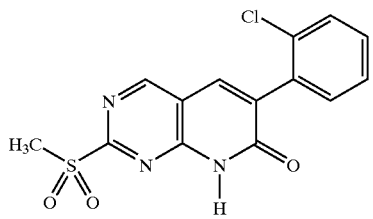

Sulfone 2

This example illustrates a method for producing 6-(2-chlorophenyl)-2-methanesulfonyl-pyrido[2,3-d]pyrimidin-7-ol (Sulfone 2) starting with ethyl 4-chloro-2-methylthiopyrimidine-5-carboxylate.

Step 2.1 Preparation of ethyl 4-amino-2-methylthiopyrimidine-5-carboxylate

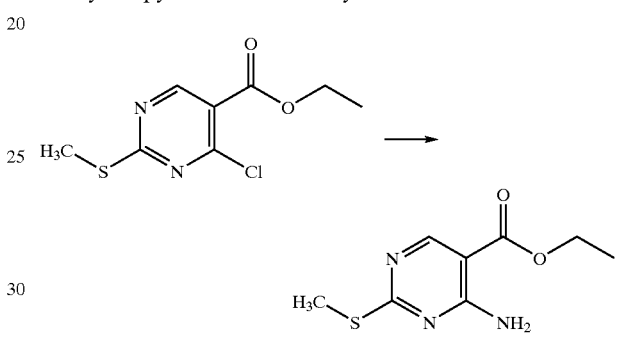

A solution of ethyl 4-chloro-2-methylthiopyrimidine-5-carboxylate (25.4 g, 106 mmol, Aldrich Chemical Co., Milwaukee, Wis., USA) in 300 mL of tetrahydrofuran was treated with 50 mL of triethylamine and 40 mL of aqueous ammonium hydroxide. After stirring for 4 hours, 300 mL of water was added and the phases were separated. The organic layer was washed with 300 mL of brine, concentrated in vacuo, dissolved in methylene chloride, dried over sodium sulfate, filtered and concentrated in vacuo to give 16.5 g (95%) of ethyl 4-amino-2-methylthiopyrimidine-5-carboxylate as a white solid.

Step 2.2 Preparation of 4-amino-2-methylthiopyrimidine-5-methanol

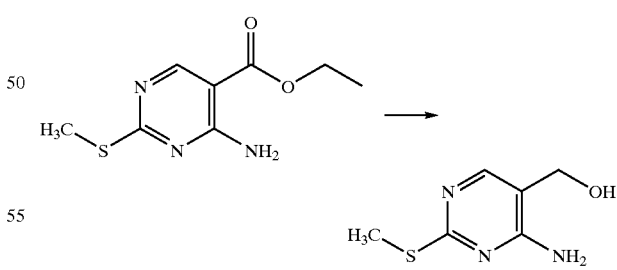

To a 0° C. solution of lithium aluminum hydride (175 mmol) in 175 mL of diethyl ether was added a solution of 4-amino-2-methylthiopyrimidine-5-carboxylate (34.7 g, 163 mmol) in 500 mL of dry tetrahydrofuran over a period of 1.5 hours. The reaction mixture was slowly warmed to ambient temperature and then cooled back to 0° C. before quenching with 7 mL of water, 7 mL of 2 M sodium hydroxide solution, followed by 14 mL of water. The resulting suspension was filtered and the filter residue was washed with 2×300 mL of ethyl acetate. The filtrates were combined and concentrated to give 23.0 g (83%) of 4-amino-2-methylthiopyrimidine-5-methanol as a white solid.

Step 2.3 Preparation of 4-amino-2-methylthiopyrimidine-5-carboxaldehyde

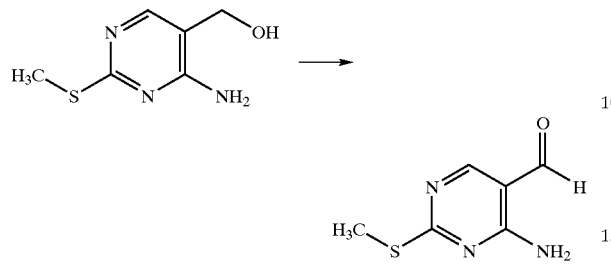

A suspension of 4-amino-2-methylthiopyrimidine-5-methanol (21.8 g, 128 mmol) in 800 mL of methylene chloride was treated with activated manganese oxide powder (63.0 g, 725 mmol). The reaction mixture was stirred for 18 hours, then filtered through a pad of celite. The filter residue was repeatedly washed with a solution of hot methylene chloride and methanol. The filtrates were combined and concentrated to give 17.5 g (81%) of 4-amino-2-methylthiopyrimidine-5-carboxaldehyde as a white solid.

Step 2.4 Preparation of 6-(2-chlorophenyl)-2-methylthio-pyrido[2,3-d]pyrimidin-7-ol

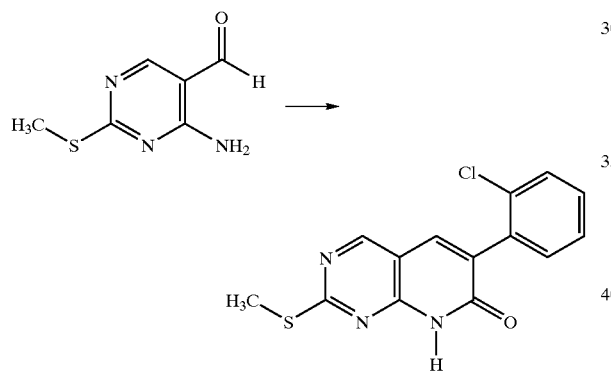

To a solution of 4-amino-2-methylthiopyrimidine-5-carboxaldehyde (21.7 g, 128 mmol) and ethyl-2-chlorophenylacetate (31.3 g, 158 mmol) in 250 mL of dry 1-methyl-2-pyrrolidinone was added potassium carbonate (63.0 g, 491 mmol). The reaction mixture was stirred at 95° C. for 16 hours and monitored by TLC (20:80, ethyl acetate/hexanes). An additional 12.0 g (60 mmol) of ethyl-2-chlorophenylacetate was added and the reaction mixture was stirred at 95° C. for another 16 hours. The cooled reaction mixture was filtered, and the filtered solids were washed with ethyl acetate. The filtrates were combined and diluted with 400 mL of water and 300 mL of ethyl acetate. The organic phases was separated, washed with brine, dried over sodium sulfate, filtered and concentrated in vacuo until a yellow precipitate formed. The resulting solid was washed with ethyl acetate and dried to yield a minor amount of product. Most of the product remained in the aqueous layer and slowly precipitated out upon standing. The precipitate was filtered and washed with water and ethyl acetate. This procedure was repeated six times yielding a total of 31.9 g (82%) of 6-(2-chlorophenyl)-2-methanesulfonyl-pyrido[2,3-d]pyrimidin-7-ol (mass spec. M+=303, mp=234.5–235.3° C.).

Step 2.5 Preparation of 6-(2-chlorophenyl)-2-methanesulfonyl-pyrido[2,3-d]pyrimidin-7-ol

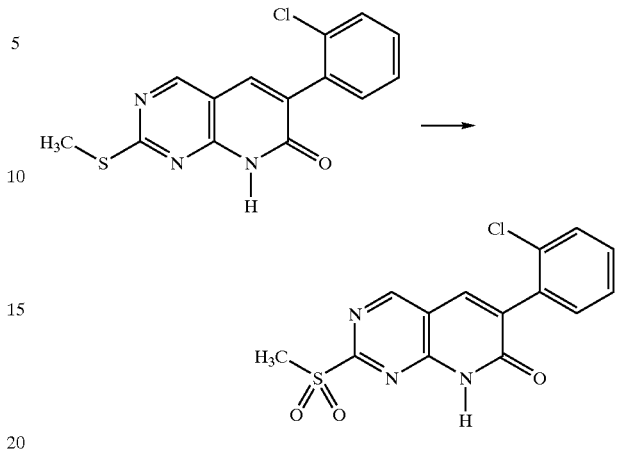

To a solution of 6-(2-chlorophenyl)-2-methylthio-pyrido[2,3-d]pyrimidin-7-ol (25.2 g, 82.9 mmol) in 700 mL of tetrahydrofuran was added a slurry of Oxone™ (105 g, 171 mmol) in 200 mL of water. The reaction mixture was stirred for 5 hours, filtered, then concentrated in vacuo. The resulting slurry was filtered and the collected solid was washed with water and dried to give 23.2 g (83%) of 6-(2-chlorophenyl)-2-methanesulfonyl-pyrido[2,3-d]pyrimidin-7-ol (Sulfone 2) as a light-yellow solid. (mass spec. M+H+= 336, mp=215.1–221.1° C.).

Example 3

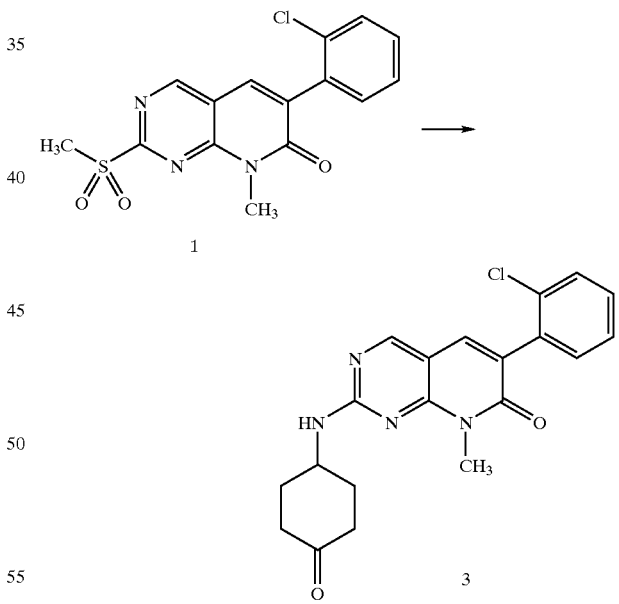

Step 1

A mixture of 3.1 g (8.9 mmol) of sulfone 1 and 2.8 g (17.7 mmol) of 1,4 dioxa-spiro[4,5]dec-8-ylamine (see WO 99/01452 for preparation) in 15 mL of NMP was stirred at 80° C. for 16 h, diluted with water, stirred, filtered and dried to obtain 3.7 g of ketal intermediate as a yellow solid.

Step 2

A solution of 3.8 g (8.9 mmol) of ketal in 40 mL of 80% aqueous acetic acid was stirred at 65° C. for 4 h, cooled, poured into water and extracted with ethyl acetate. The organic fraction was washed with saturated sodium bicarbonate and brine, dried over sodium sulfate and concentrated under reduced pressure. The residue was purified by flash chromatography (gradient elution: 20–30% acetone/hexane) to give 2.4 g as a white solid (mass spec. MH$^+$= 383).

Example 4

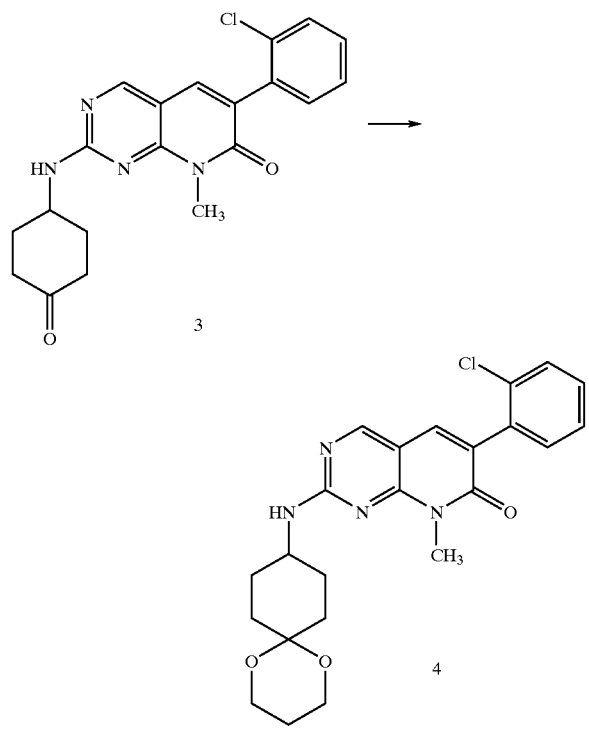

A mixture of 0.4 g (1.05 mmol) of compound 3, 0.23 ml (3.2 mmol) of 1,3-propanediol and 0.25 g (1.3 mmol) of pTsOH.H$_2$O in 15 mL of toluene was heated at reflux through a Dean-Stark trap. After 16 h, the reaction was cooled to room temperature, poured into aqueous sodium bicarbonate and extracted with ethyl acetate. The extracts were washed with brine, dried over sodium sulfate and concentrated under reduced pressure. The residue was purified by flash chromatography (gradient elution: 2–3% acetone/hexane) to give 0.3 g as a white solid (mass spec. MH$^+$=441. Mpt. 196.1–196.5° C.).

Example 5

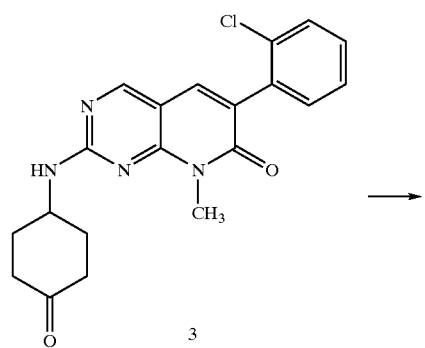

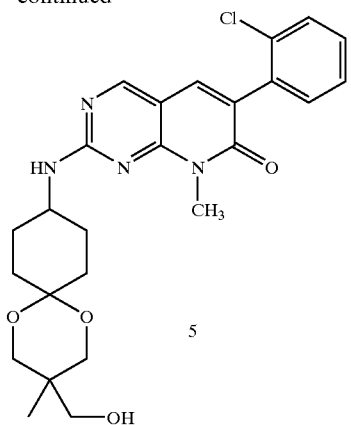

A mixture of 0.3 g (0.78 mmol) of compound 3, 0.29 g (2.4 mmol) of 1,1,1-tris(hydroxymethyl)ethanol and 0.19 g (1 mmol) of p-TsOH.H$_2$O in 10 mL of toluene was refluxed for 16 h, cooled to room temperature, poured into aqueous sodium bicarbonate and extracted with ethyl acetate. The extracts were washed with brine, dried over sodium sulfate and concentrated under reduced pressure. The residue was purified by flash chromatography (eluting with ethyl acetate) and the product converted to the HCl salt with HCl/ethyl ether to give 0.2 g as a white solid (mass spec. M$^+$=485. Mpt. 180.3–181.2).

Example 6

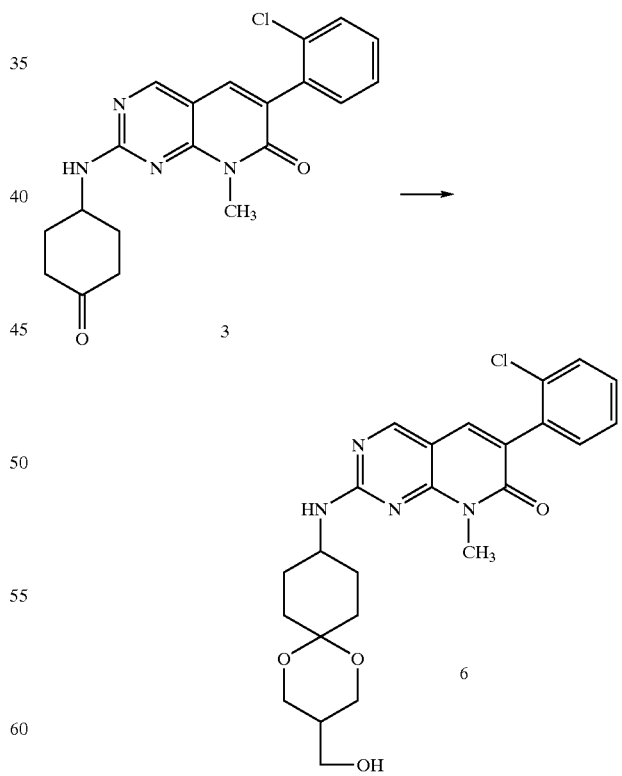

A mixture of 0.1 g (0.26 mmol) of compound 3, 0.09 g (0.81 mmol) of 2-(hydroxymethyl)-1,3-propanediol and 0.065 g (0.34 mmol) of p-TsOH.H$_2$O in 5 mL of toluene was refluxed for 16 h, cooled to room temperature, poured into aqueous sodium bicarbonate and extracted with ethyl acetate. The extracts were washed with brine, dried over sodium sulfate and concentrated under reduced pressure. The residue was purified by flash chromatography (eluting with ethyl acetate) and the product converted to the HCl salt with HCl/ethyl ether to give 0.08 g as a white solid (mass spec. M⁺=471. Mpt. 146–150).

Example 7

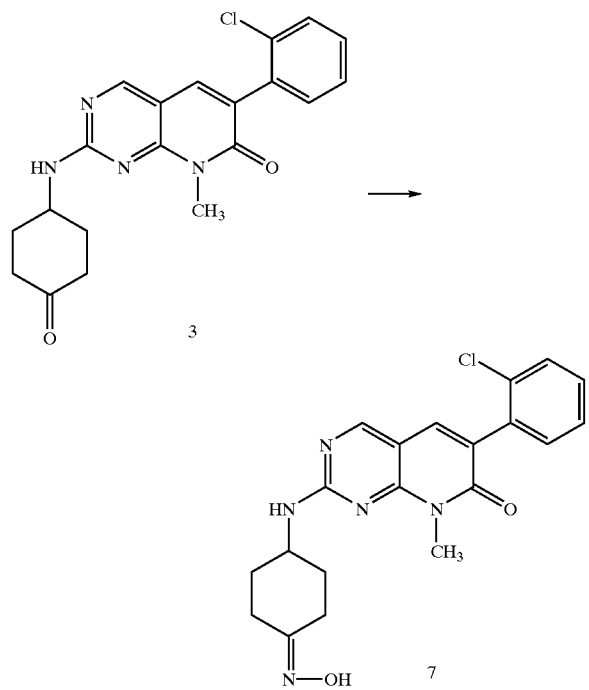

A mixture of 0.2 g (0.5 mmol) of compound 3 and 0.16 g (2.4 mmol) of hydroxylamine hydrochloride in 5 mL of pyridine was heated at 65° C. After 2 h, the reaction was cooled to room temperature and poured into water. The product was filtered, washed with water and dried to give a white solid, 0.21 g (mass spec. MH⁺=398. Mpt. >300°).

Example 8

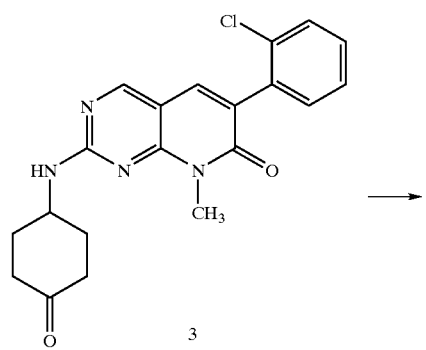

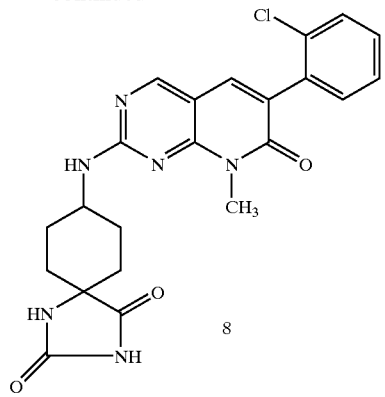

A mixture of 0.26 g (0.79 mmol) of compound 3, 0.077 g (1.2 mmol) of KCN and 0.23 g (2.4 mmol) of ammonium carbonate in 10 mL of 50% aqueous ethanol was heated to 65° C. After 16 h, the reaction mixture was diluted with 10 mL of water and heated to reflux. After 15 min, the reaction was cooled and the product isolated by filtration. The product was suspended in methyl alcohol and excess HCl/ethyl ether was added. The solution was concentrated under reduced pressure and the residue was stirred with ethyl ether, filtered and dried to afford 0.24 g of product as a white solid (mass spec. MH⁺=453. Mpt.=>300).

Example 9

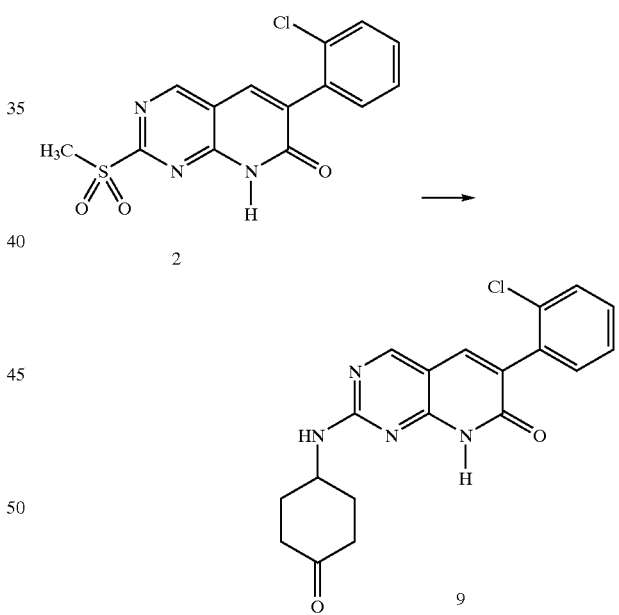

Step 1

A mixture of 0.1 g (0.3 mmol) of sulfone 2 and 0.94 g (0.6 mmol) of 1,4 dioxa-spiro[4,5]dec-8-ylamine (see WO 99/01452 for preparation) in 5 mL of NMP was stirred at 80° C. for 16 h, cooled to room temperature, poured into saturated aqueous sodium bicarbonate solution and extracted with ethyl acetate. The extracts were washed with water and brine, then dried over sodium sulfate. The solution was concentrated under reduced pressure and purified by flash chromatography (gradient elution: 40–80% ethyl acetate/hexane) to afford 0.1 g of ketal intermediate as a white solid (mass spec. MH⁺=413).

Step 2

A solution of 2.35 g (5.7 mmol) of ketal in 40 mL of 80% aqueous acetic acid was stirred at 65° C. for 3 h, cooled, poured into water filtered and dried to give 0.8 g of ketone (mass spec. MH⁺=369) as a yellow solid. A sample was converted to the HCl salt with HCl/ethyl ether (mass spec. MH⁺=369. Mpt.=265.5–269.9° C.).

Example 10

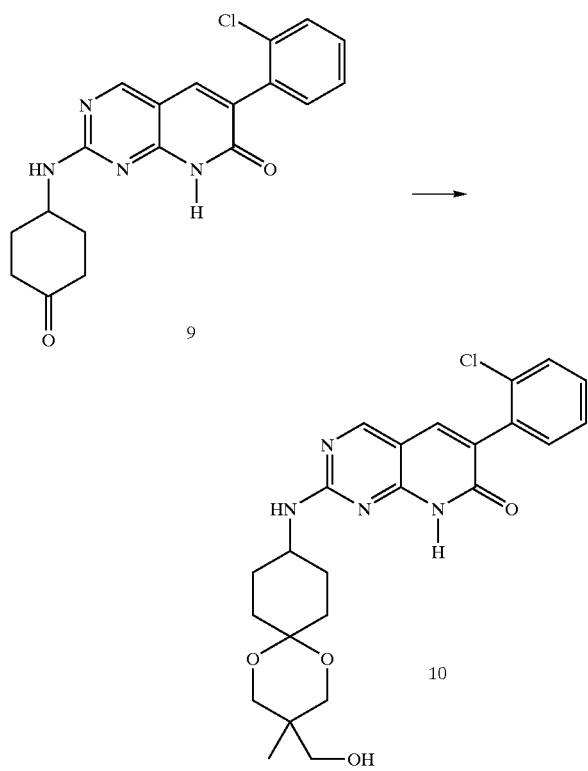

A mixture of 0.2 g (0.54 mmol) of compound 9, 0.2 g (1.7 mmol) of 1,1,1-tris(hydroxymethyl)ethanol and 0.13 g (0.7 mmol) of p-TsOH.H₂O in 30 mL of toluene was refluxed for 16 h, cooled to room temperature and filtered. The white solid product was isolated as a p-toluene sulfonic acid salt (0.19 g) (mass spec. MH⁺=470. Mpt.=223–226.5° C.).

Example 11

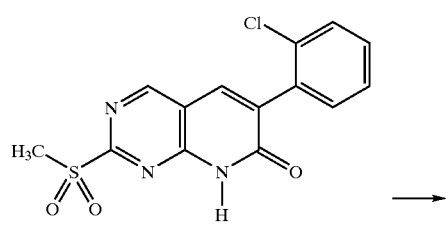

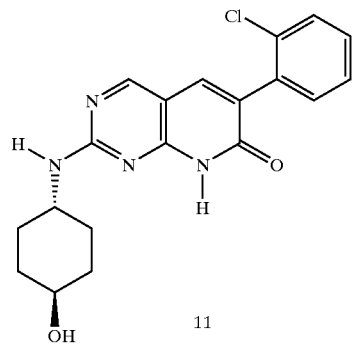

To a solution of sulfone 2 (0.45 g, 1.3 mmol) in 3 mL of 1-methyl-2-pyrrolidinone was added trans-4-aminocyclohexanol (0.54 g, 4.7 mmol). The reaction mixture was stirred at 70° C. for 2 hours, cooled, and diluted with ethyl acetate until precipitate started to form. The resulting suspension was filtered and the solid was washed with water and ethyl acetate, and dried to give 0.40 g (78%) of the title compound as a light yellow solid (mass spec. M+H⁺=371, mp=191.1–194.3° C.). The free base was taken up in ethyl acetate and treated with a 1M solution of HCl/Et₂O to form the hydrochloride salt of 2-(trans-4-hydroxycyclohexylamino)-6-(2-chlorophenyl)-pyrido[2,3-d]pyrimidin-7-ol (11) as a white powder with a melting point of 263.2–264.0° C.

Example 12

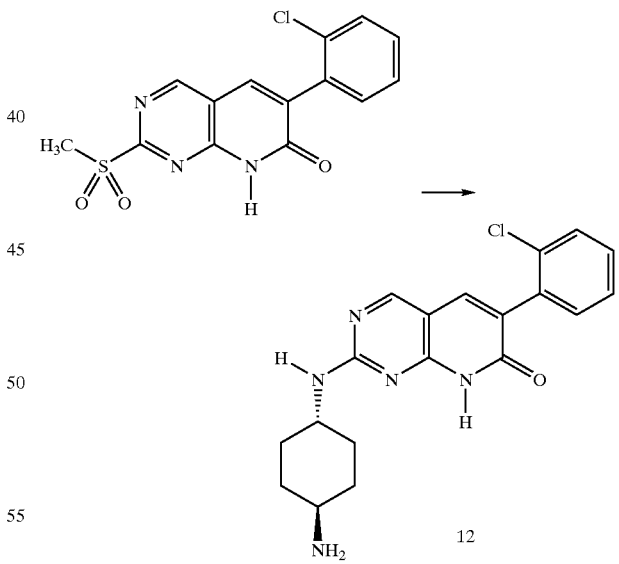

To a solution of sulfone 2 (1.27 g, 3.78 mmol) in 15 mL of 1-methyl-2-pyrrolidinone was added trans-1,4-diaminocyclohexane (3.75 g, 32.8 mmol). The reaction mixture was stirred at 65° C. for 1.5 hours, cooled, and diluted with 80 mL of ethyl acetate. The resulting suspension was filtered and washed several times with ethyl acetate and methanol. The solid was dried to yield 1.31 g (94%) of 2-(trans-4-aminocyclohexylamino)-6-(2-chlorophenyl)- pyrido[2,3-d]pyrimidin-7-ol as an off-white powder (mass spec. M+H$^+$=370). The free base was taken up in ethyl acetate and treated with a 1 M solution of HCl/Et$_2$O to form the dihydrochloride salt of the title compound as a white powder with a melting point of >300° C.

Example 13

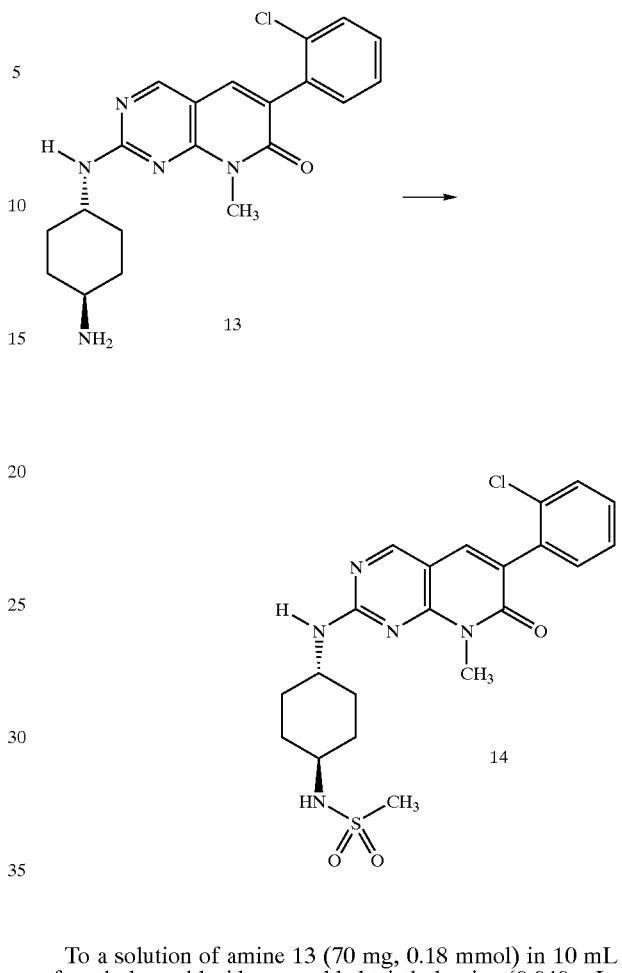

Example 14

To a solution of sulfone 1 (0.36 g, 1.0 mmol) in 10 mL of 1-methyl-2-pyrrolidinone was added trans-1,4-diaminocyclohexane (1.05 g, 9.20 mmol). The reaction mixture was stirred at 80° C. for 20 minutes, cooled, and diluted with ethyl acetate. A small amount of precipitate formed and the suspension was filtered. Water was added to the organic layer and extracted with 3×60 mL of ethyl acetate. The combined organic layers were washed with brine, dried over sodium sulfate, and concentrated to give a yellow liquid. Purification by column chromatography (50:50, methanol/methylene chloride) gave 0.25 g (62%) of 2-(trans-4-aminocyclohexylamino)-6-(2-chlorophenyl)-8-methyl-pyrido[2,3-d]pyrimidin-7-one as a yellow foam (mass spec. M+H$^+$=384, mp=190.3–191.4° C.). The free base was taken up in ethyl acetate and treated with a 1 M solution of HCl/Et$_2$O to form the dihydrochloride salt of the title compound as a white powder with a melting point of 224.0–228.5° C.

To a solution of amine 13 (70 mg, 0.18 mmol) in 10 mL of methylene chloride was added triethylamine (0.040 mL, 0.29 mmol) and methane sulfonic anhydride (50 mg, 0.29 mmol). The reaction mixture was stirred for 1 hour and concentrated in vacuo. Purification by column chromatography (3:97, methanol/methylene chloride) gave 78 mg (93%) of 2-(trans-4-methanesulfonylaminocyclohexylamino)-6-(2-chlorophenyl)-8-methyl-pyrido[2,3-d]pyrimidin-7-one as a white solid (mass spec. M+H$^+$=462, mp=260.9–261.1° C.). The free base was taken up in ethyl acetate and treated with a 1 M solution of HCl/Et$_2$O to form the hydrochloride salt of the title compound as a white powder with a melting point of 250.8–252.2° C.

Example 15

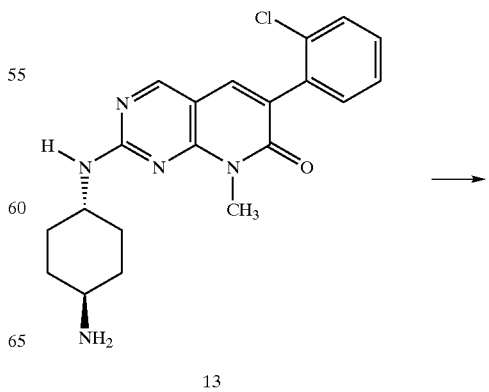

-continued

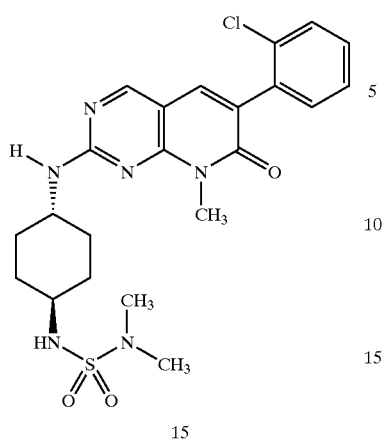

15

To a solution of amine 13 (116 mg, 0.302 mmol) in 15 mL of methylene chloride was added triethylamine (0.050 mL, 0.36 mmol) and dimethylsulfamoyl chloride (0.075 mL, 0.696 mmol). The reaction mixture was refluxed for 1 hour. An additional 0.075 mL (0.696 mmol) of dimethylsulfamoyl chloride was added and the reaction mixture was refluxed for additional 16 hours, cooled, concentrated in vacuo and purified by column chromatography (3:97, methanol/methylene chloride) to give 90 mg (61%) of 2-(trans-4-N,N-dimethylsulfonylaminocyclohexylamino)-6-(2-chlorophenyl)-8-methyl-pyrido[2,3-d]pyrimidin-7-one as a white solid (mass spec. M+H$^+$=491, mp=226.5–229.0° C.). The free base was dissolved in methylene chloride and treated with a 1M solution of HCl/Et$_2$O to form the hydrochloride salt of the title compound as a pale yellow powder with a melting point of 160.0–168.0° C.

Example 16

This example illustrates the synthesis 2-(trans-4-methanesulfonylamidocyclohexylamino)-6-(2-chlorophenyl)-pyrido[2,3-d]pyrimidin-7-one starting with of 6-(2-chlorophenyl)-2-methanesulfonyl-pyrido[2,3-d]pyrimidin-7-ol.

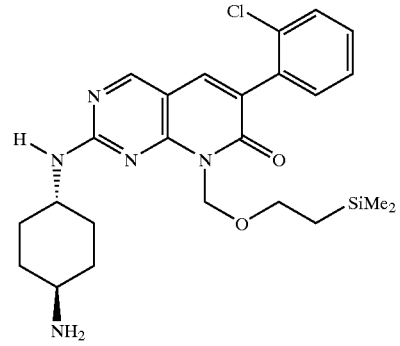

2

-continued

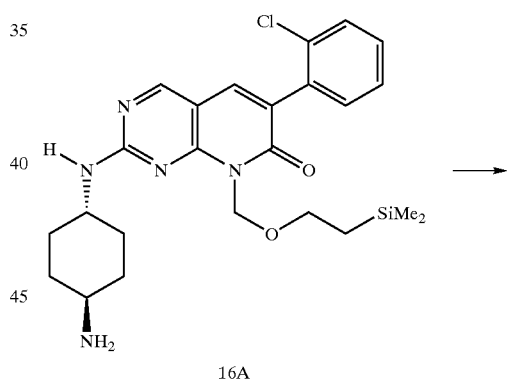

16A

To a solution of sulfone 2 (1.84 g, 5.48 mmol) in 18 mL of dry 1-methyl-2-pyrrolidinone was added sodium hydride (0.31 g, 7.75 mmol, 60% dispersion in mineral oil). The reaction mixture was stirred for 10 minutes until gas evolution subsided, then 2-(trimethylsilyl)ethoxymethyl chloride (0.10 mL, 5.7 mmol) was added dropwise over a period of 5 minutes. The reaction mixture was stirred for 1.5 hours, after which a solution of trans-1,4-diaminocyclohexane (6.24 g, 54.6 mmol) in 20 mL of dry 1-methyl-2-pyrrolidinone was added to the reaction mixture. The resulting reaction mixture was stirred for 30 minutes and poured into 60 mL of water. The resulting cloudy mixture was extracted with 2×100 mL of ethyl acetate. The combined organic layers were washed with 2×150 mL of brine, dried over sodium sulfate and concentrated in vacuo to give a crude brown liquid. Purification by column chromatography (5–50:95–50, methanol/methylene chloride) gave 1.66 g (61%) of product 16A as a yellow foam (mass spec. M+H$^+$= 500, mp=96.5–105.0° C.).

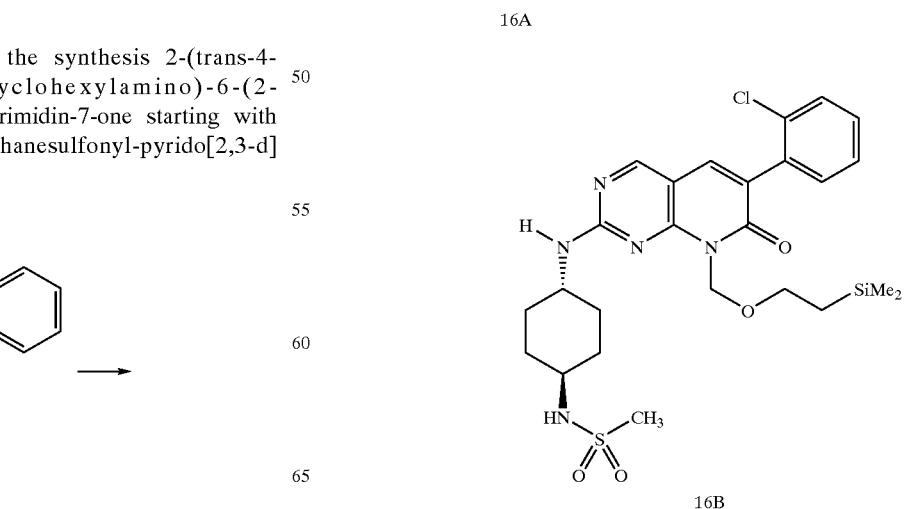

16A

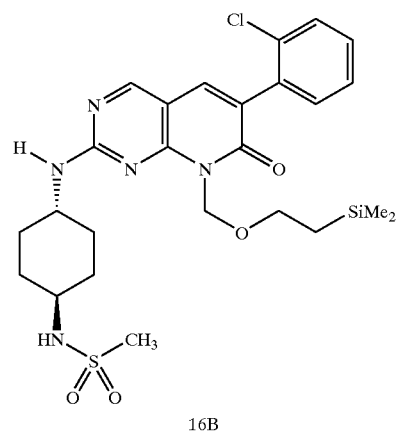

16B

To a solution of amine 16A (0.46 g, 0.91 mmol) in 20 mL of methylene chloride were added triethylamine (0.15 mL, 1.1 mmol) and methane sulfonic anhydride (0.18 g, 1.1 mmol). The reaction mixture was stirred for 19 hours, and then concentrated in vacuo. Purification by column chromatography (3:97, methanol/methylene chloride) gave 0.34 g (65%) of product 16B as a white solid (mass spec. M+H$^+$= 578, mp=231–232.5° C.)

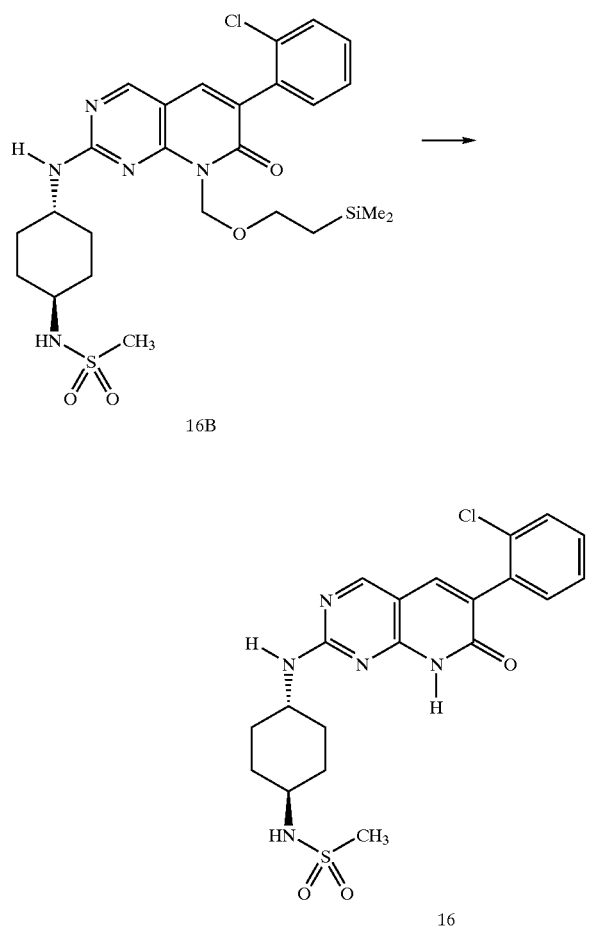

16B

16

The SEM-protected pyridone 16B (320 mg, 0.553 mmol) was suspended in 20 mL of methanol and treated with 10 mL of 10% hydrochloric acid. The reaction mixture was refluxed for 26 hours, cooled, then concentrated in vacuo until precipitate began to form. The resulting suspension was filtered, washed with water and ethyl acetate, then dried to give a white solid. Another crop of solids was obtained by reconcentration of the mother liquor and filtration to give a total of 221 mg (85%) of the hydrochloric acid salt of 2-(trans-4-methanesulfonylaminocyclohexylamino)-6-(2-chlorophenyl)-pyrido[2,3-d]pyrimidin-7-one (16) as a white solid (mass spec. M+H$^+$=448, mp>300° C.).

Example 17

This example illustrates the synthesis 2-(trans-4-N,N-dimethylsulfonylaminocyclohexylamino)-6-(2-chlorophenyl)-pyrido[2,3-d]pyrimidin-7-one starting with the SEM-protected pyridone.

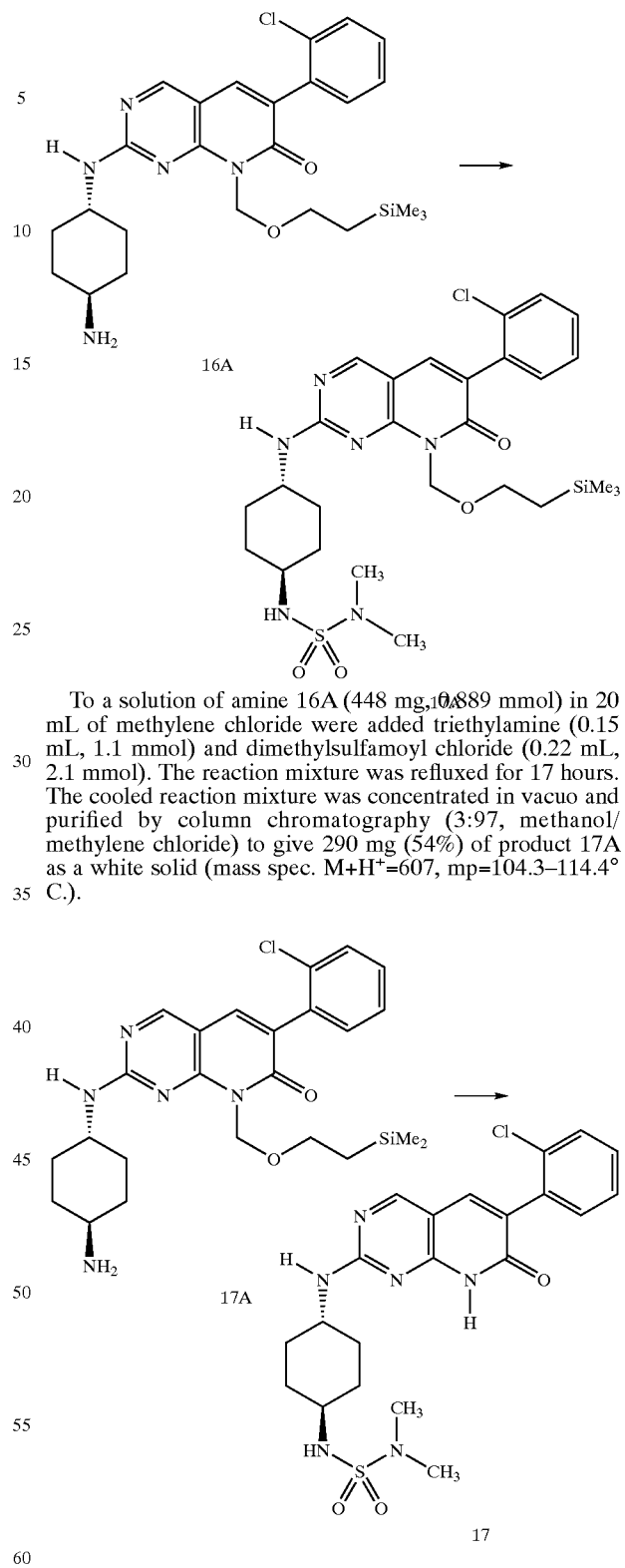

16A

17A

17

To a solution of amine 16A (448 mg, 0.889 mmol) in 20 mL of methylene chloride were added triethylamine (0.15 mL, 1.1 mmol) and dimethylsulfamoyl chloride (0.22 mL, 2.1 mmol). The reaction mixture was refluxed for 17 hours. The cooled reaction mixture was concentrated in vacuo and purified by column chromatography (3:97, methanol/methylene chloride) to give 290 mg (54%) of product 17A as a white solid (mass spec. M+H$^+$=607, mp=104.3–114.4° C.).

The SEM-protected compound 17A (270 mg, 0.445 mmol) was suspended in 30 mL of methanol and treated with 20 mL of 10% hydrochloric acid. The reaction mixture was refluxed for 2 days, cooled, then concentrated in vacuo until precipitate began to form. The resulting suspension was filtered, washed with water and ethyl acetate, then dried to give 205 mg (90%) of the hydrochloric acid salt of 2-(trans- 4-dimethylsulfonylamidocyclohexylamino)-6-(2-chlorophenyl)-pyrido[2,3-d]pyrimidin-7-one (17) as a white solid (mass spec. M+H+=477, mp=262.2–262.5° C.).

Example 18

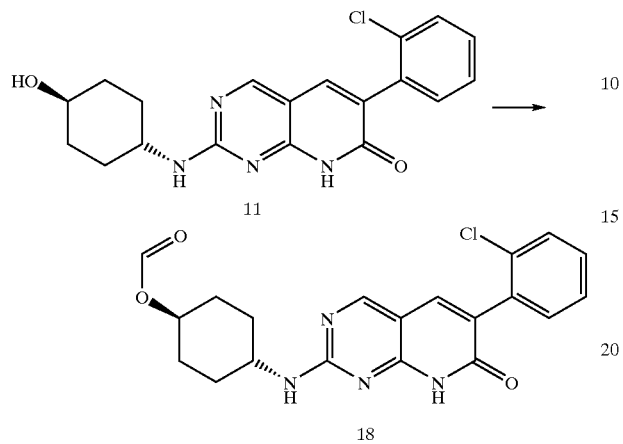

18

A mixture of compound 11 (300 mg, 0.8 mmol) and 96% formic acid (3 mL) was stirred at 60° C. for 3 h then at 25° C. overnight. The reaction mixture was concentrated under reduced pressure, triturated with ether, filtered and dried to give 320 mg of 6-(2-chlorophenyl)-2-(4-trans-formyloxy-cyclohexylamino)-8H-pyrido[2,3-d]pyrimidin-7-one. (Mass spec. MH+=399, mpt.>300° C.).

Example 19

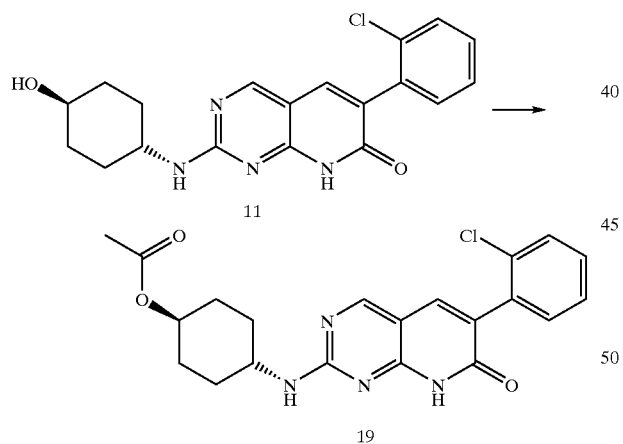

19

A suspension of compound 11 (300 mg, 0.8 mmol), acetic anhydride (0.23 mL, 2.4 mmol) and pyridine (0.26 mL, 3.2 mmol) in methylene chloride (3 mL) was refluxed for 3 days. The reaction was filtered and the precipitate was purified by column chromatography on silica gel using 97:3 CH$_2$Cl$_2$/MeOH to obtain 158 mg of the purified product. Addition of hydrochloric acid (1.0 M/Et$_2$O, 2.0 equivalents) gave the salt which was filtered and dried to give 155 mg of 6-(2-chlorophenyl)-2-(4-trans-acetyloxy-cyclohexylamino)-8H-pyrido[2,3-d]pyrimidin-7-one (19). (Mass spec. MH+= 413, mpt.>300° C.).

Example 20

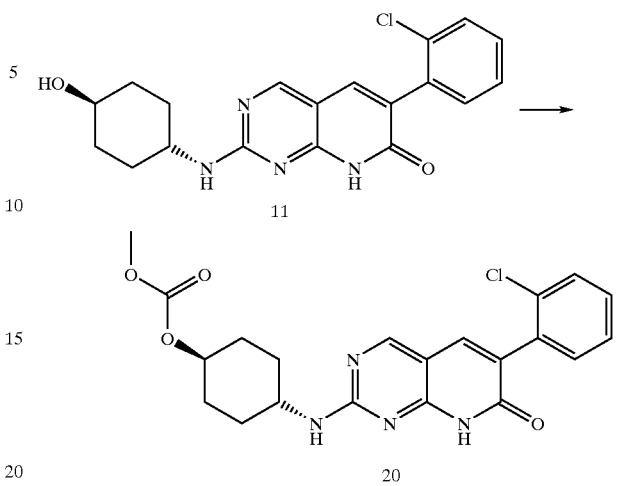

20

A suspension of compound 11 (250 mg, 0.68 mmol) and 4-(dimethylamino) pyridine (DMAP) (6.8 mg, 0.06 mmol) in THF (5 mL) was cooled in an ice bath and dimethylpyrocarbonate (0.7 mL, 6.8 mmol) was added and the mixture was stirred at 25° C. for 18 h. The reaction was filtered and the precipitate was purified by column chromatography on silica gel using 98:2 CH$_2$Cl$_2$/MeOH to obtain 33 mg of the purified product. Addition of hydrochloric acid (1.0 M/Et$_2$O, 2.0 equivalents) gave the salt which was filtered and dried to give 34 mg of 6-(2-chlorophenyl)-2-(4-trans-methoxycarbonyloxycyclohexylamino)-8H-pyrido[2,3-d]pyrimidin-7-one (20). (Mass spec. MH+=429).

Example 21

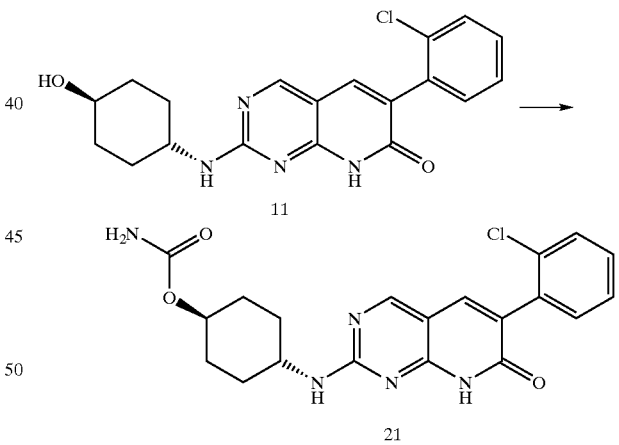

21

A suspension of compound 11 (308 mg, 0.83 mmol) in methylene chloride (5 mL) was cooled in an ice bath and chlorosulfonylisocyanate (0.08 mL, 0.87 mmol) was added. The mixture was stirred at 25° C. for 18 h, and then treated with water (0.5 mL). The biphasic mixture was stirred for 8 h, filtered and the precipitate was purified by column chromatography on silica gel using 97:3 CH$_2$Cl$_2$/MeOH to obtain 108 mg of pure product. Addition of hydrochloric acid (1.0 M/Et$_2$O, 2.0 equivalents) gave the salt which was filtered and dried to give 94 mg of. 6-(2-chlorophenyl)-2-(4-carbamoyloxycyclo-hexylamino)-8-pyrido[2,3-d] pyrimidin-7-one (21). (Mass spec. MH+=414, mpt. 291.0–293.5° C.).

Example 22

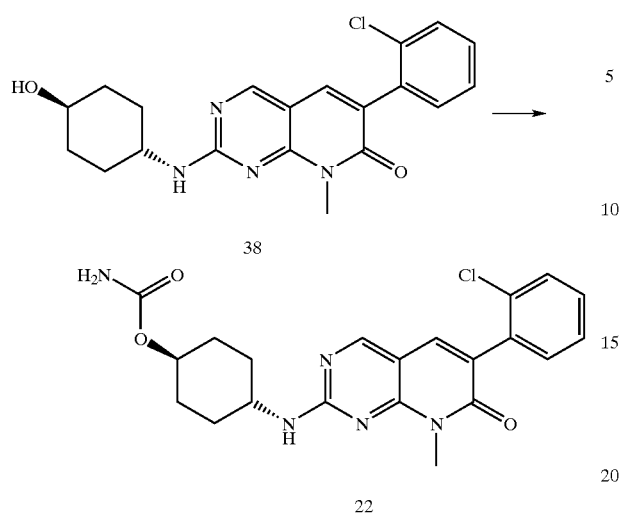

A suspension of compound 38, see Example 38, (190 mg, 0.49 mmol) in methylene chloride (5 mL) was cooled in an ice bath and chlorosulfonylisocyanate (0.05 mL, 1.01 mmol) was added. the resulting mixture was stirred at 25° C. for 18 h, and then treated with water (0.5 mL). The biphasic mixture was stirred for 8 h, filtered and the precipitate was purified by column chromatography on silica gel using 97:3 $CH_2Cl_2$/MeOH to obtain 108 mg of the purified product. Addition of hydrochloric acid (1.0 M/$Et_2O$, 2.0 equivalent gave the salt which was filtered and dried to give 94 mg product 22. (Mass spec. MH+=428, mpt. 234.7–235.4° C.).

Example 23

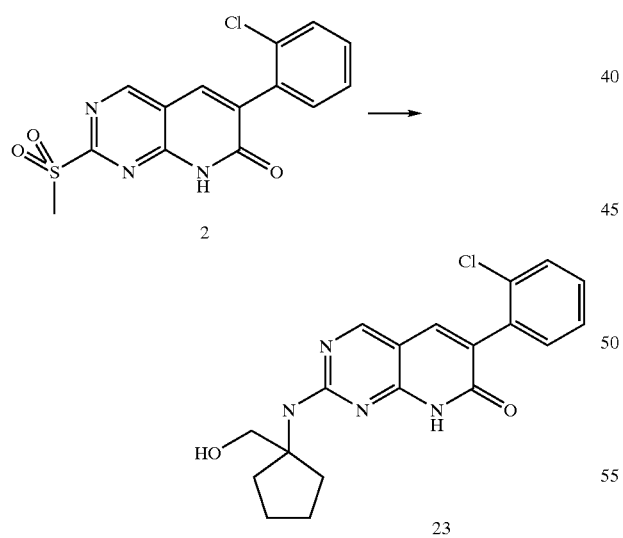

Sulfone 2 (500 mg, 1.5 mmol) was combined with 1-hydroxymethyl-cyclopentylamino (686 mg, 5.96 mmol) and 1-methyl-2-pyrrolidinone (1 mL). The mixture was heated to 100° C. for 3 h and then cooled to room temperature. Methanol (3 mL) was added. The suspension was stirred for 10 min, filtered and the precipitate was washed thoroughly with methanol, dried and suspended in ethyl acetate. Addition of hydrochloric acid (1.0 M/$Et_2O$, 2.0 equivalents) gave the salt which was filtered and dried to give 235 mg of product 23. (Mass spec. MH+=371, mpt. 290–293° C.).

Example 24

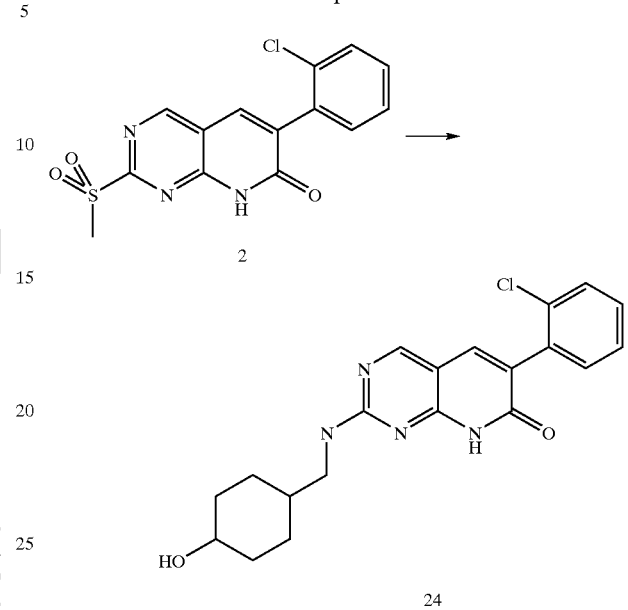

Sulfone 2 (250 mg, 0.71 mmol) was combined with 4-aminomethyl-cyclohexanol (630 mg, 3.4 mmol) and 1-methyl-2-pyrrolidinone (0.5 mL). The mixture was heated to 95° C. for 3 h and then cooled to room temperature. The mixture was purified by column chromatography on silica gel using 96:4 $CH_2Cl_2$. The column fractions containing product were combined and concentrated to a solid that was suspended in ethyl acetate. Addition of hydrochloric acid (1.0 M/$Et_2O$, 2.0 equivalents) gave the salt which was filtered and dried to give 85 mg of product 24. (Mass spec. MH+=385, mpt. 205–213° C.).

Example 25

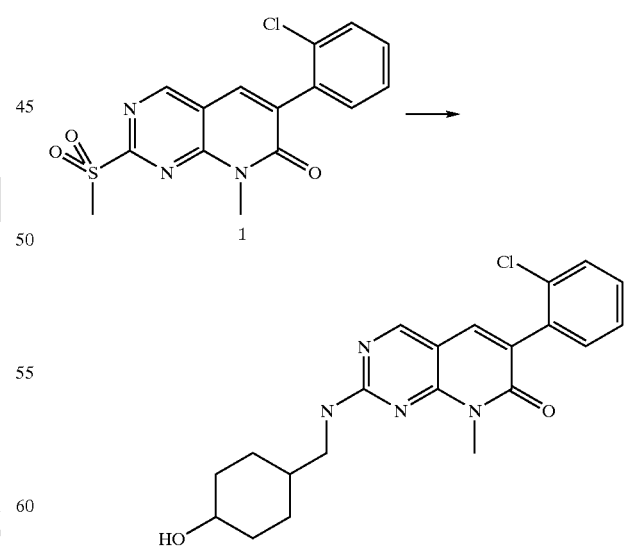

Sulfone 1 (500 mg, 1.42 mmol) was combined with 4-aminomethyl-cyclohexanol (630 mg, 3.4 mmol) and 1-methyl-2-pyrrolidinone (0.5 mL). The mixture was heated to 95° C. for 3h and then cooled to room temperature. The mixture was purified by column chromatography on silica gel using 96:4 CH₂Cl₂. The column fractions containing product were combined and concentrated to a solid that was suspended in ethyl acetate. Addition of hydrochloric acid (1.0 M/Et₂O, 2.0 equivalents) gave the salt which was filtered and dried to give 79 mg of product 25. (Mass spec. MH+=399, mpt. 148–151.5° C.).

Example 26

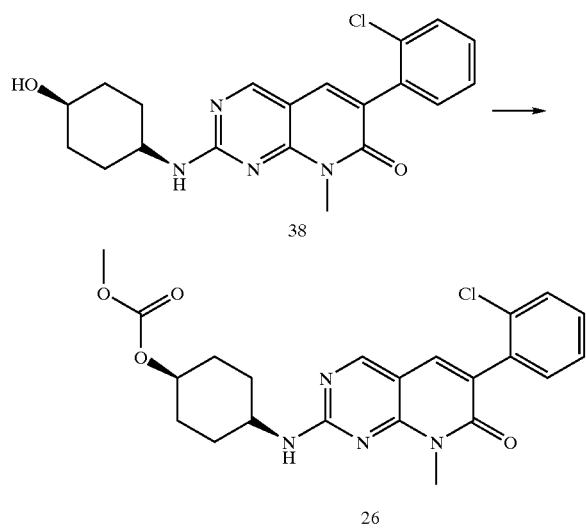

A suspension of compound 38 (350 mg, 0.9 mmol) and 4-(dimethylamino) pyridine (DMAP) (55.5 mg, 0.45 mmol) in THF (5 mL) was cooled in an ice bath and dimethylpyrocarbonate (0.3 mL, 2.8 mmol) was added. The resulting mixture was stirred at 25° C. for 18 h, filtered and the precipitate was purified by column chromatography on silica gel using 99:1 CH₂Cl₂/MeOH to obtain 205 mg of the purified product. Addition of hydrochloric acid (1.0 M/Et₂O, 2.0 equivalents) gave the salt which was filtered and dried to give 200 mg of product 26. (Mass spec. MH+=443: mpt 213.9–214.4° C.).

Example 27

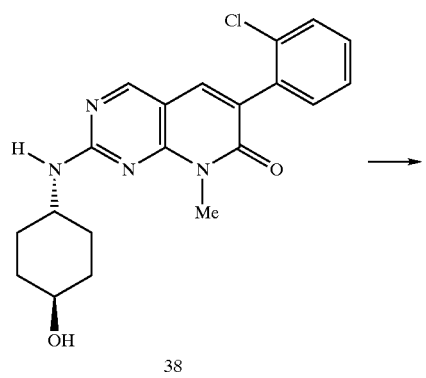

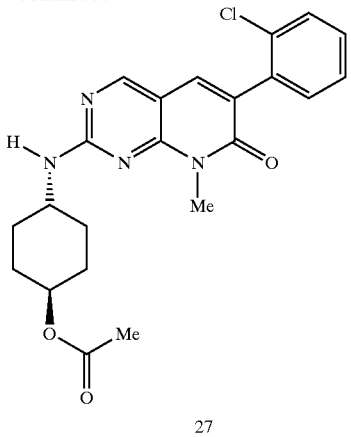

To a solution of compound 38 (0.36 g, 0.94 mmol) in 10 mL of methylene chloride at room temperature was sequentially added pyridine (0.60 g, 7.6 mmol) and acetic anhydride (0.58 g, 5.6 mmol). The resulting mixture was stirred at room temperature for three days, then concentrated under reduced pressure. The resulting residue was purified by column chromatography to yield 250 mg of a gray solid as the pure product. (mass spec. MH⁺=427, mpt. 200.9–201.2° C.).

Example 28

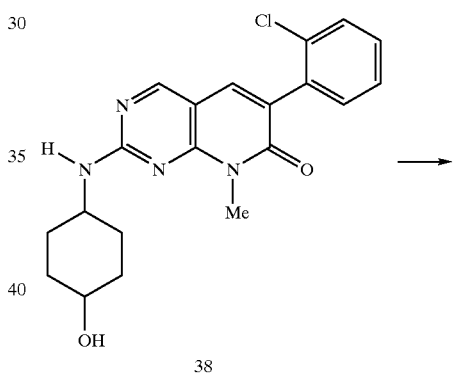

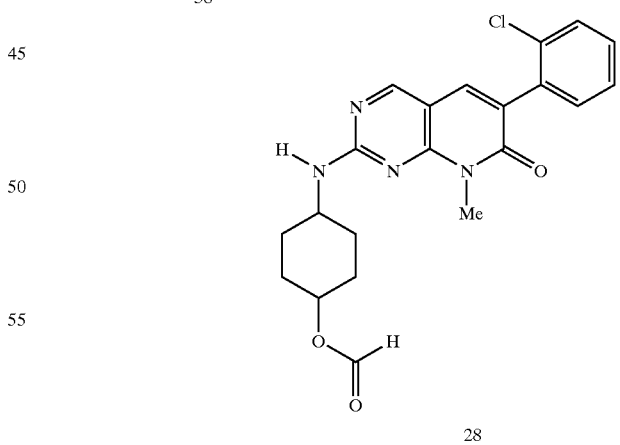

A solution of compound 38 (0.34 g, 0.89 mmol) in 6 mL formic acid was stirred at 60° C. for three days. The resulting mixture was concentrated under reduced pressure. The resulting foam was diluted with hexane and concentrated to yield a solid. Purification by column chromatography gave 340 mg of produce 28 as a powdery, brown solid. (Mass spec. MH⁺=413, mpt. 196.1–196.6° C.).

Example 29

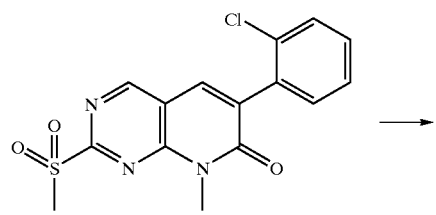

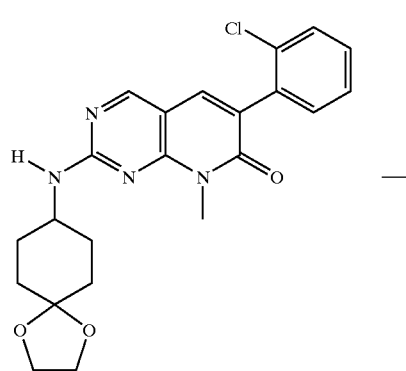

29

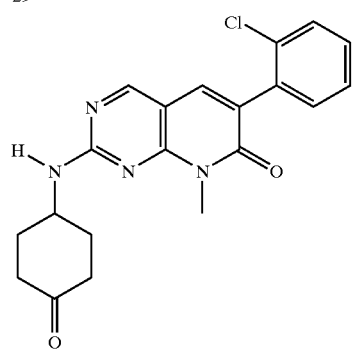

3

A mixture of 1,4 dioxa-spiro[4,5]dec-8-ylamine (see WO 99/01452 for preparation) (0.157 g, 1.00 mmole), N-methylpyrrolidinone (1 mL) and sulfone 1 (0.350 g, 1.00 mmole) was stirred at 100° C. for 2 hours. The reaction mixture was cooled and poured into water, extracted with ethyl acetate, washed with saturated brine, dried with magnesium sulfate, and evaporated in vacuo. The crude product was purified by flash chromatography on silica gel (0–3% methanol/dichloromethane). The column fractions containing product were combined and concentrated in vacuo. A portion of the concentrate (0.100 g) was taken up in methanol, treated with hydrochloric acid (1.0 M/Et$_2$O, 1.0 equivalent), and re-evaporated to dryness, then washed with ethyl ether, filtered, and dried to give 0.070 g of the hydrochloride salt of compound 29 (M$^+$=427).

To the remaining free base (0.167 g, 3.56 mmole) in 5 mL THF was added 2 N aqueous hydrochloric acid (1 mL). After 6 hours, the reaction mixture was poured into saturated sodium bicarbonate solution and extracted with ethyl acetate. The organic layers were combined, washed with saturated brine, dried with magnesium sulfate, and evaporated in vacuo. The residue was purified by flash chromatography on silica gel (20–30% acetone/hexanes). The column fractions containing product were combined and concentrated in vacuo. The product was disoolved in methanol, treated with hydrochloric acid (1.0 M/Et$_2$O, 1.0 equivalent), re-evaporated to dryness, washed with ethyl ether, filtered, and dried to give 0.102 g of the hydrochloride salt compound (M$^+$=382).

Example 30

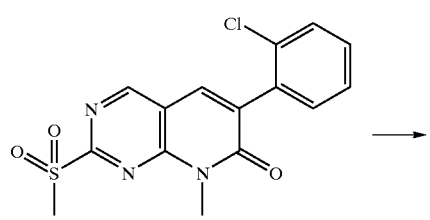
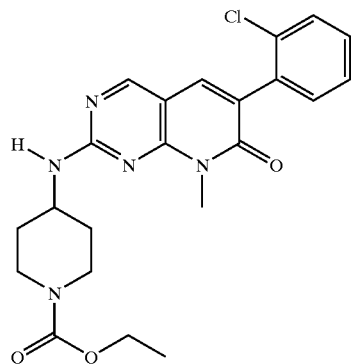

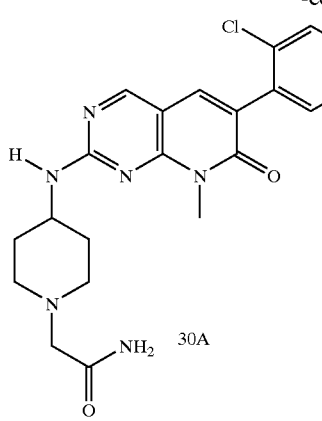

30A

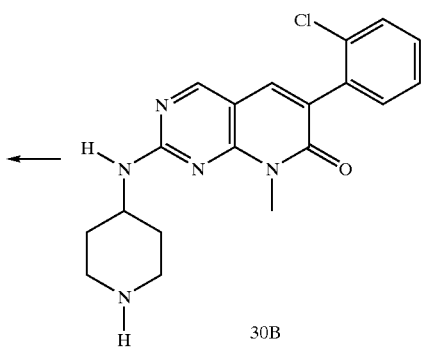

30B

A solution of sulfone 1 (0.500 g, 1.43 mmole) in ethyl 4-amino-1-piperidinecarboxylate (1.0 mL, 5.83 mmole) was stirred at 120° C. for 3 hours. The reaction mixture was poured into water and extracted with dichloromethane. The organic layers were combined, dried with magnesium sulfate, and concentrated in vacuo. The residue was purified by flash chromatography on silica gel (20–30% acetone/hexanes). The column fractions containing product were combined and concentrated in vacuo.

The purified ethyl carbamate (0.617 g, 1.40 mmole) was added to a hot ethanolic solution of potassium hydroxide (6.58 g, 117 mmole; 37 mL EtOH) and stirred at 80° C. for 3 hours. The reaction mixture was then chilled in an ice bath and quenched with an aqueous solution of citric acid (6.6 g, 31.4 mmole; 37 mL $H_2O$). The resulting solution was concentrated in vacuo to provide a thick aqueous solution, which was extracted with ethyl acetate. The organic layers were combined, dried with sodium carbonate, and concentrated—in vacuo. The residue was purified by flash chromatography on silica gel (10–30% methanol/dichloromethane). The column fractions containing product were combined and concentrated in vacuo to provide 30B.

A portion of the piperidine product was dissolved in methanol and treated with 1 eq 1 N HCl/ether. The solution was concentrated in vacuo. The dry residue was washed with ethyl ether and dried to provide the hydrochloride salt of compound 30B (mp>300.0 C.).

A solution of the compound 30B (0.100 g, 0.270 mmole) and bromoacetamide (0.100 g, 0.724 mmole) in 2 mL of DMF was heated to 120° C. over several hours. The reaction mixture was cooled and purified by flash chromatography on silica gel (3–5, 10% [1:9 ammonium hydroxide/methanol]/dichloromethane). The column fractions containing product were combined, concentrated in vacuo, dissolved in methanol and treated with hydrochloric acid (1.0 M/$Et_2O$, 1.0 equivalent). The solution was concentrated, washed with ethyl ether, filtered, and dried to give 0.117 g of the hydrochloride salt of compound 30A (mp 76.3–136.5; M+. 427).

Example 31

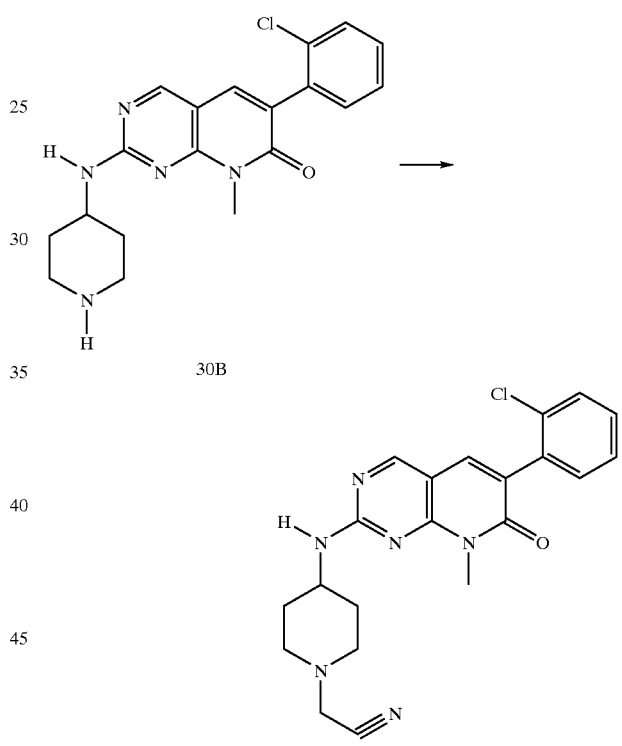

A mixture of compound 30B (0.100 g, 0.270 mmole), bromoacetonitrile (0.091 mL, 1.35 mmole) and sodium carbonate (0.114 g, 1.35 mmole) in 1 mL of DMF was stirred at room temperature. The mixture was then purified by flash chromatography on silica gel (2–5% [1:9 ammonium hydroxide/methanol]/dichloromethane). The column fractions containing product were combined and concentrated in vacuo to yield 0.086 g of the desired product. A portion of this free base (0.016 g) was dissolved in methanol and treated with hydrochloric acid (1.0 M/$Et_2O$, 1.0 equivalent). The solution was concentrated washed with ethyl ether, filtered, and dried to give 0.012 g of the hydrochloride salt of Compound 31 (mp 228.3–228.9; M+. 409).

Example 32

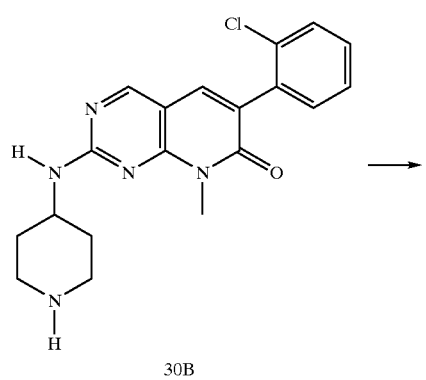

30B

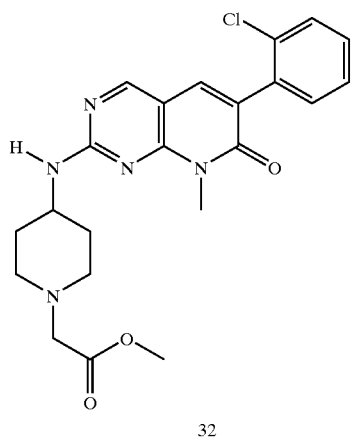

32

A mixture of compound 30B (0.050 g, 0.135 mmole) and methyl bromoacetate (0.030 mL, 0.317 mmole) in 1 mL of DMF was stirred at room temperature. The mixture was purified by flash chromatography on silica gel (10–40% methanol/dichloromethane+1% ammonium hydroxide). The column fractions containing product were combined and concentrated in vacuo. The residue was dissolved in methanol and treated with hydrochloric acid (1.0 M/Et$_2$O, 1.0 equivalent). The mixture was concentrated, washed with ethyl ether, filtered, and dried to give 0.013 g of the hydrochloride salt of Compound 32 (mp 150–168; M+. 442).

Example 33

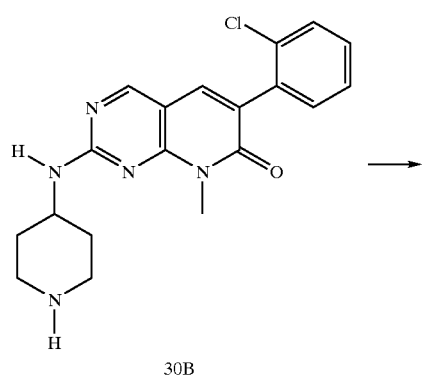

30B

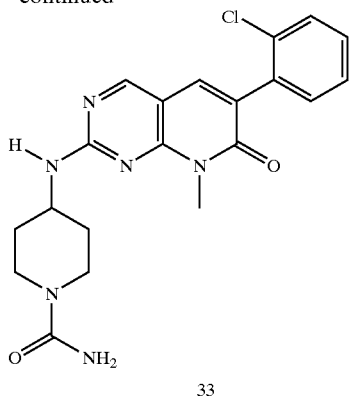

33

The compound 30B (0.050 g, 0.135 mmole) was taken up in 1 mL of THF with trimethylsilyl isocyanate (0.021 mL, 0.149 mmole) and stirred at room temperature for 3 hours, then evaporated in vacuo. The residue was purified by flash chromatography on silica gel (10% [1:9 ammonium hydroxide/methanol]/dichloromethane). The column fractions containing product were combined and concentrated in vacuo. The final product was taken up in methanol, treated with hydrochloric acid (1.0 M/Et$_2$O, 1.0 equivalent), and re-evaporated to dryness, then washed with ethyl ether, filtered, and dried to give 0.057 g of the hydrochloride salt of Compound 33 (mp 192.0–202.0; M+. 413).

Example 34

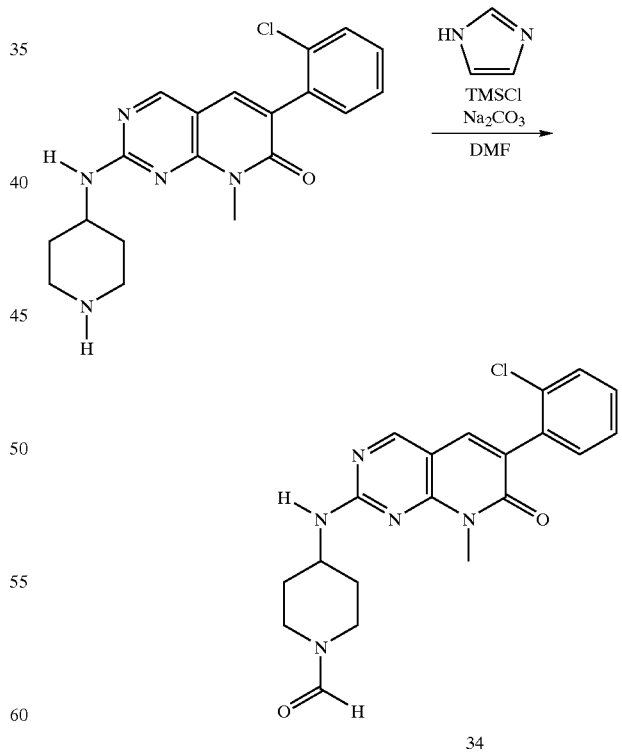

34

Imidazole (0.28 g, 4.06 mmole) and sodium carbonate (0.43 g, 4.06 mmole) were combined with DMF (0.63 mL, 8.11 mmole), to which chlorotrimethylsilane (0.63 mL, 4.06 mmole) was added dropwise. The slurry was stirred at room temperature for 20 minutes before adding Compound 30B (0.50 g, 1.35 mmole) as a dry powder. The reaction was stirred at room temperature for 2 hours, then poured into water and extracted with dichloromethane and ethyl acetate. The combined organic extracts were washed with saturated brine, dried with magnesium sulfate, and evaporated in vacuo. The residue was purified by flash chromatography (2–3% methanol/dichloromethane) and the column fractions containing product were combined and concentrated in vacuo. The final product was taken up in methanol, treated with hydrochloric acid (1.0 M/Et2O, 1.0 equivalent) and re-evaporated to dryness, then washed with ethyl ether, filtered, and dried to give 0.259 g of the hydrochloride salt of Compound 34 (mp 105.0–115.0° C., M+. 427).

A portion of the free base of Compound 35A (0.030 g, 0.084 mmole) was taken up in 1 mL DMF with bromoacetonitrile (0.009 mL, 0.126 mmole) and sodium carbonate (0.015 g, 0.141 mmole) and stirred at room temperature for 3 hours, then purified by flash chromatography on silica gel (1–10% [1:9 ammonium hydroxide/methanol]/dichloromethane). The column fractions containing product were combined and concentrated in vacuo. The final product was taken up in methanol, treated with hydrochloric acid (1.0 M/Et$_2$O, 1.0 equivalent), and re-evaporated to dryness, then washed with ethyl ether, filtered, and dried to give 0.006 g of the hydrochloride salt of Compound 35B (M+. 395).

Example 35

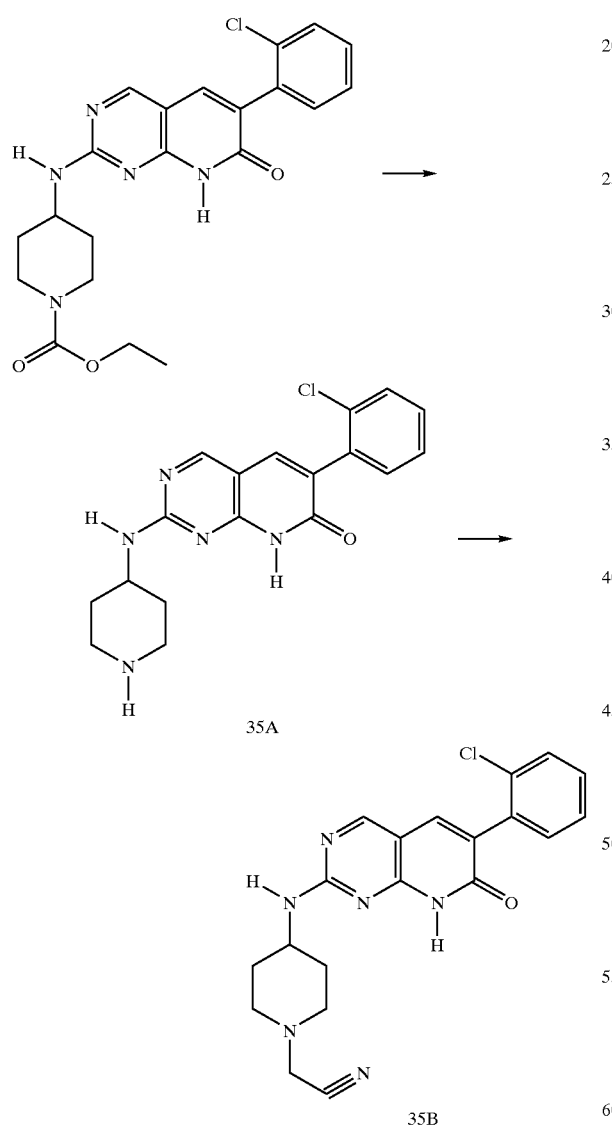

35A

35B

The ethyl carbamate was made from the corresponding benzyl sulfone in the manner already described, and cleaved to the piperidine intermediate 35A (mp>300.0) with iodotrimethylsilane.

Example 36

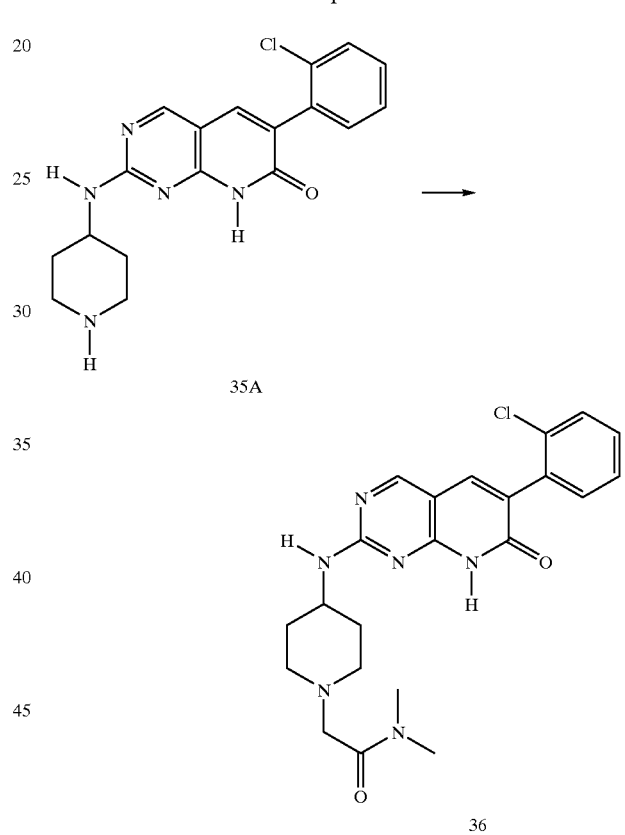

35A

36

A portion of the free base of Compound 35A (0.050 g, 0.141 mmole) was taken up in 1 mL DMF with 2-chloro-N,N-dimethylacetamide (0.026 g, 0.211 mmole) and N,N-diisopropylethylamine (0.037 mL, 0.211 mmole) and stirred at 60° C. for 3 hours and at 120° C. for 2 hours, then purified by flash chromatography on silica gel (3–20% [1:9 ammonium hydroxide/methanol]/dichloromethane). The column fractions containing product were combined and concentrated in vacuo. The final product was taken up in methanol, treated with hydrochloric acid (1.0 M/Et$_2$O, 1.0 equivalent), and re-evaporated to dryness, then washed with ethyl ether, filtered, and dried to give 0.006 g of the hydrochloride salt of Compound 36 (mp 103.0–120.0° C.).

Example 37

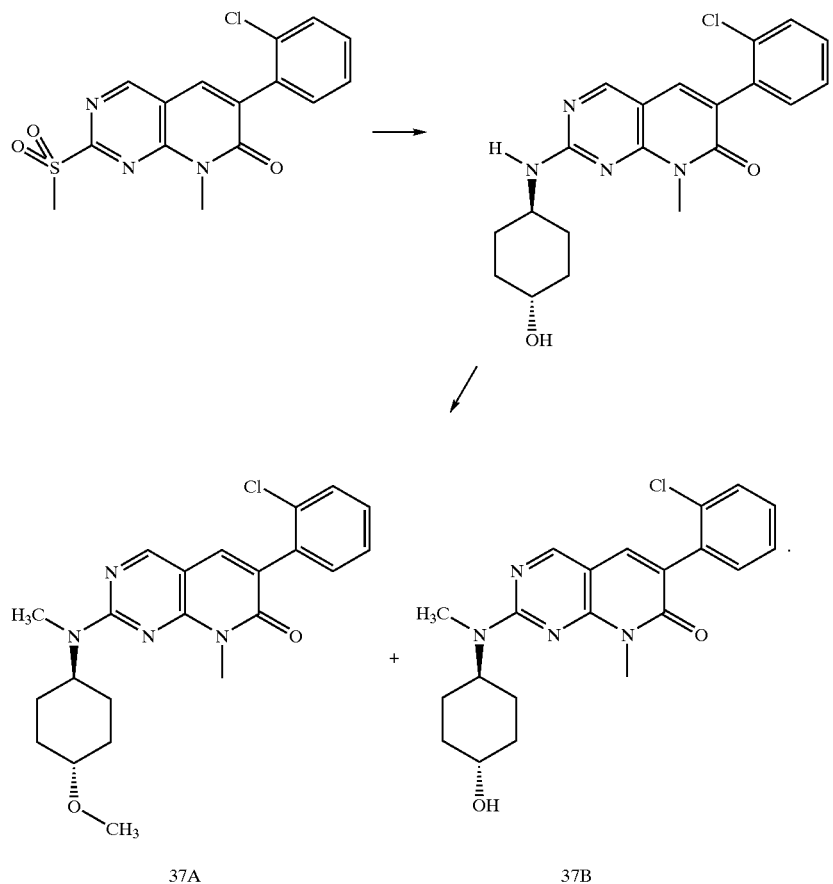

Compound 11 was taken up in 5 mL tetrahydrofuran with potassium tert-butoxide (0.95 g, 8.42 mmole) and methyl iodide (0.11 mL, 1.68 mmole). After stirring at rt for four hours, the reaction mixture was purified by flash chromatography (1–3% methanol/dichloromethane; 25–35% acetone/hexanes) to yield two products as shown above (i.e., compounds 37A and 37B). These were individually taken up in methanol, treated with hydrochloric acid (1.0 M/Et$_2$O, 1.0 equivalent), and re-evaporated to dryness, then washed with ethyl ether, filtered, and dried to give 0.157 g of the bis-methylated product (compound 37A) (mp 182.3–183.1° C.) and 0.069 g of the monomethylated product (compound 37B) (mp 218.2–218.5° C.).

Example 38

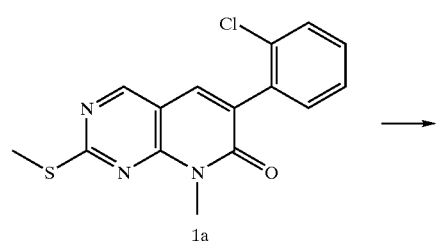

-continued

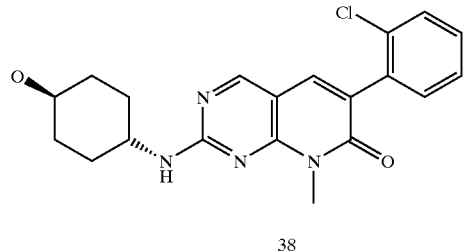

Sulfide 1a (317 mg, 1.0 mmole) was dissolved in NMP (0.3 mL) and to this solution was added trans 4-aminocyclohexanol (570 mg, 5 mmoles). The reaction was heated at 120° C. for 12 hours. Reaction cooled to room temperature and added to water (50 mL) and extracted with ethyl acetate. The organic layers were combined, washed 2 times with water, and concentrated in vacuo. The residue was purified by column chromatography on silica gel using 10:90 MeOH/CH$_2$Cl$_2$. The column fractions containing the desired product were combined and concentrated to yield a foam. The foam was suspended in MeOH followed by the addition of hydrochloric acid (1.0 M/Et$_2$O, 1.0 equivalent) to give the salt of Compound 38. The solvent was evaporated. The resulting solid was diluted with a mixture of Et$_2$O/MeOH, filtered and dried. Yield 282 mg. Mp 163.4–171.1° C. MS (M+H)$^+$385.

Example 39

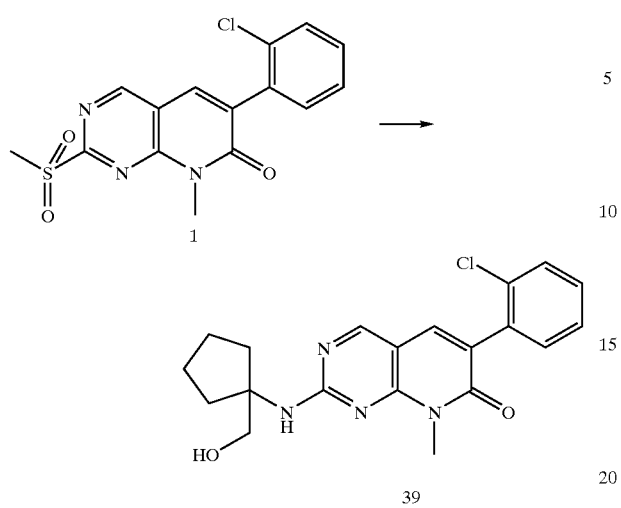

Sulfone 1 (350 mg, 1.0 mmole) was combined with 1-amino-1-cyclopentane methanol (345 mg, 3.0 mmoles) and NMP (0.3 mL) and stirred at 120° C. for 1 hour. Reaction mixture was added to water and extracted with ethyl acetate. The organic layers were combined, washed two times with water and concentrated under vacuum to give the crude product. The residue was purified by column chromatography on silica gel using 10:90 MeOH/CH$_2$Cl$_2$. The fractions containing the desired product were combined and evaporated in vacuo to give the desired product as a foam. The residue was suspended in MeOH, added hydrochloric acid (1.0 M/Et$_2$O, 1 equivalent), stirred for 20 minutes and concentrated under reduced pressure. The residue was stirred with a mixture of MeOH/Et$_2$O for one hour, and filtered to provide the product 39 as a white solid. Yield 263 mg. Mp 213.7–214.6° C. MS (M+H)$^+$385.

Example 40

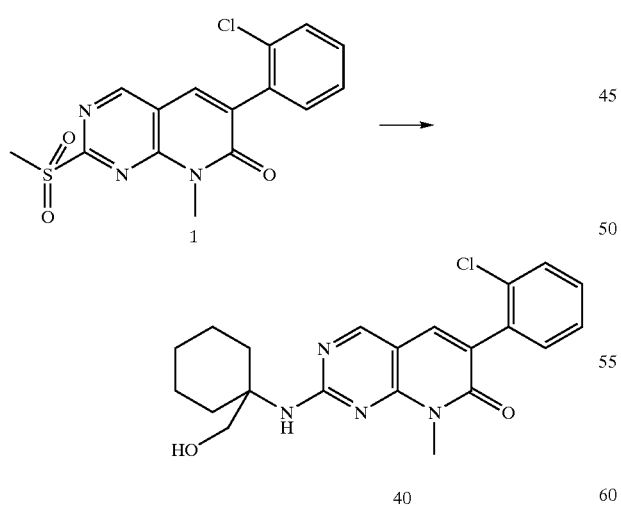

Sulfone 1 (350 mg, 1.0 mmole) was combined with 1-amino-1-cyclohexane methanol (387 mg, 3.0 mmoles) and NMP (0.3 mL) and stirred at 120° C. for 90 minutes. The reaction mixture was cooled to room temperature, added to water and extracted with ethyl acetate. The organic layers were combined, dried over MgSO$_4$ and concentrated under reduced pressure. The residue was purified by column chromatography on silica gel using 10:90 MeOH/CH$_2$Cl$_2$. The fractions containing the desired product were combined and evaporated under reduced pressure to give the desired product as a foam. The foam was suspended in MeOH and hydrochloric acid was added (1.0 M Et$_2$O, 1.0 equivalent). The mixture was stirred for 20 minutes, evaporated in vacuo, stirred with a mixture of MeOH/Et$_2$O for 2 hours, filtered, and dried to give product 40 as a white solid. Yield 242 mg. Mp 185–188.6° C. MS (M+H)$^+$399.

Example 41

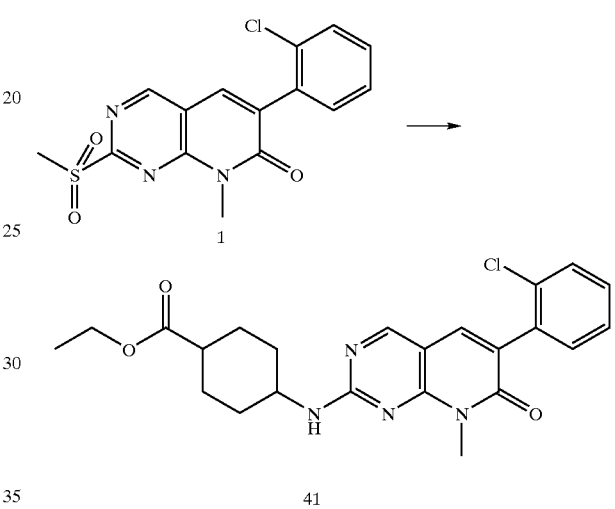

Sulfone 1 (350 mg, 1.0 mmole) was combined with cis/trans ethyl aminocyclohexanecaboxylate (520 mg, 3 mmoles), and stirred at 100° C. for 30 minutes. The resulting solution was cooled to room temperature and purified by column chromatography on silica gel using 65:35 hexane/acetone. The fractions containing the desired product were combined and concentrated to yield a foam. The residue was suspended in MeOH and a solution of hydrochloric acid (1.0 M/Et$_2$O 1.0 equivalent) was added. The resulting mixture was stirred for 30 minutes and the solution was evaporated. The resulting residue was stirred with a mixture of MeOH/Et$_2$O, for one hour, and filtered to give product 41 as a white solid. Yield 414 mg. Mp 192.1–198.3° C. MS (M+H)$^+$441.

Example 42

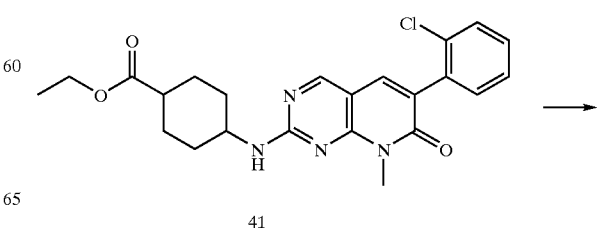

119

-continued

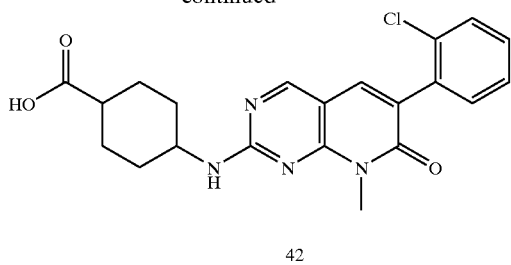

42

To a solution of compound 41 (300 mg, 0.67 mmole) in EtOH was added a concentrated aqueous hydrochloric acid solution (3.0 mL). The resulting solution was refluxed for 24 hours. Additional hydrochloric acid was added (1.0 mL) and the solution was refluxed for additional 24 hours. Reaction mixture was evaporated to dryness under reduced pressure, and dried under high vacuum to give the hydrochloride salt of Compound 42 as a white solid. Yield: 225 mg. Mp:263.6–264.2° C. MS: (M+H)$^+$413.

Example 43

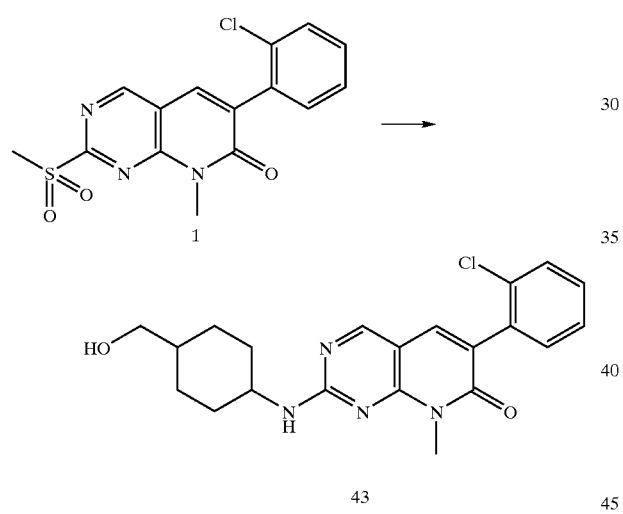

Sulfone 1 (350 mg, 1.0 mmole) was combined with 4-aminocyclohexylmethanol (1:1 cis/trans) (Chem.Ber:96;1963;2377–2386) (400 mg, 3.3 mmoles) and NMP (0.4ml) and stirred at 100° C. for one hour. The reaction mixture was cooled to room temperature, added to water, and extracted with ethyl acetate. The organic layer were combined, washed five times with water, dried over MgSO$_4$ and concentrated to give the crude product as an oil. The residue was purified by column chromatography on silica gel using 70:30 hexane/acetone. The fractions containing the desired product were combined and concentrated under reduced pressure to give the product as a foam. This material was suspended in MeOH and acidified with hydrochloric acid (1.0 M/Et$_2$O, 1 equivalent), stirred at room temperature for 30 minutes, and concentrated under reduced pressure. The resulting residue was stirred with a mixture of MeOH/Et$_2$O, for 2 hours, filtered, and dried to give the hydrochloride salt of Compound 43 as a white solid. Yield 335 mg. Mp 153.6–157° C. MS (M+H)$^+$399.

120

Example 44

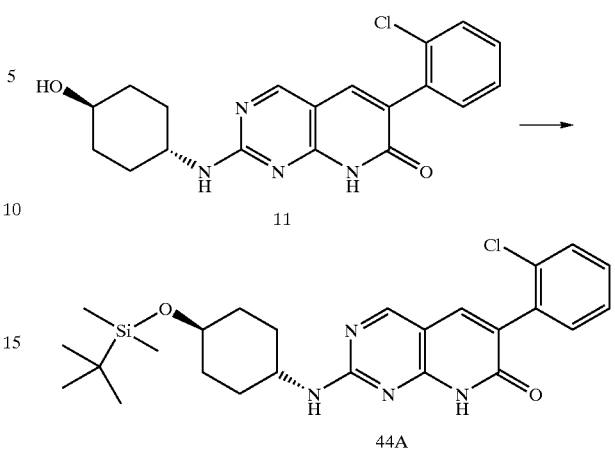

Step 1

To a suspension of Compound 11 (3.0 g, 8.1 mmoles) was in NMP (35 mL) was added tert-butyldimethylsilylchloride (1.7 g, 11.3 mmoles) and imidazole (1.2 g, 17.6 mmoles). The reaction mixture was stirred at 50° C. for 12 hours, cooled to room temperature and added to water (150–200 mL). The mixture was stirred for an hour, and filtered to give Compound 44A as a white solid. Yield 3.71. Mp 289.9–291.4° C. MS (M+H)$^+$485.

Step 2: Alkylation

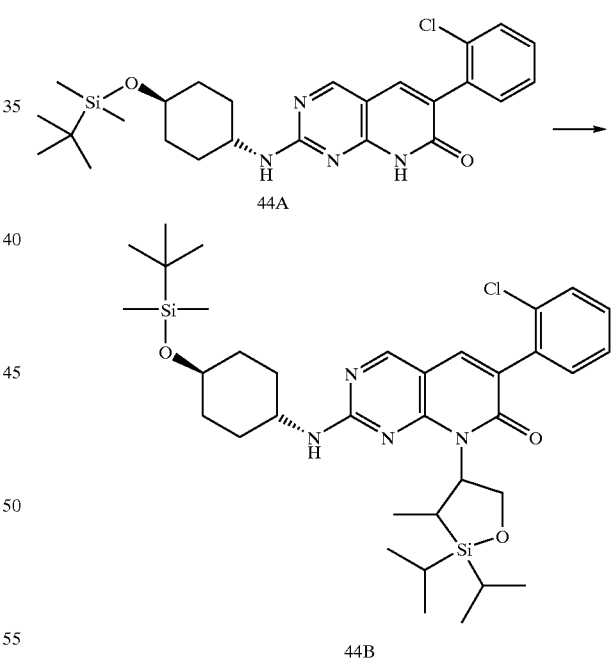

To a suspension of the silyl protected alcohol 44A (483 mg, 1.0 mmole) in NMP was added sodium hydride (44 mg, 1.1 mmole (60% oil dispersion). The reaction mixture was stirred for 25 minutes, after which 2-(iodoethoxy)tri-isopropylsilane (328 mg, 1.0 mmole) was added, and the resulting mixture was stirred at room temperature for 4 hours. The reaction mixture was added to water and extracted with ethyl acetate. The organic layers were combined, washed 5 times with water, dried over MgSO$_4$, and concentrated to give the silyl protected intermediate 44B as an oil. The residue was purified by column chromatography on silica gel using 25:75 acetone/hexane to give the product 44B as an oil. Yield 650 mg. MS (M+H)$^+$685.

Step 3: Deprotection

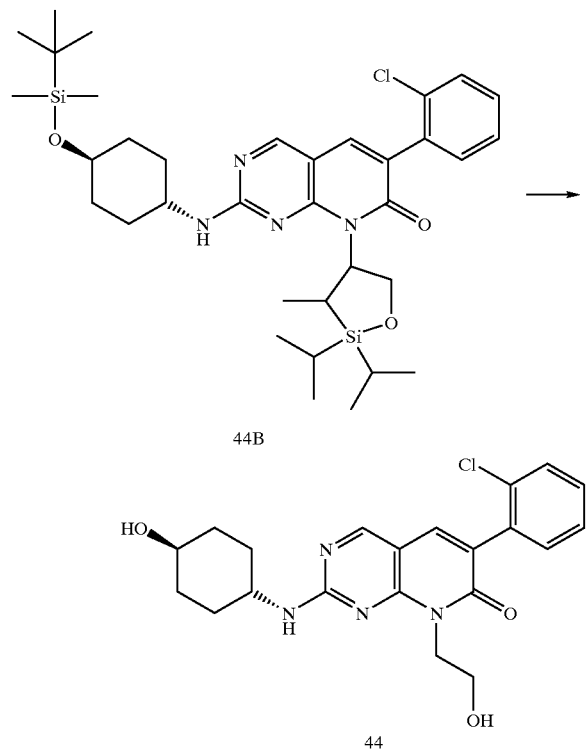

44B

44

To a solution of Compound 44B (650 mg, 0.94 mmole) in THF (15 mL) was added tetrabutylammonium fluoride (1.0 M in THF, 1.1 equivalents). The resulting solution was stirred at room temperature for 12 hours, added to water and extracted with ethyl acetate. The organic layers were combined, dried over MgSO$_4$ and concentrated to give the product as an oil. The residue was purified by column chromatography on silica gel using 90:10 CH$_2$Cl$_2$/MeOH to give product 44 as an oil. This was suspended in MeOH and acidified with hydrochloric acid (1.0 M/Et$_2$O, 1 equivalent), stirred for 20 minutes, concentrated, and again diluted with a mixture of Et$_2$O/MeOH and stirred for 2 hours. The solution was filtered to give the hydrochloride salt of Compound 44 as a white solid. Yield 270 mg. MP210.5–212.0° C. MS (M+H)$^+$415.

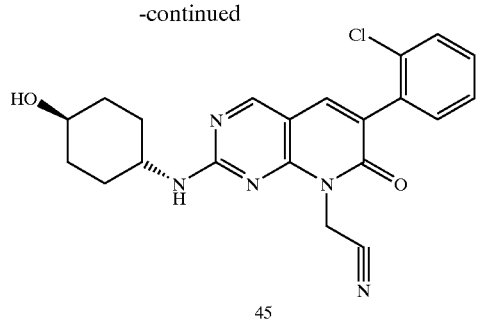

45

Step 1: Alkylation

To a solution of the silyl protected alcohol 44A (483 mg, 1.0 mmole) in NMP was added sodium hydride (44 mg, 1.1 mmole, 60% oil dispersion). The reaction mixture was stirred at room temperature for 25 minutes. To this solution was added iodoacetonitrile (0.167 mg, 1.0 mmole), and the resulting solution was stirred at room temperature for 4 hours. The reaction mixture was added to water and extracted with ethyl acetate. The organic layers were combined, washed 5 times with water, dried over MgSO$_4$, and concentrated to provide an oil. This residue was purified by column chromatography on silica gel with 25:75 acetone/hexane to give the product as a white solid. Yield 480 mg. Mp 193–195.8° C. MS (M+H)$^+$524

Step 2: Deprotection

To a solution of the product from Step 1 above (480 mg, 0.92 mmole) in THF was added tetabutylammonium fluoride (1.0 M/THF, 1.1 equivalent) and stirred at room temperature for 12 hours. The reaction mixture was added to water and extracted with ethyl acetate. The organic layers were combined, dried over MgSO$_4$, and concentrated to give the product as an oil. The residue was purified by column chromatography on silica gel using 90:10 CH$_2$Cl$_2$/MeOH to give the product 45 as a white solid. Yield 260 mg. Mp 245.8–246.8° C. MS (M+H)$^+$410.

To a suspension of the product 45 in MeOH, was added a solution of hydrochloric acid (1.0 M/Et$_2$O, 1 equivalent). The mixture was stirred at room temperature for 30 minutes and concentrated. The residue was stirred in a mixture of Et$_2$O/MeOH, for 2 hours, and filtered to give the hydrochloride salt of compound 45 as a white solid. Yield 255 mg. Mp 232.1–233.4° C. MS (M+H)$^+$ 410.

Example 45

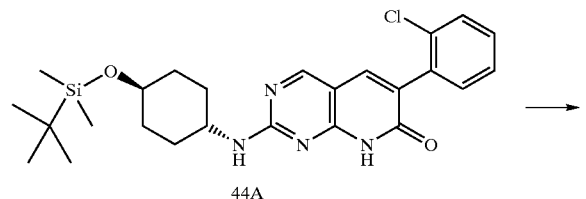

44A

Example 46

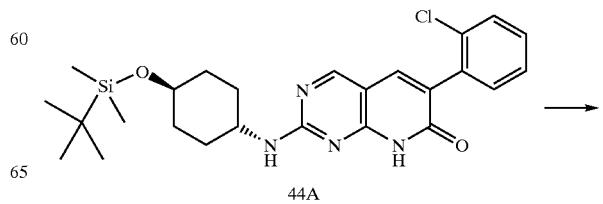

44A

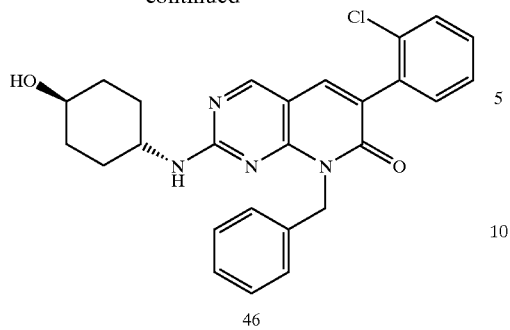

46

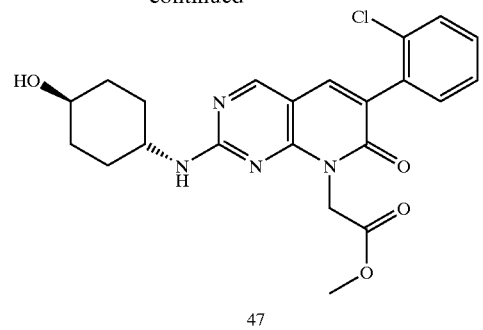

47

Step 1: Alkylation

To a suspension of the silyl protected alcohol 44A (483 mg, 1.0 mmole) in NMP was added sodium hydride (44 mg, 1.1 mmole, 60% oil dispersion), and the resulting solution was stirred at room temperature for 30 minutes. To this reaction mixture was added benzyl bromide (0.12 ml, 1.0 mmole), and stirred at room temperature for 12 hours, after which the reaction mixture was added to water and extracted with ethyl acetate. The organic layers were combined, washed five times with water, dried over MgSO$_4$, concentrated and purified by column chromatography on silica gel using 25:75 acetone/hexane to give the product as a white solid. Yield 502 mg. Mp 188.8–191.0° C. MS (M+H)$^+$ 575

Step 2: Deprotection

To a solution of the material from Step 1 above (480 mg, 0.84 mmole) in THF was added tetrabutylammonium fluoride (1.0 M/THF, 1.1 equivalent). The resulting mixture was stirred at room temperature for 12 hours, added to water and extracted with ethyl acetate. The organic layers were combined, dried over MgSO$_4$, concentrated and purified by column chromatography on silica gel using 10:90 MeOH/CH$_2$Cl$_2$ to give product 46 as a white solid. Yield 320 mg. Mp 119–131° C. MS (M+H)$^+$ 461.

To a solution of the material from above in MeOH was added hydrochloric acid (1.0 M/Et$_2$O, 1 equivalent). The resulting solution was stirred at room temperature for 20 minutes and concentrated to give a foam. The foam was dissolved in a mixture of Et$_2$O/MeOH and stirred for 2 hours and filtered to give the hydrochloride salt of Compound 46 as a white solid. Yield 305 mg. Mp 202–206° C. MS (M+H)$^+$ 461.

Example 47

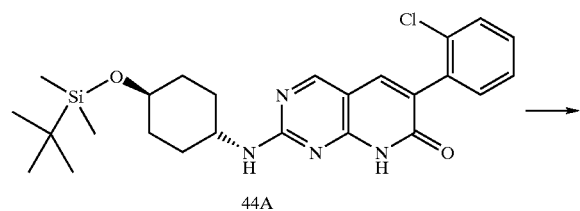

44A

Step 1: Alkylation

To a suspension of the silyl protected alcohol 44A in NMP was added sodium hydride (44 mg, 1.1 equivalent (60% oil dispersion)). The resulting solution was stirred at room temperature for 25 minutes. To this solution was added methyl bromoacetate (0.095 ml, 1.0 mmole) and stirred at room temperature for 12 hours. The reaction mixture was added to water and extracted with ethyl acetate. The organic layers were combined, washed five times with water, dried over MgSO$_4$, concentrated and purified by column chromatography on silica gel using 25:75 acetone/hexane to give the product as a white solid. Yield 480 mg. Mp 182–187° C. MS (M+H)$^+$=557.

Step 2: Deprotection

To a solution of the material from Step 1 above (480 mg, 0.86 mmole) in tetrahydrofuran (15 mL) was added tetrabutylammonium fluoride (1.0 M/THF, 1 equivalent). The resulting mixture was stirred at room temperature for 12 hour, added to water and extracted with ethyl acetate. The organic layers were combined, dried over MgSO$_4$, and concentrated to give the product 47 as a foam. Yield 225 mg. Mp 118–130° C. MS (M+H)$^+$ 443.

Example 48

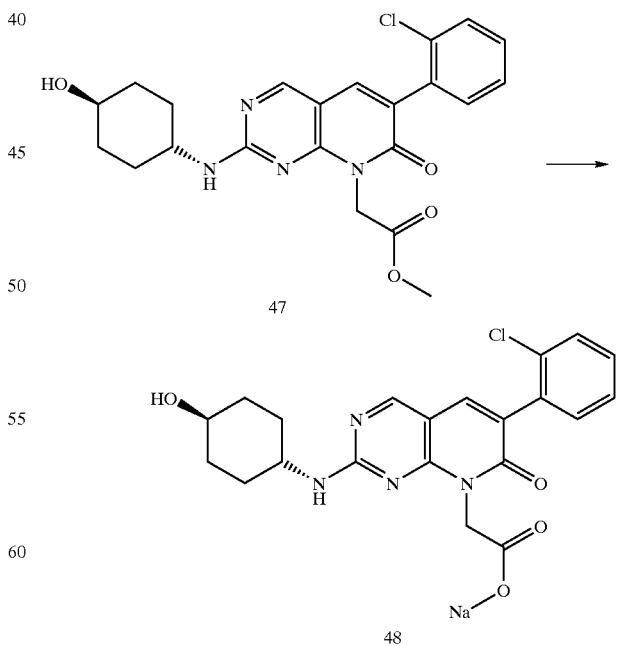

47

48

To a suspension of Compound 47 (210 mg, 0.475 mmole) in MeOH (4.0 mL) was added a solution of aqueous sodium hydroxide (0.477 mL of 1.0 N NaOH). The resulting mixture was stirred at room temperature for 5 days and evaporated to dryness. The residue was diluted with Et₂O, stirred for two hours, filtered, and dried to give the product 48 as a light yellow solid. Yield 205 mg. Mp 260–265° C. MS (M+H)⁺ 429.

Example 49

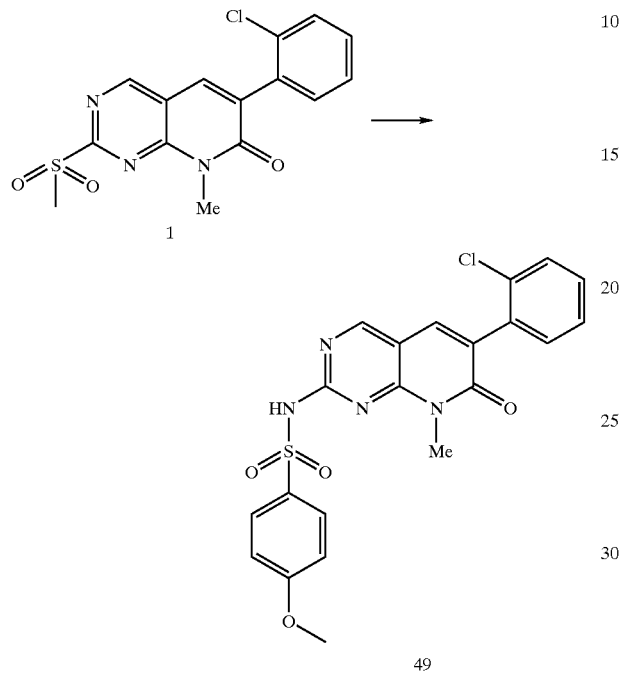

49

To a solution of 4-methoxybenzenesulfonamide (0.417 g, 2.23 mmol) in 3 mL of N-methylpyrrolidinone was added 60% sodium hydride (107 mg, 2.68 mmol) at room temperature. The mixture was stirred for 10 minutes. The sulfone 1 (189 mg) was then added, and the resulting mixture was stirred at 130° C. for 6 hours. The reaction mixture was cooled to room temperature and added to water (50 mL). The resulting solid was filtered, washed successively with water, ethyl acetate and methanol, and dried in vacuo to give product 49 (190 mg), mp>300° C.; ms 457 (M+H)⁺.

Example 50

6-(2-chlorophenyl)-2-(N-2-cyanoethylpiperidyl-4-amino)-pyrido[2,3-d]-pyrimidin-7-ol Step 1: Preparation of 4-trifluoroacetamido-1-benzylpiperidine

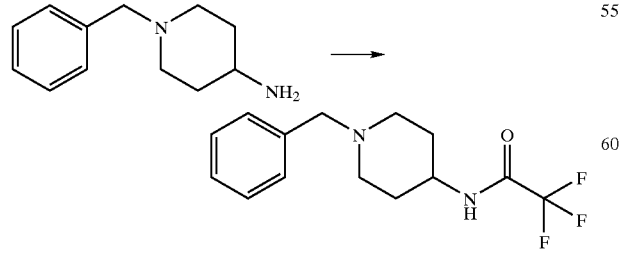

To a cooled (5° C.) solution of 25 g (131 mmol) of 4-amino-1-benzylpiperidine and 15.36 g (152 mmol) of triethylamine in 130 mL of dichloromethane was added 28 g (18.8 mL, 133 mmol) of trifluoroacetic anhydride dropwise over a period of 30 to 45 min. at such a rate that the reaction temperature was kept between 5° C. to 10° C. After addition was completed, the reaction mixture was stirred for another 15 min. The solvent and volatile were removed under reduced pressure. The residue was dissolved in 100 mL of ethyl acetate and was then diluted with 100 mL of hexane. The solution was filtered over a cake of silica gel (50 g) and was washed with 1 liter of 50% ethyl acetate in hexane. The filtrate was concentrated under reduced pressure to give 37 g (quantitative yield) of the desired 4-trifluoroacetamido-1-benzylpiperidine, (light yellow solid).

Step 2: Preparation of 4-trifluoroacetamidopiperidine

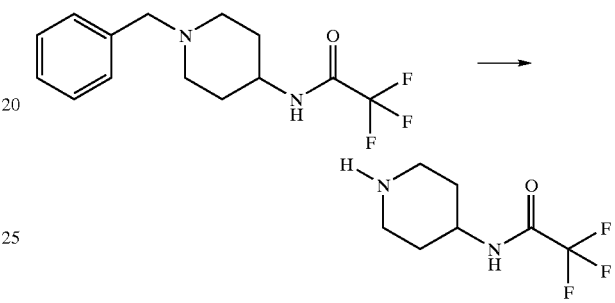

A 500 mL, three-necked round-bottomed flask under nitrogen was charged with 4 g of 10% Palladium on Carbon, and 100 mL of methanol. The suspension was cooled to 5° C. and 10 g of ammonium formate was added in one batch (evolution of gas was observed). A solution of 10 g (35 mmol) of the 4-trifluoroacetamido-1-benzylpiperidine in 100 mL of methanol was then added dropwise gradually. The resulting reaction mixture was refluxed for 2.5 hr. and then at room temperature overnight. The catalyst was filtered off through Celite under a blanket of nitrogen and washed with ethanol. The filtrate was concentrated under reduced pressure to give 6.9 g (quantitative yield) of a light yellow solid of the title compound.

Step 3: Preparation of N-(2-cyanoethyl)-4-aminopiperidine

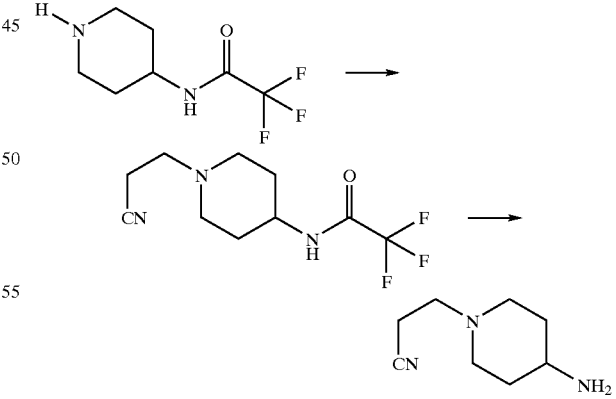

A mixture of 3 g (15.3 mmol) of 4-trifluoroacetamidopiperidine, 3 g (4.25 mL, 30.6 mmol) of triethylamine, 3 mL (45.9 mmol) of acrylonitrile in 10 mL of THF was stirred at room temperature for 17 hr. The solvent and volatile were evaporated under reduced pressure. The residue was dissolved in 20 mL of methanol and 4 mL of 30% NH₄OH and the solution was refluxed for 5 hr.

The solvent was evaporated under reduced pressure and the residue was purified by column chromatography on silica gel eluting first with 500 mL of dichloromethane, then 500 mL of 0.5% methanol/dichloromethane, followed by 1000 mL of 9:1:0.1 dichloromethane/methanol/ammonium hydroxide to give 0.7 g (30% yield) of the N-(2-cyanoethyl)-4-aminopiperidine.

Step 4: Preparation of 6-(2-chlorophenyl)-2-(N-2-cyanoethylpiperidyl-4-amino)-pyrido[2,3-d]-pyrimidin-7-ol

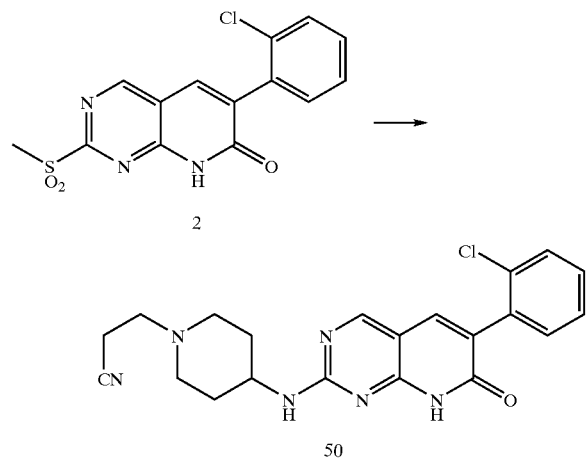

A mixture of 0.2 g (0.58 mmol) of sulfone 2,6-(2-chlorophenyl)-2-methanesulfonyl-pyrido[2,3-d]pyrimidin-7-ol, 0.18 g (1.16 mmol) of N-(2-cyanoethyl)-4-aminopiperidine in 0.5 mL of NMP was heated in a 60° C. oil bath for 2.5 hr., cooled and diluted with 5 mL of dichloromethane. The solution was purified by column chromatography on 40 g of silica gel using 200 mL of dichloromethane to elute out the NMP, then followed with 5% methanol/dichloromethane to elute out the product. The product containing fractions were combined and concentrated. Ether was added to the product and after trituration, the solid was filtered, washed with ether and dried, affording 165 mg (70% yield) of the desired product. About 50 mg of this solid was dissolved in 3 mL of dichloromethane. 1 mL of 1 M HCl/ether solution was added and the mixture was stirred for 1 hr at room temperature. The solvent was evaporated under reduced pressure to afford 54 mg of compound 50. (mass spec. MH⁺=408, mpt. 217.5–219.5° C.).

Example 51

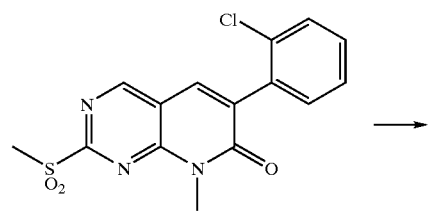

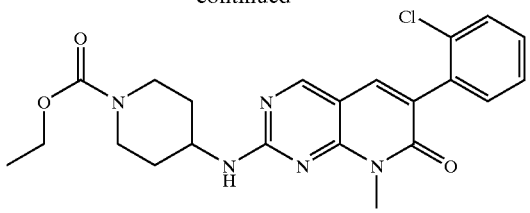

A mixture of 2 g (5.8 mmol) of 6-(2-chlorophenyl)-2-methanesulfonyl-pyrido[2,3-d]pyrimidin-7-ol, 1.97 g (11.4 mmol) of ethyl 4-amino-1-piperidine carboxylate in 2 mL of NMP was heated in a 60° C. oil bath for 1.5 hr. The suspension soon turned into a clear brown solution. The mixture was partitioned between 150 mL of water and 150 mL of ethyl acetate. The aqueous layer was extracted once more with 150 mL of ethyl acetate. The combined ethyl acetate solution was washed with water, 2×150 mL, then brine and dried, filtered and the filtrate was concentrated under reduced pressure. After trituration in ether and removal of solvent under reduced pressure, 2.5 g (quantitative yield) of compound 51 was isolated. About 0.13 g of this material was dissolved in 1.5 mL of ethyl acetate and 1 mL of 1 M HCl in ether was added. The suspension was stirred at room temperature for 1 hr., diluted with ether, filtered, and washed with ether affording 0.12 g of the hydrochloric salt of compound 51. (Mass spec. M⁺=441.9, mpt. 190–191° C.).

Example 52

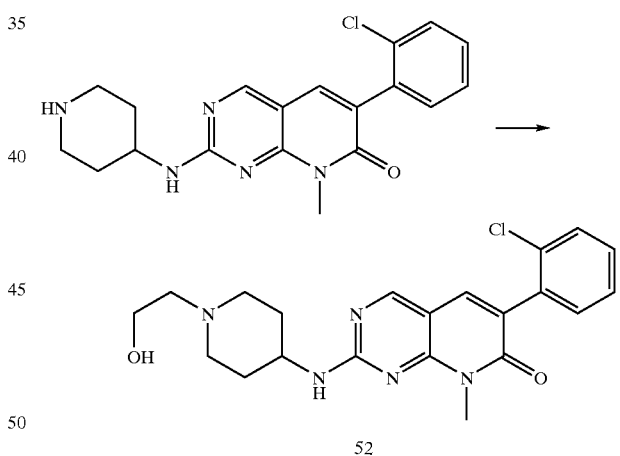

A mixture of 0.3 g (0.8 mmol) of 6-(2-chloropheny)-2-(piperidyl-4-amino)-pyrido[2,3-d]pyrimidin-7-ol, 0.3 g (2.4 mmol) of 2-bromoethanol, 0.22 mL (1.6 mmol) of triethylamine, 1.5 mL of NMP and 10 mL of toluene was stirred in a 100° C. oil bath for 2.5 hr. The mixture was diluted with 75 mL of ethyl acetate and 100 mL of water. Layers were separated and the aqueous layer was extracted again with ethyl acetate (2×75 mL). The combined organic solution was then washed with brine, filtered and concentrated under reduced pressure. The residue was dissolved in a small amount of methanol and was purified by column chromatography on 40 g of silica gel using 8.5:1.5:0.2 ethyl acetate/methanol/ammonium hydroxide to give 0.115 g of white solid, (35% yield). This was dissolved in 2 mL of EtOAc and 2 mL of 1 M HCl in ether was added. The suspension was stirred at room temperature for 30 min. Filtered and dried, affording 0.13 g of compound 52. (Mass spec. MH+=414, mpt. 265.9–266.6° C.).

Example 53

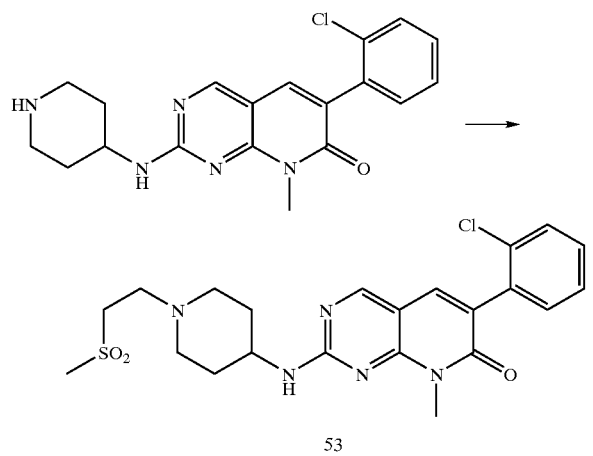

A mixture of 0.2 g (0.54 mmol) of 6-(2-chlorophenyl)-2-(piperidyl-4-amino)-pyrido[2,3-d]pyrimidin-7-ol, 0.11 g (1.6 mmol) of methyl vinyl sulfone, 0.5 mL of triethylamine in 5 mL of THF was stirred at room temperature for 17 hrs. Triethylamine and THF were evaporated under reduced pressure. The residue was partitioned between 75 mL of water and 100 mL of ethyl acetate. After layers were separated, the aqueous layer was extracted again with 75 mL of ethyl acetate. The combined organic solution was washed with water, brine, dried, and filtered. The filtrate was concentrated under reduced pressure. The crude product was purified by column chromatography on 40 g of silica gel using 90:10:5 dichloromethane/ethyl acetate/ammonium hydroxide. The recovered product was dissolved in 1.5 mL of ethyl acetate and 2 mL of 1 M HCl in ether was added. The suspension was stirred for 1 hr., filtered and washed with ether affording 165 mg of the hydrochloride salt of compound 53 (HCl salt). (Mass spec. MH$^+$=476, mpt.204.6–205.6° C.).

Example 54

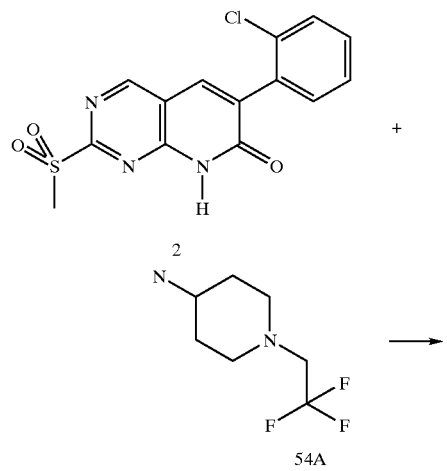

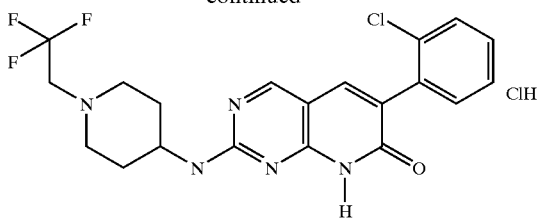

Preparation of 4-amino-1-(2,2,2-trifluoroethyl)-piperidine, 54A

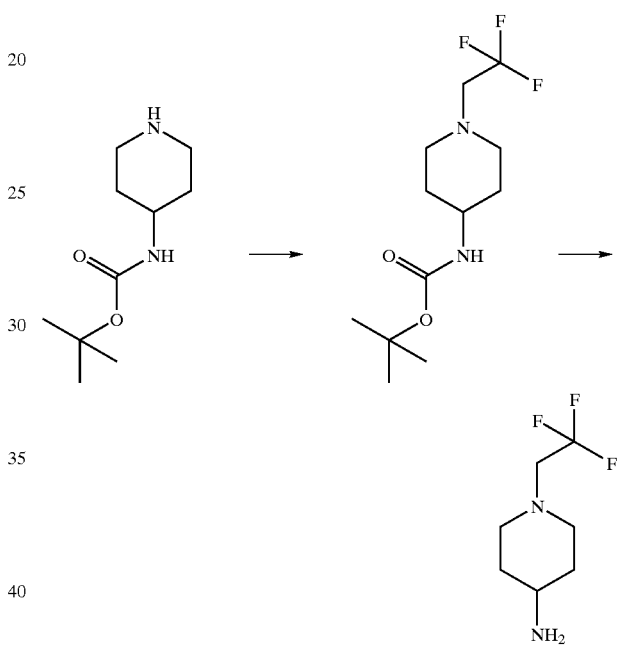

A solution of 4-N-BOC-aminopiperidine (commercially available) (5 g, 24.96 mmol), 2,2,2-trifluoroethyl trichloromethane sulfonate (7.03 g, 1 eq), and potassium carbonate (4.1 g, 1.2 eq) in acetone (80 mL) was stirred at reflux for 17 hours. The solvent was removed under reduced pressure at 40° C. and ethyl acetate (250 mL) and water (150 mL) were added to the residue. The organic layer was separated, washed consecutively with water (1×150 mL) and brine (1×200 mL), dried over magnesium sulfate, filtered, and concentrated to provide a dark colored solid. Purification by chromatography on silica gel using 15% ethyl acetate in hexanes as the eluent gave 4-N-BOC-amino-1-(2,2,2-trifluoroethyl)-piperidine (4.45 g) as an off-white powder, m.p. 99.2–99.8° C., (M+H)+=283. This amine was then taken up in dioxane (80 mL) and HCl gas was bubbled through the solution for 10 minutes (a precipitate formed almost immediately). The reaction vessel was capped tightly, stirred for 1.5 hours and concentrated to provide a white powder. This HCl salt was dissolved in 42 mL of 0.5 M sodium methoxide in methanol solution and stirred at room temperature for 3 hours. The solution was then filtered through a medium frit and the filtrate was concentrated. The residue was diluted with ethyl acetate (100 mL) and the solids were crushed up and the mixture was filtered. Concentration of the filtrate afforded 4-amino-1-(2,2,2-trifluoroethyl)-piperidine, 54A, as a dark colored oil (1.0 g), (M+H)+=183.

Sulfone 2 (200 mg, 0.614 mmol), compound 54A (224 mg, 2 eq) and N-methyl pyrrolidinone (0.3 mL) were mixed in a 10 mL flask and stirred at 110° C. for 10 minutes. The reaction was cooled and then methanol (10 mL) was added and the solid was crushed up and filtered and collected to give an off-white powder. The free amine was dried under high vacuum at 56° C. for 2 hours, m.p.=267.4–267.6° C., (M+H)+=438. This free amine was then take up in dioxane (20 mL) at room temperature and with stirring was added a solution of 1 M HCl in diethyl ether (0.5 mL, 1.3 eq). The resulting mixture was stirred at room temperature for 1 hour, filtered and dried under high vacuum at 56° C. for 8 hours to yield Compound 54 as an off-white powder. M.p.= 260.0–265.0° C., (M+H)+=438 (free amine).

Example 55

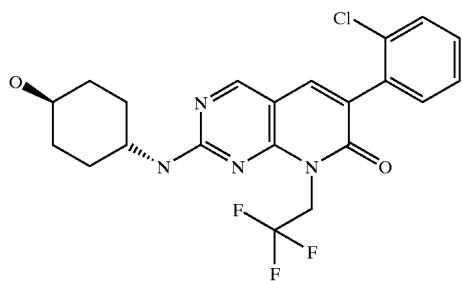

Preparation of 55B

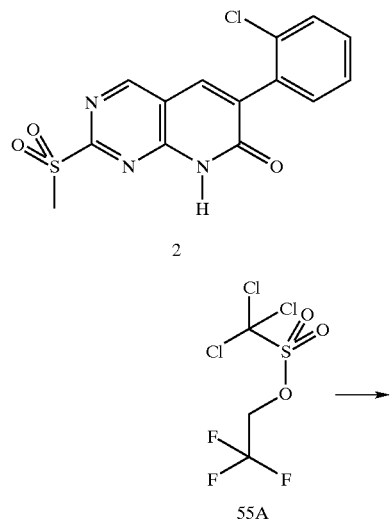

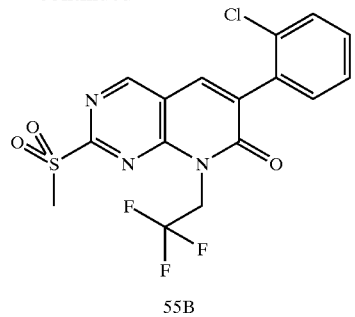

55B

To a 0° C. solution of Sulfone 2 (1.485 g, 4.56 mmol) in dimethylformamide (25 mL) was added 60% sodium hydride (200 mg, 1.1 eq). The resulting mixture was stirred vigorously at 0° C. for 15 minutes, afterwhich 2,2,2,-trifluoroethyltrichloromethane sulfonate 55A (4.2 g, 3.3 eq) in dimethyformamide (15 mL) was added. The resulting mixture was stirred from 0° C. to room temperature for 4 days. The reaction mixture was diluted with ethyl acetate (300 mL) and water (100 mL). The organic layer was separated and washed with water (100 mL) and brine (2×100 mL), dried over magnesium sulfate, filtered and concentrated. The residue was washed several times with ether/hexanes, decanting the supernatant each time. Concentrating and drying the residue under high vacuum afforded compound 55B as a semi-solid in quantitative yield.

Preparation of 55

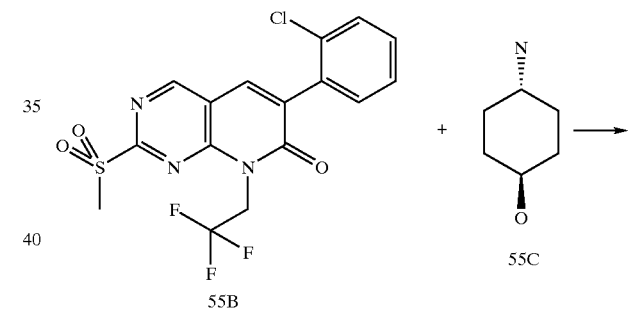

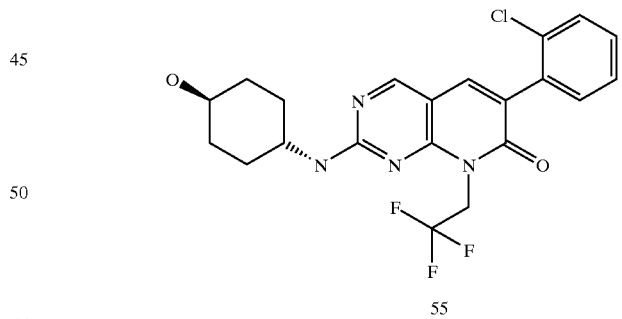

Compound 55B (0.9 g, 2.15 mmol), compound 55C (743 mg, 3 eq) and N-methyl pyrolidinone were added to a 10 mL flask and stirred at 110° C. for 25 minutes. The reaction mixture was cooled, diluted with 10 mL of methanol, and concentrated. The residue was dissolved in ethyl acetate (35 mL) and washed with water (7×25 mL) and brine (1×25 mL). The organic layer was dried over magnesium sulfate, filtered and concentrated. Purification by Preparative Thin Layer Chromatography on 3 (20×40 cm, 1000 μM) plates with 5% methanol in dichloromethane as the eluent gave 55 as an off-white powder, m.p.=227.2–230.4, (M+H)+=453.

Example 56

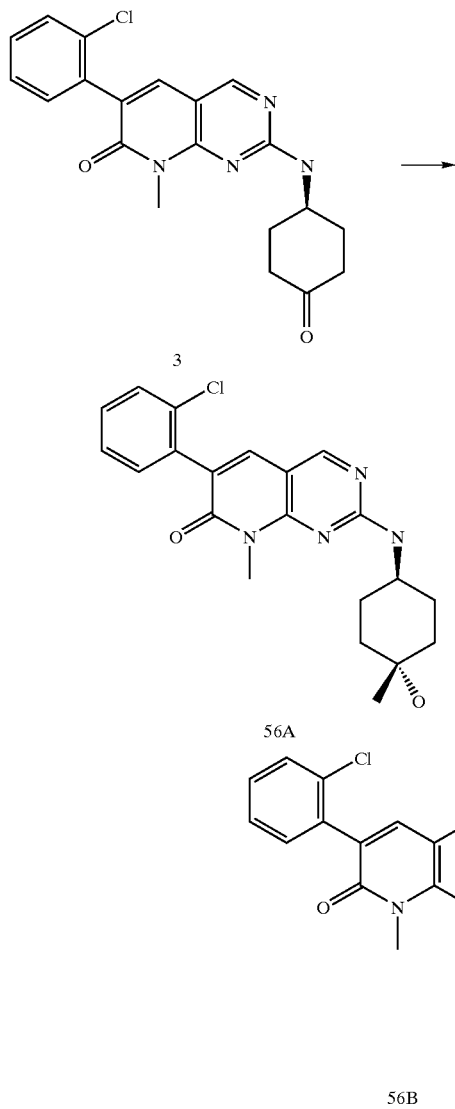

Compound 3 (0.13 g, 0.34 mmol) was dissolved in dry tetrahydrofuran and stirred in an ice bath. Methyl magensium chloride (3 M solution in THF, 0.25 mL, 0.75 mmol) was added dropwise. The reaction was stirred at room temperature for 1 hour. The reaction was recooled in an ice bath and a saturated solution of ammonium chloride (2 mL) was added, followed by water. The reaction mixture was extracted two times with ethyl acetate and the combined ethyl acetate layers were dried over sodium sulfate. After concentration, the reaction mixture was purified and the isomers separated by chromatography on silica gel in 5% methanol/dichloromethane. The less polar product fraction was assigned as the trans-isomer (i.e., compound 56A) and was found to be pure by reverse phase HPLC. The more polar product fraction was assigned as the cis-isomer (i.e., compound 56B) and was found to have a cis:trans ratio of 98:2 by reverse phase HPLC. Each product fraction was separately dissolved in dichloromethane, treated with 1 equivalent of 1 M HCl in ether, and evaporated to a foamy residue. 13 mg of the trans-isomer, HCl salt of compound 56A (mass spec. MH$^+$=399, melting pt.=155–168° C.), and 26 mg of the cis-isomer, HCl salt of compound 56B (mass spec. MH$^+$=399, melting pt.=156°–169° C.) were obtained.

Example 57

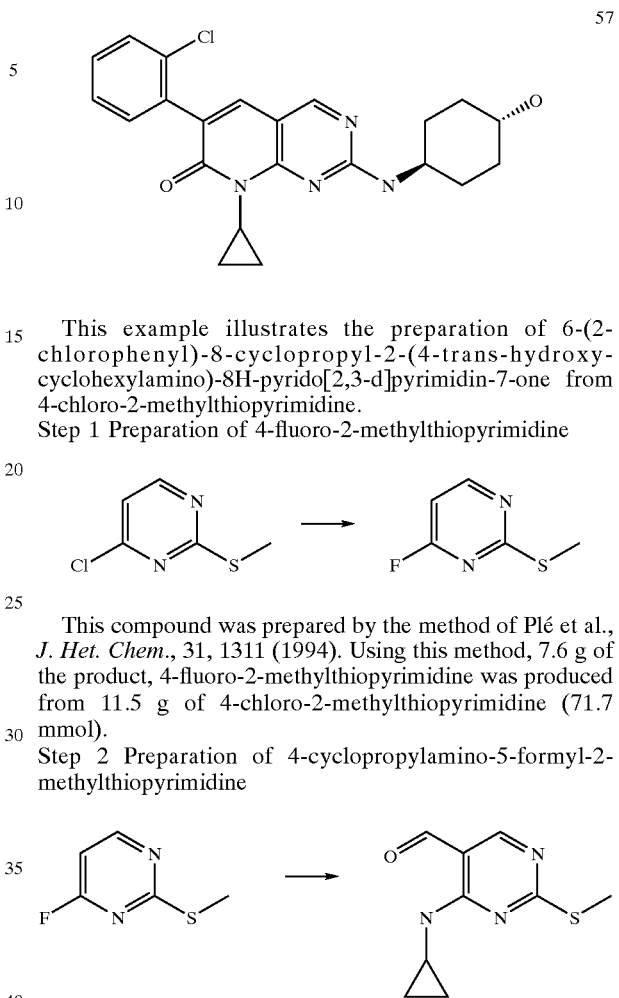

This example illustrates the preparation of 6-(2-chlorophenyl)-8-cyclopropyl-2-(4-trans-hydroxy-cyclohexylamino)-8H-pyrido[2,3-d]pyrimidin-7-one from 4-chloro-2-methylthiopyrimidine.

Step 1 Preparation of 4-fluoro-2-methylthiopyrimidine

This compound was prepared by the method of Plé et al., J. Het. Chem., 31, 1311 (1994). Using this method, 7.6 g of the product, 4-fluoro-2-methylthiopyrimidine was produced from 11.5 g of 4-chloro-2-methylthiopyrimidine (71.7 mmol).

Step 2 Preparation of 4-cyclopropylamino-5-formyl-2-methylthiopyrimidine

Butyl lithium (10.2 mL, 2.5 M solution in hexanes) was added to 55 mL of THF (distilled from sodium/benzophenone) at −30° C. The butyl lithium solution was moved to an ice bath and diisopropylamine (4 mL, 28.9 mmol) was added dropwise. The reaction was stirred for 30 minutes and then cooled to approximately −80° C. in a dry ice/ether bath. A solution of 4-fluoro-2-methylthiopyrimidine (1.6 g, 11.1 mmol) in 4 mL THF was added dropwise and the resulting reaction mixture was stirred for 2 hours. Ethyl formate (2.1 mL, 22.2 mmol, treated with K$_2$CO$_3$ and distilled from P$_2$O$_5$) was then added dropwise and the resulting reaction mixture was stirred for another 1 hour. Additional 0.1 eq of ethyl formate was added and the reaction mixture was stirred for another 1 hour. Cyclopropylamine (1.5 mL, 22.2 mmol, Aldrich Chemical) and water were added and the reaction stirred for 90 minutes. Approximately 50 mL of 1 M HCl/ether was added and the reaction mixture was stirred to room temperature. More water was added and the THF was removed by evaporation. The residual material was extracted twice with dichloromethane. The combined dichloromethane layers were dried over sodium sulfate and evaporated to a syrup. This residue was purified by chromatography on silica gel in 7% methanol/dichloromethane.

Fractions containing imine were combined, concentrated, treated with 10 equivalents of 3 M aqueous HCl in THF for 3 hours, neutralized with sodium bicarbonate solution, concentrated and extracted with dichloromethane. The dichloromethane was washed with water and bicarbonate solution, dried over sodium sulfate and concentrated. The resulting material was combined with the previously purified material to yield 1.8 g of 4-cyclopropylamino-5-formyl-2-methylthiopyrimidine.

Step 3

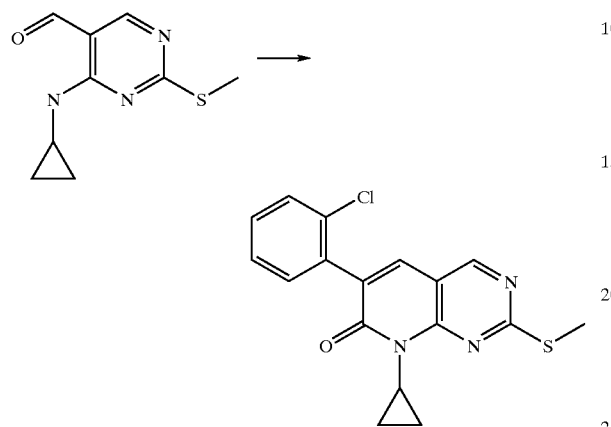

4-Cyclopropylamino-5-formyl-2-methylthiopyrimidine (1.8 g, 8.6 mmol) was dissolved in 17 mL of 1-methyl-2-pyrrolidinone. Ethyl 2-chlorophenylacetate (2.1 g, 10.75 mmol) and potassium carbonate were added and the mixture was stirred overnight at 95° C. A total of 0.8 g more ester was added and the reaction was stirred overnight again. The reaction mixture was partitioned into 120 mL ethyl acetate and 100 mL water. After separation, the aqueous layer was extracted one time more with ethyl acetate. The combined ethyl acetate layers were washed with brine, dried over sodium sulfate, concentrated and purified by chromatography on silica gel 60 with 20–25% ethyl acetate/hexanes to yield 1.78 g of the product.

Step 4

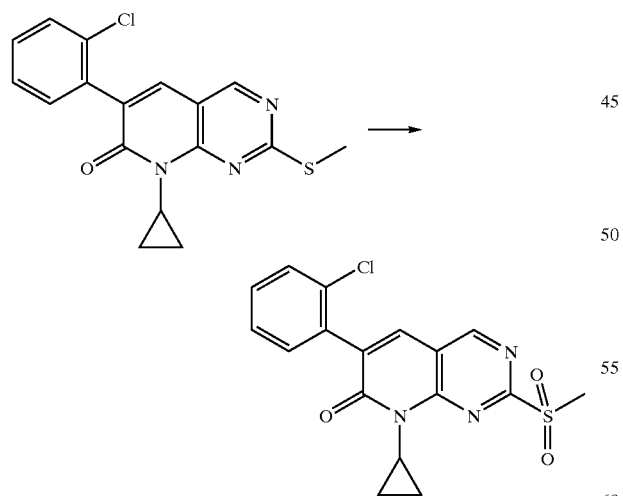

The product of Step 3 (1.66 g, 4.82 mmol) was dissolved in 20 mL THF and cooled in an ice bath. A solution of Oxone® (5.9 g, 9.64 mmol) in water was added dropwise. The ice bath was removed and the reaction was stirred overnight. The reaction was filtered, approximately 40 mL of water was added and the mixture was stirred for 30 minutes. Solids were filtered off, resuspended in water and stirred for another 60 minutes. The mixture was filtered, rinsed with water and 20% ether/hexanes and dried to yield 1.08 g of the product.

Step 5

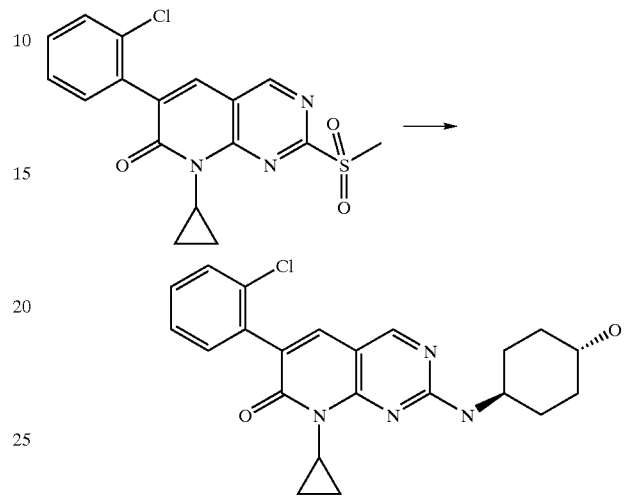

The product of Step 4 (0.35 g, 0.93 mmol), trans-4-aminocyclohexanol (0.322 g, 2.79 mmol, TCI America) and 0.5 mL 1-methyl-2-pyrrolidinone were combined and heated to 90° C. After one hour, the reaction was cooled to room temperature, and ethyl acetate and water were added. The layers were separated and the aqueous layer was extracted with ethyl acetate again. The combined organic layers were washed with brine, dried over sodium sulfate, concentrated and purified on silica gel 60 in 5% methanol/dichloromethane. After evaporation of the product fractions, the residue was redissolved in methanol/dichloromethane and treated with one equivalent of 1 M HCl/ether. The solution was evaporated and the residue was triturated in 20% ether/hexanes and dried to yield 366 mg of the product (HCl salt of compound 57). Mass spec. MH$^+$=411, melting pt.=241.7–242.3° C.

Example 58

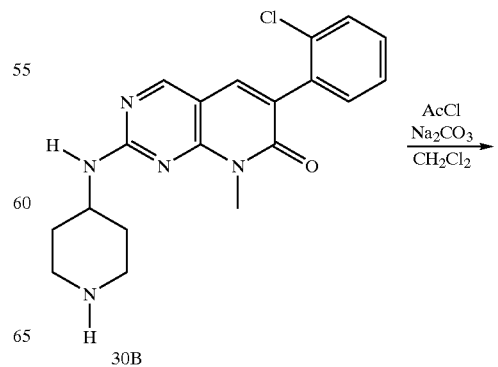

30B

-continued

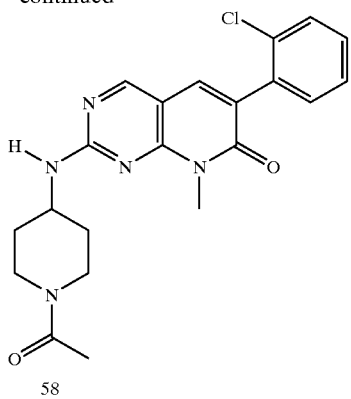

58

Compound 30B (0.300 g, 0.811 mmole), acetyl chloride (0.061 mL, 0.852 mmole), and sodium carbonate (0.090 g, 0.852 mmole) were taken up in 5 mL of dichloromethane and stirred overnight at room temperature. After 18 hours, the reaction was purified by flash chromatography (3–5% (1:9 ammonium hydroxide/methanol)/dichloromethane), and the column fractions containing product 58 were combined and concentrated in vacuo. The final product was taken up in methanol, treated with hydrochloric acid (1.0 M/Et$_2$O, 1.0 equivalent) and re-evaporated to dryness, then washed with ethyl ether, filtered, and dried to give 0.288 g of the hydrochloride salt of compound 58 (mp 215.3–218.6° C., M+. 427).

Example 59

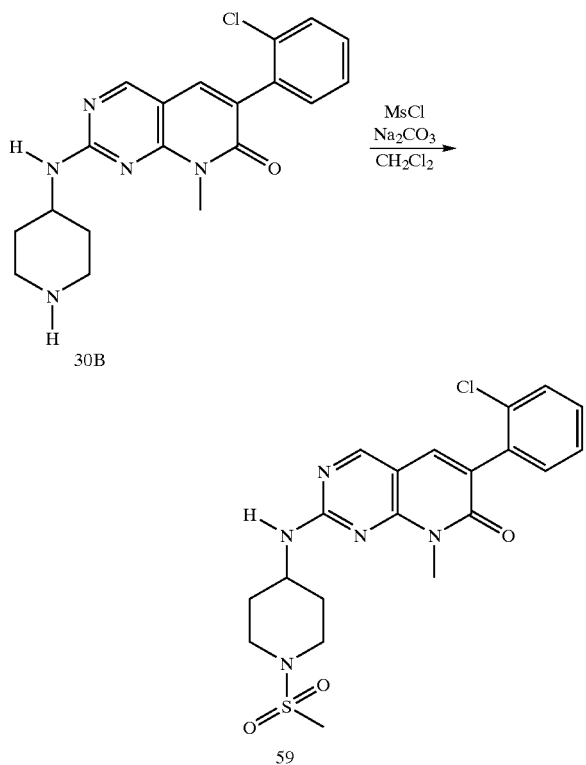

Compound 30B (0.300 g, 0.811 mmole), methanesulfonyl chloride (0.066 mL, 0.852 mmole), and sodium carbonate (0.090 g, 0.852 mmole) were taken up in 5 mL of dichloromethane and stirred overnight at room temperature. After 18 hours, the reaction was purified by flash chromatography (3–5% (1:9 ammonium hydroxide/methanol)/dichloromethane), and the column fractions containing product 59 were combined and concentrated in vacuo. The final product was taken up in methanol, treated with hydrochloric acid (1.0 M/Et$_2$O, 1.0 equivalent) and re-evaporated to dryness, then washed with ethyl ether, filtered, and dried to give 0.326 g of the hydrochloride salt of compound 59 (mp 185.0–194.0° C., M+=427).

Example 60

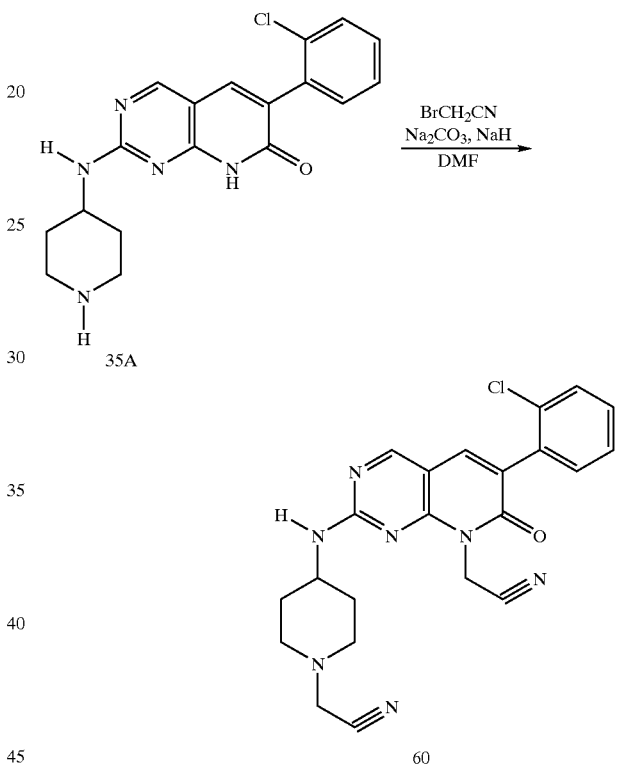

Compound 35A (0.086 g, 0.242 mmole), sodium carbonate (0.026 g, 0.242 mmole), and bromoacetonitrile (0.016 mL, 0.242 mmole) were taken up in 2 mL of DMF. After 30 minutes at room temperature, the initial starting material was consumed. Sodium hydride (60% in oil, 0.011 g, 0.266 mmole) was added and stirred another 30 minutes at rt before adding another 1 eq of bromoacetonitrile (0.016 mL, 0.242 mmole) and stirring at rt overnight. The reaction was purified by flash chromatography (1–5% (1:9 ammonium hydroxide/methanol)/dichloromethane), and the column fractions containing product 60 were combined and concentrated in vacuo. The final product was taken up in methanol, treated with hydrochloric acid (1.0 M/Et$_2$O, 1.0 equivalent) and re-evaporated to dryness, washed with ethyl ether, filtered, and dried to give 0.054 g of the hydrochloride salt of compound 60 (mp 143.0–158.5° C.).

Example 61

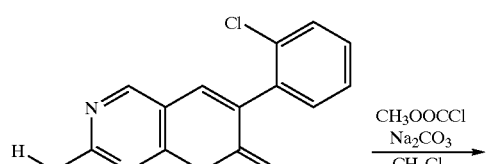

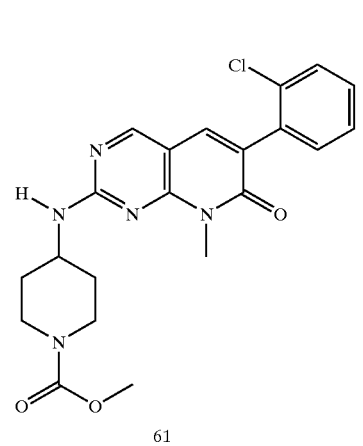

Compound 30B (0.709 g, 1.92 mmole), methyl chloroformate (0.16 mL, 2.01 mmole), and sodium carbonate (0.213 g, 2.01 mmole) were taken up in 5 mL of dichloromethane and stirred overnight at room temperature. After 18 hours, the reaction was purified by flash chromatography (2–10% (1:9 ammonium hydroxide/methanol)/dichloromethane), and the column fractions containing product 61 were combined and concentrated in vacuo. The final product was taken up in methanol, treated with hydrochloric acid (1.0 M/Et$_2$O, 1.0 equivalent), re-evaporated to dryness, washed with ethyl ether, filtered, and dried to give 0.063 g of the hydrochloride salt of compound 61 (mp 133.5–136.5° C.).

Example 62

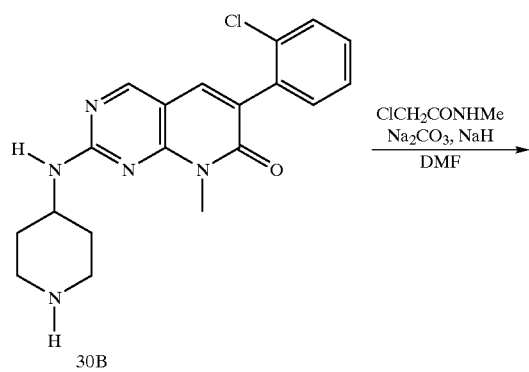

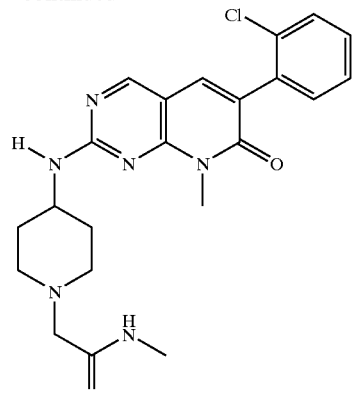

Compound 30B (1.0 g, 2.81 mmole), sodium carbonate (0.447 g, 4.22 mmole), and 2-chloro-N-methylacetamide (0.453 g, 4.22 mmole) were taken up in 5 mL of DMF and stirred overnight at room temperature. After 20 hrs, the reaction was purified by flash chromatography (3–5% (1:9 ammonium hydroxide/methanol)/dichloromethane), and the column fractions containing product 62 were combined and concentrated in vacuo. The final product was taken up in methanol, treated with hydrochloric acid (1.0 M/Et$_2$O, 1.0 equivalent) and re-evaporated to dryness, then washed with ethyl ether, filtered, and dried to give 0.708 g of the hydrochloride salt of compound 62, (mp 64.0–102.6° C.).

Example 63

This example illustrates an alternative method of synthesizing compound 30B.

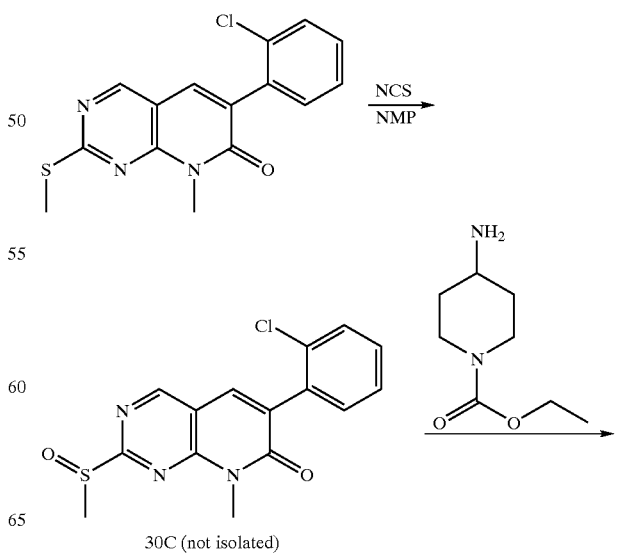

-continued

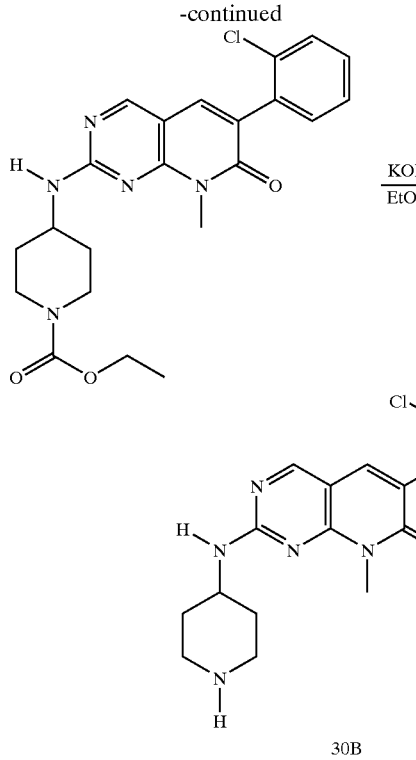

30B

The methyl sulfide (15 g, 49.4 mmole) was taken up in 70 mL of NMP and stirred at room temperature; to this solution was added a solution of N-chlorosuccinimide (7.6 g, 56.8 mmole) in 6 mL of NMP with added water (0.87 mL, 48.1 mmole). The initial slurry quickly dissolved to a clear yellow solution. After 20 minutes at room temperature the sulfoxide 30C was then treated with ethyl 4-amino-1-piperidinecarboxylate (12.7 mL, 74.1 mmole). The reaction quickly darkened, warmed to the touch, and was left to stir at room temperature for 4 days. At the end of this period, the opaque yellow suspension was transferred to a large Erlenmeyer flask with 250 mL of water and stirred in an ice bath for 4 hours. The suspension was then filtered to collect a yellow cake, which was rinsed with water and hexanes and dried in vacuo. The ethyl carbamate intermediate showed excess mass, not reducing below 31.6 g despite prolonged drying.

Potassium hydroxide (111 g, 1.98 mol) was taken up in 400 mL of ethanol and heated until dissolved, and then cooled slightly before adding the carbamate intermediate from above (theoretically 49.4 mmole). The solution was stirred at reflux for 3 hours, then cooled to rt before placing in an ice bath for neutralization with aqueous citric acid (111 g, 577 mmole, dissolved in 400 mL of water). The solution was stirred for 30 minutes, then evaporated in vacuo to an aqueous syrup. This syrup was extracted with methylene chloride (×3); the combined extracts were washed with saturated brine, dried with sodium carbonate, and evaporated in vacuo to yield 12 g yellow foam (32.4 mmmole).

A portion (500 mg) of this foam was purified by flash chromatography (5–20% methanol/dichloromethane+1% ammonium hydroxide), and the column fractions containing product were combined and concentrated in vacuo. The purified product was taken up in methanol, treated with 2 equivalents 1 N HCl/Et₂O, and evaporated in vacuo; the resulting solids were washed with ethyl ether and collected to yield 520 mg of the bis hydrochloride salt of compound 30B, (mp>300 C., (M+H)+ 370).

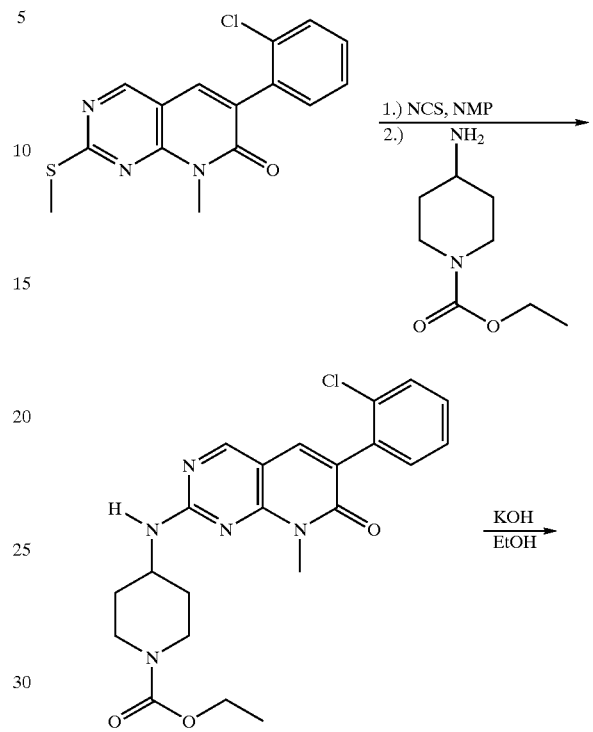

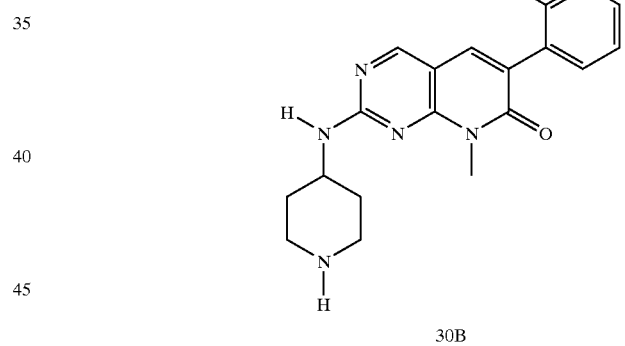

30B

The methyl sulfide (15 g, 49.4 mmole) was taken up in 70 mL of NMP and stirred at room temperature; to this solution was added a solution of N-chlorosuccinimide (7.6 g, 56.8 mmole) in 6 mL of NMP and water (0.87 mL, 48.1 mmole). The initial slurry quickly dissolved to a clear yellow solution. After 20 minutes at room temperature, ethyl 4-amino-1-piperidinecarboxylate (12.7 mL, 74.1 mmole) was added to the solution, and stirred at room temperature for 4 days. The opaque yellow suspension was transferred to a large Erlenmeyer flask with 250 mL of water and stirred in an ice bath for 4 hours. The suspension was then filtered to collect a yellow cake, which was rinsed with water and hexanes and dried in vacuo. The ethyl carbamate intermediate showed excess mass, not reducing below 31.6 g despite prolonged drying.

Potassium hydroxide (111 g, 1.98 mol) was taken up in 400 mL of ethanol and heated until dissolved, and then cooled slightly before adding the carbamate intermediate from above (theoretically 49.4 mmole). The solution was stirred at reflux for 3 hours, then cooled to rt before placing in an ice bath for neutralization with aqueous citric acid (111 g, 577 mmole, dissolved in 400 mL of water). The solution was stirred for 30 minutes, then evaporated in vacuo to an aqueous syrup. This syrup was extracted with methylene chloride (×3); the combined extracts were washed with saturated brine, dried with sodium carbonate, and evaporated in vacuo to yield 12 g yellow foam (32.4 mmole).

A portion (500 mg) of this foam was purified by flash chromatography (5–20% methanol/dichloromethane+1% ammonium hydroxide), and the column fractions containing product were combined and concentrated in vacuo. The purified product was taken up in methanol, treated with 2 equivalents 1 N HCl/Et$_2$O, and evaporated in vacuo; the resulting solids were washed with ethyl ether and collected to yield 520 mg of the bis hydrochloride salt compound 30B (mp>300° C., (M+H)+370).

Example 64

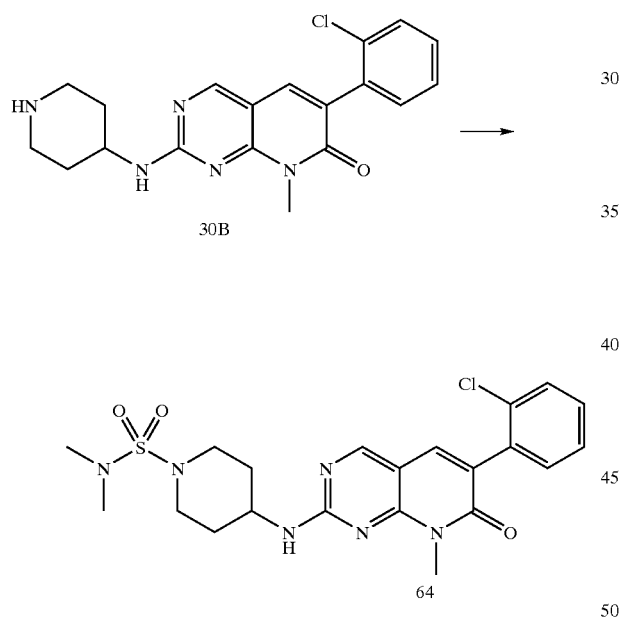

64

Example 65

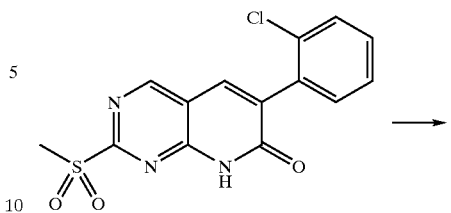

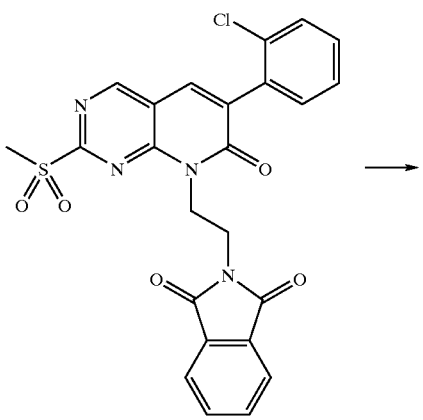

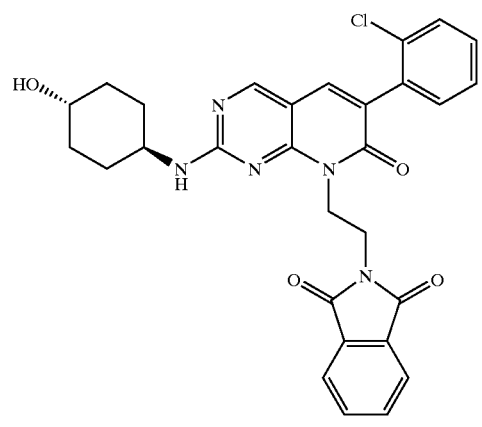

65

To a solution of 0.25 g (0.68 mmol) of compound 30B and 0.11 g (0.74 mmol) of dimethylsulfamoyl chloride in 20 mL of dichloromethane was added 0.11 mL (0.81 mmol) of triethylamine. The mixture was heated to reflux for 6 hr and the solvent was removed under reduced pressure and the residue was purified by column chromatography on 40 g of silica gel using 5% methanol/ethyl acetate to afford 200 mg white powder. This was dissolved in 2 mL of ethyl acetate and 0.75 mL of 1 M HCl/Ether was added. This was stirred for 1 hr and solvent was evaporated under reduced pressure to give the HCl salt of compound 64, (200 mg). mass spec. MH$^+$=477, mp 207.2–208° C.).

To a cooled (5° C.) suspension of 0.914 g (2.7 mmol) of 6-(chlorophenyl)-2-methanesulfonyl-pyrido[2,3-d]pyrimidin-7-ol, 1.041 g (5.4 mmol) of N-(2-hydroxyethyl)-phthalimide, 1.43 g (5.4 mmol) of triphenylphosphine in 15 mL of 1,4-dionxane was added dropwise a solution of 0.95 g (0.86 mL, 5.4 mmol) diethylazodicarboxylate in 5 mL of 1,4-dioxane over a period of 30 min. After addition was completed, the ice-water cooling bath was removed. The suspension soon turned into a clear light brown solution. This was allowed to stir at room temperature overnight. The reaction mixture was concentrated under reduced pressure and purified by column chromatography on 120 g of silica gel using 90:10:0.5 ethyl acetate/dichloromethane/ammonium hydroxide to obtain 0.38 g of the N-ethylphthalimide intermediate. A mixture of 0.18 g (0.35 mmol) of this intermediate and 0.05 g (0.42 mmol) of trans-4-aminocyclohexanol in 1 mL of NMP was heated to 120° C. for 30 min. The reaction mixture was cooled, diluted with 75 mL of water and extracted with ethyl acetate (3×75 mL). The combined ethyl acetate solution was washed with water (3×75 mL), brine, dried, filtered and concentrated. The material was purified by column chromatography on 40 g of silica eluting with 5% methanol/dichloromethane affording 45 mg of compound 65. (mass spec. MH+=544, mp 208–210° C.).

Example 66

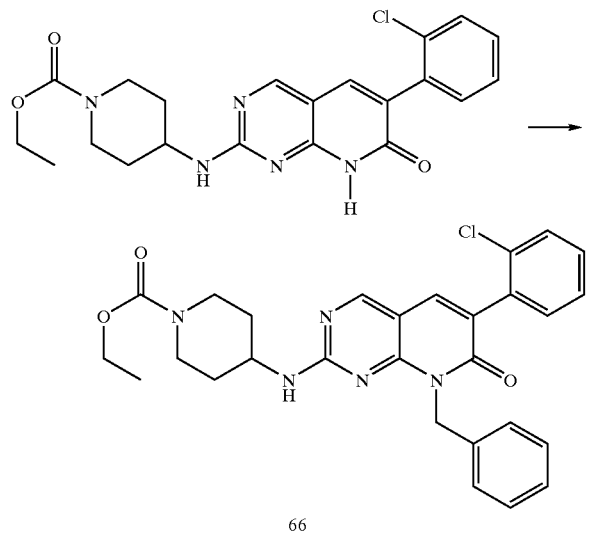

66

To a suspension of 0.179 g (0.4 mmol) of the 6-(2-chlorophenyl)-2-(N-carbethoxypiperidyl-4-amino)pyrido[2,3-d]-pyrimidin-7-ol in 1 mL of DMF at room temperature under nitrogen was added 0.012 g (0.46 mmol) of sodium hydride (95%) all at once. Evolution of gas was observed and after 5 min. the suspension turned into a clear yellow solution. This was allowed to stir at room temperature for 30 min., then 0.068 g (0.05 mL, 0.4 mmol) of benzyl bromide was added via a syringe. The reaction mixture was allowed to stir overnight, quenched with concentrated aqueous ammonium chloride solution and extracted with ethyl acetate (3×60 mL). The combined ethyl acetate solution was washed with water (3×60 mL), brine, dried, filtered and concentrated. The material was purified by column chromatography on 40 g of silica using 20% ethyl acetate/ dichloromethane to afford 75.6 mg of product 66. This was dissolved in 2 mL of ethyl acetate and 1 mL of 1 M HCl/ether was added. The suspension was stirred for 1 hr and concentrated to give 74 mg of the hydrochloric salt of compound 66. (mass spec. MH+=518, mp. 162–173° C.).

Example 67

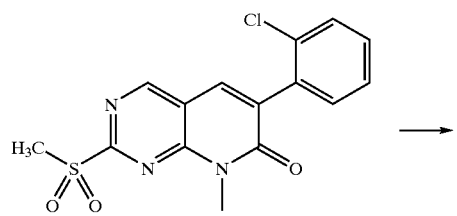

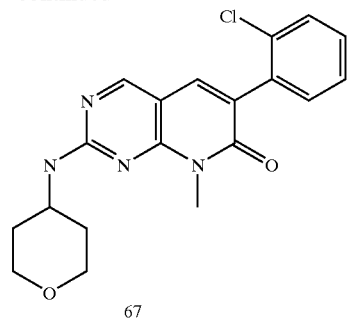

67

A mixture of 0.350 g (1.0 mmol) of sulfone and 0.303 g (3.0 mmol) of 4-amino-tetrahydropyran in 0.7 mL of NMP was heated at 100° C. After 1 hour the reaction was cooled, poured into water and extracted with ethyl acetate. The organic fraction was washed 5 times with water and once with brine, dried over magnesium sulfate and concentrated under reduced pressure. The residue was purified by column chromatography (5% methanol/dichloromethane) to yield compound 67 as a foam. The residue was suspended in MeOH and hydrochloric acid (1.0 M/Et₂O, 1 equivalent) was added. The resulting mixture was stirred for 20 minutes and concentrated under reduced pressure. The residue was stirred with a mixture of MeOH/Et₂O, for 1 hour, the hydrochloric salt of compound 67 was filtered off as a white solid. Yield 330 mg. Mp 217.2–218.9° C. MS (M+H)+ 371.

Example 68

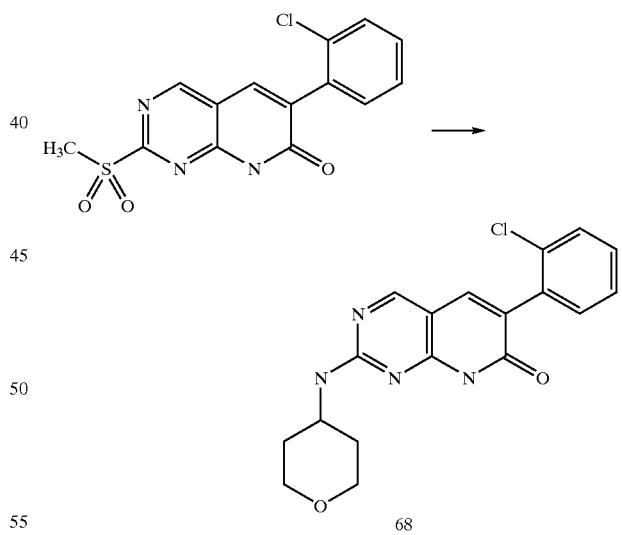

68

The sulfone (350 mg, 1.04 mmol) was combined with 4-aminotetrahydropyran (303 mg, 3.0 mmol) and 0.7 mL NMP, heated at 100° C. for 30 minutes. Cooled to room temperature, added to water, and filtered to give comopund 68 as a brown solid. The solid was dissolved in MeOH and made acidic with hydrochloric acid (1.0 M/Et₂O), and evaporated. This residue was purified on silica gel using 10:90 MeOH/CH₂Cl₂. The fractions containing the hydrochloric acid salt of compound 68 were combined and evaporated under reduced pressure to give the hydrochloric acid salt of compound 68 as a white foam. The residue was suspended in MeOH and addition of hydrochloric acid (1.0 M/Et$_2$O, 1 equivalent), stirred for 20 minutes and concentrated under reduced pressure. The residue was stirred with a mixture of MeOH/Et$_2$O, for 1 hour, the product was filtered off as a white solid. Yield 228 mg. Mp>300° C. MS (M+H)$^+$ 357.

Example 69

This example illustrates the synthesis 2-(trans-4-methoxycarboxamidocyclohexylamino)-6-(2-chlorophenyl)-8H-pyrido[2,3-d]pyrimidin-7-one starting with the SEM-protected pyridone.

Step 1

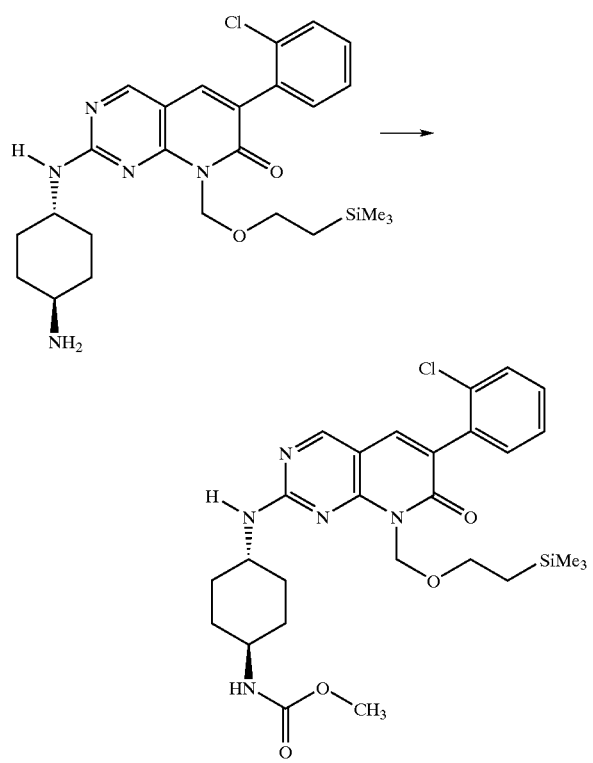

To a 0° C. solution of the amine (218 mg, 0.436 mmol) in 10 mL of anhydrous tetrahydrofuran were added dimethyl pyrocarbonate (0.080 mL, 0.746 mmol) dimethylamino pyridine (2 mg, 0.016 mmol). The reaction mixture was stirred at 0° C. for 15 min and then slowly warmed to ambient temperature overnight. The crude reaction mixture was concentrated in vacuo and purified by column chromatography (5:95, methanol/methylene chloride) to give 230 mg (95%) of the product as a white solid (mass spec. M+H$^+$=558, mp=110.0–112.0° C.).

Step 2

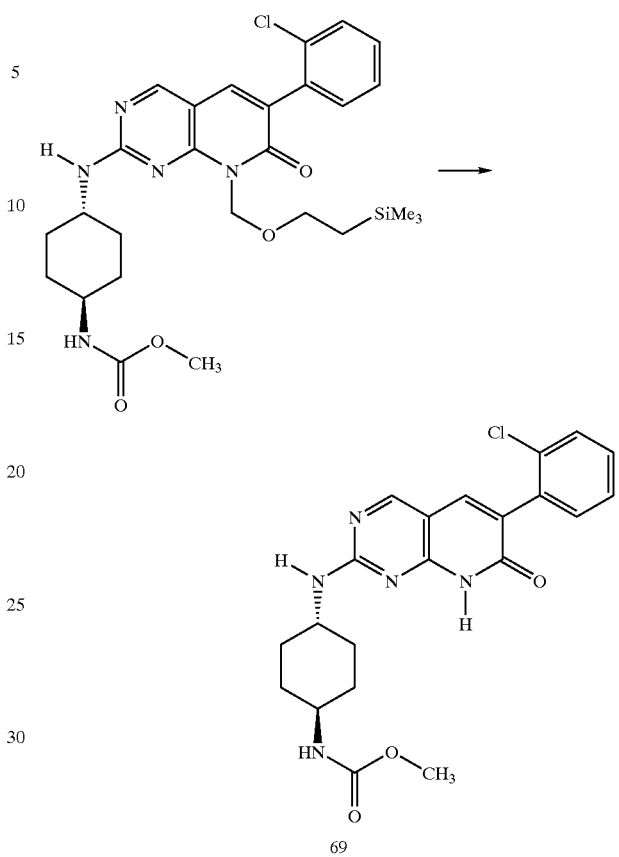

The SEM-protected pyridone (320 mg, 0.553 mmol) from Step 1 was suspended in 10 mL of methanol and treated with 10 mL of 10% hydrochloric acid. The reaction mixture was refluxed for 24 hours, cooled, then concentrated in vacuo until precipitate began to form. The resulting suspension was filtered, washed with water and ethyl acetate, then dried to give 95 mg (53%) of the hydrochloric acid salt of 2-(trans-4-methoxycarboxamido-cyclohexylaino)-6-(2-chlorophenyl)-8H-pyrido[2,3-d]pyrimidin-7-one 69 as a white solid (mass spec. M+H$^+$=428, mp=294.6–296.8° C.).

Example 70

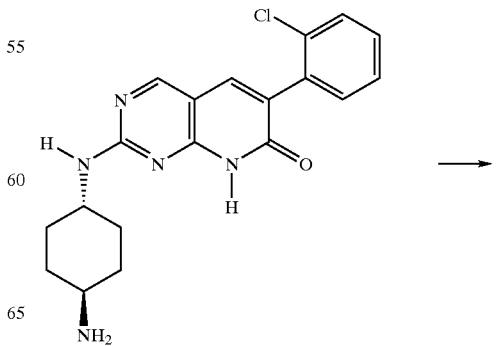

149

-continued

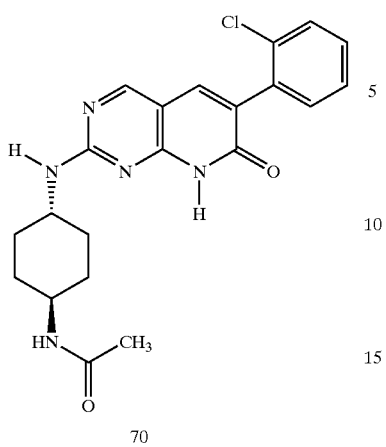

70

The amine (0.49 mg, 1.3 mmol) was suspended in 6 mL of acetic anhydride and stirred at ambient temperature for 16 hours. The reaction mixture was diluted with ethyl acetate and filtered. The collected solids were washed with water and ethyl acetate and then dried to give 2-(trans-4-methylcarboxamidocyclohexylamino)-6-(2-chlorophenyl)-pyrido[2,3-d]pyrimidin-7-one as a white solid. The free base was suspended in ethyl acetate and treated with a 1 M solution of HCl/ether to form 0.51 g (87%) of the hydrochloric acid salt of compound 70 as a white powder (mass spec. M+H$^+$=412, mp>300° C.).

Example 71

This example illustrates the synthesis 2-(trans-4-amidocarboxamido-cyclohexylamino)-6-(2-chlorophenyl)-8H-pyrido[2,3-d]pyrimidin-7-one starting with the SEM-protected pyridone.

Step 1

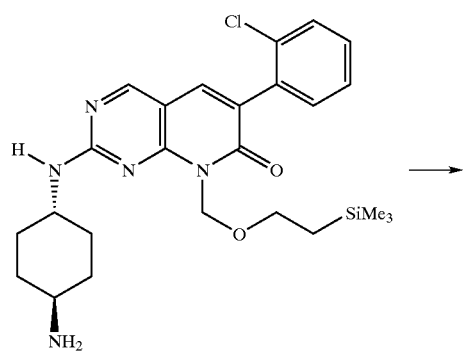

150

-continued

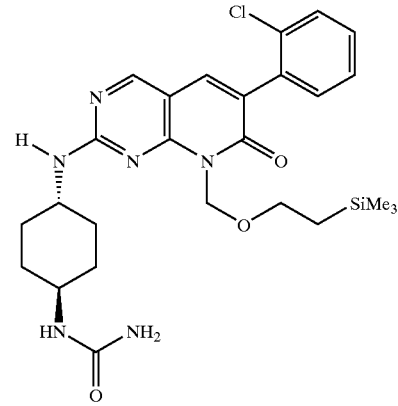

To a solution of the amine (0.20 g, 0.39 mmol) in 15 mL of methylene chloride was added trimethylsilyl isocyanate (0.12 mL, 0.73 mmol) and was stirred at ambient temperature for 5 hours. The reaction mixture was quenched with 5 mL of methanol, concentrated in vacuo, and purified by column chromatography (5:95, methanol/methylene chloride) to give 0.14 g (66%) of the product as a white solid (mass spec. M+H$^+$=543, mp=182.2–188.9° C.).

Step 2

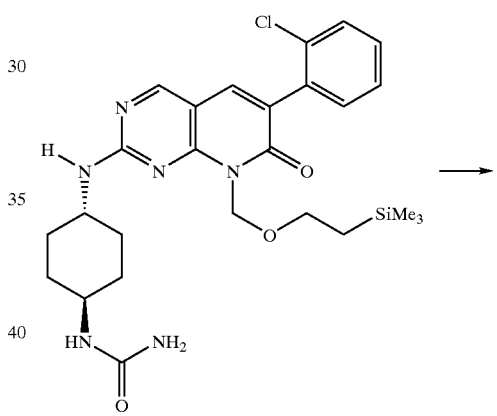

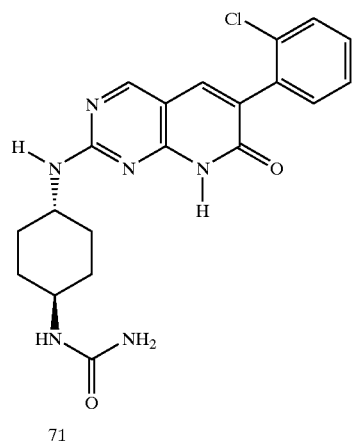

71

The SEM-protected compound (130 mg, 0.245 mmol) from Step 1 was suspended in 5 mL of methanol and treated with 5 mL of 10% hydrochloric acid. The reaction mixture was refluxed for 18 hours. The resulting suspension was filtered and the collected solids were washed with water, ethyl acetate, and dried to give 68 mg (62%) of the hydrochloric acid salt of 2-(trans-4-amidocarboxamidocyclohexylamino)-6-(2-chlorophenyl)-8H-pyrido[2,3-d]pyrimidin-7-one (71) as a white solid (mass spec. M+H⁺=413, mp>300° C.).

Example 72

This example illustrates the synthesis 2-(cis-4-methanesulfonylamido-cyclohexylamino)-6-(2-chlorophenyl)-pyrido[2,3-d]pyrimidin-7-one starting with 6-(2-chlorophenyl)-2-methanesulfonyl-pyrido[2,3-d]pyrimidin-7-ol.

Step 1

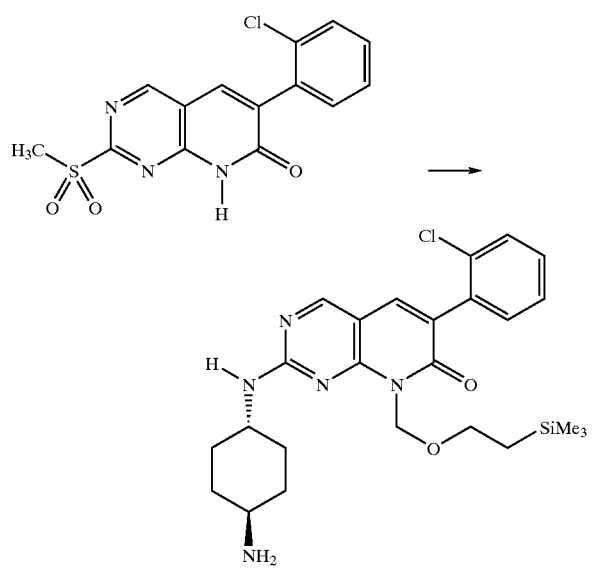

To a 0° C. solution of the sulfone (1.93 g, 5.75 mmol) in 15 mL of dry 1-methyl-2-pyrrolidinone was added sodium hydride (0.160 g, 6.33 mmol, 95% dry powder). The reaction mixture was stirred for 10 minutes until gas evolution subsided, then 2-(trimethylsilyl)ethoxymethyl chloride (1.10 mL, 6.22 mmol) was added dropwise over a period of 5 minutes. The reaction mixture was stirred for 30 minutes, then was added to a 0° C. cooled flask containing cis-1,4-diaminocyclohexane (6.27 g, 54.9 mmol, TCI America, Portland, Oreg., mixture of cis and trans isomers). The reaction mixture was stirred for 3 hours at ambient temperature. 100 mL of water and 100 mL of ethyl acetate were added, the layers were partitioned and the aqueous layer was extracted with another 100 mL portion of ethyl acetate. The combined organic layers were washed with 4×200 mL of brine, dried over sodium sulfate and concentrated in vacuo to give a crude yellow liquid. Purification by column chromatography (30–40:70–60, methanol/methylene chloride and ammonium hydroxide) gave 1.62 g (56%) of the product as a light yellow foam (mass spec. M+H⁺=500, mp=79.0–81.5° C.

Step 2

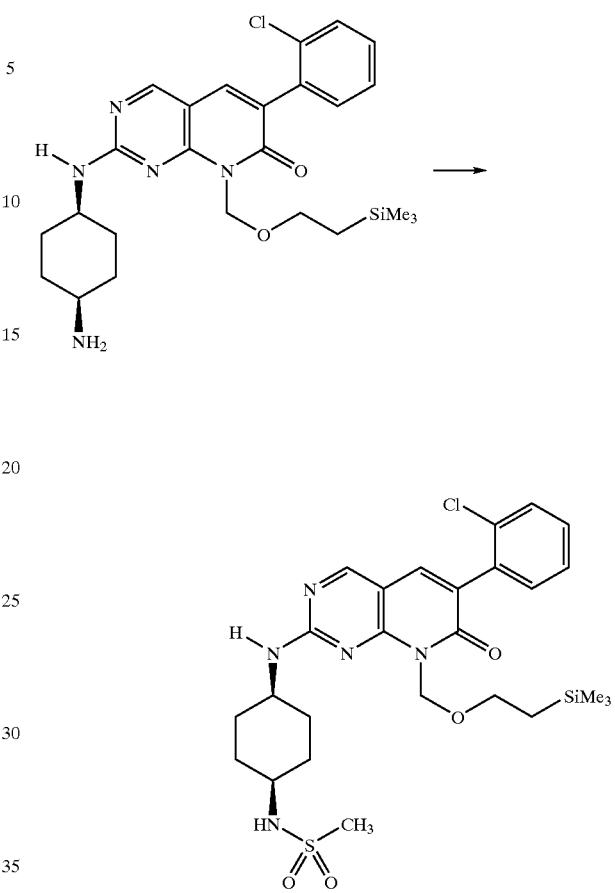

To a solution of the amine (0.26 g, 0.53 mmol) from Step 1 in 12 mL of methylene chloride were added triethylamine (0.11 mL, 0.79 mmol) and methane sulfonic anhydride (0.18 g, 1.0 mmol). The reaction mixture was stirred for 3 hours, and then concentrated in vacuo. Purification by column chromatography (3:97, methanol/methylene chloride) gave 0.30 g (98%) of the product as a white foam (mass spec. M+H⁺=578, mp=117.0–144.0° C.). The product was isolated as a mixture of cis and trans stereoisomers in an 82:18 ratio, respectively, as determined by ¹H NMR spectroscopy.

Step 3

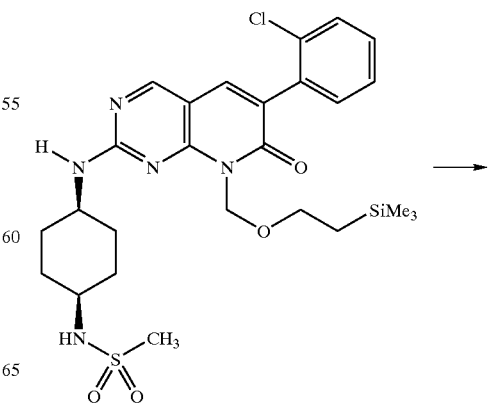

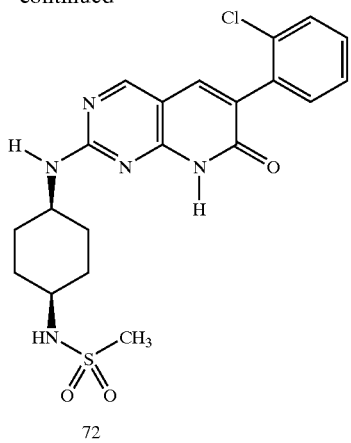

72

The SEM-protected pyridone (0.29 g, 0.50 mmol) from Step 2 was suspended in 10 mL of methanol and treated with 10 mL of 10% hydrochloric acid. The reaction mixture was refluxed for 5 hours, cooled, then concentrated in vacuo until precipitate began to form. The resulting suspension was filtered, washed with water and ethyl acetate, then dried to give 0.17 g (70%) of the hydrochloric acid salt of 2-(cis-4-methanesulfonylamino-cyclohexylamino)-6-(2-chlorophenyl)-8H-pyrido[2,3-d]pyrimidin-7-one (72) as a white solid (mp>300° C.). The product was isolated as a mixture of cis and trans stereoisomers in an 82:18 ratio, respectively, as determined by $^1$H NMR spectroscopy.

Example 73

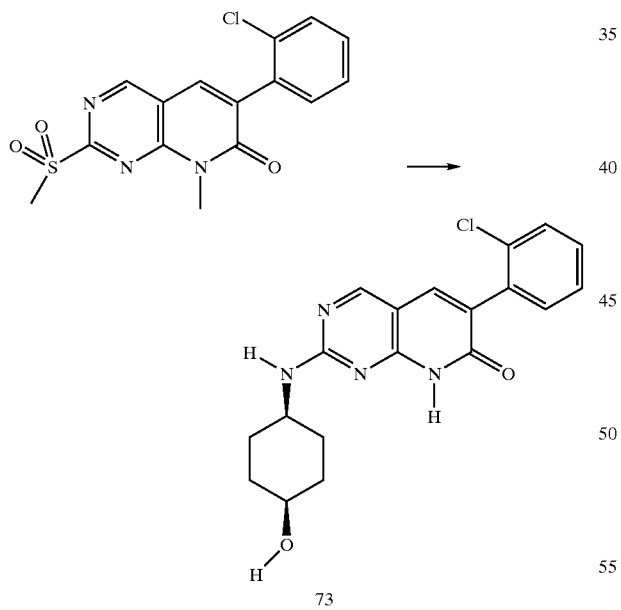

To a solution of the sulfone (0.20 g, 0.57 mmol) and triethylamine (0.24 mL, 1.7 mmol) in 25 mL of tetrahydrofuran was added cis-4-aminocyclohexanol (Aust. J. Chem., 1961,14,610). The reaction mixture was stirred at 80° C. for 48 h, cooled, then added 1 N HCl. Extracted with chloroform, washed with sodium bicarbonate solution and brine, dried over magnesium sulfate. Filtered and concentrated to give 0.398 g crude solid, which was purified column chromatography (4% methanol in dichloromethane) to give 0.118 g (54%) 2-(cis-4-hydroxycyclohexylamino)-6-(2-chlorophenyl)-8-methyl-8H-pyrido[2,3-d]pyrimidin-7-one (73) as a white solid (mass spec. M+H$^+$=385, mp=209.5–216.5° C.).

Example 74

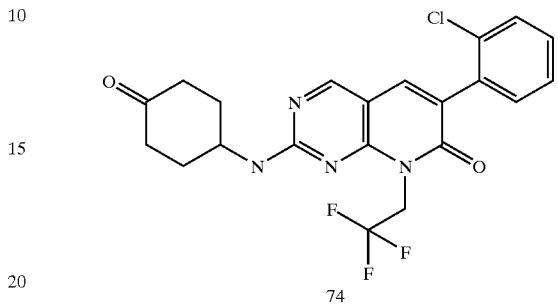

74

Preparation of 74B:

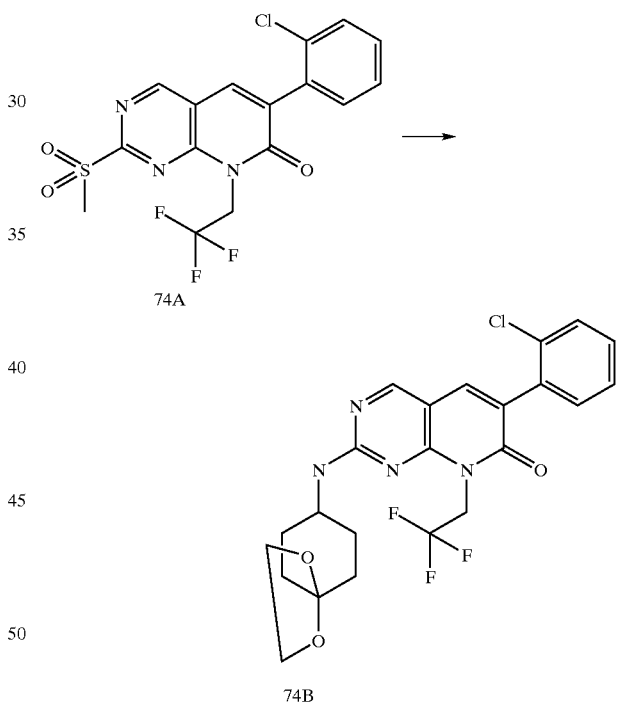

Compound 74A (800 mg, 1.91 mmol), 1,4-dioxa-spiro[4,5]dec-8-ylamine (see WO 99/001452 for preparation), and N-methyl pyrrolidinone (0.5 mL) were mixed together and heated to 110° C. with stirring. After 35 minutes, the reaction was cooled to room temperature, diluted with ethyl acetate (25 mL)/water (25 mL), partitioned, and the layers were separated. The organic layers were combined, washed with water (2×25 mL) and brine (1×25 mL), dried over magnesium sulfate, filtered and concentrated to give compound 74B as an off-white powder (990 mg, (M+H)$^+$=495, M.P.= 200.0–206.5° C.).

Preparation of compound 74:

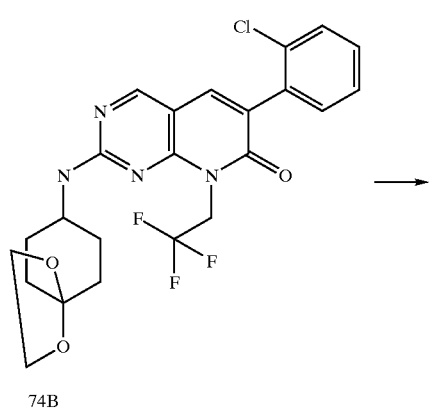

74B

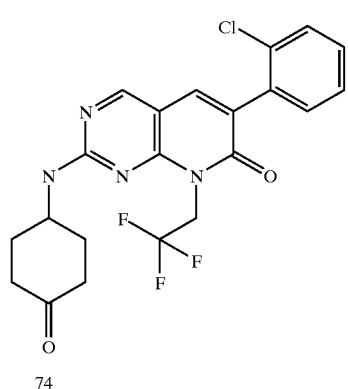

74

Compound 74B (990 mg) was taken up in 10 mL of 80% acetic acid$_{(aq)}$ and heated to 65° C. with stirring for 4 hours. The reaction mixture was extracted with ethyl acetate (1×70 mL). The organic layer was washed with saturated sodium bicarbonate (4×50 mL) until pH=8 and brine (1×50 mL), dried over magnesium sulfate, filtered and concentrated to give a crude yield of 800 mg. Purification by Preparative TLC using 70% ethyl acetate in hexanes afforded 349 mg of compound 74 (M+H)=451, M.P.=251.2–252° C.).

Example 75

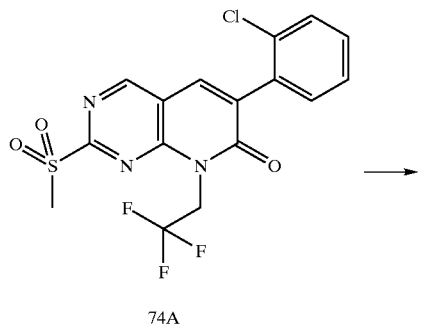

74A

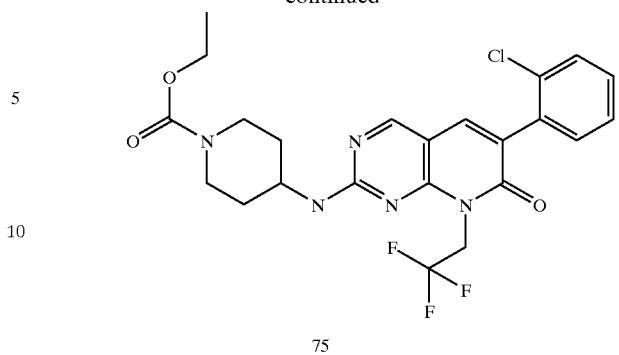

75

Compound 74A (2 g, 4.79 mmol), ethyl 4-amino-1-piperidine carboxylate (Aldrich, 2.5 g, 3 eq) and N-methyl pyrrolidinone (1.5 mL) were mixed together and stirred at 110° C. for 3.5 hours. The reaction mixture was cooled to room temperature and diluted with ethyl acetate (80 mL) and water (20 mL). The organic layer was separated, washed with water (2×25 mL) and brine (1×25 mL), dried over magnesium sulfate, filtered and then concentrated. The crude material was purified on silica gel eluting with a gradient of 25% to 50% ethyl acetate in hexanes, affording 1.023 g of the free amine ((M+H)$^+$=510, M.P.=194.2–221.4° C.). 200 mg of the free amine was dissolved in ethyl acetate (15 mL) and then added 1.0 M HCl in diethyl ether (0.5 mL, 1.25 eq) and stirred for 1 hour. The solvent was then removed under reduced pressure at 50° C. Added 20 mL of diethyl ether to the residue and crushed up the solids. The resulting slurry was stirred for 30 minutes, filtered and the off-white powder was dried under high vacuum at 56° C. for 2 hours to give 65 mg of compound 75 ((M+H)$^+$=510, M.P.=107.0–110.0° C.).

Example 76

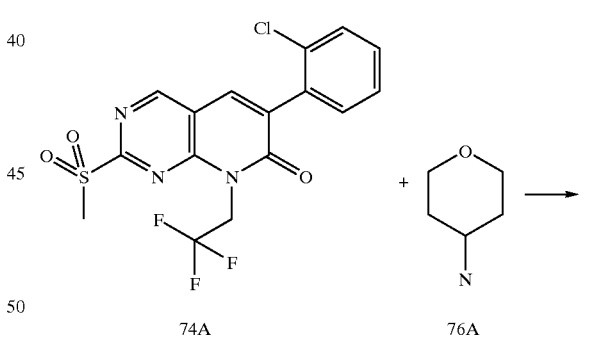

74A        76A

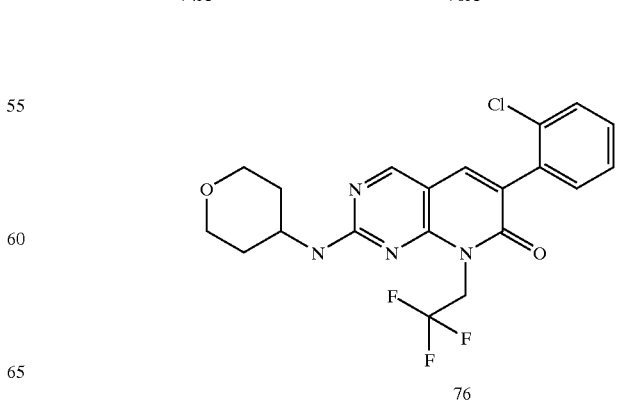

76

Compound 74A (365 mg, 0.87 mmol), 4-aminotetrahydropyran, 76A, (265 mg, 3 eq) and N-methylpyrrolidinone (0.3 mL) were mixed together and heated at 110° C. for 30 minutes. The reaction was cooled to room temperature and diluted with ethyl acetate (30 mL) and water (25 mL). The organic layer was separated, washed with water (2×25 mL) and brine (1×25 mL), dried over magnesium sulfate, filtered and concentrated to give 440 mg of the crude material. Purification by Preparative TLC eluting with 70% ethyl acetate in hexanes afforded the free amine (405 mg) as an off-white powder ((M+H)$^+$=439, M.P.=200.9–202.1° C.). The free amine was dissolved in ethyl acetate (25 mL) and then 1.0 M HCl in diethyl ether (1.4 mL, 1.5 eq) was added and the resulting mixture was stirred for 1 hour. Then the solvent was removed under reduced pressure at 50° C., and the resulting residue was dried under high vacuum at 56° C. to give 339 mg of the hydrochloric acid salt of compound 76, ((M+H)$^+$=439, M.P.=198.2–201° C.).

Example 77
Preparation of Compound 77B

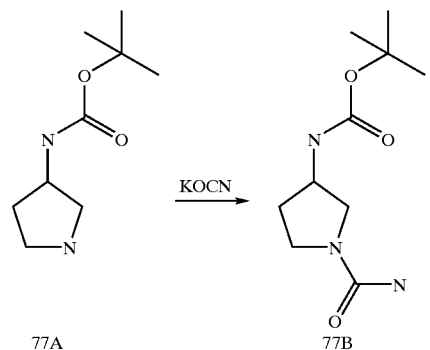

Compound 77A (TCI Chemicals, 5 g, 26 mmol), and potassium cyanate (10.1 g, 5 eq) were dissolved in methanol (60 mL) and water (60 mL). The resulting mixture was heated to 80° C. with stirring for 4 hours and then stirred at room temperature for 24 hours. The reaction mixture was diluted with ethyl acetate (350 mL). The organic layer was separated, washed with brine (5×150 mL) and dilute HCl/brine (1×150 mL), and concentrated to about 50 mL when solids began to form. These solids were filtered and dried to give compound 77B (2 g, (M+H)$^+$=230, M.P.=170.4–173.5° C.).

Preparation of Compound 77C:

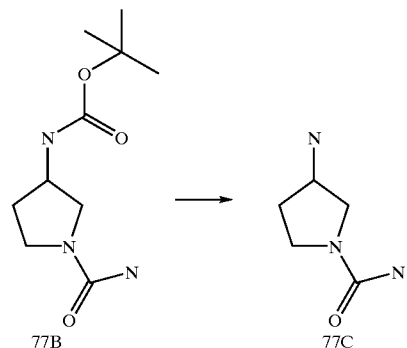

Compound 77B (2 g) was taken up in dioxane (125 mL) and HCl$_{(g)}$ was bubbled through the heterogeneous mixture for 15 minutes and then the vessel was capped tightly and stirred for 5 hours. The solvent was removed under reduced pressure at 50° C. The crude material was taken up in methanol (250 mL) and 2.5 mL of sodium methoxide in methanol (25 wt %, 1 eq) was added. The resulting mixture was stirred for 1 hour and then concentrated to about 75 mL and filtered through a medium frit. The filtrate was concentrated and dried to give compound 77C (1.76 g, (M+H)$^+$= 130).

Preparation of Compound 77:

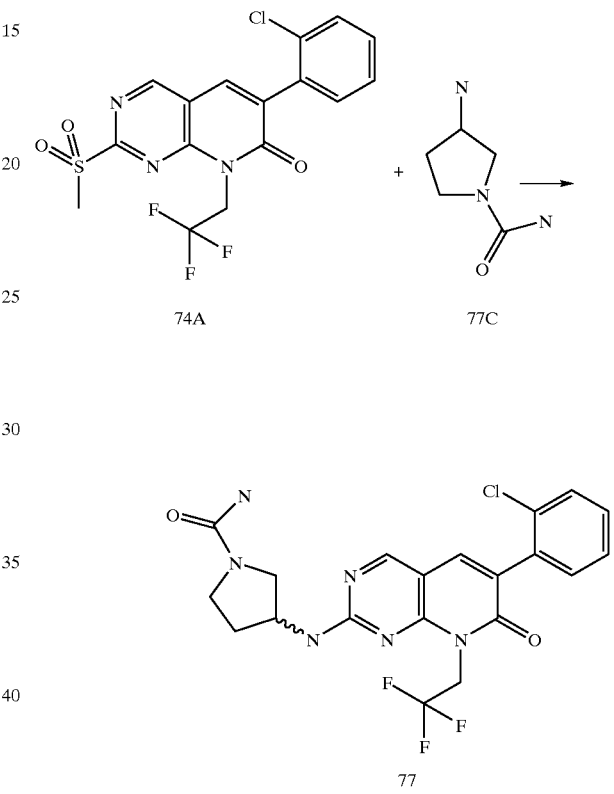

Compound 74A (500 mg, 1.2 mmol), compound 77C (660 mg, 3 eq) and N-methyl pyrrolidinone (0.8 mL) were mixed together and heated at 110° C. with stirring for 30 minutes. The reaction mixture was cooled to room temperature and diluted with ethyl acetate (80 mL) and water (40 mL). The organic layer was separated, washed with water (2×40 mL) and brine (1×40 mL), dried over magnesium sulfate, filtered and concentrated to give the crude product. Purification by Preparative TLC eluting with neat ethyl acetate gave compound 77 as a free amine (120 mg). The free amine was then dissolved in ethyl acetate (25 mL) and 1 M HCl in diethyl ether (0.4 mL, 1.5 eq) was added and the resulting mixture was stirred for 1 hour. The solvent was removed under reduced pressure at 50° C. and the resulting residue was dried under high vacuum at 56° C. to give the HCl salt of 77 as an off-white powder (126 mg, (M+H)$^+$=467, M.P.= 164.5–168.0° C.).

Example 78

2-(4-tetrahydrothiopyranylamino)-6-(2-chlorophenyl)-8-methyl-8H-pyrido[2,3-d]pyrimidin-7-one Step 1

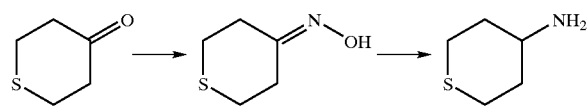

A mixture of 5 g (43 mmol) of tetrahydrothiopyran-4-one, 29.26 g (215 mmol) of sodium acetate trihydtate and 14.94 g (215 mmol) of hydroxylamine hydrochloride in 200 mL of ethanol was refluxed for 6 hours. The mixture was diluted with 400 mL of ice-water mixture and extracted with ethyl acetate (2×150 mL). The extract was washed with brine, dried, filtered and concentrated under reduced pressure to yield 5.6 g (quantitative yield) of the oxime, (white solid). 2 g (15 mmol) of this oxime in 30 mL of THF was added dropwise to 76 mL (76 mmol) of 1 M LAH/THF solution at room temperature. After addition was completed, the mixture was refluxed for 7 hours and was cooled to 5° C. 2.9 mL of water was added cautiously dropwise to the reaction mixture, followed by 2.9 mL of 15% aqueous NaOH and 8.7 mL of water. The suspension was stirred for 30 minutes and filtered over Celite and washed with 300 mL of ethyl acetate. The filtrate was removed under reduced pressure (<50° C.) to afford 1.62 g of 4-aminotetrahydrothiopyran, (92.3% yield).

Step 2

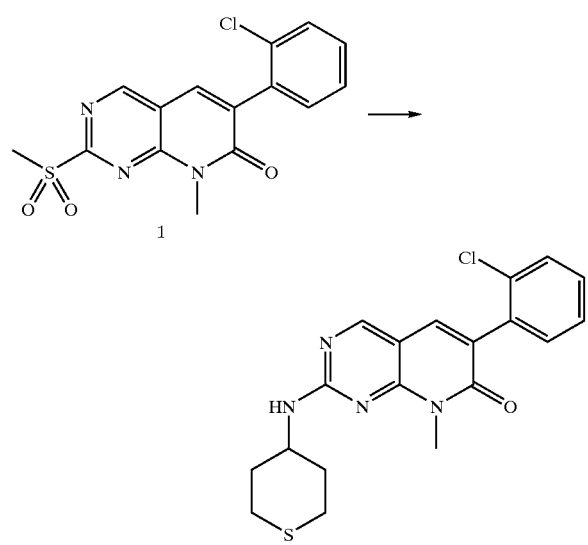

A mixture of 1 g (2.9 mmol) of sulfone 1 and 0.67 g (5.7 mmol) of 4-aminotetrahydrothiopyran in 1.5 mL of NMP was heated in a 85° C. oil bath for 1.5 hours until the reaction was completed. The reaction mixture was cooled, diluted with 100 mL of water and extracted with ethyl acetate (2×75 mL). The combined ethyl acetate solution was washed again with water (2×75 mL), brine, dried, filtered and concentrated under reduced pressure. The compound was purified by column chromatography on silica gel (100 g) using 5% methanol in dichloromethane to afford 0.77 g (77% yield). 0.2 g of this sulfide in 2 mL of dichloromethane was stirred with 0.62 mL (1.2 eq) of 1 M HCl/Ether for 30 minutes. The solvent was evaporated to afford 206 mg of the desired HCl salt of 2-(4-tetrahydrothiopyranylamino)-6-(2-chlorophenyl)-8-methyl-8H-pyrido[2,3-d]pyrimidin-7-one, (mass spec. MH$^+$=387, mp 232.1–233.1° C.).

Example 79

2-(S-oxo-4-tetrahydrothiopyranylamino)-6-(2-chlorophenyl)-8-methyl-8H-pyrido[2,3-d]pyrimidin-7-one

2-(S,S-dioxo-4-tetrahydrothiopyranylamino)-6-(2-chlorophenyl)-8-methyl-8H-pyrido[2,3-d]pyrimidin-7-one

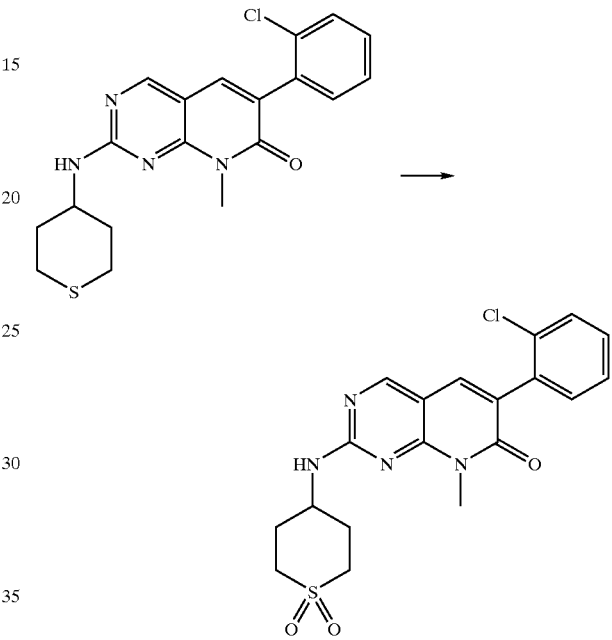

To a cooled (5° C.) solution of 0.2 g (0.5 mmol) of the sulfide in 50 mL of dichloromethane was added 0.13 g (0.57 mmol) of 77% 3-chloroperbenzoic acid. After 15 min, TLC of an aliquot of the reaction showed the sulfide was completely converted to the sulfoxide (n=1) and trace of the sulfone (n=2). An additional 0.04 g of 77% 3-chloroperbenzoic acid was added and the mixture was stirred for another 30 minutes as more sulfoxide was converted to the sulfone. The mixture was poured into aqueous 10% sodium bisulfite solution and extracted with dichloromethane. The organic solution was washed with aqueous 10% sodium bicarbonate solution and then brine, dried, filtered, and concentrated. Purification and separation of sulfoxide and sulfone was done on three 20×40 cm preparative TLC SiO$_2$ plates eluting with 5% methanol in dichloromethane. 68 mg of the sulfoxide (racemate) was recovered and dissolved in 3 mL of dichloromethane. 0.25 mL of 1 M HCl/Ether was added and the suspension was stirred for 30 minutes. Solvent was evaporated under reduced pressure to afford 70 mg of the HCl salt of the desired sulfoxide. (mass spec. MH$^+$=403, m.p.205.6–207.3° C.)

From the preparative TLC plates were also recovered 0.15 g of the sulfone (Higher R$_f$). This was dissolved in 3 mL of dichloromethane and 0.54 mL of 1 M HCl/Ether was added. The suspension was stirred for 30 minutes, filtered and washed with ether to afford 122 mg of the HCl salt of the desire sulfone. (Mass spec. MH$^+$=419, m.p).

Example 80

This example illustrates an alternative method for producing 6-(2-chlorophenyl)-8-methyl-2-methylthio-8-hydropyridino[2,3-d]pyrimidin-7-one (VI)

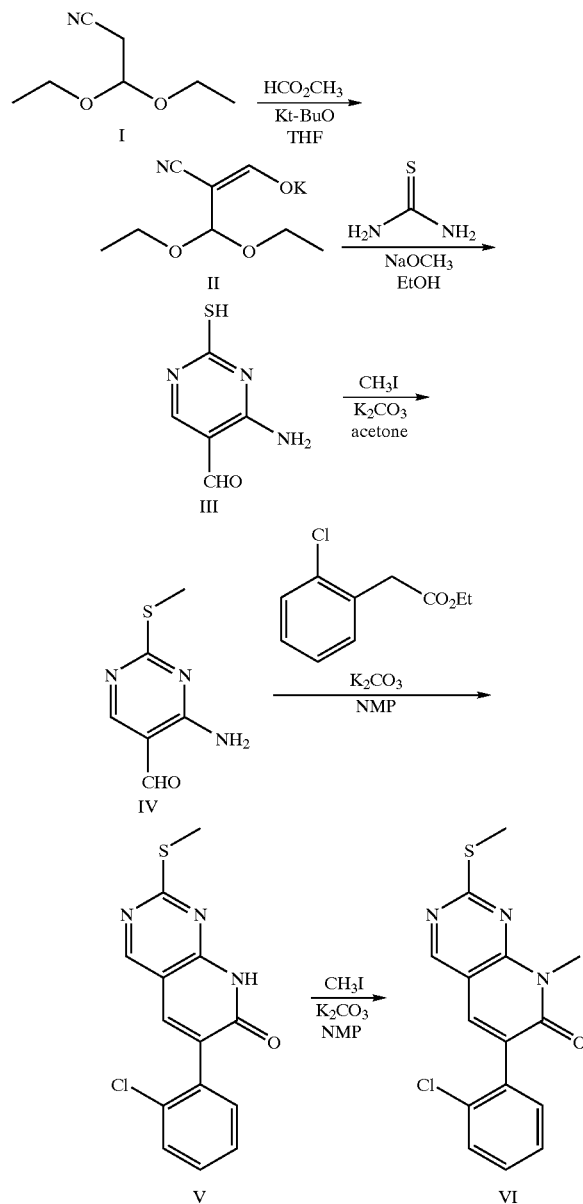

Preparation of 3,3-Diethoxy-2-formylpropionitrile Potassium Salt (II)

To a stirred solution of 3,3-diethoxypropane-nitrile (I, 283.80 g, 1.98 moles) and methyl formate (148.80 g, 2.48 moles) in anhydrous THF (1.1 L) at 10° C. was added 1.0 M potassium tert-butoxide in THF (2.2 L, 2.2 moles). Temperature was maintained in the range of 10° C. to 15° C. throughout the 45 minute addition. Following the addition, the resulting slurry was stirred 2 hours at ambient room temperature. Hexane (400 mL) was then added and stirring was continued for another 20 min. The slurry was filtered and the cake washed with 1/1 hexanes/THF and dried overnight at 60° C. in a vacuum oven. The yield of pale tan powder was 302.5 grams (73.0%). $^1$H-NMR (CD$_3$OD) was consistent with the desired structure II.

Preparation of 4-Amino-2-sulfanylpyrimidine-5-carbaldehyde (III)

A slurry of thiourea (92.8 g, 1.22 moles) in ethanol (90 mL) was heated under reflux and vigorously stirred. To this slurry was added a suspension of 3,3-diethoxy-2-formylpropionitrile potassium salt II (222.20 g, 1.06 moles) in 25% sodium methoxide/methanol (85.5 mL, 0.37 mole) and ethanol (285 mL) in five aliquots over a 10 minute period while maintaining reflux conditions (alternatively, the latter slurry may be heated to 50° C. to give a homogenous solution for the addition). An additional portion of ethanol (150 mL) was added to facilitate stirring. The thick slurry became a bright yellow color following the addition and was held under reflux for an additional 1 hour. The mixture was then cooled and evaporated to near dryness on a rotoevaporator. The residue was dissolved in water (940 mL). Crude product was precipitated from solution by the addition of 30% acetic acid (280 mL) and isolated via filtration using a medium frit sintered glass filtration funnel. The cake was washed with water (800 mL). Purification via trituration in hot water (1 L) for 30 minutes, followed by cooling and filtration gave 118.9 grams (72.3%) of product as a bright yellow solid after drying overnight at 60° C. in a vacuum oven (subsequent preparations have demonstrated that this trituration is unnecessary). An HPLC gave purity as 98.67%. $^1$H-NMR (DMSO-d$_6$) was consistent with desired structure III.

Preparation of 4-Amino-2-methylthiopyrimidine-5-carbaldehyde (IV)

To a solution of 4-amino-2-sulfanyl-pyrimidine-5-carbaldehyde III (100.00 g, 644.4 mmoles) and 325 mesh potassium carbonate (178.10 g, 1.29 moles) in acetone (1.5 L) was added iodomethane (128.10 g, 902.2 mmoles) dropwise over 20 minutes with mild cooling. The mixture was stirred at ambient room temperature over the weekend. TLC showed remaining III and an additional aliquot of iodomethane was added (8 mL) and stirring was continued overnight. TLC again showed some III remaining and an addition portion of iodomethane was added (8 mL) and stirring was continued another 24 hour period. An HPLC showed 95.9% S-alkylated product and 3.7% of compound III. The reaction mixture was stripped to near dryness on a rotoevaporator. Water (1 L) was added to the residue and the product was collected via filtration and washed with water (200 mL). The product was dried overnight in a vacuum oven at 60° C. Yield was 103.37 grams (94.8%). An HPLC showed 95.8% IV and 4.2% III.

Preparation of 6-(2-chlorophenyl)-2-methylthio-8-hydropyridino[2,3-d]pyrimidin-7-one (V)

A mixture of IV (10.00 g, 59.1 mmoles), ethyl 2-(2-chlorophenyl)acetate (14.40 g, 71.8 mmoles), NMP (115 mL) and 325 mesh potassium carbonate (29.00 g, 209.8 mmoles) was heated at 95° C. overnight. The reaction mixture was cooled and diluted with water (800 mL). The resulting slurry was stirred overnight and filtered to isolate product (V). The filter cake was washed with water and dried at 60° C. in a vacuum oven overnight. Isolated yield was 14.9 grams (83.0%) of dark tan solid. Analysis by an HPLC showed 98.3% purity.

Preparation of 6-(2-Chlorophenyl)-8-methyl-2-methylthio-8-hydropyridino[2,3-d]pyrimidin-7-one (VI)

A mixture of V (0.25 g, 0.82 mmole), NMP (5 mL), potassium carbonate (0.11 g, 0.82 mmole), and iodomethane (0.14 g, 0.96 mmole) was stirred under nitrogen at ambient room temperature overnight. Water (15 mL) was added and stirring was continued for 24 hours. The slurry was filtered and the filter cake washed with water (10 mL). An HPLC showed 97.8% purity.

Example 81

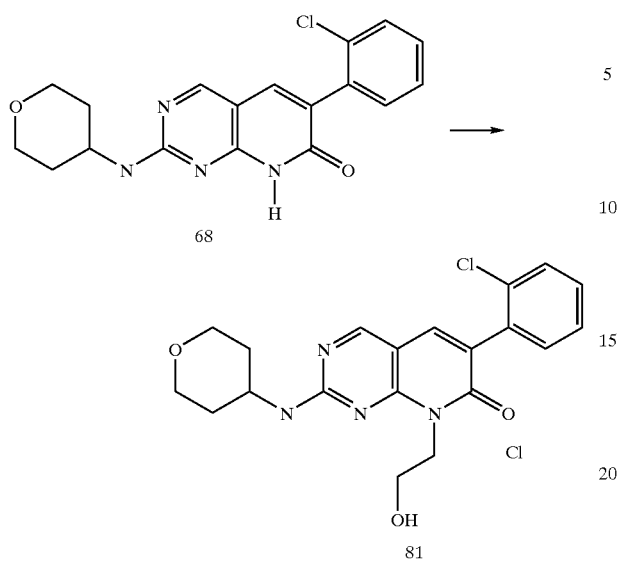

To pyridone 68 (1.6 g, 4.5 mmol) in NMP (10 mL) was added sodium hydride (188 mg, 4.7 mmol) and the mixture was stirred for 45 min followed by addition of (2-iodoethoxy) triisopropylsilane (1.62 g, 5 mmol). After 12 h the mixture was poured into water, extracted into ethyl acetate, dried over sodium sulfate concentrated under vacuum and the residue was by column chromatography on silica gel using 95:5 dichloromethane/methanol. The column fractions containing product were combined and concentrated in vacuo to a solid which was suspended in ethyl acetate. Addition of hydrochloric acid (1.0 M/Et$_2$O, 1.2 equivalents) gave the salt which was filtered and dried to give 262 mg of desired product. Mass spec. MH+=401, mpt.217–220.

Example 82

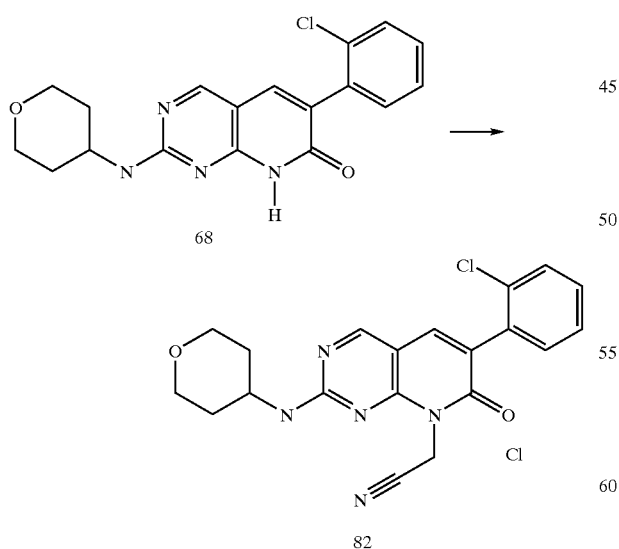

To pyridone 68 (500 mg, 1.4 mmol) in NMP (5 mL) was added sodium hydride (56 mg, 1.4 mmol) and the mixture was stirred for 45 min followed by addition of iodoacetonitrile (0.11 mL, 1.54 mmol). After 12 h the mixture was poured into water, extracted into ethyl acetate, dried over sodium sulfate concentrated under vacuum and the residue was by column chromatography on silica gel using 97:3 dichloromethane/methanol. The column fractions containing product were combined and concentrated in vacuo to a solid which was suspended in ethyl acetate. Addition of hydrochloric acid (1.0 M/Et$_2$O, 1.2 equivalents) gave the salt which was filtered and dried to give 62 mg of desired product. Mass spec. MH+=395, mpt.230.2–230.4.

Example 83

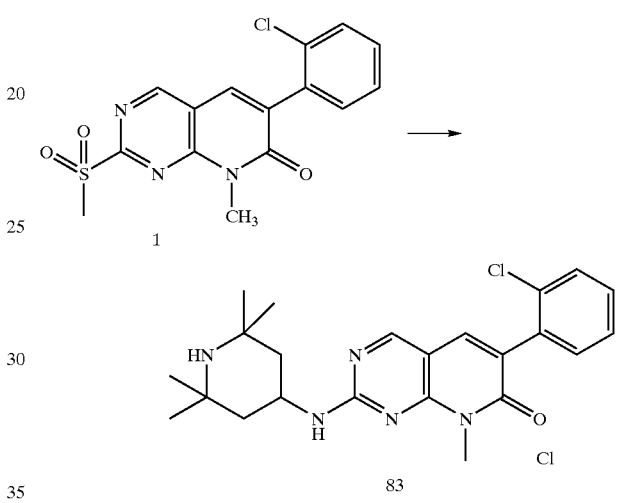

To sulfone 1 (0.4 g, 1.2 mmol) in NMP (1 mL) was added 4-amino-2,2,6,6-tetramethylpiperidine (0.74 mg, 4.7 mmol) and the mixture was stirred for 20 min at 75° C. The mixture was diluted with water (30 mL), and the suspension was stirred for 30 min. The solid was filtered and washed with 100 mL of water and 50 mL of ether. After air-drying for 30 minutes, 0.376 g of the desired product was obtained. To 0.27 g of this solid in 2 mL of dichloromethane was added hydrochloric acid (1.0 M/Et$_2$O, 1.2 equivalents), and the resulting salt was filtered and dried to give 264 mg of desired product. Mass spec. MH+=426, mpt.>300° C.

Example 84

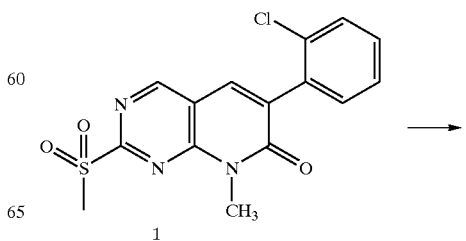

-continued

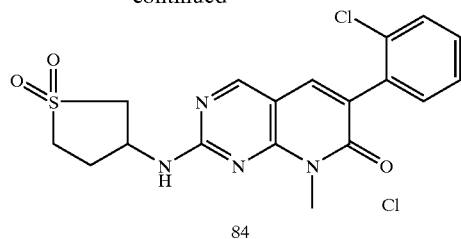

84

To sulfone 1 (0.16 g, 0.47 mmol) in NMP (1 mL) was added tetrahydro-3-thiophene amine 1,1-dioxide (0.19 g, 1.4 mmol) and the mixture was stirred for 30 min at 70° C. The mixture was diluted with water and the solid was filtered and washed with water and ether. The crude solid was then purified by column chromatography on silica gel using 5:95:0.01 methanol/dichloromethane/NH$_4$OH. The resulting solid was suspended in dichloromethane and hydrochloric acid (1.0 M/Et$_2$O, 1.2 equivalents) was added. The resulting salt was filtered and dried to give 150 mg of desired product. Mass spec. MH+=405, mpt.256–260.

Example 85

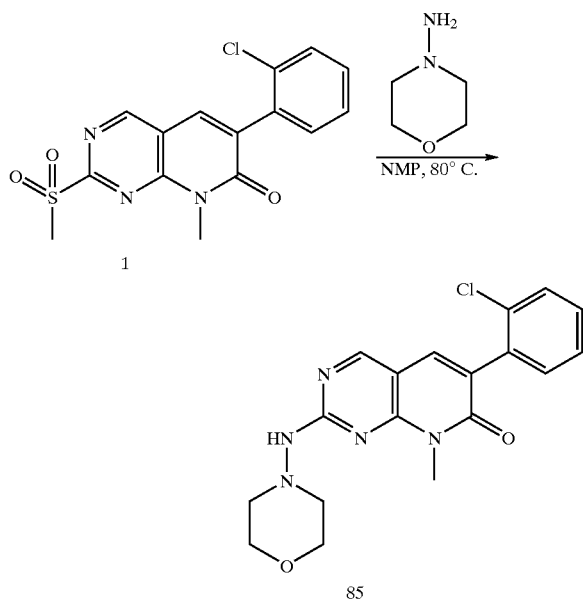

85

A mixture of sulfone 1 (105 mg, 0.3 mmoles) was and 4-aminomorpholine (0.3 mL, 3.0 mmoles) was stirred at 60° C. overnight. The reaction mixture was cooled and chromatographed on silica gel eluting with dichloromethane to give white powder (91 mg, (M+H)+=372, M.P.= 243.3–244.0° C.).

Example 86

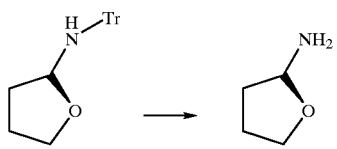

-continued

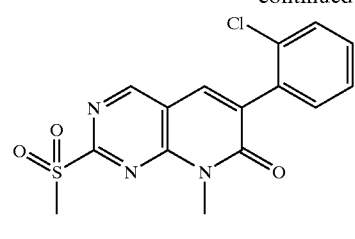

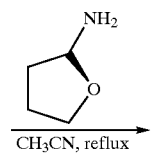

Step 1

A mixture of S-3-(N-tritylamino)tetrahydrofuran (prepared according to the literature procedure, Barlos, Kleomenis; Papaioannou, Dionysios; Patrianakou, Stella; Sanida, Chariklia; Tsegenidis, Theodoros; J.Chem.Soc-.Chem.Commun.; EN; 6; 1987; 474–475) (5.12 g, 0.0155 mol) and concentric hydrochloric acid (5 mL) was heated in ethanol (60 mL) to reflux for 15 min, and concentrated. The residue was stirred in hot ether (100 mL), filtered, washed with ether and dried in vacuo to afford (S)-3-aminotetrahydrofuran hydrochloride.

Step 2

A mixture of the sulfone 1 (1.877 g), (S)-3-aminotetrahydrofuran hydrochloride (0.66 g) and di-isopropyl amine (3.73 mL) was refluxed in dry acetonitrile (20 mL) until TLC indicated the sulfone was consumed. The solvent was removed, and residue was partitioned between ethyl acetate and brine. The organic layer was separated, dried and concentrated. The crude product was purified by column chromatograph on silica gel (1% MeOH/CH$_2$Cl$_2$) to yield the desired product (0.6 g). The product was dissolved in MeOH/CH$_2$Cl$_2$ and treated with 2 mL of 1 N HCl in ether, evaporated and dried to give the hydrochloride salt, MP 171.9–173° C., MS 357 (M+H).

Example 87

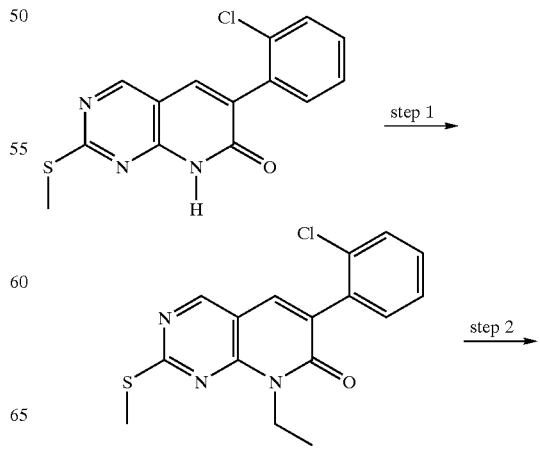

-continued

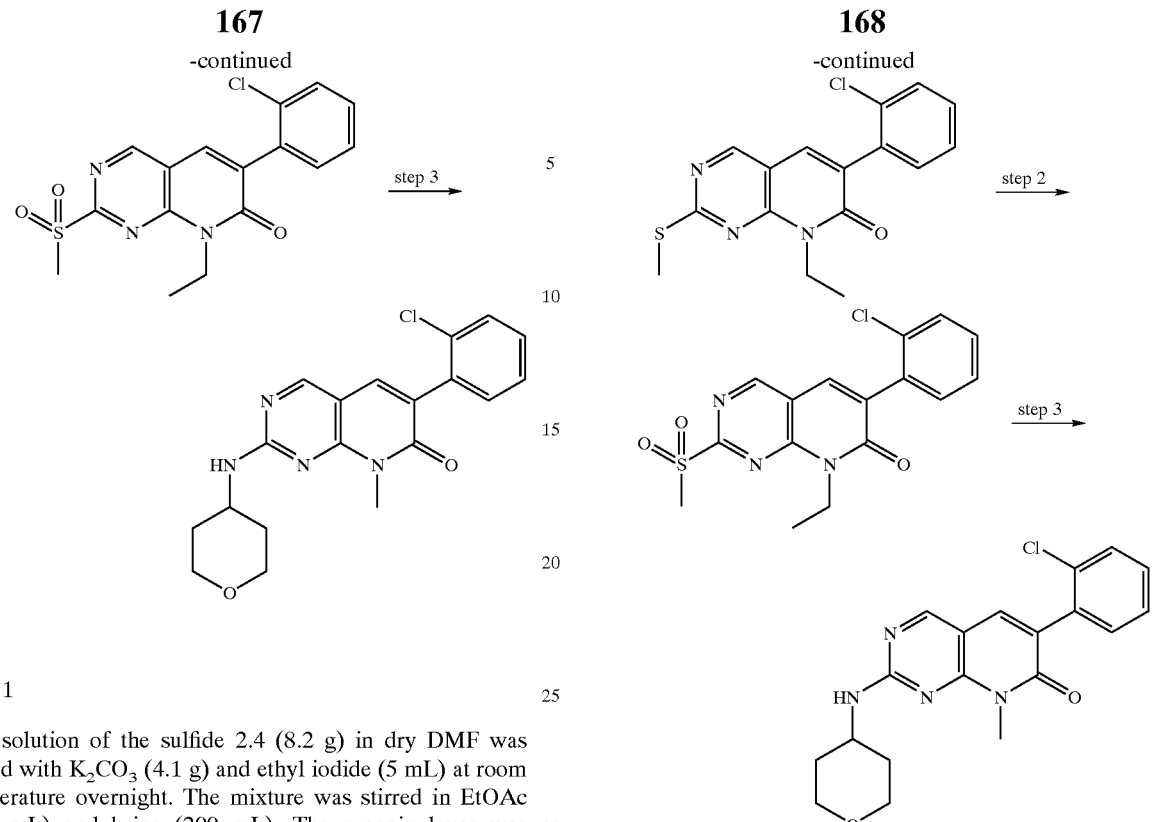

Step 1

A solution of the sulfide 2.4 (8.2 g) in dry DMF was stirred with K$_2$CO$_3$ (4.1 g) and ethyl iodide (5 mL) at room temperature overnight. The mixture was stirred in EtOAc (300 mL) and brine (200 mL). The organic layer was separated, washed with brine, dried and concentrated to give the crude product.

Step 2

To a solution of the above product in THF (170 mL) was added Oxone® (41 g) in water (170 mL) at 0–5° C. The mixture was stirred at room temperature for 4 h and diluted with EtOAc (600 mL) and water (200 mL). The organic layer was separated, washed with brine (3×), dried and concentrated to give the sulfone.

Step 3

A mixture of the sulfone (2.23 g) and 4-aminotetrahydropyran (1.17 g) in NMP (0.4 mL) was stirred at 120° C. for 1 h and then cooled to room temperature. Methanol (5 mL) was added and the mixture was stirred for 10 min. The solids were filtered and washed with cold methanol. The resulting solid was dissolved in CH$_2$Cl$_2$ and treated with 5 mL of 1–2 N HCl in methanol. After evaporation of the solvent, the residue was recrystallized from isopropanol/ethyl acetate to give the final product (1.45 g). MP 185.3–190.1° C.

Example 88

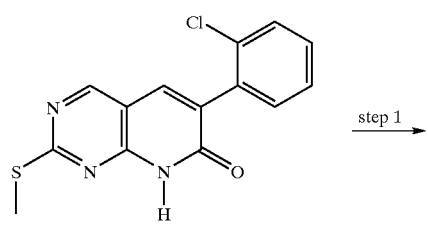

step 1

Step 1

A mixture of the sulfide (5.0 g), isobutyren oxide (3 mL) and potassium carbonate (2.6 g) in DMF (20 mL) was stirred at 80° C. overnight. Additional isobutyren oxide (1.0 mL) was added and the mixture was stirred for additional 8 h. After aqueuos workup with EtOAc and brine, 5.8 g of crude product was obtained.

Step 2

To the above sulfide (5.8 g) in THF (150 mL) at 0–5° C. was added a solution of Oxone® (3.5 g) in water (150 mL). The mixture was slowly warmed to room temperature and stirred for 4 hours. EtOAC (400 mL) was added and the layers were separated. The organic layer was washed with brine (3×200 mL), dried over sodium sulfate, filtered and concentrated to give the desired sulfone (6.0 g), which was used without purification in the next step.

Step 3

A mixture of the sulfone (5.0 g) and 4-aminotetrahydrothiopyran (2.4 g) in NMP (4 mL) was stirred at 100° C. for 1 h. Aqueous workup with EtOAc and brine gave the crude product, which was purified by column chromatograph (silica gel, 30–35% EtOAc/hexanes) to give 2.3 g of a solid. MP 105–108.5° C., MS 445 (M+H).

Step 4

To a solution of the above compound (2.3 g) in 90 mL of CH$_2$Cl$_2$ at 0–5° C. was added a solution of MCPBA (2.6 g) in 70 mL of CH$_2$Cl$_2$. The mixture was then stirred at room temperature overnight and concentrated. The residue was partitioned between EtOAc and brine. The organic layer was separated, washed with sat. NaHCO$_3$ (5×), dried, concentrated and purified by column chromatograph (silica gel, 2–3% MeOH/CH$_2$Cl$_2$). The product (1.3 g) was dissolved in CH$_2$Cl$_2$/EtOAc and treated with 3 mL of 1 M HCl in ether. The resulting solid was filtered, washed with ether, and recrystallized from MeOH/EtOH to give the hydrochloride salt (0.65 g), MP 223.72–230.2° C., MS 477 (M+H).

Example 89

Sulfone 89

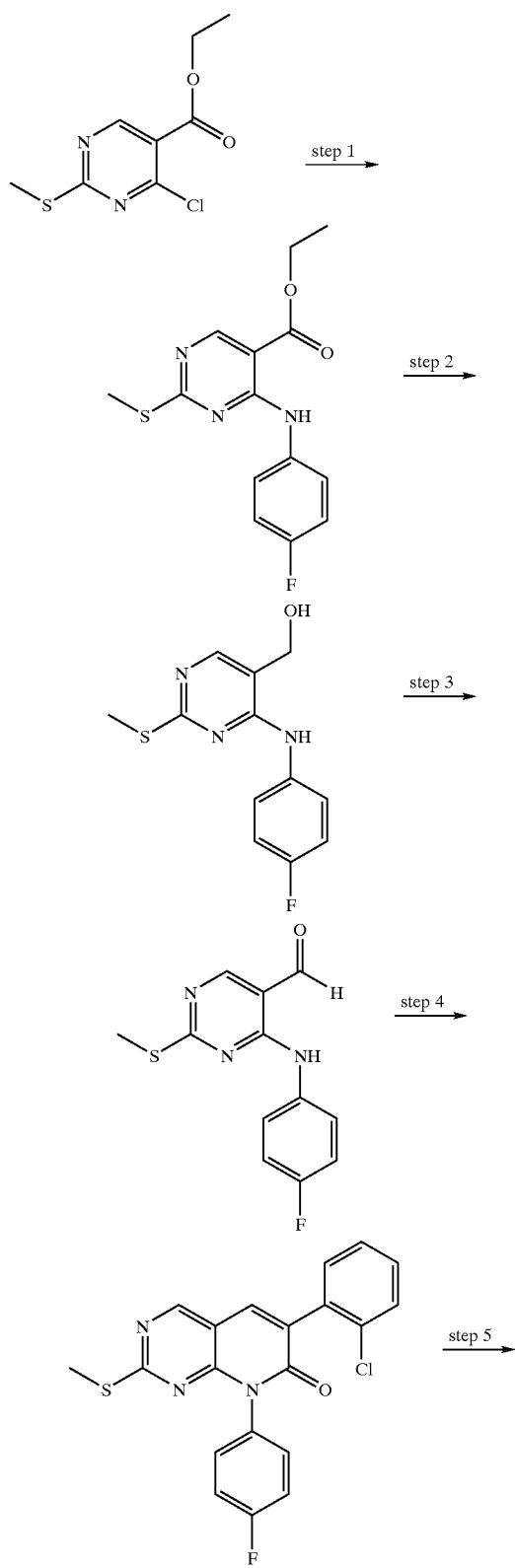

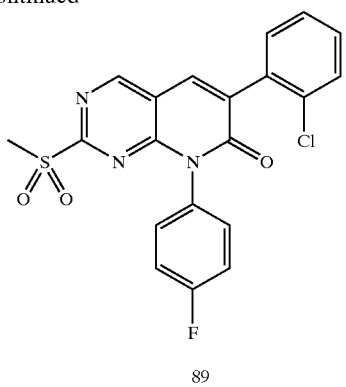

89

Step 1

To a solution of ethyl 4-chloro-2-methylthiopyrimidine-5-carboxylate (Aldrich, 24 g, 103 mmol) in 250 mL of acetonitrile at room temperature was added 4-fluoroaniline (22.75 g, 205 mmol). After stirring for two days, the mixture was heated at 60° C. for four hours. The resulting solid was filtered and washed with EtOAc. The filtrate was concentrated, diluted in EtOAc (300 L), washed with brine, dried (MgSO$_4$), filtered and concentrated to provide a crude product. The crude product was stirred with hexanes (400 mL) and then filtered to give 23 g of the ethyl 4-(4-fluorophenyl)amino-2-methylthiopyrimidine-5-carboxylate as a white solid.

Step 2

Lithium aluminum hydride (3.0 g) was stirred in dry tetrahydrofuran (300 mL) at 5° C. and treated dropwise with a solution of ethyl 4-(4-fluorophenyl)amino-2-methylthio-pyrimidine-5-carboxylate (22.5 g) in dry tetrahydrofuran (250 mL). The reaction mixture was stirred overnight at room temperature. Additional 1.0 M solution of lithium aluminum hydride in THF (55 mL) was added at 5° C. and the mixture was stirred for three hours at room temperature. Water (9 mL) was added dropwise and the resulting mixture was stirred for 30 minutes, after which an aqueous solution of sodium hydroxide (2M, 9 mL) was added dropwise, followed by water (12 mL). The resulting suspension was stirred for 17 hours at room temperature and then filtered. The filter residue was washed with tetrahydrofuran (2×, 100 mL) and the combined filtrate and washings were concentrated. The residue was suspended in ethyl acetate/hexane-1/2 (200 mL) and the solid was filtered and dried to provide 14 g of 4-(4-fluorophenyl)amino-2-methylthiopyrimidine-5-methanol as a yellow solid.

Step 3

A solution of 4-(4-fluorophenyl)amino-2-methylthiopyrimidine-5-methanol (14.5 g) in 260 mL of dichloromethane was treated with manganese dioxide (58 g). The resulting suspension was stirred for 5 hours and filtered through celite. The filter residue was washed with dichloromethane (100 mL) and the combined filtrate and washings were concentrated to give a solid. The solid was stirred with ether (100 mL) and filtered to give 8.6 g of the 4-(4-fluorophenyl)amino-2-methylthiopyrimidine-5-carboxaldehyde as a white solid.

Step 4

The aldehyde (8.6 g, 0.033 mol), ethyl o-chlorophenylacetate (8 g) and 1,3,4,6,7,8-hexahydro-2H-pyrimido[1,2a]pyrimidine polymer bound (base from Aldrich, 2.5 g) were mixed in NMP (60 mL) and stirred at 120° C. for 4 days. Additional 1.4 g of the base was added and the mixture was stirred at 120° C. for additional 3 days.

The reaction mixture was cooled to room temperature, filtered through a pad of celite and washed with NMP (10 mL). The filtrate was poured to water (600 mL) and extracted with EtOAc (3×500 mL). The organic layers were combined, washed with brine (3×), dried over Na2SO4, filterd and concentrated. Trituation of the resulting solid with hot ether gave the product (6.5 g).

Step 5

To a solution of the above sulfide (6.4 g) in THF (70 mL) was added solution of Oxone™ (27.3 g) in water (90 mL) at 0–5° C. The mixture was then stirred at room temperature for 5 h and diluted with EtOAc (600 mL) and water (250 mL). The organic layer was separated, washed with brine (3×), dried over $Na_2SO_4$, filtered and concentrated to give the sulfone 89 (5.5 g). MP 115.5–117° C., MS 430 (M+H).

Example 90

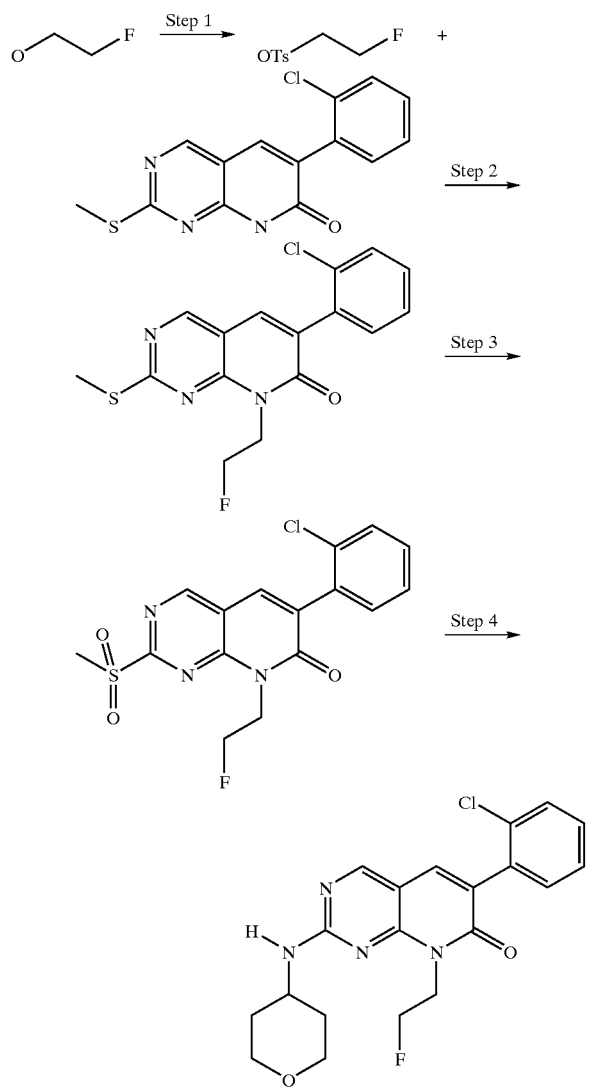

Step 1

To a solution of 2-fluoroethanol (13.85 g, 216.2 mmol, Aldrich Chemicals) and pyridine (50 mL) in dichloromethane (50 mL) with stirring at 0° C. was added toluenesulfonyl chloride (61.9 g, 1.5 equivalents). The resulting mixture was stirred for five hours at 0° C. and then kept in a fridge overnight. The next day the reaction was quenched with 150 mL of ice-water, removed dichloromethane and pyridine under reduced pressure at 0° C. and diluted with ethyl acetate (600 mL). The aqueous layer was separated and extracted with ethyl acetate (1×200 mL). The organic layers were combined, washed with 0.5 N HCl (3×200 mL) until pH=2, washed with saturated sodium bicarbonate (2×200 mL) and brine (1×200 mL), dried over magnesium sulfate, filtered and concentrated to yield a colorless oil which crystallized upon standing to give the tosylate (46.5 g, $M^+$=218) as a white powder.

Step 2

To a 0° C. solution of the sulfide 2.4 (4.06 g, 13.4 mmol) in DMF (200 mL) was added 60% NaH dispersion in oil (0.59 g, 1.1 equivalents). The resulting mixture was stirred at 0° C. for 30 minutes and a solution of the above tosylate (3.8 g, 1.3 equivalents) in DMF (25 mL) was added dropwise. The resulting mixture was stirred from 0° C. to room temperature overnight and then diluted with ethyl acetate (600 mL) and water (200 mL). The organic layer was separated, washed with water (3×200 mL), saturated sodium bicarbonate (1×200 ml) and brine (2×200 mL), dried over magnesium sulfate, filtered and concentrated to give a semi-solid material (9.16 g). Hexanes (400 mL) were added to the crude material and stirred for 15 minutes. The solvent was decanted, and the residue was concentrated to give the N-monofluoroethyl compound (4.92 g, $(M+H)^+$=350, M.P.= 114.7–118.1° C.) as a tan powder.

Step 3

To a 0° C. solution of the N-monofluoroethyl compound above (4.8 g, 13.4 mmol) in tetrahydrofuran (75 mL) was added dropwise a solution of Oxone® (20.6 g, 2.5 equivalents) in water (75 mL). After addition was complete, the ice bath was removed and the resulting mixture was stirred at room temperature for seven hours, then kept at 0° C. overnight. The reaction was stirred an addition 5 hours at room temperature, then diluted with ethyl acetate (600 mL) and water (250 mL). The organic layer was separated, washed with water (3×250 mL) and brine (1×250 mL), dried over magnesium sulfate, filtered and concentrated to give the desired sulfone (5.4 g,$(M+H)^+$=382, M.P.=156.0–168.0° C.) as a tan-yellowish powder.

Step 4

A mixture of the sulfone above (2.7 g, 7.07 mmol), 4-amino-tetrahydropyran (2.15 g, 3 equivalents) and NMP (2.7 mL) was stirred at 110° C. for 3.5 hours. Then the heat and stirring were turned off and the mixture was left to stand overnight. The next day, ethyl acetate (180 mL) and water (65 ml) were added and the layers were partitioned and then separated. The organic layer was washed with water (2×65 mL) and brine (1×65 mL), dried over magnesium sulfate, filtered and concentrated to give 2.6 g of the crude product. Purification by column chromatography on silica gel eluting with 25% ethyl acetate in hexanes afforded the free amine (1.267 g, $(M+H)^+$=403). The free amine was taken up in dichloromethane (50 mL) and with stirring was added 1M HCl in diethyl ether (4.5 mL, 1.5 equivalents). The resulting mixture was stirred for 5 minutes and then the solvent was removed under reduced pressure at 55° C. Drying under high vacuum at 56° C. for 24 hours gave the desired compound (1.247 g, $(M+H)^+$=403) as the HCl salt.

Example 91

Sulfide hydrazide 91

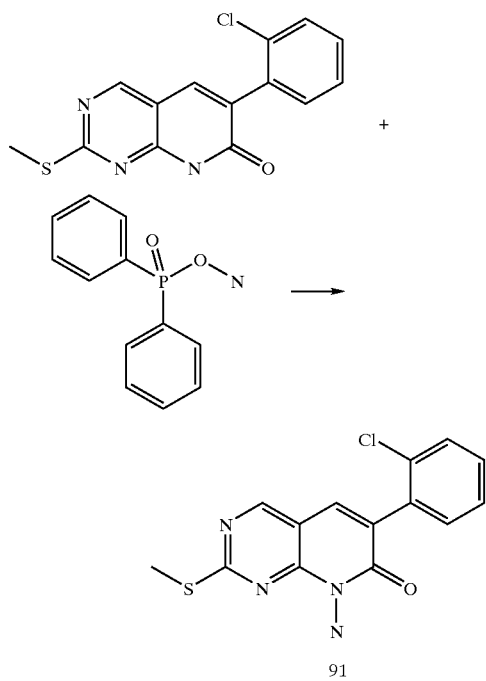

To a solution of sulfide 2.4 (2.10 g, 6.59 mmol) in DMF (60 mL) at 0° C. was added a 60% dispersion of sodium hydride in oil (266 mg, 1.0 equivalents). The resulting mixture was stirred at 0° C. for 30 minutes, then diphenyl phosphinyl-O-hydroxylamine (Tet. Let., vol 23, No. 37, 3835–3836, 1982) (1.854 g, 1.26 equivalents) was added in one portion. After 1 minute, a voluminous precipitate formed and an additional 100 mL of DMF was added to allow stirring. Stirred for 1 hour and the reaction was poured into ethyl acetate (700 mL) and water (200 mL) mixture. The aqueous layer was separated and extracted with ethyl acetate (125 mL). The combined ethyl acetate layers were washed with water (5×150 mL) and brine (1×150 mL), dried over magnesium sulfate, filtered and concentrated to give the sulfide hydrazide (2.3 g, M.P.=183.4–184.2° C., (M+H)$^+$= 319) as an off-white powder.

Example 92

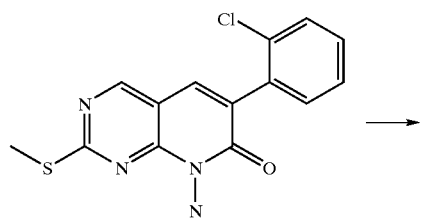

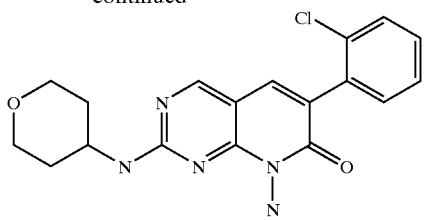

The sulfide hydrazide 91 (250 mg, 0.78 mmol) and 4-amino-tetrahydropyran (397 mg, 5 equivalents) were combined and stirred at 150° C. for 10 hours. The reaction mixture was cooled to room temperature and diluted with ethyl acetate (35 mL) and water (25 mL). The organic layer was separated, washed with water (2×25 mL) and brine (1×25 mL), dried over magnesium sulfate, filtered and concentrated to give the crude product (300 mg). Purification by preparative TLC eluting with 5% methanol in dichloromethane afforded the free amine (209 mg, M.P.= 117.4–121.3° C., (M+H)$^+$=372.1). The free amine (200 mg, 0.538 mmol) was taken up in dichloromethane (5 mL) and ethyl acetate (20 mL). To this solution was added 1 M HCl in diethyl ether (0.8 mL, 1.5 equivalents) and stirred for 2 hours. The solvent was remove under reduced pressure at 55° C. and dried under vacuum at 56° C. for 24 hours to give the desired compound (171 mg, M.P.=207.1–215.9° C., (M+H)$^+$=372) as an off-white powder.

Example 93

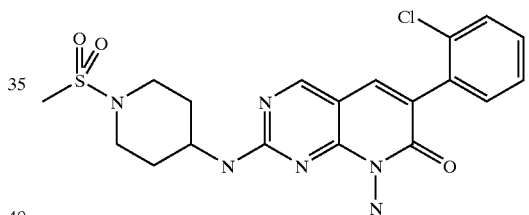

Step A: Preparation of benzyl 1-benzylpiperidin-4-ylcarbamate

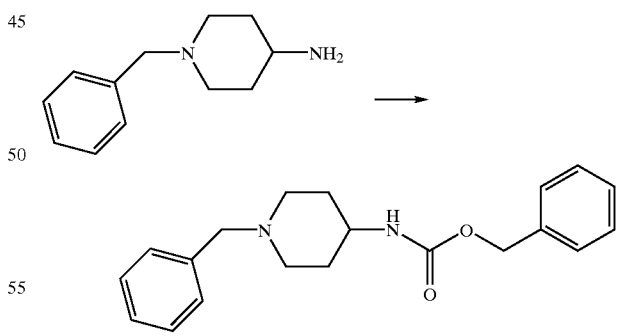

To a 0° C. solution of 4-amino-1-benzylpiperidine (41.2 g, 216.5 mmol) and triethylamine (51.3 mL, 369 mmol) in 600 mL of tetrahydrofuran was added benzyl chloroformate (31 mL, 217 mmol) dropwise over a period of 30 to 45 min. at such a rate that the reaction temperature was kept between 5° C. and 10° C. After the addition was complete, the reaction mixture was allowed to warm to room temperature and stir for 12 hours. The solvent and volatiles were removed under reduced pressure. Water (500 mL) and ethyl acetate (1.2 L) were then added and the phases were separated. The organic layer was washed with saturated aqueous sodium bicarbonate solution (2×, 150 mL) and brine, dried over MgSO₄, filtered and concentrated to yield a tan liquid which was purified via column chromatography (SiO₂, EtOAc/Hexane-30/70 to EtOAc-100) to provide 27.8 g of the amine as a white solid (mass spec. M+=324, MP=79.1–79.6° C.).

Step B: Preparation of benzyl piperidin-4-ylcarbamate

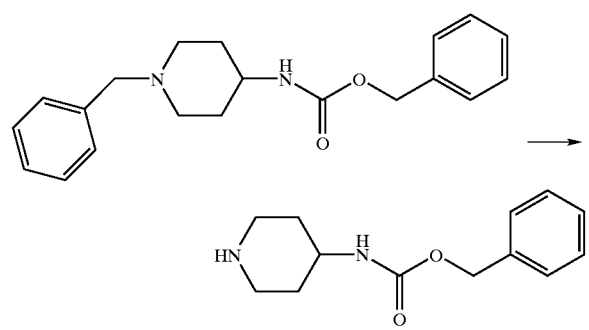

To a solution of benzyl amine (27.8 g, 85.7 mmol) in 400 mL of methylene chloride at room temperature was added dropwise a solution of 1-chloro-ethylchloroformate (25.4 g, 178 mmol) in 50 mL of methylene chloride via an addition funnel. After addition was complete, the reaction mixture was stirred at room temperature for 3 hours. The solvent and volatiles were removed under reduced pressure and methanol (500 mL) was added. The reaction mixture was heated to reflux with stirring for 1 hour, cooled to room temperature and concentrated to yield 26.3 g of the piperidine as an off-white solid (mass spec. M+1=235, MP=190.7–192.2° C.).

Step C: Preparation of benzyl 1-(methylsulfonyl)piperidin-4-ylcarbamate

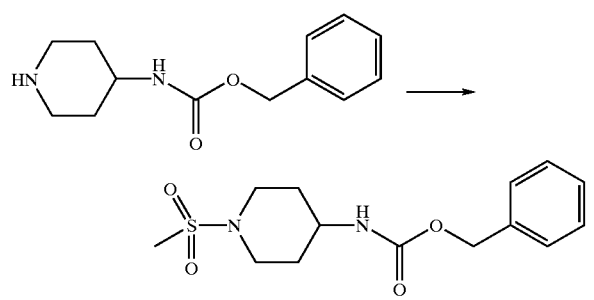

The protected piperidine (10 g, 42.7 mmol) and triethylamine (12 mL, 86.7 mmol) was dissolved in 500 mL of methylene chloride at room temperature. Methane sulfonyl-chloride (4.3 mL, 55.5 mmol) in 20 mL of methylene chloride was added dropwise via an addition funnel. The reaction mixture was stirred at room temperature for 3 hours. The solvent and volatiles were removed under reduced pressure. Ethyl acetate (500 mL) and an aqueous solution of hydrochloric acid (0.5M, 350 mL) were added to the reaction mixture and the two phases were separated. The organic layer was washed with an aqueous solution of hydrochloric acid (0.5 M, 2×100 mL), saturated aqueous sodium bicarbonate solution (3×100 mL) and brine, dried over MgSO₄, filtered and concentrated to provide 9.2 g of the methane sulfonamide (MP=148.6–152.8° C.).

Step D: Preparation of 1-(methylsulfonyl)piperidin-4-amine

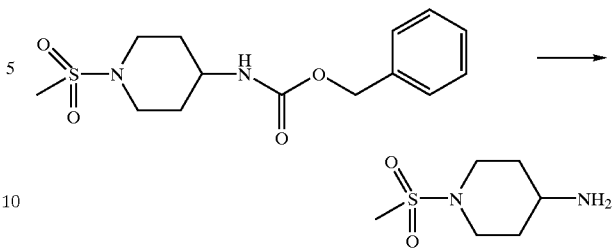

To a solution of methane sulfonamide (9.2 g, 29.5 mmol) in 200 mL of tetrahydrofuran at room temperature in a 500 mL round-bottomed flask under a nitrogen atmosphere was added palladium on Carbon (10%, 2–3 g). The reaction vessel was flushed with hydrogen gas (3×). A balloon of hydrogen gas was put on the reaction flask and the solution was stirred for 15 hours (more catalyst added and the hydrogen balloon was refilled as necessary). Methylene chloride (100 mL) was added to the reaction and it was filtered through a celite pad. Filtrate was concentrated to provide 4.63 g of the desired amine (mass spec. M+1=179, MP=65.3–65.7° C.).

Step E

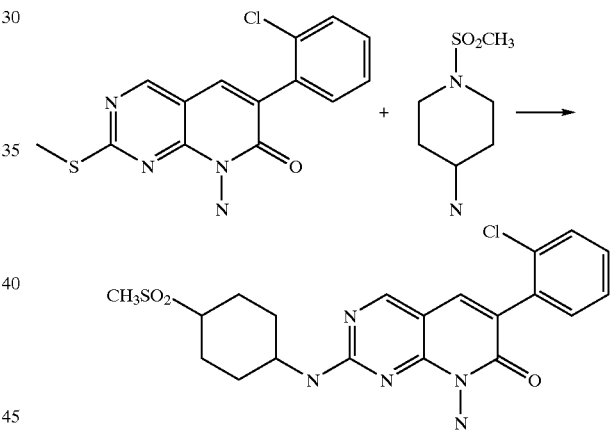

A mixture of the sulfide hydrazide 91 (255 mg, 0.8 mmol), 4-amino-1-methanesulfonylpiperidine (200 mg, 1.4 eq) and NMP (0.3 mL) was stirred at 150° C. for 2 days. The resulting mixture was diluted with methanol (8 mL), ethyl acetate (180 mL) and water (65 mL). The organic layer was separated, washed with water (2×60 mL) and brine (1×60 mL) and concentrated to give 640 mg of the crude product. Purification by preparative TLC eluting with 8% methanol in dichloromethane gave the free amine (180 mg, M.P.= 180.0–194.0° C., (M+H)⁺=449).

To a solution of the free amine (180 mg, 0.40 mmol) in ethyl acetate (150 mL), dichloromethane (20 mL) and methanol (3 mL) was added 1 M HCl in diethyl ether (0.6 mL, 1.5 equivalents). The resulting mixture was stirred for 2 hours and then the solvent was removed under reduced pressure. The residue was dried under high vacuum at 56° C. for 18 hours to give the desired compound (168 mg, M.P.= 180.7–213.2° C., (M+H)⁺=449) as an off-white powder.

Example 94

1,1-Dioxo-4-aminothiopyran

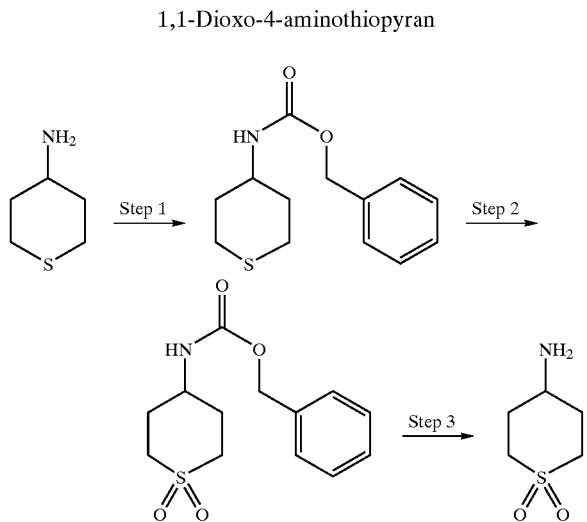

Step 1

To a 0° C. mixture of 1.0 N NaOH (25 mL, 25 mmol) and 4-aminotetrahydrothiopyran (2.34 g, 20 mmol) was added dropwise benzylchloroformate, 3.14 mL (22 mmol). The reaction mixture was stirred at room temperature for 1 hour, filtered, washed 2 times with water, stirred with hexane, filtered and dried in a vacuum oven to yield 4.4 g of the carbamate as a white solid. (M+H)$^+$ 252

Step 2

To a solution of the carbamate (40 g, 159 mmol) in dichloromethane was added 3-chloroperoxybenzoic acid (75%, 75 g, 320 mmol) in portions over an hour. The reaction mixture was stirred for 12 hours, filtered, washed 2 times with a 10% solution of sodiun sulfite, washed 3 times with a 10% solution of sodium bicarbonate, dried with magnesium sulfate, and concentrated under reduced pressure to give the sulfone (37.5 g). M$^+$=283

Step 3

To a mixture of the sulfone (3.0 g, 10.6 mmol) in 50 mL of ethanol was added 5% palladium on carbon (300 mg). The reaction mixture was hydrogenated using a Paar hydrogenator at 40 psi for 8 hours. The resulting solution was filtered through celite, and the filtrate was concentrate to give 1.5 g of the amine. (M+H)$^+$ 150

Example 95

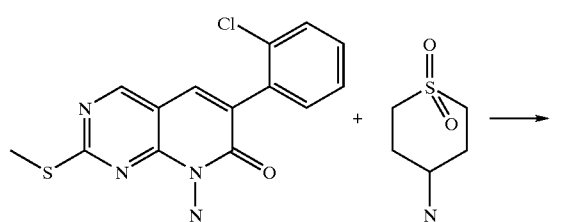

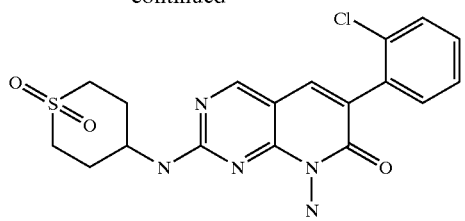

A mixture of the sulfide hydrazide 91 (660 mg, 2.07 mmol), the amino-sulfone (500 mg, 2 equivalents), and NMP (0.5 mL) was stirred at 150° C. for 3 days. By TLC, there was still significant starting material present so additional amino-sulfone (200 mg, 1.34 mmol) was added and the mixture was stirred for one more day. By TLC, there was no more starting material remaining. The reaction mixture was cooled to room temperature, diluted with methanol (230 mL) and dichloromethane (150 mL) and 10 g of silica gel was added. The mixture was concentrated, and the residue was loaded onto a Flash Column (silica gel, 20 g) and eluted with 1% methanol in dichloromethane to give 623 mg of an impure product. This mixture was further purified on preparative TLC eluting with neat ethyl acetate to give the free amine (70 mg, (M+H)$^+$=420). The free amine (70 mg, 0.17 mmol) was taken up in dichloromethane (10 mL) and methanol (10 mL) and then 1 M HCl in diethyl ether (0.3 mL, 1.5 equivalents) was added. The resulting mixture was stirred for 5 minutes, concentrated and dried under high vacuum at 56° C. for 16 hours to afford the desired product (62 mg, M.P.=240.0–243.0° C.) as an off-white powder.

Example 96

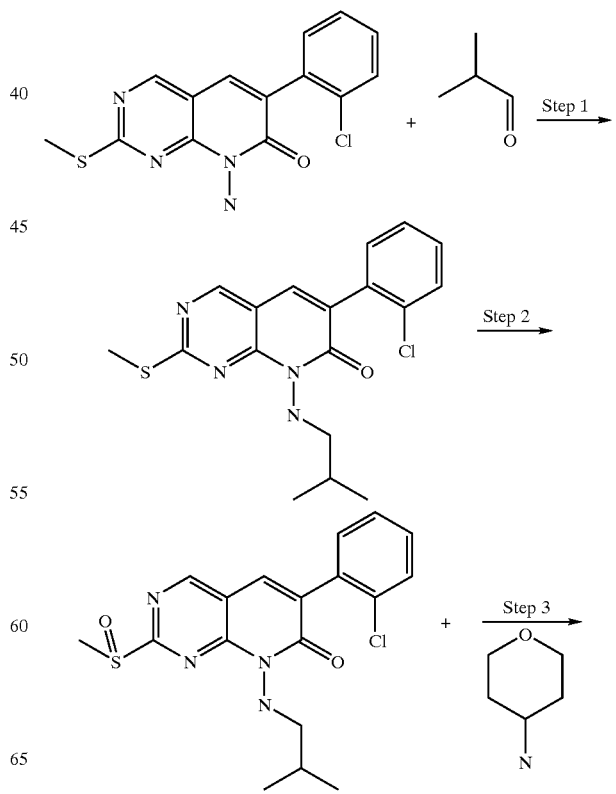

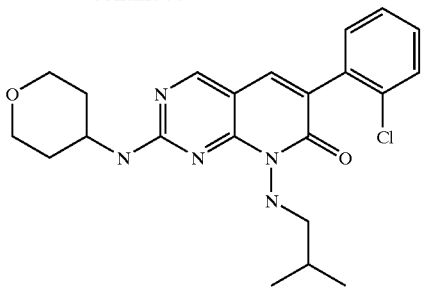

Step 1

To a solution of the sulfide hydrazide 91 (291 mg, 0.913 mmol) in methanol (30 mL) and acetic acid (10 mL) was added isobutyraldehyde (0.11 mL, 1.3 equivalents) followed by sodium cyanoborohydride (58 mg, 1 equivalent). The resulting mixture was stirred at room temperature for 40 minutes and then diluted with ethyl acetate (175 mL). The organic layer was separated, washed with saturated sodium bicarbonate (4×60 mL) until basic and with brine (1×60 mL), dried over magnesium sulfate, filtered and concentrated to give 400 mg of the crude product. Purification by Preparative TLC, eluting with 20% ethyl acetate in hexanes, afforded the N-alkylated sulfide hydrazide (319 mg, $(M+H)^+=375$) as an off-white foamy powder.

Step 2

To a 0° C. solution of the N-alkylated sulfide hydrazide (319 mg, 0.85 mmol) in tetrahydrofuran (15 mL) was added dropwise a solution of Oxone® (523 mg, 1 equivalent) in water (15 mL). The resulting mixture was gradually warmed to room temperature over a four hour period and then diluted with ethyl acetate (300 nmL). The organic layer was separated, washed with water (4×150 mL) and brine (1×50 mL), dried over magnesium sulfate, filtered and concentrated to give the desired compound as an off white foam (308 mg, $(M+H)^+=391$).

Step 3

A mixture of the N-alkylated sulfoxide hydrazide (300 mg, 0.768 mmol), 4-amino-tetrahydropyran (233 mg, 3 equivalents) and NMP was stirrred at 80° C. for 35 minutes. The reaction mixture was cooled to room temperature and diluted with ethyl acetate (90 mL). The organic layer was separated, washed with water (3×25 mL) and brine (1×25 mL), dried over magnesium sulfate, filtered and concentrated to give 327 mg of the crude product. Purification by preparative TLC, eluting with 5% methanol in dichloromethane, gave the free amine. The free base was then dissolved in dichloromethane (20 nmL) and 1 M HCl in diethyl ether (1.15 mL, 1.5 equivalents) was added at room temperature. The resulting mixture was stirred for two minutes and then the solvent was removed under reduced pressure. Drying the residue under high vacuum at 56° C. for 24 hours gave the desired compound (239 mg, M.P.= 111.3–117.5° C., $(M+H)^+=428$) as an off-white powder.

Example 97

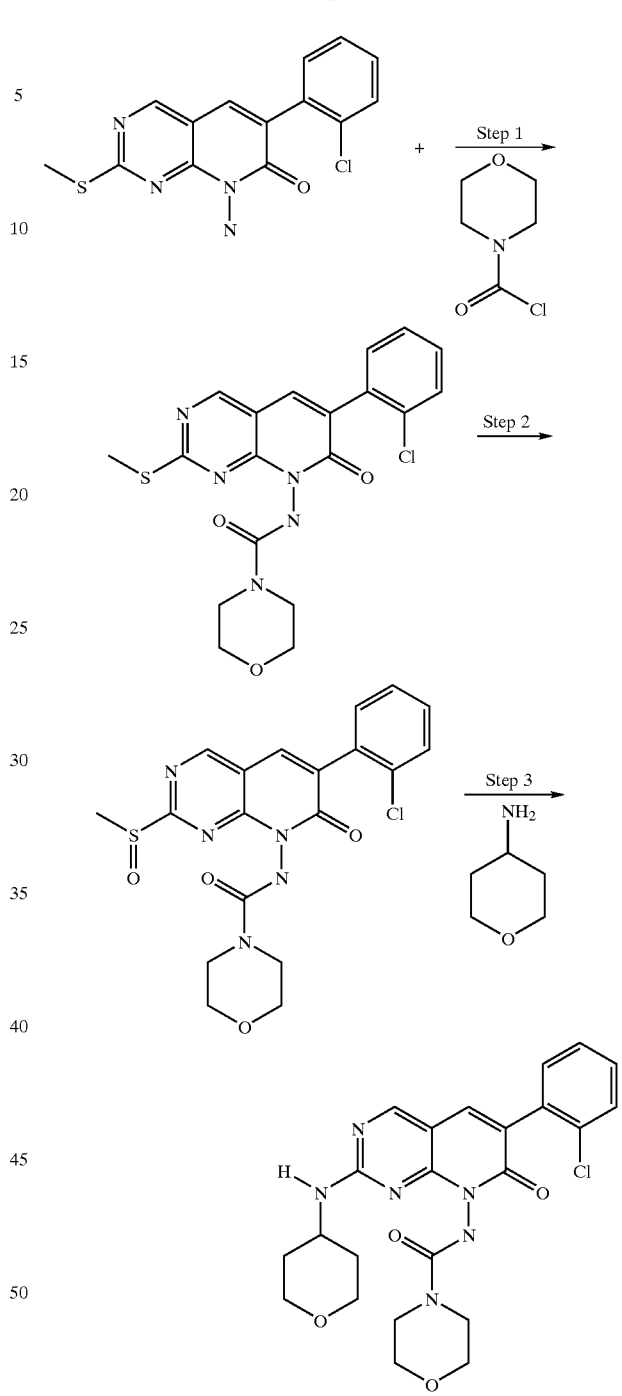

Step 1

A mixture of the sulfide hydrazide 91 (500 mg, 1.57 mmol) and 4-morpholine carbonyl chloride (0.5 mL, 2.6 equivalents) in pyridine (40 mL) was stirred at 90° C. for 7 hours. Pyridine was removed under reduced pressure at 50° C., and the residue was diluted with ethyl acetate (175 mL). The organic layer was washed with dilute HCl/brine (3×75 mL) and brine (75 mL), dried over magnesium sulfate, filtered and concentrated to give the N-acylated sulfide hydrazide ($(M+H)^+=432$) in quantitative yield.

Step 2

To a 0° C. solution of the N-acylated sulfide hydrazide (0.785 mmol) in tetrahydrofuran (15 mL) was added dropwise a solution of Oxone® (483 mg, 1 equivalent) in water (15 mL). The resulting solution was gradually warmed to room temperature over a four hour period and diluted with ethyl acetate (175 mL) and water (50 mL). The organic layer was separated, washed with water (3×50 mL) and brine (1×50 mL), dried over magnesium sulfate, filtered and concentrated to give the N-acylated sulfoxide hydrazide (209 mg, (M+H)$^+$=448) as a foam.

Step 3

A mixture of the N-acylated sulfoxide hydrazide (209 mg, 0.0468 mmol), 4-amino-tetrahydropyran (142 mg, 3 equivalents) and NMP was stirred at 90° C. for 1 hour, cooled to room temperature and diluted with ethyl acetate (35 mL) and water (25 mL). The organic layer was separated, washed with water (2×25 mL) and brine (1×25 mL), dried over magnesium sulfate, filtered and concentrated to give 293 mg of the crude product. Purification by preparative TLC, eluting with 5% methanol in dichloromethane, gave the free amine (36 mg, (M+H)$^+$= 485). The free base was dissolved in dichloromethane and then 1.0 M HCl in diethyl ether (0.11 mL, 1.5 equivalents) was added and the resulting mixture was stirred for 2 hours. The solvent was removed under reduced pressure at 55° C. and dried under high vacuum at 56° C. for 24 hours to give the desired compound (38 mg, (M+H)$^+$=485) as an off-white powder.

Example 98

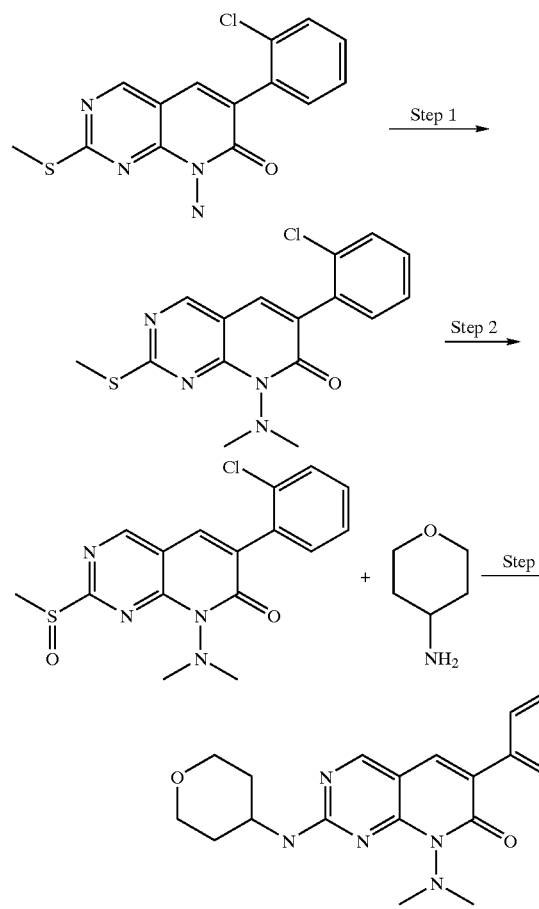

Step 1

To a solution of the sulfide hydrazide 91 (500 mg, 1.57 mmol) in acetonitrile (10 mL) was added 37% formaldehyde $_{(aq)}$ (0.65 mL, 5 equivalents) followed by sodium cyanoborohydride (155 mg, 1.6 equivalents). The resulting mixture was stirred for 15 minutes, and then acetic acid was added as required to maintain a neutral pH. The resulting mixture was stirred for 2 hours, occasionally adding acetic acid to keep the pH neutral. The reaction mixture was diluted with ethyl acetate (300 mL) and water (150 mL). The organic layer was separated, washed with saturated sodium bicarbonate (3×150 mL) and brine (1×150 mL), dried over magnesium sulfate, filtered and concentrated to give 651 mg of the crude product. Purification by flash column chromatography, eluting with 15% ethyl acetate in hexanes, afforded the N,N-dialkylated sulfide hydrazide (37 mg, (M+H)$^+$=347).

Step 2

To a 0° C. solution of the N,N-dialkylated sulfide hydrazide (37 mg, 0.107 mmol) in tetrahydrofuran (3 mL) was added dropwise a solution of Oxone® (66 mg, 1 equivalent) in water (3 mL). The resulting mixture was gradually warmed to room temperature over a 4 hour period, stored overnight at 0° C., and diluted with ethyl acetate (35 mL) and water (20 mL). The organic layer was separated, washed with water (2×20 mL) and brine (1×20 mL), dried over magnesium sulfate, filtered and concentrated to give the N,N-dialkylated sulfoxide hydrazide (35 mg, (M+H)$^+$= 363).

Step 3

A mixture of the N,N-dialkylated sulfoxide hydrazide (35 mg, 0.0965 mmol), 4-amino-tetrahydropyran (39 mg, 4 equivalents) and NMP was stirred at 80° C. for 35 minutes. The reaction mixture was cooled to room temperature and diluted with ethyl acetate (35 mL) and water (25 mL). The organic layer was separated, washed with water (2×25 mL) and brine (1×25 mL), dried over magnesium sulfate, filtered and concentrated to give 39 mg of the crude product. Purification by preparative TLC, eluting with 5% methanol in dichloromethane, afforded the free amine (29 mg). The free amine was dissolved in dichloromethane (5 mL) and 1 M HCl in diethyl ether (0.1 mL, 1.5 equivalents) was added. The resulting mixture was stirred for 2 minutes. The solvent was removed under reduced pressure, and the residue was dried under high vacuum at 56° C. for 24 hours to give the desired product (29 mg, (M+H)$^+$=400) as an off-white powder.

Example 99

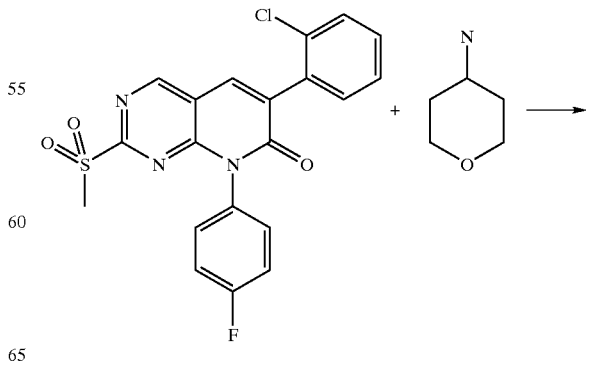

89

-continued

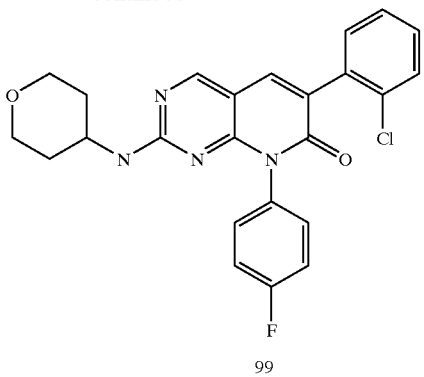

99

A mixture of the sulfone 89 (354 mg, 0.823 mmol), 4-amino-tetrahydropyran (250 mg, 3 equivalents) and NMP (0.3 mL) was stirred at 110° C. for 35 minutes. The reaction mixture was cooled to room temperature and diluted with ethyl acetate (170 mL) and water (70 mL). The organic layer was separated, washed with water (2×70 mL) and brine (1×70 mL), dried over magnesium sulfate, filtered and concentrated to give 393 mg of the crude product. Purification by preparative TLC, eluting with 65% ethyl acetate in hexanes, gave the free amine (261 mg, (M+H)$^+$=451, M.P.=281.7–283.4° C.). The amine was dissolved in dichloromethane (15 mL) and methanol (2 mL) and 1 M HCl in diethyl ether (0.8 mL, 1.5 eq) was added. The resulting mixture was stirred for 1 hour, after which the solvent was removed under reduced pressure and the material was dried under high vaccum at 56° C. to give the desired compound (252 mg, (M+H)$^+$=451, M.P.=150.0–154.0° C.).

Example 100

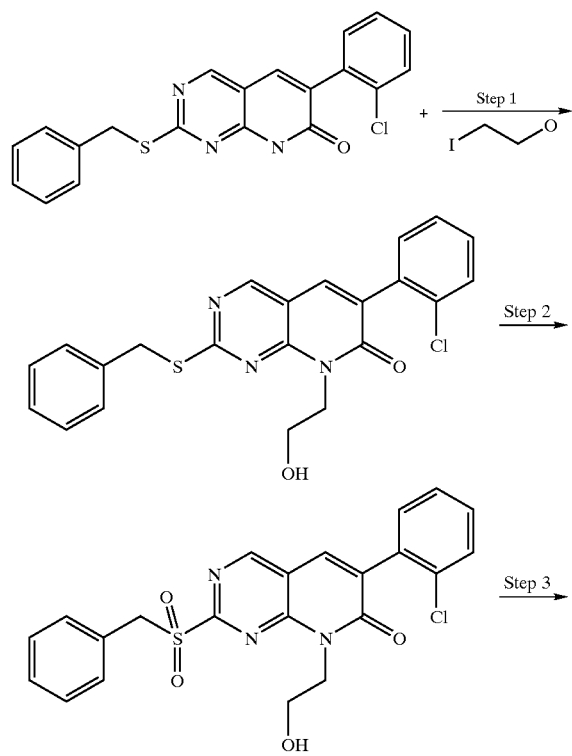

-continued

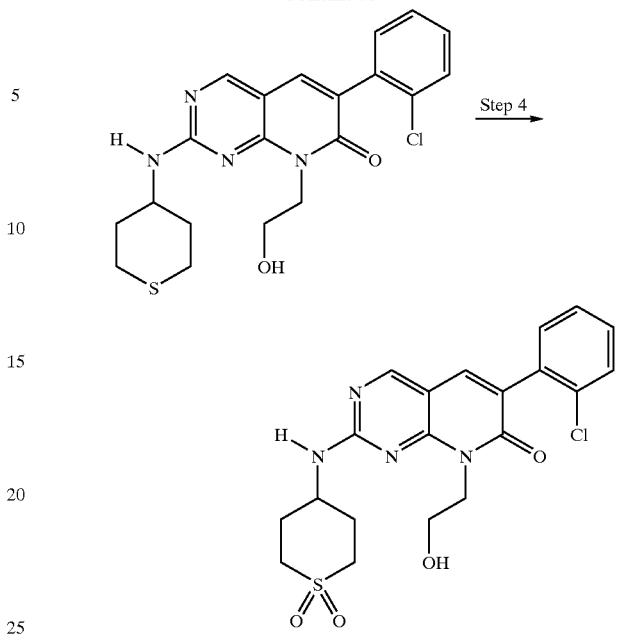

Step 1

To a solution of the benzyl sulfide (5 g, 12.1 mmol) in DMF (50 mL) was added potassium carbonate (1.05 equivalents, 1.76 g) followed by 2-iodoethanol (1.42 mL, 1.5 equivalents), and the resulting mixture was stirred at room temperature overnight. The reaction mixture was diluted with ethyl acetate (300 mL) and water (150 mL). The organic layer was separated and concentrated to a volume of about 150 mL without heating. The white solid was collected by vacuum filtration and air dried on the frit for two hours. The solid was dried further under vacuum to give the N-alkylated hydroxyethyl sulfide (4.139 g, M.P.=155.6° C.–156.2° C.(M+H)$^+$=424).

Step 2

To a 0° C. solution of the N-alkylated hydroxyethyl sulfide (4.13 g, 9.06 mmol) in tetrahydrofuran (200 mL) was added dropwise a solution of Oxone® (11.13 g, 2 equivalents) in water (200 mL). After addition was complete, the ice bath was removed and the resulting mixture was stirred at room temperature overnight. The reaction mixture was poured into a mixture of ethyl acetate (700 mL) and water (400 mL). The organic layer was separated, washed with water (7×500 mL) and brine (5×500 mL), dried over magnesium sulfate, filtered and concentrated to give 2.2 g of N-alkylated hydroxyethyl sulfone. Some of the compound had crystallized when drying over magnesium sulfate and in the separatory funnel. The aqueous layers were combined, and further extracted with dichloromethane (3×300 mL). To these extracts, the magnesium sulfate drying powder from the first organic phase was added and the slurry was stirred overnight. The mixture was filtered and concentrated to give another 2 g of the desired product (M.P.=197.1–198.7, (M+H)$^+$=456).

Step 3

A mixture of the N-alkylated hydroxyethyl sulfone (1 g, 2.19 mmol), 4-amino-tetrahydrothiopyran (385 mg, 1.5 equivalents) and NMP (0.5 mL) was stirred at 100° C. for 2.5 hours. The reaction mixture was cooled to room temperature, diluted with ethyl acetate (50 mL) and water (40 nmL) and stirred for 20 minutes. The organic layer was separated, washed with water (2×45 mL) and brine (1×45 mL), dried over magnesium sulfate, filtered and concentrated to give 1 g of the crude product. Purification by flash column chromatography on silica gel eluting with 20% ethyl acetate in dichloromethane afforded the desired compound (519 mg, M.P.=195.1–195.4° C., (M+H)$^+$=417) as an off-white powder.

Step 4

To a 0° C. solution of the sulfide free amine (500 mg, 1.2 mmol) in dichloromethane (50 mL) was added dropwise a solution of MCPBA (724 mg, 3.5 eq) in dichloromethane (50 mL). The resulting mixture was gradually warmed from 0° C. to room temperature overnight. The reaction mixture was concentrated under reduced pressure at 55° C., and the resulting residue was diluted with ethyl acetate (180 mL) and saturated sodium bicarbonate (60 mL). The organic layer was separated, washed with saturated sodium bicarbonate (3×60 mL) and bine (1×60 mL), dried over magnesium sulfate, filtered and concentrated to give 528 mg of the crude sulfone free amine. Purification by flash column chromatography on silica gel eluting with a gradient of 1% methanol in dichloromethane to 2% methanol in dichloromethane gave the sulfone free amine (279 mg, M.P.=155.0–155.9° C., (M+H)$^+$=449) as an off-white powder. The free amine (278 mg, 0.62 mmol) was taken up in ethyl acetate (50 mL) and then 1 M HCl in diethyl ether (1 mL, 1.5 equivalents) was added. The resulting mixture was stirred for 1 hour and then the solvent was removed under reduced pressure. The residue was dried under high vacuum at 56° C. to give the desired compound (242 mg, M.P.=182.0–186.0, (M+H)$^+$=449) as an off-white powder.

Example 101

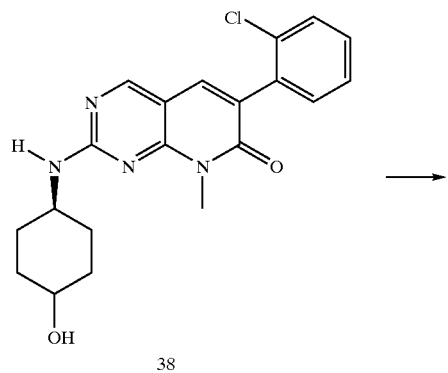

38

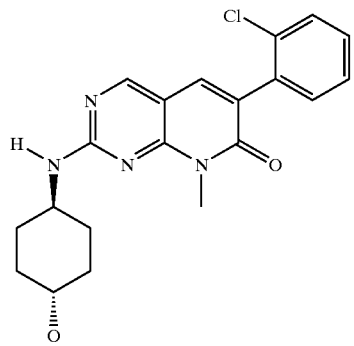

101

A mixture of silver nitrate (1.10 g, 6.50 mmole) and sodium hydroxide (0.52 g, 13.0 mmole) in 5 mL of water was stirred for 15 minutes at room temperature. The resultant silver oxide was collected by vacuum filtration, washed with water, and dried in vacuo before adding to a solution of trans-aminocyclohexanol adduct 38 (0.500 g, 1.30 mmole) in 2 mL of tetrahydrofuran, to which methyl iodide (0.16 mL, 2.60 mmole) was also added. The reaction mixture was stirred at 40° C. overnight, then raised to 60° C. for 5 days, adding more methyl iodide (1.30 mmole, 0.08 mL) after the first day at 60° C.

Purification by flash chromatography (10–50% acetone/hexanes) yielded the desired product as shown above, as well as the N-methylated isomer. Each product was individually taken up in methanol, treated with hydrochloric acid (1.0 M/Et$_2$O, 1.0 equivalent), and re-evaporated to dryness, then washed with ethyl ether, filtered, and dried to give 0.157 g of the desired O-methylated product (mp 189.0–192.0° C.) and 0.069 g of the N-methylated product (mp 130.3–130.5° C.).

Example 102

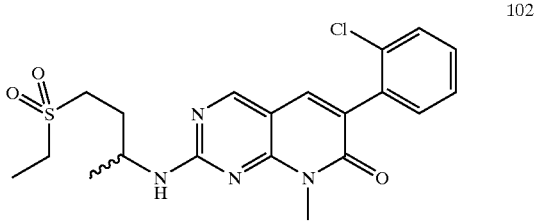

102

Step A: Preparation of 4-ethylsulfanyl-butan-2-one

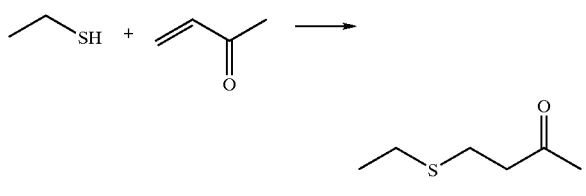

To a 5° C. solution of ethanethiol (6.2 g, 7.4 mL, 0.1 mol), 3 drops of DBU in 50 mL of THF was added dropwise methyl vinyl ketone (7.3 g, 8.45 mL, 0.105 mol). The solution mixture was allowed to stir overnight at ambient temperature. The mixture was then concentrated in vacuo to afford 13.6 g of the desired ketone.

Step B: Preparation of 4-ethylsulfanyl-butan-2-one oxime

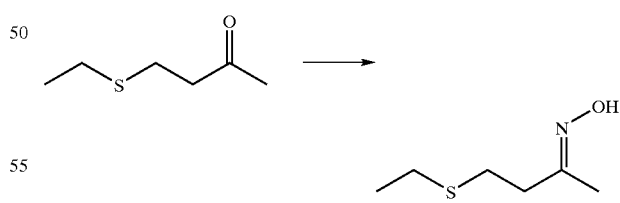

A mixture of 4-ethylsulfanyl-butan-2-one (13.6 g, 0.1 mol), sodium acetate trihydrate (68 g, 0.5 mol) and hydroxylamine hydrochloride (34.7 g, 0.5 mol) in 500 mL of ethanol was heated to refluxed for 3 hours. The mixture was cooled and concentrated in vacuo. The residue was diluted with water and extracted with ethyl acetate (2×200 mL). The organic layers were combined, washed with brine, dried, filtered and concentrated in vacuo to afford 14.7 g of the oxime.

Step C: Preparation of 2-amino-4-ethylsulfanyl-butane

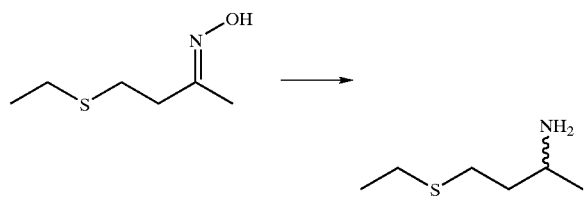

To a solution of lithium aluminum hydride (1 M, 120 mL, 0.12 mol) in tetrahydrofuran was added dropwise 4-ethylsulfanyl-butan-2-one oxime (6 g, 0.04 mol) in 30 mL of tetrahydrofuran. After addition was completed, the mixture was stirred at reflux for 4 hours. The suspension was cooled with an ice-water bath and water (4.6 mL) and 20 mL of tetrahydrofuran were added dropwise, followed by an aqueous solution of sodium hydroxide (15%, 4.6 mL). Additional water (13.8 mL) was then added and the reaction mixture was stirred for 30 minutes, filtered through a celite pad and rinsed with ethyl acetate (300 mL). The filtrate was dried (brine, MgSO$_4$) and evaporated under reduced pressure to afford 3.43 g of 2-amino4-ethylsulfanyl-butane (mass spec. M+1=134).

Step D: Preparation of 102A and 102B

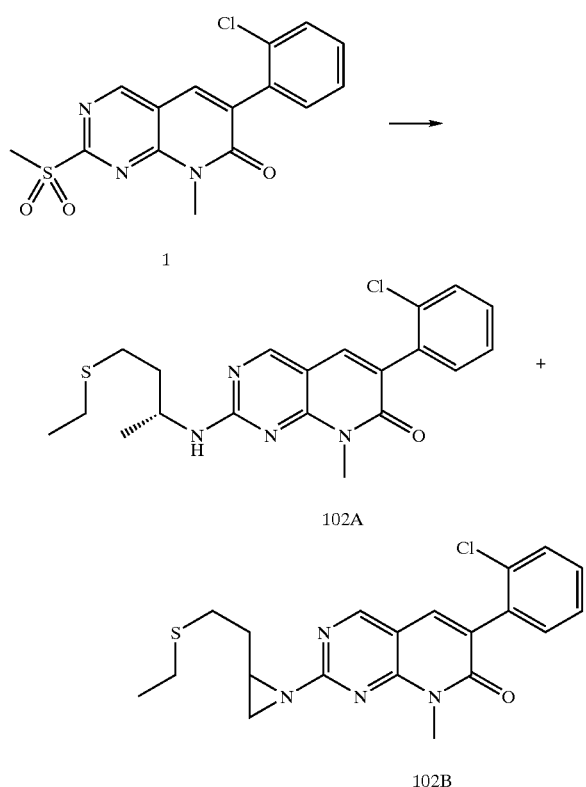

A solution of the sulfone 1 (0.55 g, 1.6 mmol) and 2-amino-4-ethylsulfanyl-butane (0.63 g, 4.8 mmol) in 10 mL of tetrahydrofuran was refluxed for 1 hour. The solution was cooled and concentrated in vacuo and the product was purified by column chromatography with silica eluting with 5% ethyl acetate in dichloromethane to afford 421 mg of a racemic mixture of 102A (mass spec. M+1=403) and 31 mg of the aziridine compound 102B (mass spec. M+1=401, MP=160–167° C.).

Step E: Preparation of 102:

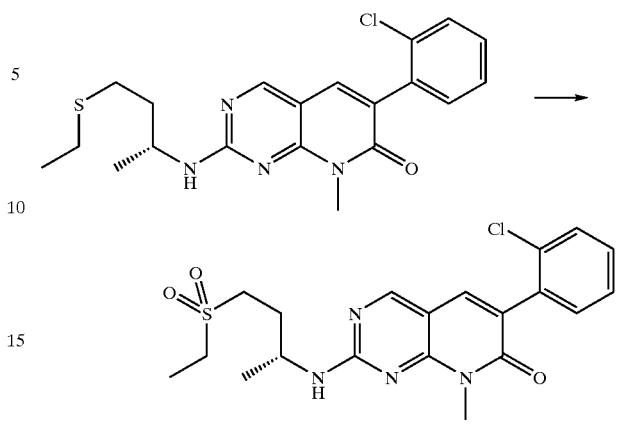

To a cooled solution of the sulfide 102A (0.371 g, 0.92 mmol) in dichloromethane at 5° C. was added the 3-chloroperbenzoic acid (0.43 g, 1.94 mmol) in two batches over a period of 30 minutes. The mixture was allowed to stir overnight at ambient temperature. The reaction mixture was quenched with an aqueous sodium sulfite solution (10%, 100 mL), then washed with cold saturated aqueous sodium bicarbonate solution (100 mL). The organic solution was dried (brine, MgSO$_4$), evaporated under reduced pressure, and purified via column chromatography (SiO$_2$, 2.5% methanol in dichloromethane) affording 379 g of sulfone. This was dissolved in 3 mL of dichloromethane and hydrochloric acid in ether (1M, 1 mL) was added. The suspension formed was stirred for 30 minutes, filtered and rinsing with ether yielded 346 mg of the hydrochloride salt of the desired sulfone 102 (mass spec. M+1=435, MP =160.1–167° C.).

Example 103

This example illustrate an assay protocol for determining in vitro inhibition of p-38 (MAP) Kinase.

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. Biol. Chem.* Vol. 266(7), 4220–4227, (1991).

The phosphorylated form of the recombinant p38 MAP kinase was expressed with SEK-1 and MEKK in *E. Coli* and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Compounds of the invention were active in this assay. The p-38 inhibitory activities (expressed as IC$_{50}$, the concentration causing 50% inhibition of the p-38 enzyme being assayed) of some compounds of the invention are:

| CPD # (from Table 1) | IC$_{50}$ (M) |
|---|---|
| 1 | $2.05 \times 10^{-8}$ |
| 2 | $4.19 \times 10^{-8}$ |
| 11 | $4.80 \times 10^{-9}$ |
| 24 | $3.55 \times 10^{-8}$ |
| 29 | $4.15 \times 10^{-8}$ |
| 37 | $3.05 \times 10^{-8}$ |
| 38 | $6.2 \times 10^{-9}$ |
| 41 | $5.1 \times 10^{-9}$ |
| 44 | $7.8 \times 10^{-9}$ |
| 63 | $7.30 \times 10^{-9}$ |
| 73 | $2.09 \times 10^{-8}$ |
| 126 | $3.00 \times 10^{-10}$ |
| 128 | $6.00 \times 10^{-10}$ |
| 136 | $8.20 \times 10^{-9}$ |

Example 104

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis:

THP-1 cells were suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 min., at 37° C. LPS (Sigma St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. GUT. Vol. 39(5), 684–689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The IC$_{50}$ value was defined as the concentration of the test compound corresponding to half-maximal reduction in 450 nm absorbance.

Example 105

This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18–21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by CO$_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

Example 106

This example illustrates an alternative method for producing 6-(2-chlorophenyl)-8-methyl-2-methylthio-8-hydropyridino[2,3-d]pyrimidin-7-one (VI)

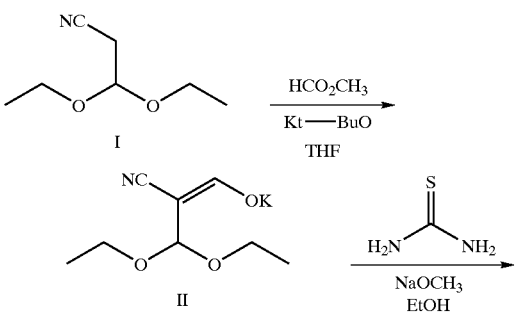

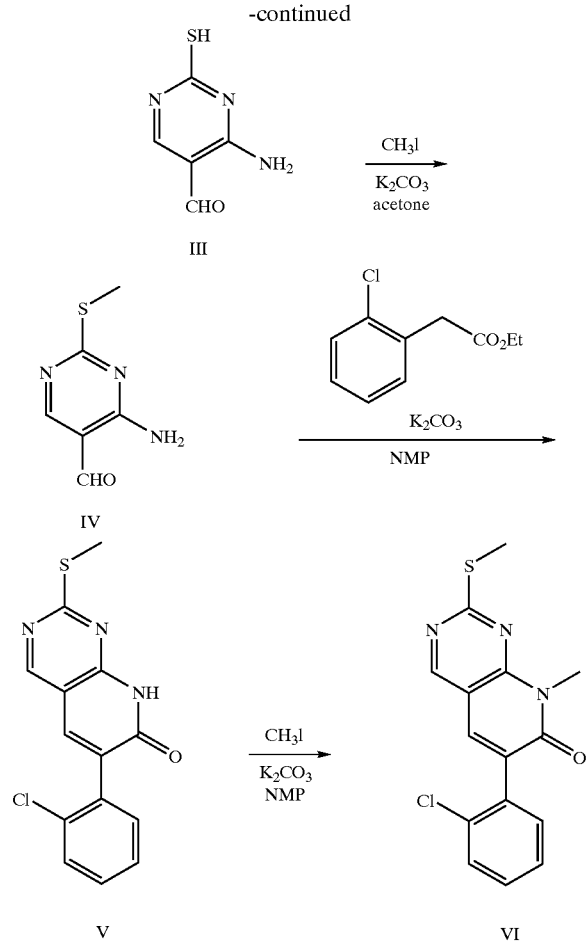

Preparation of 3,3-Diethoxy-2-formylpropionitrile Potassium Salt (II)

To a stirred solution of 3,3-diethoxypropane-nitrile (I, 283.80 g, 1.98 moles) and methyl formate (148.80 g, 2.48 moles) in anhydrous THF (1.1 L) at 10° C. was added 1.0 M potassium tert-butoxide in THF (2.2 L, 2.2 moles). Temperature was maintained in the range of 10° C. to 15° C. throughout the 45 minute addition. Following the addition, the resulting slurry was stirred 2 hours at ambient room temperature. Hexane (400 mL) was then added and stirring was continued for another 20 min. The slurry was filtered and the cake washed with 1/1 hexanes/THF and dried overnight at 60° C. in a vacuum oven. The yield of pale tan powder was 302.5 grams (73.0%). $^1$H-NMR (CD$_3$OD) was consistent with the desired structure II.

Preparation of 4-Amino-2-sulfanylpyrimidine-5-carbaldehyde (III)

A slurry of thiourea (92.8 g, 1.22 moles) in ethanol (90 mL) was heated under reflux and vigorously stirred. To this slurry was added a suspension of 3,3-diethoxy-2-formylpropionitrile potassium salt II (222.20 g, 1.06 moles) in 25% sodium methoxide/methanol (85.5 mL, 0.37 mole) and ethanol (285 mL) in five aliquots over a 10 minute period while maintaining reflux conditions (alternatively, the latter slurry may be heated to 50° C. to give a homogenous solution for the addition). An additional portion of ethanol (150 mL) was added to facilitate stirring. The thick slurry became a bright yellow color following the addition and was held under reflux for an additional 1 hour. The mixture was then cooled and evaporated to near dryness on a rotoevaporator. The residue was dissolved in water (940 mL). Crude product was precipitated from solution by the addition of 30% acetic acid (280 mL) and isolated via filtration using a medium frit sintered glass filtration funnel. The cake was washed with water (800 mL). Purification via trituration in hot water (1 L) for 30 minutes, followed by cooling and filtration gave 118.9 grams (72.3%) of product as a bright yellow solid after drying overnight at 60° C. in a vacuum oven (subsequent preparations have demonstrated that this trituration is unnecessary). An HPLC gave purity as 98.67%. $^1$H-NMR (DMSO-d$_6$) was consistent with desired structure III.

Preparation of 4-Amino-2-methylthiopyrimidine-5-carbaldehyde (IV)

To a solution of 4-amino-2-sulfanyl-pyrimidine-5-carbaldehyde III (100.00 g, 644.4 mmoles) and 325 mesh potassium carbonate (178.10 g, 1.29 moles) in acetone (1.5 L) was added iodomethane (128.10 g, 902.2 mmoles) dropwise over 20 minutes with mild cooling. The mixture was stirred at ambient room temperature over the weekend. TLC showed remaining III and an additional aliquot of iodomethane was added (8 mL) and stirring was continued overnight. TLC again showed some III remaining and an addition portion of iodomethane was added (8 mL) and stirring was continued another 24 hour period. An HPLC showed 95.9% S-alkylated product and 3.7% of compound III. The reaction mixture was stripped to near dryness on a rotoevaporator. Water (1 L) was added to the residue and the product was collected via filtration and washed with water (200 mL). The product was dried overnight in a vacuum oven at 60° C. Yield was 103.37 grams (94.8%). An HPLC showed 95.8% IV and 4.2% III.

Preparation of 6-(2-chlorophenyl)-2-methylthio-8-hydropyridino[2,3-d]pyrimidin-7-one (V)

A mixture of IV (10.00 g, 59.1 mmoles), ethyl 2-(2-chlorophenyl)acetate (14.40 g, 71.8 mmoles), NMP (115 mL) and 325 mesh potassium carbonate (29.00 g, 209.8 mmoles) was heated at 95° C. overnight. The reaction mixture was cooled and diluted with water (800 mL). The resulting slurry was stirred overnight and filtered to isolate product (V). The filter cake was washed with water and dried at 60° C. in a vacuum oven overnight. Isolated yield was 14.9 grams (83.0%) of dark tan solid. Analysis by an HPLC showed 98.3% purity.

Preparation of 6-(2-Chlorophenyl)-8-methyl-2-methylthio-8-hydropyridino[2,3-d]pyrimidin-7-one (VI)

A mixture of V (0.25 g, 0.82 mmole), NMP (5 mL), potassium carbonate (0.11 g, 0.82 mmole), and iodomethane (0.14 g, 0.96 mmole) was stirred under nitrogen at ambient room temperature overnight. Water (15 mL) was added and stirring was continued for 24 hours. The slurry was filtered and the filter cake washed with water (10 mL). An HPLC showed 97.8% purity.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A method of reducing the development of a p38 mediated disorder, which method comprises:
administering to a mammal in need of such treatment a therapeutically effective amount of a compound of Formula I

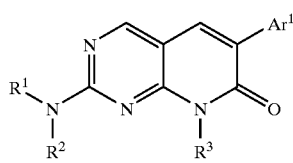

Formula I or salts thereof,
wherein:
$R^1$ is hydrogen or alkyl;
$R^2$ is substituted cycloalkyl, heterosubstituted cycloalkyl, heteroalkylsubstituted cycloalkyl, heterosubstituted cycloalkyl-alkyl, heterocyclyl, heterocyclyl spiro cycloalkyl, aralkoxy, alkoxy, -alkylene-S(O)$_n$-alkyl (where n is 1 or 2) or —SO$_2$Ar$^2$;
$R^3$ is hydrogen, amino, monoalkylamino, dialkylamino, acylamino, —NR$^a$ C(—O)—R$^b$ (where R$^a$ is hydrogen or alkyl and R$^b$ is heterocyclyl or heteroalkyl), alkyl, cycloalkyl, phthalimidoalkyl, aryl, aralkyl, haloalkyl, heteroalkyl, cyanoalkyl, -alkylene-C(O)—R (where R is hydrogen, alkyl, hydroxy, alkoxy, amino, monoalkylamino or dialkylamino) or acyl; and
each of Ar$^1$ and Ar$^2$ is independently aryl;
wherein said p38 mediated disorder is selected from the group consisting of Alzheimer's disease, adult respiratory distress syndrome, and chronic obstructive pulmonary disease.

2. The method of claim 1 wherein Ar$^1$ is an optionally substituted phenyl.

3. The method of claim 2, wherein Ar$^1$ is a phenyl group independently substituted with one or two halo, alkyl or methoxy groups.

4. The method of claim 3, wherein Ar$^1$ is 2-chlorophenyl, 2-methylphenyl or 2-methoxyphenyl.

5. The method according to claim 4 wherein said compound is of the formula:

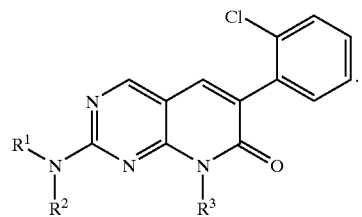

6. The method according to claim 1, wherein $R^3$ is hydrogen, amino, monoalkylamino, dialkylamino, acylamino, —NR$^a$—C(=O) R$^b$ (where R$^a$ is hydrogen or alkyl and R$^b$ is heterocyclyl or heteroalkyl), alkyl, haloalkyl, cycloalkyl, cyanomethyl, phthalimidoalkyl, heteroalkyl, aryl, aralkyl or -alkylene-C(O) R.

7. The method according to claim 6, wherein $R^3$ is hydrogen, amino, dimethylamino, isopropylamino, (morpholinoformyl)amino, methyl, 2,2,2-trifluoroethyl, cyclopropyl, cyanomethyl, phthalimidoalkyl, 2-hydroxyethyl, 4-fluorophenyl, benzyl, carboxymethyl or methoxycarbonylmethyl.

8. The method according to claim 7, wherein $R^3$ is hydrogen or methyl.

9. The method according to claim 1, wherein $R^3$ is hydrogen or methyl, and Ar$^1$ is a phenyl group independently substituted with one or two halo, alkyl or methoxy groups.

10. The method according to claim 1, wherein $R^1$ is hydrogen or methyl.

11. The method according to claim 10, wherein $R^1$ is hydrogen.

12. The method according to claim 1, wherein $R^2$ is heterosubstituted cycloalkyl, heteroalkylsubstituted cycloalkyl, aralkoxy, alkoxy, alkylsulfonyl-alkyl or heterocyclyl.

13. The method according to claim 12, wherein $R^2$ is heterosubstituted cycloalkyl or heterocyclyl.

14. The method according to claim 13, wherein $R^2$ is 4-hetero-substituted cyclohexyl.

15. The method according to claim 14, wherein $R^2$ is 4-hydroxy-cyclohexyl.

16. The method according to claim 13, wherein $R^2$ is heterocyclyl.

17. The method according to claim 16, wherein $R^2$ is a substituted piperidinyl group.

18. The method according to claim 16, wherein $R^2$ is N-methanesulfonyl-piperidin-4-yl.

19. The method according to claim 16, wherein $R^2$ is a 4-tetrahydropyranyl group.

20. The method according to claim 1, wherein $R^2$ is heterosubstituted cycloalkyl or heterocyclyl, and Ar$^1$ is a phenyl group independently substituted with one or two halo, alkyl or methoxy groups.

21. The method according to claim 20, wherein $R^3$ is hydrogen.

22. The method according to claim 20, wherein $R^3$ is methyl.

23. The method according to claim 1, wherein $R^2$ is alkylsulfonyl-alkyl.

24. The method according to claim 23, wherein $R^2$ is selected from the group consisting of (1,1-dimethyl-2-methylsulfonyl)ethyl and (1,1-dimethyl-3-methylsulfonyl)propyl.

* * * * *